United States Patent
South et al.

(10) Patent No.: US 9,765,348 B2
(45) Date of Patent: Sep. 19, 2017

(54) MICROORGANISMS ENGINEERED TO USE UNCONVENTIONAL SOURCES OF NITROGEN

(71) Applicant: Novogy, Inc., Cambridge, MA (US)

(72) Inventors: Colin R. South, Lexington, MA (US); Arthur J. Shaw, IV, Belmont, MA (US)

(73) Assignee: Novogy, Inc., Cambridge, MA (US)

( * ) Notice: Subject to any disclaimer, the term of this patent is extended or adjusted under 35 U.S.C. 154(b) by 49 days.

(21) Appl. No.: 14/759,878

(22) PCT Filed: Jan. 6, 2014

(86) PCT No.: PCT/US2014/010332
§ 371 (c)(1),
(2) Date: Jul. 8, 2015

(87) PCT Pub. No.: WO2014/107660
PCT Pub. Date: Jul. 10, 2014

(65) Prior Publication Data
US 2016/0115492 A1    Apr. 28, 2016

Related U.S. Application Data

(60) Provisional application No. 61/782,351, filed on Mar. 14, 2013, provisional application No. 61/748,901, filed on Jan. 4, 2013.

(51) Int. Cl.
| | |
|---|---|
| C12N 1/20 | (2006.01) |
| C12N 15/81 | (2006.01) |
| C12N 9/14 | (2006.01) |
| C12N 9/88 | (2006.01) |
| C12P 3/00 | (2006.01) |
| C12N 15/70 | (2006.01) |

(52) U.S. Cl.
CPC ............. *C12N 15/815* (2013.01); *C12N 1/20* (2013.01); *C12N 9/14* (2013.01); *C12N 9/88* (2013.01); *C12N 15/70* (2013.01); *C12N 15/81* (2013.01); *C12P 3/00* (2013.01); *C12Y 308/01* (2013.01); *C12Y 402/01069* (2013.01)

(58) Field of Classification Search
CPC ................................. C12N 1/20; C12N 9/14
USPC ............................................. 435/252.3, 320.1
See application file for complete search history.

(56) References Cited

U.S. PATENT DOCUMENTS

| | | |
|---|---|---|
| 2011/0127108 A1 | 6/2011 | Teichert |
| 2011/0129566 A1 | 6/2011 | Van Vuuren et al. |

OTHER PUBLICATIONS

Cameron SM, Durchschein K, Richman JE, Sadowsky MJ, Wackett LP. 2011. New Family of Biuret Hydrolases Involved in s-Triazine Ring Metabolism. ACS Catal. 1:1075-1082.
Copley, Shelley D., Evolution of Efficient Pathways for Degradation of Anthropogenic Chemicals. Nat Chem Biol. Aug. 2009; 5(*): 559-566 doi:10.1038/nchembio.197.
Dodge AG, Wackett LP, Sadowsky MJ. 2012. Plasmid Localization and Organization of Melamine Degradation Genes in *Rhodococcus* sp. Strain Mel. Applied and Environmental Microbiology 78:1397-1403.
Eaton RW, Karns JS. 1991. Cloning and analysis of s-triazine catabolic genes from *Pseudomonas* sp. strain NRRLB-12227. Journal of Bacteriology 173:1215-1222.
Eaton RW, Karns JS. 1991. Cloning and comparison of the DNA encoding ammelide aminohydrolase and cyanuric acid amidohydrolase from three s-triazine-degrading bacterial strains. Journal of Bacteriology 173:1363-1366.
El-Sayed WS, El-Baz AF, Othman AM. 2006. Biodegradation of melamine formaldehyde by *Micrococcus* sp. strain MF-1 isolated from aminoplastic wastewater effluent. International Biodeterioration & Biodegradation 57:75-81.
Kamo T, Endo M, Sato M, Kasahara R, Yamaya H, Hiradate S, Fujii Y, Hirai N, Hirota M. 2008. Limited distribution of natural cyanamide in higher plants: Occurrence in *Vicia villosa* subsp. *varia*, V. *cracca*, and *Robinia* pseudo-acacia. Phytochemistry 69:1166-1172.
Kamo T, Sato M, Kato K, Hiradate S, Nakajima E, Fujii Y, Hirota M. 2006. Quantification of Cyanamide Contents in Herbaceous Plants. Bioscience, Biotechnology, and Biochemistry 70:2310-2312.
Karns JS. 1999. Gene Sequence and Properties of ans-Triazine Ring-Cleavage Enzyme from *Pseudomonas*sp. Strain NRRLB-12227. Applied and Environmental Microbiology 65:3512-3517.
Leeson A, Hapeman CJ, Shelton DR. 1993. Biomineralization of atrazine ozonation products. Application to the development of a pesticide waste disposal system. J. Agric. Food Chem. 41:983-987.
Maier-Greiner UH, Obermaier-Skrobranek BM, Estermaier LM, Kammerloher W, Freund C, Wülfing C, Burkert UI, Matern DH, Breuer M, Eulitz M. 1991. Isolation and properties of a nitrile hydratase from the soil fungus *Myrothecium verrucaria* that is highly specific for the fertilizer cyanamide and cloning of its gene. Proceedings of the National Academy of Sciences 88:4260-4264.
Martinez B, Tomkins J, Wackett LP, Wing R, Sadowsky MJ. 2001. Complete Nucleotide Sequence and Organization of the Atrazine Catabolic Plasmid pADP-1 from *Pseudomonas*sp. Strain ADP. Journal of Bacteriology 183:5684-5697.
Mäser P, Sütterlin C, Kralli A, Kaminsky R. 1999. A Nucleoside Transporter from *Trypanosoma brucei* Involved in Drug Resistance. Science 285:242-244.
Schwarzer C, Auer B, Klima J, Haselwandter K. 1998. Physiological and electron microscopical investigations on syntrophic dicyandiamide degradation by soil bacteria. Soil Biology and Biochemistry 30:385-391.
Seffernick JL, De Souza ML, Sadowsky MJ, Wackett LP. 2001. Melamine Deaminase and Atrazine Chlorohydrolase: 98 Percent Identical but Functionally Different. Journal of Bacteriology 183:2405-2410.

(Continued)

*Primary Examiner* — Tekchand Saidha
(74) *Attorney, Agent, or Firm* — Albert Shung

(57) ABSTRACT

Disclosed are genetically engineered organisms, such as yeast and bacteria, that have the ability to metabolize atypical nitrogen sources, such as melamine and cyanamide. Fermentation methods using the genetically engineered organisms are also described. The methods of the invention are robust processes for the industrial bioproduction of a variety of compounds, including commodities, fine chemicals, and pharmaceuticals.

19 Claims, 29 Drawing Sheets

(56) References Cited

OTHER PUBLICATIONS

Seffernick JL, Dodge AG, Sadowsky MJ, Bumpus JA, Wackett LP. 2010. Bacterial Ammeline Metabolism via Guanine Deaminase. Journal of Bacteriology 192:1106-1112.

Shapir N, Cheng G, Sadowsky MJ, Wackett LP. 2006. Purification and Characterization of TrzF: Biuret Hydrolysis by Allophanate Hydrolase Supports Growth. Applied and Environmental Microbiology 72:2491-2495.

Shapir N, Osborne JP, Johnson G, Sadowsky MJ, Wackett LP. 2002. Purification, Substrate Range, and Metal Center of AtzC: the N-Isopropylammelide Aminohydrolase Involved in Bacterial Atrazine Metabolism. Journal of Bacteriology 184:5376-5384.

Shelton DR, Karns JS, McCarty GW, Durham DR. 1997. Metabolism of Melamine by Klebsiella terragena. Applied and Environmental Microbiology 63:2832-5.

Strong LC, Rosendahl C, Johnson G, Sadowsky MJ, Wackett LP. 2002. Arthrobacter aurescens TC1 Metabolizes Diverse s-Triazine Ring Compounds. Applied and Environmental Microbiology 68:5973-5980.

Sýkora V, Pitter P, Bittnerová I, Lederer T. 2001. Biodegradability of ethylenediamine-based complexing agents. Water Research 35:2010-2016.

Ulanov A, Widholm JM. 2007. Effect of the expression of cyanamide hydratase on metabolites in cyanamide-treated soybean plants kept in the light or dark. Journal of Experimental Botany 58:4319-4332.

Wackett LP. 1999. Microbial Enzymes in Biodegradation, p. 95-103. In Fass, R, Flashner, Y, Reuveny, S (eds.), Springer US.

Zeyer J, Bodmer J, Hütter R. 1981. Microbial degradation of Ammeline. Zentralblatt füur Bakteriologie Mikrobiologie und Hygiene: I. Abt. Originale C: Allgemeine, angewandte und ökologische Mikrobiologie 2:289-298.

Cheng et al., "Allophanate Hydrolase, Not Urease, Functions in Bacterial Cyanuric Acid Metabolism," Appl Environ Microb, 71(8): 4437-4445 (Aug. 2005).

De Souza et al., "The atzABC Genes Encoding Atrazine Catabolism Are Located on a Self-Transmissible Plasmid in Pseudomonas sp. Strain ADP," Appl Environ Microb, 64(6): 2323-2326 (Jun. 1998).

Fruchey et al., "On the Origins of Cyanuric Acid Hydrolase: Purification, Substrates, and Prevalence of AtzD from Pseudomonas sp. Strain ADP," Appl Environ Microb, 69(6): 3653-3657 (Jun. 2003).

Shapir et al., "Evolution of Catabolic Pathways: Genomic Insights into Microbial s-Triazine Metabolism," J Bacteriol, 189(3): 674-682 (Feb. 2007).

Takagi et al., "Biodegradation of Melamine and its Hydroxy Derivatives by a Bacterial Consortium Containing a Novel Nocardioides Species," Appl Microbiol Biotechnol, 94: 1647-1656 (2012).

Shapir, et al., "Purification and Characterization of Allophanate Hydrolase (AtzF) from Pseudomonas sp. Straing ADP," J Bacteriol, 187(11): 3731-3738 (2005).

Figure 2

| Compound | Formula | % N |
|---|---|---|
| Hydrazine | $N_2H_4$ | 88% |
| 5-Aminotetrazole | $CH_3N_5$ | 82% |
| Tetrazole | $CH_2N_4$ | 80% |
| Melamine | $C_3H_6N_6$ | 67% |
| Cyanamide | $CH_2N_2$ | 67% |
| 2-Cyanoguanidine | $C_2H_4N_4$ | 67% |
| Sodium azide | $NaN_3$ | 65% |
| Carbohydrazide | $CH_6N_4O$ | 62% |
| 1,2,3-Triazole | $C_2H_3N_3$ | 61% |
| 1,2,4-Triazole | $C_2H_3N_3$ | 61% |
| 1,3-Diaminoguanidine HCL | $CH_7N_5 \cdot HCl$ | 56% |
| Ammeline | $C_3H_5N_5O$ | 55% |
| 1,3,5-triazine | $C_3H_3N_3$ | 52% |
| Aminoacetonitrile | $C_2H_4N_2$ | 50% |
| Cyanoethylhydrazine | $C_3H_7N_3$ | 49% |
| Azodicarbonamide | $C_2H_4O_2N_4$ | 48% |
| Biurea | $C_2H_6N_4O_2$ | 47% |
| Formamidoxime | $CH_4N_2O$ | 47% |
| 1,2-Dimethylhydrazine | $C_2H_8N_2$ | 47% |
| 1,1-Dimethylhydrazine | $C_2H_8N_2$ | 47% |
| ethylhydrazine | $C_2H_8N_2$ | 47% |
| Ethylenediamine | $C_2H_8N_2$ | 47% |
| Sodium dicyanamide | $C_2N_3Na$ | 47% |
| Guanidine carbonate | $CH_5N_3 * \frac{1}{2} H_2CO_3$ | 47% |
| Methylamine | $CH_5N$ | 45% |
| Ammelide | $C_3H_4N_4O_2$ | 44% |
| Hydroxylamine | $NH_2OH$ | 42% |
| Malononitrile | $C_3H_2N_2$ | 42% |
| Biuret | $C_2H_5N_3O_2$ | 41% |
| Diethyltriamine | $C_4H_{13}N_3$ | 41% |

Figure 2 (continued)

| | | |
|---|---|---|
| Hexamethylenetetramine | $C_6H_{12}N_4$ | 40% |
| Triethylenetetramine | $C_6H_{18}N_4$ | 38% |
| 1,3-Diaminopropane | $C_3H_{10}N_2$ | 38% |
| Triethylenetetramine | $C_6H_{18}N_4$ | 38% |
| 1,3-Diaminopropane | $C_3H_{10}N_2$ | 38% |
| Hydroxyurea | $CH_4N_2O_2$ | 37% |
| Tetraethylenepentamine | $C_8H_{23}N_5$ | 37% |
| Thiourea | $CH_4N_2S$ | 37% |
| Succinonitrile | $C_4H_4N_2$ | 35% |
| Calcium cyanamide | $CaCN_2$ | 35% |
| Cyanuric acid | $C_3H_3N_3O_3$ | 33% |
| Aminoethylpiperazine | $C_6H_{15}N_3$ | 33% |
| Piperazine | $C_4H_{10}N_2$ | 33% |
| Dimethylamine | $C_2H_7N$ | 31% |
| Ethylamine | $C_2H_7N$ | 31% |
| dalfampridine | $C_5H_6N_2$ | 30% |
| Tetranitromethane | $CN_4O_8$ | 29% |
| Imidazolidinyl urea | $C_{11}H_{16}N_8O_8$ | 29% |
| Trinitromethane | $CHN_3O_6$ | 28% |
| malonamide | $C_3H_6N_2O_2$ | 27% |
| Chloramine | $NH_2Cl$ | 27% |
| Allophante | $C_2H_3N_2O_3$ | 27% |
| Trimethylamine | $C_3H_9N$ | 24% |
| Nitromethane | $CH_3NO_2$ | 23% |
| Acetaldoxime | $C_2H_5NO$ | 23% |
| Diazolidinyl urea | $C_8H_{14}N_4O_7$ | 20% |
| 1,2-Cyclohexanedione dioxime | $C_6H_{10}N_2O_2$ | 20% |
| Acetone oxime | $C_3H_7NO$ | 19% |
| Thioacetamide | $C_2H_5NS$ | 19% |
| Sodium thiocyanate | $NaSCN$ | 17% |
| Isothiazole | $C_3H_3NS$ | 16% |
| Thiazole | $C_3H_3NS$ | 16% |

Figure 2 (continued)

| | | |
|---|---|---|
| Dimethylacetamide | $C_4H_9NO$ | 16% |
| Isothiazolinone | $C_3H_3NOS$ | 14% |
| Methylene blue | $C_{16}H_{18}N_3SCl$ | 13% |
| Diethanolamine | $C_4H_{11}NO_2$ | 13% |
| Aspartame | $C_{14}H_{18}N_2O_5$ | 10% |
| Benzisothiazolinone | $C_7H_5NOS$ | 7% |
| Acesulfame potassium | $C_4H_4KNO_4S$ | 7% |

Figure 3

| Enzyme | Gene | Source | EC | Genbank | Genbank Protein or Nucleotide Region |
|---|---|---|---|---|---|
| Melamine deaminase | trzA | Williamsia sp. NRRL B-15444R (formerly R. corallinus) | 3.5.4.- | JN241635 | |
| Melamine deaminase | triA | Pseudomonas sp. strain NRRL B-12227 (formerly Acidovorax citrulli) | 3.5.4.- | AF312304 | |
| Guanine (ammeline) deaminase | guaD | E. coli K12 strain MG1566 | 3.5.4.3 | NC_000913 | REGION: 3023788..3025107 |
| Guanine (ammeline) deaminase | blr3880 | Bradyrhizobium japonicum USDA 110 | 3.5.4.3 | NC_004463 | REGION: 4303362..4304759 |
| Guanine (ammeline) deaminase | GUD1/YDL238C | S. cerevisiae | 3.5.4.3 | Z74286 | |
| Guanine (ammeline) deaminase | YALI0E25740p | Y. lipolytica CLIB122 | 3.5.4.3 | NC_006071 | REGION: complement(3051691..3053046) |
| ammelide hydrolase | trzC | Pseudomonas sp. strain NRRL B-12227 (formerly Acidovorax citrulli) | 3.5.3.- | AAK00493 | |
| ammelide hydrolase | trzC | Rhodococcus sp. Mel | 3.5.3.- | AEX65049 | |
| N-isopropylammelide isopropylamino hydrolase | atzC | Pseudomonas sp. strain ADP | 3.5.99.4 | NC_004956 | REGION: complement(70219..71430) |
| Cyanuric acid amidohydrolase | trzD | Pseudomonas sp. strain NRRL B-12227 (formerly Acidovorax citrulli) | 3.5.2.15 | AF086815 | |
| Cyanuric acid amidohydrolase | atzD (trzD) | Rhodococcus sp. Mel | 3.5.2.15 | JN241637 | AEX65082 |
| Cyanuric acid amidohydrolase | atzD | Pseudomonas sp. strain ADP | 3.5.2.15 | NC_004956 | REGION: 101053..102144 |
| Biuret amidohydrolase | atzE | Pseudomonas sp. strain ADP | 3.5.1.84 | NC_004956 | REGION: 102427..103800 |
| Biuret amidohydrolase | trzE | Rhodococcus sp. Mel | 3.5.1.84 | AEX65081 | |
| Biuret amidohydrolase | trzE | Rhizobium leguminosarum bv. viciae 3841 | 3.5.1.84 | YP_770628 | |
| Allophanate hydrolase | atzF | Pseudomonas sp. strain ADP | 3.5.1.54 | NC_004956 | REGION: 104283..106100 |
| Allophanate hydrolase | DUR1,2 | S. cerevisiae | 6.3.4.6 / 3.5.1.54 | YSCUAMD | |
| Allophanate hydrolase | YALI0E07271g | Y. lipolytica CLIB122 | 6.3.4.6 / 3.5.1.54 | XM_503658 | |

Figure 11

| MOPS defined medium | mM |
|---|---|
| Glucose | 11.1 |
| $K_2HPO_4$ | 1.32 |
| $K_2SO_4$ | 0.28 |
| $FeSO_4$ | 0.01 |
| $CaCl_2$ | 5E-04 |
| $MgCl_2$ | 0.52 |
| NaCl | 50 |
| MOPS | 40 |
| Tricine | 4 |
| $(NH_4)_6Mo_7O_{24}$ | 3E-06 |
| $H_3BO_3$ | 4E-04 |
| $CoCl_2$ | 3E-05 |
| $CuSO_4$ | 1E-05 |
| $MnCl_2$ | 8E-05 |
| $ZnSO_4$ | 1E-05 |

|  | Optical Density 600 nm | | | |
| --- | --- | --- | --- | --- |
|  | NS100 | NS101 | NS111 | NS112 |
| no nitrogen | 0.18 | 0.19 | 1.31 | 0.99 |
| 10 mM urea | 3.12 | 3.60 | 3.68 | 3.05 |
| 10 mM cyanamide | 0.05 | 4.66 | 3.09 | 0.15 |

|  | Optical Density 600 nm | | |
|---|---|---|---|
|  | NS98 | NS99 | NS100 |
| no nitrogen | 1.43 | 1.37 | 1.09 |
| 10 mM urea | 5.09 | 5.26 | 5.22 |
| 10 mM biuret | 2.55 | 2.18 | 1.21 |

Figure 29

| Plasmid | Description | Genotype |
|---|---|---|
| pNC10 | *E. coli* and *S. cerevisiae* cloning/shuttle vector | Amp, ura3 |
| pNC53 | *E. coli* promoter (pTac)-terminator (trpT') cloning vector (AJS52) | Amp, ura3 |
| pNC67 | *E. coli*, *S. cerevisiae*, and *Y. lipolytica* shuttle vector | Amp, ura3, Hyg, Nat |
| pNC85 | *E. coli triA* expression vector (AJS69) | Amp, ura3 |
| pNC86 | *E. coli trzA, guaD, trzC* expression vector (AJS67) | Amp, ura3 |
| pNC87 | *E. coli trzD, trzE*, DUR1,2 expression vector (AJS68) | Amp, ura3 |
| pNC93 | *S. cerevisiae cah* expression vector (AJS76) | Amp, ura3, Hyg |
| pNC96 | *S. cerevisiae trzE MEL* expression vector (AJS79) | Amp, ura3, Hyg |
| pNC97 | *S. cerevisiae trzE RI* expression vector (AJS80) | Amp, ura3, Hyg |
| pNC101 | E. coli *trzC_12227, guaD, triA* expression vector (AJS83) | Amp, ura3 |
| pNC120 | E. coli *trzD_12227, trzE*, DUR1,2 *trzC_12227, guaD, triA* expression vector (AJS88a) | Amp, ura3 |
| pNC121 | E. coli *atzD_ADP, trzE*, DUR1,2 *trzC_12227, guaD, triA* expression vector (AJS88b) | Amp, ura3 |

Figure 30

| Strain | Description | Culture Collection Designation |
|---|---|---|
| NS21 | Eschericha coli K12 | NRRL B-3707 |
| NS88 | Eschericha coli K12 with pNC85 | |
| NS89 | Eschericha coli K12 with pNC86 | |
| NS90 | Eschericha coli K12 with pNC87 | |
| NS91 | Eschericha coli K12 with pNC53 | |
| NS93 | Eschericha coli K12 with pNC85 selected for ammeline utilization | |
| NS103 | Eschericha coli K12 with pNC101 | |
| NS106 | Eschericha coli MG1655 | ATCC 47076 |
| NS107 | Eschericha coli B | ATCC 11303 |
| NS108 | Eschericha coli Crooks | ATCC 8739 |
| NS109 | Eschericha coli K12 with pNC120 | |
| NS110 | Eschericha coli K12 with pNC121 | |
| NS120 | Eschericha coli MG1655 with pNC53 | |
| NS121 | Eschericha coli MG1655 with pNC121 | |
| NS122 | Eschericha coli B with pNC121 | |
| NS123 | Eschericha coli Crooks with pNC53 | |
| NS124 | Eschericha coli Crooks with pNC121 | |
| NS8 | Saccharomyces cerevisiae | NRRL Y-2223 |
| NS22 | Saccharomyces cerevisiae industrial ethanol strain | |
| NS98 | Saccharomyces cerevisiae industrial ethanol strain with pNC96 | |
| NS99 | Saccharomyces cerevisiae industrial ethanol strain with pNC97 | |
| NS100 | Saccharomyces cerevisiae industrial ethanol strain with pNC67 | |
| NS101 | Saccharomyces cerevisiae industrial ethanol strain with pNC93 | |
| NS111 | Saccharomyces cerevisiae NRRL Y-2223 with pNC93 | |
| NS112 | Saccharomyces cerevisiae NRRL Y-2223 with pNC67 | |

Figure 31

*E. coli* Media

| | mM |
|---|---|
| MOPS defined medium | |
| Glucose | 11.1 |
| $K_2HPO_4$ | 1.32 |
| $K_2SO_4$ | 0.28 |
| $FeSO_4$ | 0.01 |
| $CaCl_2$ | 5E-04 |
| $MgCl_2$ | 0.52 |
| NaCl | 50 |
| MOPS | 40 |
| Tricine | 4 |
| $(NH_4)_6Mo_7O_{24}$ | 3E-06 |
| $H_3BO_3$ | 4E-04 |
| $CoCl_2$ | 3E-05 |
| $CuSO_4$ | 1E-05 |
| $MnCl_2$ | 8E-05 |
| $ZnSO_4$ | 1E-05 |
| Nitrogen source as indicated | 0.25-10 |

Additionally 100 ug/mL ampicillin is added for plasmid maintenance.

Figure 32

<u>S. cerevisiae Media</u>
YNB media (Per liter)
- Glucose        20 g
- Biotin 2 µg
- Calcium pantothenate 400 µg
- Folic acid 2 µg
- Inositol 2000 µg
- Niacin 400 µg
- p-Aminobenzoic acid 200 µg
- Pyridoxine hydrochloride 400 µg
- Riboflavin 200 µg
- Thiamine hydrochloride 400 µg
- Boric acid 500 µg
- Copper sulfate 40 µg
- Potassium iodide 100 µg
- Ferric chloride 200 µg
- Manganese sulfate 400 µg
- Sodium molybdate 200 µg
- Zinc sulfate 400 µg
- Potassium phosphate monobasic 1 g
- Magnesium sulfate 500 mg
- Sodium chloride 100 mg
- Calcium chloride 100 mg Additionally a nitrogen source at 10 mM concentration is added, as well as the antibiotics hygromycin (300 ug/mL) or nourseothricin (100 ug/mL) as appropriate for plasmid maintenance.

Figure 33

SC amino acid composition (total 2 g/L)

| SC amino acids | mg/L |
|---|---|
| Adenine | 21 |
| L-Alanine | 85.6 |
| L-Arginine | 85.6 |
| L-Asparagine | 85.6 |
| L-Aspartic Acid | 85.6 |
| L-Cysteine | 85.6 |
| Glutamine | 85.6 |
| L-Glutamic Acid | 85.6 |
| Glycine | 85.6 |
| L-Histidine | 85.6 |
| Myo-Inositol | 85.6 |
| L-Isoleucine | 85.6 |
| L-Leucine | 173.4 |
| L-Lysine | 85.6 |
| L-Methionine | 85.6 |
| Para-AminoBenzoic Acid (PABA) | 8.6 |
| L-Phenylalenine | 85.6 |
| L-Proline | 85.6 |
| L-Serine | 85.6 |
| L-Threonine | 85.6 |
| L-Tryptophan | 85.6 |
| L-Tyrosine | 85.6 |
| Uracil | 85.6 |
| L-Valine | 85.6 |

SEQUENCE LISTING

```
<160> NUMBER OF SEQ ID NOS: 76

<210> SEQ ID NO 1
<211> LENGTH: 1818
<212> TYPE: DNA
<213> ORGANISM: Pseudomonas sp.

<400> SEQUENCE: 1
atgaatgacc gcgcgcccca ccctgaaaga tctggtcgag tcacgccgga tcacctgacc      60
gatctggctt cctatcaggc tgcctatgcc gccggtacag acgccgccga cgtcatttcg     120
gacctgtatg cccgtatcaa agaagacggc gaaaatccga tctggattag cctgttgccc     180
ttggaaagcg cattggcgat gctggccgac gcgcagcaac gcaaggacaa gggagaagcg     240
ttgccgctct ttggcatccc cttcggcgtc aaggacaaca tcgacgtcgc aggccttccg     300
acgactgccg ggtgtacggg gttcgcgcgt acgccccgac agcacgcctt cgtcgtacag     360
cgcctggtgg acgctggcgc gatcccgatc ggaaaaacga acctcgatca attcgcgacc     420
gggttgaacg gcactcgcac gccgtttggc attccgcgct gcgtgttcaa cgagaactac     480
gtatccggcg gctccagcag tggctccgca gtggccgtcg ccaacggcac ggtaccgttc     540
tcgctcggga cggacactgc cggttccggc cgcattcctg ctgcgttcaa caatctggtg     600
ggcttgaaac cgaccaaagg cctgttctcg ggcagtggac tggttcccgc ggcgcgaagc     660
cttgactgca tcagcgtcct cgcccatacc gtagatgacg cccttgcggt cgcacgcgtc     720
gccgccggct acgatgctga tgacgctttt tcgcgcaagg cgggcgccgc cgcactgaca     780
gaaaagagtt ggcctcgtcg cttcaatttc ggggtcccag cggcggaaca tcgccagttt     840
ttcggtgacg cggaagccga ggcgcttttc aataaagcgg ttcgcaagct tgaagagatg     900
ggtggcacct gcatctcgtt tgactatacc cccttcaggc aggctgctga actgctctac     960
gccggcccct gggttgcgga gcgcctggcg gccatcgaga gccttgcgga cgagcatccc    1020
gaggtgctcc acccggtcgt tcgtgacatc atcttgtccg cgaagcgaat gagcgcagtc    1080
gacacgttca acggtatcta tcgcctggcc gaccttgtca gggctgcaga gagcacttgg    1140
gaaaagatcg atgtgatgct gctgccgacg gcgccgacca tctacactgt agaagacatg    1200
ctcgccgatc cggtacgcct caacagcaat ctgggcttct acacgaactt cgtgaacttg    1260
```

```
atggatttgt ccgcgattgc tgttcccgca ggcttccgaa ccaatggcct gccatttggc    1320
gtcactttca tcggtcgggc gttcgaagat ggggcgatcg caagcttggg aaaagctttc    1380
gtggagcacg acctcgccaa gggcaacgcg ccacggcgg cgccacccaa ggataccgtc     1440
gcaatcgccg tggtaggtgc acatctctcc gaccagccct gaatcatca gctcacggag     1500 agcggcggaa agctacgggc aacaacgcgt actgcgccgg gatatgcctt gtacgcactc    1560
cgtgatgcga cgccggctaa gcctggaatg ttgcgcgacc agaatgcggt cgggagcatc    1620
gaagtggaaa tctgggatct gccggtcgcc gggttcggtg cgtttgtaag tgaaattccg    1680
gcgccgttgg gtatcgggac aataacactc gaagacggca gccatgtgaa aggctttctg    1740
tgcgagccac atgccatcga gacggcgctc gacatcactc actacggcgg ctggcgagca    1800
tacctcgcgg ctcaatag                                                  1818

<210> SEQ ID NO 2
<211> LENGTH: 5508
<212> TYPE: DNA
<213> ORGANISM: Saccharomyces cerevisiae

<400> SEQUENCE: 2
atgacagtta gttccgatac aactgctgaa atatcgttag gttggtcaat ccaagactgg      60
attgatttcc acaagtcatc aagctcccag gcttcactaa ggcttcttga atcactacta     120
gactctcaaa atgttgcgcc agtcgataat gcgtggatat cgctaatttc aaaggaaaat     180
ttactgcacc aattccaaat tttaaagagc agagaaaata agaaactct acctctctac      240 ggtgtcccta ttgctgttaa ggacaacatc gacgttagag gtctacgcac caccgctgca    300
tgtccatcct ttgcatatga gccttccaaa gactctaaag tagtagaact actaagaaat    360
gcaggtgcaa taatcgtggg taagacaaac ttggaccaat ttgccacagg attagtcggc    420
acacggtctc catatgggaa aacaccttgc gcttttagca aagagcatgt atctggtggt    480
tcctccgctg ggtcagcatc ggtggtcgcc agaggtatcg taccaattgc attgggtact    540
gatacagcag gttctggtag agtcccagcc gccttgaaca acctgattgg cctaaagcca    600
acaaagggcg tcttttcctg tcaaggtgta gttcccgctt gtaaatcttt agactgcgtc    660
tccatctttg cattaaacct aagtgatgct gaacgctgct tccgcatcat gtgccagcca    720
gatcctgata tgatgaata ttctagaccc tatgttccca acccaaagaa aaattttca    780 agcaatgtaa cgattgctat tcctaaaaat atcccatggt atggtgaaac caagaatcct    840
gtactgtttt ccaatgctgt cgaaaatcta tcaagaacgg cgctaacgt catagaaatt    900 gattttgagc ctctttttaga gttagctcgc tgtttatacg aaggtacttg ggtggccgag    960
cgttatcaag ctattcaatc gttttttggac agtaaaccac caaggaatc tttggaccct   1020 actgttattt caattataga aggggccaag aaatacagtg cagtagactg cttcagtttt   1080
gaatacaaaa gacaaggcat cttgcaaaaa gtgagacgac ttctcgaatc agtcgatgtc   1140
ttgtgtgtgc ccacatgtcc cttaaatcct actatgcaac aagttgcgga tgaaccagtc   1200
ctagtcaatt caagacaagg cacatggact aattttgtca acttggcaga tttggcagcc   1260
cttgctgttc ccgcagggtt ccgagacgat ggtttgccaa atggtattac tttaatcggt   1320
aaaaaattca cagattacgc actattagag ttggctaacc gctatttcca aaatatgttc   1380
cccaacggtt ccagaacata cggtactttt acctcttctt cagtaaagcc agcaaacgat   1440
caattagtgg gaccagacta tgacccatct acgtccataa aattggctgt tgtcggtgca   1500
catcttaagg gtctgcctct acattggcaa ttggaaaagg tcaatgcaac atatttatgt   1560
```

```
acaacaaaaa catcaaaagc ttaccagctt tttgctttgc ccaaaaatgg accagttta    1620 aaacctggtt tgagaagagt tcaagatagc aatggctctc aaatcgaatt agaagtgtac    1680
agtgttccaa aagaactgtt cggtgctttt atttccatgg ttcctgaacc attgggaata    1740
ggttcagtgg agttagaatc tggtgaatgg atcaaatcct ttatttgtga agaatctggt    1800
tacaaagcca aagtacagt tgatatcaca aagtatggtg gatttagagc atattttgaa    1860
atgttgaaga aaaagagtc ccaaaagaag aagttatttg ataccgtgtt aattgccaat    1920
agaggtgaaa ttgccgttcg tattatcaag acattaaaaa aattgggtat tagatcagtt    1980
gcagtttatt ccgaccctga taaatattct caacacgtta ctgatgcaga tgtttctgta    2040 cccttcatg gcacaaccgc agcccaaact tatttagaca tgaataagat catagatgcc    2100
gctaagcaaa ctaatgcaca ggccattatt cctggttatg gtttcttgtc ggaaaatgcg    2160 gattttctg atgcgtgcac cagtgctggc attacctttg ttggtccttc gggagatatt    2220
atcagaggtt tagggttaaa acattctgct agacagattg cacagaaggc tggcgttcct    2280
ctagtgccag gctctttgct tatcacatca gttgaagagg ctaagaaagt cgcagcggaa    2340
ttggaatacc cagttatggt gaagtcaact gctggtggcg gtggtattgg tttgcagaaa    2400
gtcgattctg aagaggacat cgagcatatt tttgagactg tgaaacatca aggtgaaaca    2460
tttttcggtg acgctggtgt atttctgaaa cggtttatcg aaaatgccag gcatgttgaa    2520
gtccaactta tgggagatgg ttttggtaag gccattgctt gggcgaacg tgattgttct    2580 ttacagcgtc gtaaccaaaa agttatcgaa gaaactcctg caccaaattt gccagaaaag    2640
acgaggttgg cgttaagaaa ggcagctgaa agtttgggat ctttattgaa ttacaagtgt    2700
gctggtacgg ttgaatttat ttacgatgag aaaaaggacg agttttactt tttagaagtt    2760
aatacaagat tacaagttga acatccaata acagaaatgg ttacagggtt agacttggtc    2820
gagtggatga tcaggattgc cgctaatgat gcacctgatt ttgattctac aaaggtagaa    2880
gtcaatgggg tttcaatgga ggcacgttta tatgctgaaa atccattgaa aaatttcaga    2940
ccttctccag gtttacttgt cgatgtgaaa tttcctgatt gggcaagagt ggatacttgg    3000
gttaagaaag gtactaatat ttctcccgaa tatgatccaa cattggccaa aattatcgtt    3060
catgggaaag accgtgatga tgcaatttcc aagttaaatc aagcgttaga agaaacaaaa    3120
gtttacggat gtattactaa cattgactac ctgaagtcta tcattaccag tgatttcttt    3180
gctaaagcaa aagtttctac aaacattttg aactcttatc aatatgagcc taccgccatc    3240
gaaattactt tgcccggtgc acacactagt attcaggatt accccggtag agttgggtac    3300
tggagaattg gtgttccgcc ctctggtcca atggacgcat attcgtttag attggcgaac    3360
agaattgttg gtaatgacta caggactcct gccattgaag taacgttgac tggtccatcc    3420
atcgttttcc attgtgaaac tgtcattgcc attactggtg gtaccgctct atgtacatta    3480
gacggccaag aaattcccca acacaaaccg gtcgaagtta gaggggatc tactttatcc    3540 attggcaagt tgacaagcgg ctgtagagca tacttaggta tcagggggtgg cattgatgtg    3600 cctaaatact tgggctctta ttctactttc actctaggaa atgtcggtgg atacaatgga    3660
agggtgctaa aacttggaga cgtactattc ttaccaagca atgaagaaaa taatcagtt    3720 gagtgccttc cacagaatat tcctcaatca ttaattcctc aaatttccga aactaaggaa    3780
tggagaattg gtgtaacatg tggtccccat gggtctccag attttttaa acctgagtcc    3840 atcgaagaat ttttcagtga gaagtggaag gttcattaca actccaatag atttggtgtc    3900
```

```
cgtttgattg gacctaaacc taagtgggca agaagtaatg gtggtgaagg tggtatgcat    3960
ccttcaaaca ctcacgatta cgtttattct ctgggtgcaa ttaatttcac gggtgatgag    4020
ccagttatta ttacttgcga tggtccttcc ttaggtggtt ttgtgtgtca agctgttgtc    4080
ccagaagcag aactgtggaa ggttggacag gttaaacccg tgattccat  tcagtttgtg    4140 ccactttctt acgaaagctc gagatcctta aggaatctc  aggaagttgc aattaaatca    4200
ttggatggta ctaagttaag gcgcttagac tctgtttcaa ttttaccatc attcgaaacg    4260
cctattcttg cacaaatgga aaagtgaat  gagctttcac caaaggttgt atacagacaa    4320
gcaggtgatc gttatgtttt ggtggaatac ggtgataatg aaatgaattt taatatttcc    4380
tatagaattg aatgcctgat ctcccttgtg aaaagaata  agactattgg tattgttgaa    4440
atgtcccaag gtgttagatc tgtgttgata gaatttgatg gttacaaagt cactcaaaaa    4500
gaattgctta agtattggt  ggcatatgaa acagaaatcc agtttgatga aaattggaag    4560
ataacttcta atataataag attaccgatg gctttcgaag actcgaagac tttggcatgt    4620
gttcaaaggt atcaagaaac aattcgttcg tctgctccat ggttgccaaa taacgttgat    4680
ttcattgcca atgtaaatgg aatttcaagg aatgaagttt atgatatgtt gtattctgcc    4740
agatttatgg ttttaggttt aggtgatgtc ttcctagggt cgccttgtgc tgttccatta    4800
gatcctcgtc acagattttt gggaagcaag tacaacccaa gtagaacata tacagaaaga    4860
ggtgcagtcg gtattggcgg tatgtatatg tgcatatatg ctgctaacag tcctggtggg    4920
taccaattag tgggtagaac aataccaatt tgggacaaac tatgtctggc cgcatcttct    4980
gaggttccgt ggttgatgaa cccatttgac caagtcgaat tttacccagt ttctgaagaa    5040
gatttggata aaatgactga agattgtgat aatggtgttt ataaagtcaa tatcgaaaag    5100 agtgttttg  atcatcaaga atacttgaga tggatcaacg caaacaaaga ttccatcaca    5160
gcattccagg agggccagct tggtgaaaga gcagaggaat tgccaaaatt gattcaaaat    5220
gcaaactctg aactaaaaga aagtgtcaca gtcaaacctg acgaggaaga agacttccca    5280
gaaggtgcag aaattgtata ttctgagtat tctgggcgtt tttggaaatc catagcatct    5340
gttggagatg ttattgaagc aggtcaaggg ctactaatta ttgaagccat gaaagcggaa    5400
atgattatat ccgctcctaa atcgggtaag attatcaaga tttgccatgg caatggtgat    5460
atggttgatt ctggtgacat agtggccgtc atagagacat tggcatga               5508
```

<210> SEQ ID NO 3
<211> LENGTH: 5463
<212> TYPE: DNA
<213> ORGANISM: Yarrowia lipolytica

<400> SEQUENCE: 3

```
atgtgcaaat caatcggctg gactattgcc gaatggaagg aggcacagac caactcgtct     60
tacgaggagg cccgacatcg actgttggac ctcgtggcca ccttcaagga ctacaagcat    120
ggtgatccgg cttggatcac tgtcgcctca acagagcata tcaacaagca atggaaggag    180
cttcagttga tgaagaagaa cccagagtcc cttcccttt  acggagttcc tttcgctgta    240
aaggacaaca ttgatgtcat cgactttccc acaaccgctg catgccccgc ctatctctac    300
atccccaagg aagacgccac catggtccgt ctgatcaaag aggctggagg tatcgttgtc    360
ggcaaaacca acctcgatca gttcgctact ggtctggtcg gaaccgatc  tccttacgga    420 aagactccca acaccttctc cgacaagcac gtatctggag ttcgtctgc  tggctctgct    480 tccgtagtcg cccgaggcct ggttcccttt tctcttggaa cagatactgc aggctcaggt    540
```

```
cggggttcccg cctctctcaa caacctggta ggcctaaagc caaccgttgg cgcattttca    600
gccaagggtg tggtacccgc ctgcaagtcg cttgattgcg tctccatttt ctcgctggtc    660
ctgtctgacg ctcagctggt gttcaacatt gccgcccact ttgacaagga cgattgctac    720
tcgcgacgtt tcccccagcg acctctcaag tcgtttggcc ccactccagt atttgccgtc    780
cccgaaaccc ctctgtggtt tggagatgag ctcaaccctg ctctcttcga cgacgccgtt    840
gagcgtttgc gacaacaggg cgtaaaggtc gtcaagattg acttcactcc tctgttcgac    900
ctcgccaagt gcctctacga aggtccctgg gtggctgagc gatacgctgc catcaaggac    960
tttgtgcaga accgaaagga agacatggac gaaactgtgt atggcattgt caagcaggct   1020
gagaacttca ctgctgcaga cgcctttgcc tacgagtaca acgacgagc cattgtgcga    1080
aagattgagg agatcttctc ttccattgac ggtctgatcg tgcccacatg tcctctattc    1140
cccaccatgg agtctgtggc taaggagcct gtcactgtca atgcccacca gggtacctac   1200
accaactttg tcaacctcgc tgatctctct gctctagcta tccctgtcgg attccgaaag   1260
gacggtttcc cctttggaat cactctcatc tctcaaaagt caacgacta cgctctgctg    1320
gacatggctc agaagttcct gcctgcttct cgacctctgg gtgctctgcc aaaggacaag   1380
ttcaccgcca agaagggaga tcttcttgcc tcttctatcg tcgacaacat gcctcgaacc   1440
atccctctgg ctgttgtagg agcccatctc accggcatgc ctctcaactg gcagcttcaa   1500
aaggtcgagg ctactcttgc ccgacgaacc aaaactgccg actactaccg actctacgct   1560
ctggcgaaca ccgtgcctac aaagcctggt ctccgacggg ttcttccctc tgacactact   1620
ctccgaggcg aggctattga ggttgaaatc tgggacgtgc cttacagaaa ctttggagag   1680
ttcgtatcaa tggtccctca tcctcttggt atcggaacca ttgagcttgc cgacggaaaa   1740
tgggtcaagg gtttcatttg cgagcagctg ggatacgacg acgctgagga catcaccaag   1800
tttggcggct ggagagcgta caaggctgag actacccaga acctggagtc caagcctttc   1860
gagactgttc tggtcgccaa ccgaggtgag attgccgttc gactcatcaa aactcttcga   1920
aagatggata ttcgagctgt ggctgtcttc tccgagcctg atcggttcgc tcaacatgtt   1980
cttgatgctg atgactctgt gtctctggaa ggtaccactg ccgccgagac ttacttgtcc   2040
atccccaaga ttatcgctgc ttgcaagaag actggagccc aagccattct tcctggctac   2100
ggtttcctgt ctgagaatgc tgacttctcc gacgcctgtg ccgaggctgg tatcgtattc   2160
attggcccca ctggtgactc cattcgaaag ctcggtctca agcactctgc acgagagatt   2220
gctcttgctt ctgacgtgcc tcttgtgccc ggtacaggcc tgatcgagac tgtttccgag   2280
gcctccgagg ctgccgagaa gctcgagtac cccctgatga tcaagagtac cgctggtgga   2340
ggtggtattg tcttcagaa ggtcgacaaa cccgaggatc tcaagcgggc ttttgagacc   2400
gtcaagcacc aaggtaagtc tttctttgga gacgatggtg tcttcatgga gcgatttgtc   2460
gagaatgctc gacacgtgga ggttcagatt cttggtgacg gcaagggcaa cgctctcgct   2520
attggcgagc gagactgttc tcttcagcga cgaaaccaga aggtcgtcga agagactcct   2580
gccccccaact tccctgctga gactcgaact cgaatgatga aggcgtccga aatgctggca   2640
aagaacctca actatcgagg tgccggcact gtggagttca ttttcgatga aagcgaaac    2700
gagttctact tccttgaggt taacgctcgt ctgcaggtcg agcatcccat cactgagtcc   2760
gtcactggac tggatcttgt cgagtggatg attctcattg gagctggcaa ggccccagac   2820
ttcgaggccc agcgtgccaa gacccccag ggtgcttcta tcgaggcccg tctgtacgcc    2880
```

```
gagaacccccg tcaaggactt tgtgccttct cccggtcagc tcaccgacgt gcagttccct   2940
agtgatgctc gagtcgacac ctgggtcagc cgtggaacca agatctcagc agagtacgat   3000
cccactcttg ccaagattat tgttcacggc tctgaccgag ctgacgccct gcgaaagctc   3060
cagagagctc tggacgagac agtggttgcc ggcgtgacca ccaacctgga ctaccttaag   3120
tccattgtcg atctcagat gttttgccgag gccaaggtgt ccacccgagt actggactct   3180
tacaactaca ctcccaatgc cattgagatc acttcccccg ctcctacac cactattcag   3240 gattaccccg gtcgaaccaa gctgtggcat attggtgttc ctccttctgg acccatggat   3300
gcctacgcct tccgggtggc caaccagatt gtgggcaacc accccaaggc tcctgctatc   3360
gaagctacac ttgtgggccc ctcaattatg ttccacagcg acactgtgat tgccatcacc   3420
ggtggatctg ctgaggccac tcttaatggt gagcccatcg agttctggaa gcctgtgact   3480
gtcaaggctg ccagactct cgcaactggc cgtctcactt ctggctgcag attgtacatt   3540
gcgattcgaa acggtctgtc tattccagag taccttggtt ctcgatccac cttcgctctc   3600
ggtaaccttg gaggcttcaa cggtcgaact ctcaagtttg gcgatgtcat tttcatgggc   3660
gagcccgagc ttccctcctg ctccattcct gctcccatct ccgagcatgc tcctgcctct   3720
gatgacatga tccccaagta tggcaacgcc tggactgttg gagtcacttg cggccctcac   3780
ggctcgccag acttttttgc tcacggctgg atggatacct tcttcgatgc caagtggaag   3840
atccattaca actccaaccg atttggtgtt cgtctgattg gccccaagcc cgagtgggct   3900
cgaaaggatg gaggagaggc tggtctgcat ccttccaacc agcacgacta tgtctactct   3960
ctgggtgcca tcaatttcac cggtgatgag cctgtcattc tgacctgcga tggtccttct   4020
ctcggtggct ttgtctgtgc tgctgttgtt gtagaggccg agctgtggaa gattggccag   4080
gtcaagcccg agacactgt gcagtttgtg cccatgacta ttgactctgc tcgacagctc   4140
aagaaggccc aggacagaac cattaccaac ctgtgcggtt cccgtacga gtctgttgat   4200 gctcttctcg ctctggagga ttacgagaac cccatcatct acaccgtccc tgcctctacc   4260
tccactcctc gagtcgtcta ccgacaggct ggagaccgat acattctggt cgagtacggt   4320
gacaacaaca tggacattaa cctgtcctat cgaatccatc ggctcattga ggaagctcag   4380
cagtctatca agggcattgt cgaaatgtct cgaggtgttc gttctgtgct gatcgagttc   4440
catccttctg cctctcgatc cactctcatg caggctttgg tcgactttga aagcgacttc   4500
cagtttgtcg agacctggca ggttccctct cgaattattc gactgccgat gtgctttgag   4560
gactccaaga ccctggacgc tgtcaaacgg taccaggaga ccattcggtc aaaggctccc   4620
tggcttccca acaacgtcga cttcattcga gacgtcaaca agttctccga ccgatctcag   4680
gtccgagaca ttgtctacac tgcccgattc ctggttctgg gtcttggaga cgtgttcctt   4740
ggtgctcctt gcgcggtacc tcttgatccc cgacacagac tgcttggaac aaagtacaat   4800
ccctctcgaa cctacactcc caacggcact gtcggaattg gaggaatgta catgtgtatc   4860
tacaccatgg aatctcctgg aggctaccag ttggttggtc gaactatccc catctgggac   4920
aagctgtctc tcggccagga ccgaccttgg ctgctgtcac ccttcgacca gattgagtac   4980
taccccgtcg acgaggagga gctcaaccac attaccaccg aggtggagaa cggtcgatat   5040
gctgtggaga tggagcagtc cgtctttgat tatggcaagt attctgcctg gctcaaggac   5100
aactctaagt ccattgaggc tcacattgct tctcaggcag agggtctgga cgacttcgcc   5160
aacctgatca aggtcgccaa cgaggatctg gcctctggaa agactggagc caccaaggag   5220
gagactcctc tgtcggcctc tgccgtccag gtcttctccg aggtcactgg ccgtttctgg   5280
```

| aagggcctgg ttgccgtcgg agatactgtt gacaagggcc agggtatcgt tgtggtggag | 5340 |
| gccatgaaga ccgagatggt cgtcaacgcc cctgttgctg aaaggttgt caagttgtac | 5400 |
| aacaccaatg agatatggt ggatactgga gattgtgtgg ctgtcatcga gcccattgtt | 5460 |
| taa | 5463 |

<210> SEQ ID NO 4
<211> LENGTH: 1374
<212> TYPE: DNA
<213> ORGANISM: Pseudomonas sp.

<400> SEQUENCE: 4

| atgaagacag tagaaattat tgaaggtatc gcctctggca gaaccagtgc gcgcgacgtg | 60 |
| tgcgaagagg cgctcgcaac catcggcgcg accgatggac tcatcaatgc ctttacatgc | 120 |
| cgtacggttg aacgagcccg cgcagaggcg gatgccatcg atgttcgacg ggcgcgcggc | 180 |
| gaggtacttc cgcctcttgc cggcctcccc tacgcggtaa agaatctgtt cgacatcgaa | 240 |
| ggcgtgacga cgcttgccgg ctcgaagatc aaccgtactc tcccgcctgc gcgcgcagac | 300 |
| gccgtgctgt tgcaacggct gaaagctgcc ggcgccgtgc tcctgggcgg cctcaatatg | 360 |
| gacgagtttg cctatggatt tacgaccgaa atacgcact atgggccgac ccggaacccg | 420 |
| catgacaccg gcgtatcgc tggtggttcg tcagggggt ctggagcggc aatcgctgcg | 480 |
| gggcaggtac cactatcgct cggatcggac accaacggtt ccatacgcgt gccagcatca | 540 |
| ttgtgtggcg tgtgggggct gaagcctacc ttcggccgcc tgtcccggcg agggacatac | 600 |
| ccgtttgttc acagcattga tcacctcggg ccattggccg atagcgtgga aggcttggcg | 660 |
| ttggcctacg atgcaatgca gggcccggat ccgctcgacc ccggatgcag cgcatcgcgc | 720 |
| atccaaccct cggtaccggt cctcagtcag ggtatcgctg gctccggat cggcgtgctg | 780 |
| ggtggctggt ttcgggacaa tgccggcccg ccgcgcgcgag ccgcggtcga tgttgccgcg | 840 |
| cttacgctcg gcgccagcga agtcgtcatg tggcccgacg cggagatcgg gcgcgcagcc | 900 |
| gccttcgtta tcactgccag cgagggaggc tgtctgcatc tcgatgatct tcgcatccgt | 960 |
| ccgcaagact tcgagcctct gtccgtagat cgctttatct cgggggtttt acaaccggtc | 1020 |
| gcgtggtact gcgtgcaca gcggtttcga cgtgtctatc gagataaggt gaatgctctt | 1080 |
| ttccgtgact gggacatatt aatcgctccc gcaacgccaa taagtgctcc cgcaatcggc | 1140 |
| accgaatgga tcgaggtaaa cggtacacgc catccgtgcc gcccggctat gggacttctc | 1200 |
| actcagccgg tctccttcgc aggctgtccg gtggtcgccg ctccaacgtg gcctggagaa | 1260 |
| aacgatggca tgccgatcgg ggtacagctc atcgcggcgc cctggaacga atctctatgc | 1320 |
| ctgcgcgcag gcaaggtatt acaagacacc ggtatcgccc gactgaaatg ttaa | 1374 |

<210> SEQ ID NO 5
<211> LENGTH: 1092
<212> TYPE: DNA
<213> ORGANISM: Pseudomonas sp.

<400> SEQUENCE: 5

| atgtatcaca tcgacgtttt ccgaatccct tgccacagcc tggtgatac atcgggtctc | 60 |
| gaggatttga ttgaaacagg ccgcgttgcc cccgccgaca tcgtcgcggt aatgggcaag | 120 |
| accgagggca atggctgcgt caacgattac acgcgtgaat acgccaccgc catgcttgct | 180 |
| gcgtgccttg ggcgtcattt gcaactccca ccccatgagg tggaaaagcg ggtcgcgttt | 240 |

-continued

```
gtgatgtcag gtgggacgga aggcgtgctg tcccccacc acacggtatt cgcaagacgt    300
ccggcaatcg acgcgcatcg tcccgctggc aaacgtctca cgcttggaat cgccttcacg    360
cgtgattttc tgccggagga aattggccgc cacgctcaga taacggagac agccggcgcc    420
gtcaaacgcg caatgcgaga tgccgggatc gcttcgattg acgatctgca ttttgtgcag    480
gtgaagtgtc cgctgctgac accagcaaag atcgcctcgg cgcgatcacg cggatgcgct    540
ccagtcacga cggatacgta tgaatcgatg ggctattcgc gcggcgcttc ggccctgggc    600
atcgctctcg ctacagaaga ggtgccctcc tcgatgctcg tagacgaatc agtgctgaat    660
gactggagtc tctcatcgtc actggcgtcg gcgtctgcag gcatcgaact ggagcacaac    720
gtggtgatcg ctattggcat gagcgagcag gccaccagtg aactggtcat tgcccacggc    780
gtgatgagcg acgcgatcga cgcggcctcg gtgcggcgaa cgattgaatc gctgggcata    840
cgtagcgatg acgagatgga tcgcatcgtc aacgtattcg ccaaagcgga ggcgagcccg    900
gacggggttg tacgaggtat gcggcacacg atgctaagtg actccgacat taattcgacc    960
cgccatgcgc gggcggtcac cggcgcggcc attgcctcgg tagttgggca tggcatggtg   1020
tatgtgtccg gtggcgccga gcatcaggga cctgccggcg cggccccttt tgcagtcatt   1080
gcccgcgctt aa                                                        1092
```

<210> SEQ ID NO 6
<211> LENGTH: 1113
<212> TYPE: DNA
<213> ORGANISM: Pseudomonas sp.

<400> SEQUENCE: 6

```
atgcaagcgc aagttttttcg agttccaatg agtaatccag ccgatgttag tggcgtagcc     60
aagctcatcg atgagggagt gatccgtgcc gaagaggtcg tctgcgttct cggcaagacc    120
gaaggcaacg gctgtgtcaa tgacttcacg cgtggctaca ccaccctcgc gttcaaggtc    180
tacttctccg agaaactggg cgtgtcccgg caagaggtcg gcgagcgcat cgctttcatc    240
atgtccggcg gtaccgaagg cgtcatggcg cctcactgca ccatcttcac cgtgcagaag    300
acggacaaca agcagaagac cgccgctgaa ggcaagcgac ttgccgttca gcagatcttt    360
acccgcgagt tcctgccgga ggagatcggc cgcatgccgc aggtcacgga aacagccgac    420
gctgttcgcc gcgccatgcg cgaagccggc atcgcggatg catccgatgt ccacttcgtt    480
caggtcaagt gcccactgct cactgccggc cgcatgcatg acgctgtcga gcgcgggcat    540
acggttgcca ccgaagatac ctatgagtcc atgggctact cccgcggcgc atccgcgctt    600
ggtatcgccc tggccctcgg ggaagtcgag aaggccaacc tcagtgatga agttattacc    660
gcagactaca gtctctactc ctcggttgcc tcaacttcgg cgggtatcga gttgatgaac    720
aacgagatca tcgtcatggg caacagccgc gcatggggtg gtgacctcgt catcggccac    780
gccgagatga aggacgccat cgacggtgca gcggtccggc aggccctgcg cgacgtcggg    840
tgctgcgaga acgacctgcc gaccgtcgac gagctcggcc gcgtggtcaa tgtatttgcc    900
aaggctgaag cctccccgga cggtgaggtt cgtaaccgcc gccacacgat gctggacgat    960
tcggacatta acagcacgcg ccatgcgcga cggtcgtca atgcagttat cgcttcgatc   1020
gtgggagatc ccatggttta tgtctccggc ggctccgagc atcagggccc cgccggtggc   1080
ggtcccgttg cagttatcgc gcgcacagct taa                                 1113
```

<210> SEQ ID NO 7
<211> LENGTH: 1113

<212> TYPE: DNA
<213> ORGANISM: Rhodococcus sp.

<400> SEQUENCE: 7

```
atgcaagcgc aagttttcg agttccaatg agtaatccag ccgatgttag tggcgtagcc      60
aagctcatcg atgagggagt gatccgtgcc gaagaggtcg tctgcgttct cggcaagacc    120
gaaggcaacg gctgtgtcaa tgacttcacg cgtggctaca ccaccctcgc gttcaaggtc    180
tacttctccg agaaactggg cgtgtccggg caagaggtcg gcgagcgcat cgctttcatc    240
atgtccggcg gtaccgaagg cgtcatggcg cctcactgca ccatcttcac cgtgcagaag    300
acggacaaca agcagaagac cgccgctgaa ggcaagcgac ttgccgttca gcagatcttt    360
acccgcgagt tcctgccgga ggagatcggc cgcatgccgc aggtcacgga aacagccgac    420
gctgttcgcc gcgccatgcg cgaagccggc atcgcggatg catccgatgt ccacttcgtt    480
caggtcaagt gcccactgct cactgccggc cgcatgcatg acgctgtcga gcgcgggcat    540
acggttgcca ccgaagatac ctatgagtcc atgggctact cccgcggcgc atccgcgctt    600
ggtatcgccc tggccctcgg ggaagtcgag aaggccaacc tcagtgatga agttattacc    660
gcagactaca gtctctactc ctcggttgcc tcaacttcgg cgggtatcga gttgatgaac    720
aacgagatca tcgtcatggg caacagccgc gcatggggtg gtgacctcgt catcggccac    780
gccgagatga aggacgccat cgacggtgca gcggtccggc aggccctgcg cgacgtcggg    840
tgctgcgaga cgacctgcc gaccgtcgac gagctcggcc gcgtggtcaa tgtatttgcc    900
aaggctgaag cctccccgga cggtgaggtt cgtaaccgcc gccacacgat gctggacgat    960
tcggacatta acagcacgcg ccatgcgcga gcggtcgtca atgcagttat cgcttcgatc   1020
gtgggagatc ccatggttta tgtctccggc ggctccgagc atcagggccc cgccggtggc   1080
ggtcccgttg cagttatcgc gcgcacagct taa                               1113
```

<210> SEQ ID NO 8
<211> LENGTH: 1320
<212> TYPE: DNA
<213> ORGANISM: Escherichia coli

<400> SEQUENCE: 8

```
atgatgtcag agaacacac gttaaaagcg gtacgaggca gttttattga tgtcacccgt      60
acgatcgata acccggaaga gattgcctct gcgctgcggt ttattgagga tggtttatta    120
ctcattaaac agggaaaagt ggaatggttt ggcgaatggg aaaacggaaa gcatcaaatt    180
cctgacacca ttcgcgtgcg cgactatcgc ggcaaactga tagtaccggg ctttgtcgat    240
acacatatcc attatccgca aagtgaaatg gtggggcct atggtgagca attgctggag    300
tggttgaata acacaccctt ccctactgaa cgtcgttatg aggatttaga gtacgcccgc    360
gaaatgtcgg cgttcttcat caagcagctt ttacgtaacg gaaccaccac ggcgctggtg    420
tttggcactg ttcatccgca atctgttgat gcgctgtttg aagccgccag tcatatcaat    480
atgcgtatga ttgccggtaa ggtgatgatg gaccgcaacg caccggatta tctgctcgac    540
actgccgaaa gcagctatca ccaaagcaaa gaactgatcg aacgctggca caaaatggt    600
cgtctgctat atgcgattac gccacgcttc gccccgacct catctcctga acagatggcg    660
atggcgcaac gcctgaaaga agaatatccg gatacgtggg tacatacca tctctgtgaa    720
aacaaagatg aaattgcctg ggtgaaatcg ctttatcctg accatgatgg ttatctggat    780
gtttaccatc agtacggcct gaccggtaaa aactgtgtct ttgctcactg cgtccatctc    840
```

| gaagaaaaag agtgggatcg tctcagcgaa accaaatcca gcattgcttt ctgtccgacc | 900 |
| tccaacctt acctcggcag cggcttattc aacttgaaaa aagcatggca gaagaaagtt | 960 |
| aaagtgggca tgggaacgga tatcggtgcc ggaaccactt tcaacatgct gcaaacgctg | 1020 |
| aacgaagcct acaaagtatt gcaattacaa ggctatcgcc tctcggcata tgaagcgttt | 1080 |
| tacctggcca cgctcggcgg agcgaaatct ctgggccttg acgatttgat tggcaacttt | 1140 |
| ttacctggca aagaggctga tttcgtggtg atggaaccca ccgccactcc gctacagcag | 1200 |
| ctgcgctatg acaactctgt ttctttagtc gacaaattgt tcgtgatgat gacgttgggc | 1260 |
| gatgaccgtt cgatctaccg cacctacgtt gatggtcgtc tggtgtacga acgcaactaa | 1320 |

<210> SEQ ID NO 9
<211> LENGTH: 1398
<212> TYPE: DNA
<213> ORGANISM: Bradyrhizobium japonicum

<400> SEQUENCE: 9

| atgaccaccg tcggtattcg cggcacgttc ttcgatttcg tcgacgatcc ctggaagcac | 60 |
| atcggcaacg agcaggcggc tgcgcgcttt catcaggacg gcctcatggt cgtcaccgac | 120 |
| ggcgtcatca aggcgttcgg tccgtacgag aagatcgccg ccgcgcatcc gggcgttgag | 180 |
| atcaccccata tcaaggaccg catcatcgtc ccgggcttca tcgacggcca catccatctg | 240 |
| cctcagaccc gcgtgctcgg tgcctatggc gagcagctct tgccgtggct gcagaagtcg | 300 |
| atctatcccg aggagatcaa gtacaaggat cgcaactacg cgcgcgaagg cgtgaagcgt | 360 |
| tttctcgatg cactgctcgc cgccggcacc accacctgcc aggccttcac cagctcctca | 420 |
| ccggtcgcga ccgaagagct gttcgaggag caagcaggc gcaacatgcg cgtgatcgcg | 480 |
| ggtctcaccg ggatcgaccg caacgcgccg gccgaattca tcgatacgcc cgagaatttc | 540 |
| tatcgcgaca gcaagcggct gatcgcgcag tatcacgaca agggccgtaa cctctacgct | 600 |
| atcacgccgc gcttcgcctt cggcgcctcg cccgagctgc tgaaggcgtg tcagcgcctc | 660 |
| aagcacgagc atccggactg ctgggtcaat acccacatct ccgagaaccc ggccgaatgc | 720 |
| agcggcgtgc tggtcgagca cccggactgc caggattatc tcggcgtcta cgagaagttc | 780 |
| gacctggtcg gcccaaagtt ctccggcggc cacggcgtct atctctcgaa caacgaattc | 840 |
| cgccgcatgt ccaagaaagg cgcggcggta gtgttctgcc cgtgctcgaa cctgttcctc | 900 |
| ggcagcggcc tgttccgtct cggccgcgcc accgatccgg agcatcgcgt gaagatgtcg | 960 |
| ttcggcaccg atgtcggcgg cggcaaccgc ttctcgatga tctccgtgct cgacgacgct | 1020 |
| tacaaggtcg gcatgtgcaa caacacgctg ctcgacggca gcatcgatcc gtcgcgcaag | 1080 |
| gacctcgcgg aagccgagcg caacaagctc tcgccctatc gtggcttctg gtcggtcacg | 1140 |
| ctcggcggcg ccgaaggcct ctacatcgac gacaagctcg gcaatttcga gcccggcaag | 1200 |
| gaggccgatt tcgtcgcgct cgatccgaac ggcggacaac tggcgcaacc ctggcaccag | 1260 |
| tcgctgattg ccgacggtgc aggtccgcgc acggttgatg aggccgcgag catgctgttc | 1320 |
| gccgtcatga tggtcggcga cgatcgctgc gtcgacgaga cctgggtgat gggcaagcgc | 1380 |
| ctctacaaga agagctga | 1398 |

<210> SEQ ID NO 10
<211> LENGTH: 1470
<212> TYPE: DNA
<213> ORGANISM: Saccharomyces cerevisiae

<400> SEQUENCE: 10

```
atgacaaaaa gtgatttatt atttgataaa ttcaacgaca acatggaaag gtttctagtt      60
ttttttggta cctttgtaga tacccctaaa ttaggagagc tgagaatcag agagaaaaca     120
tctgttggag ttctcaacgg aatcatcagg tttgtgaaca gaaattcact cgatcctgtc     180
aaagattgtt tagatcacga tagtagctta tcaccagagg atgtcacggt ggttgacata     240
attggaaaag acaagactcg aaataacagc ttttattttc caggttttgt tgacacgcat     300
aaccatgtct cgcaatatcc aaatgtcggc gtatttggga attctaccct gctggattgg     360
ctagagaagt ataccttccc catagaagcc gcactagcaa acgaaaatat tgcgagagaa     420
gtttacaata aggtaataag taagacgctt tctcacggta caacgactgt ggcttactat     480
aataccattg atctcaagtc cactaagctc ttggctcaac taagctcctt attggggcag     540
cgtgttcttg ttggaaaagt gtgcatggat accaatggtc ccgagtatta tattgaagat     600
actaaaactt cctttgaaag cactgtgaaa gttgttaagt acatacggga aaccatttgt     660
gatcccctcg taaatcctat agtgacacca aggttcgcgc cctcttgttc tagagaacta     720
atgcaacagt tgtccaagct agtcaaggat gaaaacatac acgttcaaac ccacttgtcg     780
gaaaataagg aggagataca gtgggttcaa gatttatttc ccgaatgtga gagctatact     840
gatgtatacg acaaatatgg gctgctcaca gaaaaaacag tattggcaca ttgtattcat     900
ctaacagatg ccgaagcgcg tgtgattaaa cagcgtcgct gtggtatatc tcattgtccc     960
atttccaact cctctctgac ttctggagag tgtagggttc gatggttgct ggaccagggc    1020
ataaggttg gtctaggcac cgacgtttca gccggtcatt cttgtagcat actcaccacc    1080
ggaaggcagg cctttgcagt ttcaaggcat ttggcaatga gagaaactga tcatgcaaaa    1140
ctttcagtct ccgagtgcct atttcttgct acaatgggcg gagcacaagt cttgcgtatg    1200
gatgagacct tggggacttt tgacgtcggt aagcagtttg acgctcaaat gatcgatacc    1260
aatgctcccg gctcaaacgt ggatatgttt cattggcagc taaggagaa ggatcaaatg    1320
caagagcaag agcaagagca agggcaagac ccttataaga acccaccgct gcttactaat    1380
gaagacataa tcgcaaaatg gttctttaac ggtgatgatc gcaacaccac taaagtttgg    1440
gtagccggcc agcaagtcta ccagatttag                                      1470

<210> SEQ ID NO 11
<211> LENGTH: 1356
<212> TYPE: DNA
<213> ORGANISM: Yarrowia lipolytica

<400> SEQUENCE: 11
atgactgctt caaacaccac agtttttttc ggagccatcg tcaatcccgc cagaagagca      60
cttgaatacc tgccccaagc tgctatcggt gtcaggaag gggaaatcgt cttttcgac     120
agacatgctg aatcggcttc ggcgtctgct gccacccaca acattaagaa cttcgacacg     180
gtggacttgt cgaaaccac ctcgttcctt ttccccggtt tcatcgacac tcacattcat     240
gcgccccagt accccaacag cggtattttc ggcaagacca cactgctaga ctggctgact     300
acctacacct tcccctgga gtcgtctctc aaggaccca aaatcgccca ggacgtgtac     360
tccagggtag tcaagaagac tctcgccaac ggaactacaa cggctgctta ctacgccact     420
gtccacgtgg agtccacaaa gaaactggct gacatttgtc tgtctcaagg tcagagagca     480
cttgtgggaa gagtgtgcat ggaccaaaac actcctgatt actacagaga tgcaagcgtg     540
gaggaggcca agaagagcga ccgggaagtt gttgagtata ttcagtctct taacaaaccc     600
```

```
gatcgcatcc tccccatcat cacacccgt tttgcgccct cttgcactgg tgaaatcatg      660
tcctggcagg gagactatgc ccagaagaac aacctgcaca tccagactca catttctgaa      720
aacaagggcg agattgcctg ggtcaaggag ctgtaccctg cttgcaaatc gtatgcagac      780
acataccacc agcatggact gctgacagaa aagacgcttc tggcccatgc catctatctg      840
accgacgaag aactcaacct ggtggagcag caaaagtgtg gactttccca ttgccccatt      900
tccaactcgt cgctgacatc aggcgagttc catgctcgaa aaattctcga caggaacatt      960 cccctttggtc tgggaaccga tgtttctgga ggttacgctc cttccattct cagcacagcc     1020
agacacggtc ttctggtgtc tcgtcacgtg gccatgaagt ccgaaaacga cgccgacaag     1080
ctgtctgtgg atgaggtact gtacttggcc actctgggtg gcgccgaggc tctcaaactg     1140
gactcaaaga ttggttcttt cgaggtgggc aagaagttcg acgcccagca gattgatctc     1200
gagactaacg gttctcctgt tgacattttt gactgggaat tgcctatttc cgagggaaac     1260
aagctcgaga acctggtgca caagtggttg tttaatggag acgaccgaaa cacttctact     1320
gtctgggtca acggagacaa ggtggtgacc aagtag                                1356

<210> SEQ ID NO 12
<211> LENGTH: 1437
<212> TYPE: DNA
<213> ORGANISM: Williamsia sp.

<400> SEQUENCE: 12
atgaccagaa tcgcaatcac cggcggacga gtcctgacca tggaccccga gcgccgcgtg       60
ctcgaaccag gaacggttgt ggtcgaggac cagttcatcg cacaagtggg atccccggac      120
gacgtcgaca tccgcggcgc cgaaatcatc gacgccaccg ggatggcagt gctccccggc      180
ttcgtcaaca cccacaccca cgtcccacaa atcctcctca ggggtggtgc atcccatgac      240
cgcaacctcc tcgaatggct gcacaacgtg ctctatcccg gcctcgctgc ctacacagac      300
gacgacatcc gagtcggaac actgctgtac tgcgccgaag cccttcgttc tggcatcacc      360
actgtcgtcg acaacgagga cgtccgaccc aacgacttcg cccgcgccgg ggccgccggg      420
atcggcgcct tcaccgacgc aggaatccga gccatttacg cgcgcatgta cttcgacgcg      480
ccacgcgccg aactcgaaga actcgtcgcc accatccacg ccaaggcccc cggcgccgtg      540
cgcatggacg aatcagccag caccgaccac gtactggcag acctagacca actcatcacc      600
cgccacgacc gcacagcaga tggccgcatc agggtgtggc ccgcacccgc catcccttc       660 atggtcagtg aaaaaggaat gaaggcagcg caagagatcg cagcgagccg caccgacggc      720
tggaccatgc acgtcagcga ggatcccatc gaggcccgag tgcactccat gaacgccccg      780
gaatatttac accacctcgg ctgcctcgac gaccgactcc ttgccgcgca ctgcgtgcat      840
atcgacagcc gagacatccg cctgttccgc cagcacgacg taaaaatttc tacccaacca      900
gtatcgaaca gctacctggc ggccggaatt gcaccggtcc ccgaaatgct cgcccacggc      960
gtgaccgtgg gcatcggtac cgacgacgcc aactgcaacg cagcgtgaa cctcatctcg     1020 gacatgaaag tgctagcgct cattcaccga gctgcacatc gagatgcctc aatcatcaca     1080
cctgaaaaaa tcatcgaaat ggccaccatc gacgagcccc gctgcatcgg tatggccgat     1140
cagattggtt ccctcgaggc gggtaaacgc gccgacatca tcaccctcga ccttcgtcac     1200
gcccaaacaa cccagcgca cgacttggcg gccaccatcg tctttcaggc ctacggcaac     1260
gaggtcaacg acgtcctcgt caatggctcg gtagtgatgc gcgatcgagt actttctttt     1320
ctgccgactc cccaagaaga aaaagcgctc tacgacgatg cgtcggagcg atcggctgca     1380
```

| | |
|---|---|
| atgctcgcac gggccggcct caccggcaca cgcacatggc aaacactggg atcgtag | 1437 |

<210> SEQ ID NO 13
<211> LENGTH: 1425
<212> TYPE: DNA
<213> ORGANISM: Pseudomonas sp.

<400> SEQUENCE: 13

| | |
|---|---|
| atgcaaacgc tcagcatcca gcacggtacc ctcgtcacga tggatcagta ccgcagagtc | 60 |
| cttggggata gctgggttca cgtgcaggat ggacggatcg tcgcgctcgg agtgcacgcc | 120 |
| gagtcggtgc ctccgccagc ggatcgggtg atcgatgcac gcggcaaggt cgtgttaccc | 180 |
| ggtttcatca atgcccacac ccatgtgaac cagatcctcc tgcgcggagg gccctcgcac | 240 |
| gggcgtcaac tctatgactg gctgttcaac gttttgtatc cggacaaaaa ggcgatgaga | 300 |
| ccggaggacg tagcggtggc ggtgaggttg tattgtgcgg aagctgtgcg cagcgggatt | 360 |
| acgacgatca cgacaacgc cgattcggcc atctacccag gcaacatcga ggccgcgatg | 420 |
| gcggtctatg gtgaggtggg tgtgagggtc gtctacgccc gcatgttctt tgatcggatg | 480 |
| gacgggcgca ttcaagggta tgtggacgcc ttgaaggctc gctctcccca agtcgaactg | 540 |
| tgctcgatca tggaggaaac ggctgtggcc aaagatcgga tcacagccct gtcagatcag | 600 |
| tatcatggca cggcaggagg tcgtatatca gtttggcccg ctcctgccat taccccggcg | 660 |
| gtgacagttg aaggaatgcg atgggcacaa gccttcgccc gtgatcgggc ggtaatgtgg | 720 |
| acgcttcaca tggcggagag cgatcatgat gagcggcttc attggatgag tcccgccgag | 780 |
| tacatggagt gttacggact cttggatgag cgtctgcagg tcgcgcattg cgtgtacttt | 840 |
| gaccggaagg atgttcggct gctgcaccgc acaatgtga aggtcgcgtc gcaggttgtg | 900 |
| agcaatgcct acctcggctc aggggtggcc ccgtgccag atggtgga gcgcggcatg | 960 |
| gccgtgggca ttggaacaga tgacgggaat tgtaatgact ccgtaaacat gatcggagac | 1020 |
| atgaagttta tggcccatat tcaccgcgcg gtgcatcggg atgcggacgt gctgaccca | 1080 |
| gagaagattc ttgaaatggc gacgatcgat ggggcgcgtt cgttgggaat ggaccacgag | 1140 |
| attggttcca tcgaaaccgg caagcgcgcg gaccttatcc tgcttgacct gcgtcaccct | 1200 |
| cagacgactc ctcaccatca tttggcggcc acgatcgtgt ttcaggctta cggcaatgag | 1260 |
| gtggacactg tcctgattga cggaaacgtt gtgatggaga accgccgctt gagctttctt | 1320 |
| cccctgaac gtgagttggc gttccttgag gaagcgcaga gccgcgccac agctattttg | 1380 |
| cagcggggcga acatggtggc taacccagct tggcgcagcc tctag | 1425 |

<210> SEQ ID NO 14
<211> LENGTH: 1212
<212> TYPE: DNA
<213> ORGANISM: Pseudomonas sp.

<400> SEQUENCE: 14

| | |
|---|---|
| atgagtaaag attttgattt aatcattaga aacgcctatc taagtgaaaa agacagtgta | 60 |
| tatgatattg ggattgttgg tgacagaata atcaaaatag aagctaaaat tgaaggaacc | 120 |
| gtaaaagacg aaattgatgc aaagggtaac cttgtgtctc ccggatttgt cgatgcacat | 180 |
| acccatatgg ataagtcatt tacgagcaca ggtgaaagat taccgaagtt ttggagcaga | 240 |
| ccttatacaa gggatgctgc catcgaggat ggcttgaaat attataaaaa tgctacccac | 300 |
| gaagaaataa aaagacatgt gatagaacat gctcacatgc aggtactcca tgggacttta | 360 |

```
tacacccgga cccatgtaga tgtagattca gttgctaaaa caaaagcagt ggaagcagtt      420
ttagaagcca aggaagagtt aaaggatctt atcgatatac aagtcgtagc ctttgcacag      480
agtggatttt tcgttgattt ggaatctgaa tcattgatta gaaaatcctt ggatatgggc      540
tgtgatttag ttgggggagt tgatcctgct acgcgggaaa ataatgttga gggttcttta      600
gacctatgct ttaaattagc aaaggaatac gatgttgata tcgactatca catacatgat      660
attggaactg ttggagtata ttcgataaat cgtcttgccc aaaagacaat tgaaaatggg      720
tataagggta gagtaactac gagtcatgcc tggtgttttg cagatgctcc gtccgaatgg      780
ctcgatgagg caatcccatt gtacaaggat tcgggtatga aatttgttac ctgttttagt      840
agtacaccgc ctactatgcc ggtgataaag ctgcttgaag ctggcatcaa tcttggctgt      900
gcttcggaca atatcagaga ttttttgggtt ccctttggca acggtgatat ggtacaaggg      960
gctctgatcg aaactcagag attagagtta aagacaaaca gagatttggg actaatttgg     1020
aaaatgataa cgtcagaggg tgctagagtt ttaggaattg aaaagaacta tgggatagaa     1080
gttggtaaaa aggccgatct tgttgtatta aattcgttgt caccacaatg ggcaataatc     1140
gaccaagcaa aaagactatg cgtaattaaa aatggacgta tcattgtgaa ggatgaggtt     1200
atagttgcct aa                                                          1212

<210> SEQ ID NO 15
<211> LENGTH: 735
<212> TYPE: DNA
<213> ORGANISM: Myrothecium verrucaria

<400> SEQUENCE: 15
atgtcttctt cagaagtcaa agccaacgga tggactgccg ttccagtcag cgcaaaggcc       60
attgttgact ccctgggaaa gcttggtgat gtctcctcat attctgtgga agatatcgcg      120
ttccctgcgg cagacaaact tgttgccgag gcacaggcct tgtgaaggc ccgattgagt      180 cccgaaacct acaatcactc catgcgcgtt ttctactggg gaaccgtcat cgcgagacgt      240
ttacttcccg agcaagctaa agacttgtct ccaagtacat gggcactgac atgtcttctg      300
catgacgttg gtactgcgga ggcatacttt acatctacac gaatgtcctt cgatatttac      360
ggtggcatta aggctatgga ggtgctcaag gtccttggga gtagcaccga ccaggctgag      420
gctgttgccg aggccatcat tcgtcatgag gatgtggggg tagatggcaa catcacattc      480
ctcggtcagt tgatccagct ggctacgctt tatgacaatg tcggggccta cgatgggatt      540
gatgattttg gtagctgggt tgatgacacc acacgcaaca gtatcaacac ggcattccca      600
cgacatggtt ggtgttcttg gtttgcctgc acggttcgta aggaagaaag taacaagcct      660
tggtgccaca caacgcatat ccctcagttc gataaacaga tggaagcgaa cactttgatg      720
aagccttggg agtaa                                                       735

<210> SEQ ID NO 16
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ttatcgatga taagctgtca agatgagaaa ttaattccac ggactataga ctatactaga       60
tactccgtct actgtacgat acacttccgc tcaggtcctt gtcctttaac gaggccttac      120
```

```
cactcttttg ttactctatt gatccagctc agcaaaggca gtgtgatcta agattctatc      180
ttcgcgatgt agtaaaacta gctagaccga gaaagagact agaaatgcaa aaggcacttc      240
tacaatggct gccatcatta ttatccgatg tgacgctgca gcttctcaat gatattcgaa      300
tacgctttga ggagatacag cctaatatcc gacaaactgt tttacagatt tacgatcgta      360
cttgttaccc atcattgaat tttgaacatc cgaacctggg agttttccct gaaacagata      420
gtatatttga acctgtataa taatatatag tctagcgctt tacggaagac aatgtatgta      480
tttcggttcc tggagaaact attgcatcta ttgcataggt aatcttgcac gtcgcatccc      540
cggttcattt tctgcgtttc catcttgcac ttcaatagca tatctttgtt aacgaagcat      600
ctgtgcttca ttttgtagaa caaaaatgca acgcgagagc gctaattttt caaacaaaga      660
atctgagctg cattttaca gaacagaaat gcaacgcgaa agcgctattt taccaacgaa       720
gaatctgtgc ttcattttg taaaacaaaa atgcaacgcg acgagagcgc taattttca       780 aacaaagaat ctgagctgca ttttacaga acagaaatgc aacgcgagag cgctatttta       840
ccaacaaaga atctatactt cttttttgtt ctacaaaaat gcatcccgag agcgctattt      900
ttctaacaaa gcatcttaga ttacttttt tctcctttgt gcgctctata atgcagtctc       960
ttgataactt tttgcactgt aggtccgtta aggttagaag aaggctactt tggtgtctat     1020
tttctcttcc ataaaaaag cctgactcca cttcccgcgt ttactgatta ctagcgaagc      1080
tgcgggtgca ttttttcaag ataaaggcat ccccgattat attctatacc gatgtggatt     1140
gcgcatactt tgtgaacaga agtgatagc gttgatgatt cttcattggt cagaaaatta      1200
tgaacggttt cttctatttt gtctctatat actacgtata ggaaatgttt acattttcgt     1260
attgttttcg attcactcta tgaatagttc ttactacaat ttttttgtct aaagagtaat     1320
actagagata aacataaaaa atgtagaggt cgagtttaga tgcaagttca aggagcgaaa     1380
ggtggatggg taggttatat agggatatag cacagagata tatagcaaag agatactttt     1440
gagcaatgtt tgtggaagcg gtattcgcaa tttaattaag tttaaacggc gcgcttttcc     1500
ataggctccg ccccctgac gagcatcaca aaaatcgacg ctcaagtcag aggtggcgaa     1560
acccgacagg actataaaga taccaggcgt ttccccctgg aagctccctc gtgcgctctc     1620
ctgttccgac cctgccgctt accggatacc tgtccgcctt tctcccttcg ggaagcgtgg     1680
cgctttctca tagctcacgc tgtaggtatc tcagttcggt gtaggtcgtt cgctccaagc     1740
tgggctgtgt gcacgaaccc cccgttcagc ccgaccgctg cgccttatcc ggtaactatc     1800
gtcttgagtc caacccggta agacacgact tatcgccact ggcagcagcc actggtaaca     1860
ggattagcag agcgaggtat gtaggcggtg ctacagagtt cttgaagtgg tggcctaact     1920
acggctacac tagaagaaca gtatttggta tctgcgctct gctgaagcca gttaccttcg     1980
gaaaaagagt tggtagctct tgatccggca aacaaaccac cgctggtagc ggtggttttt     2040
ttgtttgcaa gcagcagatt acgcgcagaa aaaaaggatc tcaagaagat cctttgatct     2100
tttctacggg gtctgacgct cagtggaacg aaaactcacg ttaagggatt ttggtcatga     2160
gattatcaaa aaggatcttc acctagatcc ttttaaatta aaaatgaagt tttaaatcaa     2220
tctaaagtat atatgagtaa acttggtctg acagttacca atgcttaatc agtgaggcac     2280
ctatctcagc gatctgtcta tttcgttcat ccatagttgc ctgactcccc gtcgtgtaga     2340
taactacgat acgggagggc ttaccatctg gccccagtgc tgcaatgata ccgcgagacc     2400
cacgctcacc ggctccagat ttatcagcaa taaaccagcc agccggaagg gccgagcgca     2460
gaagtggtcc tgcaacttta tccgcctcca tccagtctat taattgttgc cgggaagcta     2520
```

```
gagtaagtag ttcgccagtt aatagtttgc gcaacgttgt tgccattgct acaggcatcg    2580
tggtgtcacg ctcgtcgttt ggtatggctt cattcagctc cggttcccaa cgatcaaggc    2640
gagttacatg atcccccatg ttgtgcaaaa aagcggttag ctccttcggt cctccgatcg    2700
ttgtcagaag taagttggcc gcagtgttat cactcatggt tatggcagca ctgcataatt    2760
ctcttactgt catgccatcc gtaagatgct tttctgtgac tggtgagtac tcaaccaagt    2820
cattctgaga atagtgtatg cggcgaccga gttgctcttg cccggcgtca atacgggata    2880
ataccgcgcc acatagcaga actttaaaag tgctcatcat tggaaaacgt tcttcggggc    2940
gaaaactctc aaggatctta ccgctgttga gatccagttc gatgtaaccc actcgtgcac    3000
ccaactgatc ttcagcatct tttactttca ccagcgtttc tgggtgagca aaaacaggaa    3060
ggcaaaatgc cgcaaaaaag gaataagggc gacacggaa atgttgaata ctcatactct    3120 tccttttca atattattga agcatttatc agggttattg tctcatgagc ggatacatat    3180
ttgaatgtat ttagaaaaat aaacagcgat cgcgcggccg cgggtaataa ctgatataat    3240
taaattgaag ctctaatttg tgagtttagt atacatgcat ttacttataa tacagttttt    3300
tagttttgct ggccgcatct tctcaaatat gcttcccagc ctgcttttct gtaacgttca    3360
ccctctacct tagcatccct tccctttgca atagtcctc ttccaacaat aataatgtca    3420
gatcctgtag agaccacatc atccacggtt ctatactgtt gacccaatgc gtctcccttg    3480
tcatctaaac ccacaccggg tgtcataatc aaccaatcgt aaccttcatc tcttccaccc    3540
atgtctcttt gagcaataaa gccgataaca aaatctttgt cgctcttcgc aatgtcaaca    3600
gtacccttag tatattctcc agtagctagg gagcccttgc atgacaattc tgctaacatc    3660
aaaaggcctc taggttcctt tgttacttct tccgccgcct gcttcaaacc gctaacaata    3720
cctgggccca ccacaccgtg tgcattcgta atgtctgccc attctgctat tctgtataca    3780
cccgcagagt actgcaattt gactgtatta ccaatgtcag caaattttct gtcttcgaag    3840
agtaaaaaat tgtacttggc ggataatgcc tttagcggct taactgtgcc ctccatggaa    3900
aaatcagtca agatatccac atgtgttttt agtaaacaaa tttttgggacc taatgcttca   3960 actaactcca gtaattcctt ggtggtacga acatccaatg aagcacacaa gtttgtttgc    4020
ttttcgtgca tgatattaaa tagcttggca gcaacaggac taggatgagt agcagcacgt    4080
tccttatatg tagctttcga catgatttat cttcgtttcc tgcaggtttt tgttctgtgc    4140
agttgggtta agaatactgg gcaatttcat gtttcttcaa caccacatat gcgtatatat    4200
accaatctaa gtctgtgctc cttccttcgt tcttccttct gctcggagat taccgaatca    4260
aagctagc                                                             4268
```

<210> SEQ ID NO 17
<211> LENGTH: 6706
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
gatactttttg agcaatgttt gtggaagcgg tattcgcaat tataaacggt attttcacaa     60 ttgcaccccca gccagaccga tagccggtcg caatccgcca cccacaaccg tctacctccc    120
acagaacccc gtcacttcca ccctttttcca ccagatcata tgtcccaact tgccaaatta    180
aaaccgtgcg aatttttcaaa ataaactttg gcaaagaggc tgcaaaggag gggctggtga    240
```

-continued

```
gggcgtctgg aagtcgacca gagaccgggt tggcggcgca tttgtgtccc aaaaaacagc    300
cccaattgcc ccaattgacc ccaaattgac ccagtagcgg gcccaacccc ggcgagagcc    360
cccttctccc cacatatcaa acctccccg gttcccacac ttgccgttaa gggcgtaggg    420
tactgcagtc tggaatctac gcttgttcag actttgtact agtttctttg tctggccatc    480
cgggtaaccc atgccggacg caaaatagac tactgaaaat ttttttgctt tgtggttggg    540
actttagcca agggtataaa agaccaccgt ccccgaatta cctttcctct tcttttctct    600
ctctccttgt caactcacac ccgaaatcgt taagcatttc cttctgagta taagaatcat    660
tcaaaatgac tagaatcgct atcacaggtg gtagagtttt gactatggac cagaaagaa    720
gagtattaga accaggtaca gttgttgttg aagatcaatt cattgcacaa gtcggttcac    780
cagatgacgt agacatcaga ggtgctgaaa ttatagatgc cactggtatg gctgtattac    840
caggtttcgt taatacacat acccacgttc ctcaaatttt gttaagaggt ggtgcttcac    900
atgatagaaa tttgttggaa tggttgcaca acgtcttata tccaggtttg gctgcataca    960
ctgatgacga tatcagagtt ggtacattgt tatattgtgc tgaagcattg agatccggta   1020
ttactacagt tgtcgacaat gaagatgtta gacctaacga ttttgccaga gctggtgccg   1080
ctggtattgg tgcattcact gatgccggta tcagagcaat ctatgccaga atgtactttg   1140
atgctccaag agcagaattg gaagaattag tcgcaacaat acatgcaaaa gccctggtg   1200
ccgtaagaat ggacgaatct gcttcaaccg atcatgtttt ggcagactta gatcaattga   1260
ttaccagaca tgcacagaact gctgatggta gaattagagt atggccagct cctgcaatac   1320
cattcatggt ttctgaaaag ggtatgaagg cagcccaaga aatagctgca tccagaactg   1380
acggttggac aatgcatgtt agtgaagatc caatcgaagc cagagtccac tctatgaatg   1440
ctcctgaata tttgcatcac ttgggttgtt tagacgatag attgttagcc gctcattgcg   1500
ttcacataga ctcaagagat atcagattgt ttagacaaca tgatgttaag atatccacac   1560
aacctgtctc caatagttac ttagcagccg gtatagcacc agttcctgaa atgttggctc   1620
atggtgtcac agtaggtatt ggtaccgacg atgctaattg taacgactcc gtaaacttaa   1680
tcagtgatat gaaggttttg gcattgatac atagagctgc acacagagat gctagtatca   1740
ttaccccaga aaagataatc gaaatggcca ctattgacgg tgctagatgc attggtatgg   1800
ctgatcaaat cggttctttg gaagctggta aaagagcaga cataatcact ttggatttga   1860
gacatgcaca aaccactcct gcccacgatt tggccgctac aattgtcttt caagcttatg   1920
gtaatgaagt aaacgatgtt ttggtcaacg gttctgtagt tatgagagat agagttttgt   1980
cattcttacc aaccccctcaa gaagaaaagg ctttatacga cgatgcatct gaaagatcag   2040
cagccatgtt agccagagct ggtttgactg gtacaagaac ctggcaaact ttgggttctt   2100
aagctgcttg tacctagtgc aaccccagtt tgttaaaaat tagtagtcaa aaacttctga   2160
gttagaaatt tgtgagtgta gtgagattgt agagtatcat gtgtgtccgt aagtgaagtg   2220
ttattgactc ttagttagtt tatctagtac tcgtttagtt gacactgatc tagtattta    2280
cgaggcgtat gactttagcc aagtgttgta cttagtcttc tctccaaaca tgagagggct   2340
ctgtcactca gtcggcctat gggtgagatg gcttggtgag atctttcgat agtctcgtca   2400
agatggtagg atgatggggg aatacattac tgctctcgtc aaggaaacca caatcagatc   2460
acaccatcct ccatggtatc cgatgactct cttctccaca gttttccata ggctccgccc   2520
ccctgacgag catcacaaaa atcgacgctc aagtcagagg tggcgaaacc cgacaggact   2580
```

```
ataaagatac caggcgtttc cccctggaag ctccctcgtg cgctctcctg ttccgaccct    2640
gccgcttacc ggatacctgt ccgcctttct ccttcggga agcgtggcgc tttctcatag     2700
ctcacgctgt aggtatctca gttcggtgta ggtcgttcgc tccaagctgg gctgtgtgca    2760
cgaacccccc gttcagcccg accgctgcgc cttatccggt aactatcgtc ttgagtccaa    2820
cccggtaaga cacgacttat cgccactggc agcagccact ggtaacagga ttagcagagc    2880
gaggtatgta ggcggtgcta cagagttctt gaagtggtgg cctaactacg gctacactag    2940
aagaacagta tttggtatct gcgctctgct gaagccagtt accttcggaa aaagagttgg    3000
tagctcttga tccggcaaac aaaccaccgc tggtagcggt ggtttttttg tttgcaagca    3060
gcagattacg cgcagaaaaa aaggatctca agaagatcct ttgatctttt ctacggggtc    3120
tgacgctcag tggaacgaaa actcacgtta agggattttg gtcatgagat tatcaaaaag    3180
gatcttcacc tagatccttt taaattaaaa atgaagtttt aaatcaatct aaagtatata    3240
tgagtaaact tggtctgaca gttaccaatg cttaatcagt gaggcaccta tctcagcgat    3300
ctgtctattt cgttcatcca tagttgcctg actccccgtc gtgtagataa ctacgatacg    3360
ggagggctta ccatctggcc ccagtgctgc aatgataccg cgagacccac gctcaccggc    3420
tccagattta tcagcaataa accagccagc cggaagggcc gagcgcagaa gtggtcctgc    3480
aactttatcc gcctccatcc agtctattaa ttgttgccgg gaagctagag taagtagttc    3540
gccagttaat agtttcgcca acgttgttgc cattgctaca ggcatcgtgg tgtcacgctc    3600
gtcgtttggt atggcttcat tcagctccgg ttcccaacga tcaaggcgag ttacatgatc    3660
ccccatgttg tgcaaaaaag cggttagctc cttcggtcct ccgatcgttg tcagaagtaa    3720
gttggccgca gtgttatcac tcatggttat ggcagcactg cataattctc ttactgtcat    3780
gccatccgta agatgctttt ctgtgactgg tgagtactca accaagtcat tctgagaata    3840
gtgtatgcgg cgaccgagtt gctcttgccc ggcgtcaata cgggataata ccgcgccaca    3900
tagcagaact ttaaaagtgc tcatcattgg aaaacgttct cggggcgaa  aactctcaag    3960 gatcttaccg ctgttgagat ccagttcgat gtaacccact cgtgcaccca actgatcttc    4020
agcatctttt actttcacca gcgtttctgg gtgagcaaaa acaggaaggc aaaatgccgc    4080
aaaaaaggga ataagggcga cacggaaatg ttgaatactc atactcttcc ttttttcaata    4140 ttattgaagc atttatcagg gttattgtct catgagcgga tacatatttg aatgtattta    4200
gaaaaataaa cagcgatcgc gcggccgcgg gtaataactg atataattaa attgaagctc    4260
taatttgtga gttagtata catgcattta cttataatac agttttttag ttttgctggc    4320
cgcatcttct caaatatgct tcccagcctg cttttctgta acgttcaccc tctaccttag    4380
catcccttcc ctttgcaaat agtcctcttc aacaataat  aatgtcagat cctgtagaga    4440
ccacatcatc cacggttcta tactgttgac ccaatgcgtc tcccttgtca tctaaaccca    4500 cacgggtgt cataatcaac caatcgtaac cttcatctct tccacccatg tctctttgag    4560
caataaagcc gataacaaaa tctttgtcgc tcttcgcaat gtcaacagta cccttagtat    4620
attctccagt agctagggag cccttgcatg acaattctgc taacatcaaa aggcctctag    4680
gttcctttgt tacttcttcc gccgcctgct tcaaaccgct aacaatacct gggcccacca    4740
caccgtgtgc attcgtaatg tctgcccatt ctgctattct gtatacaccc gcagagtact    4800
gcaatttgac tgtattacca atgtcagcaa attttctgtc ttcgaagagt aaaaaaattgt    4860 acttggcgga taatgccttt agcggcttaa ctgtgccctc catggaaaaa tcagtcaaga    4920
tatccacatg tgttttagt  aaacaaattt tgggacctaa tgcttcaact aactccagta    4980
```

```
attccttggt ggtacgaaca tccaatgaag cacacaagtt tgtttgcttt tcgtgcatga      5040
tattaaatag cttggcagca acaggactag gatgagtagc agcacgttcc ttatatgtag      5100
ctttcgacat gatttatctt cgtttcctgc aggttttgt  tctgtgcagt tgggttaaga      5160
atactgggca atttcatgtt tcttcaacac cacatatgcg tatatatacc aatctaagtc      5220
tgtgctcctt ccttcgttct tccttctgct cggagattac cgaatcaaag ctagcttatc      5280
gatgataagc tgtcaaagat gagaattaat tccacggact atagactata ctagatactc      5340
cgtctactgt acgatacact tccgctcagg tccttgtcct ttaacgaggc cttaccactc      5400
ttttgttact ctattgatcc agctcagcaa aggcagtgtg atctaagatt ctatcttcgc      5460
gatgtagtaa aactagctag accgagaaag agactagaaa tgcaaaaggc acttctacaa      5520
tggctgccat cattattatc cgatgtgacg ctgcagcttc tcaatgatat tcgaatacgc      5580
tttgaggaga tacagcctaa tatccgacaa actgttttac agatttacga tcgtacttgt      5640
tacccatcat tgaattttga acatccgaac ctgggagttt tccctgaaac agatagtata      5700
tttgaacctg tataataata tatagtctag cgctttacgg aagacaatgt atgtatttcg      5760
gttcctggag aaactattgc atctattgca taggtaatct tgcacgtcgc atccccggtt      5820
cattttctgc gtttccatct tgcacttcaa tagcatatct ttgttaacga agcatctgtg      5880
cttcattttg tagaacaaaa atgcaacgcg agagcgctaa ttttttcaaac aaagaatctg     5940 agctgcattt ttacagaaca gaaatgcaac gcgaaagcgc tattttacca acgaagaatc     6000
tgtgcttcat ttttgtaaaa caaaaatgca acgcgacgag agcgctaatt tttcaaacaa     6060
agaatctgag ctgcattttt acagaacaga aatgcaacgc gagagcgcta ttttaccaac     6120
aaagaatcta tacttctttt tgttctaca  aaaatgcatc ccgagagcgc tattttctta    6180
acaaagcatc ttagattact ttttttctcc tttgtgcgct ctataatgca gtctcttgat     6240 aacttttgc  actgtaggtc cgttaaggtt agaagaaggc tactttggtg tctattttct     6300
cttccataaa aaaagcctga ctccacttcc cgcgtttact gattactagc gaagctgcgg     6360
gtgcattttt tcaagataaa ggcatccccg attatattct ataccgatgt ggattgcgca    6420
tactttgtga acagaaagtg atagcgttga tgattcttca ttggtcagaa aattatgaac     6480
ggtttcttct attttgtctc tatatactac gtataggaaa tgtttacatt ttcgtattgt     6540
tttcgattca ctctatgaat agttcttact acaattttt  tgtctaaaga gtaatactag    6600
agataaacat aaaaaatgta gaggtcgagt ttagatgcaa gttcaaggag cgaaaggtgg    6660
atgggtaggt tatatatggga tatagcacag agatatatag caaaga                  6706

<210> SEQ ID NO 18
<211> LENGTH: 8336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gtttgtggaa gcggtattcg caatttaatt aaagctggtg acaattaatc atcggctcgt       60
ataatgtgtg gaattgaatc gatataagga ggttaatcat atgactagaa tcgctatcac      120
aggtggtaga gttttgacta tggacccaga aagaagagta ttagaaccag gtacagttgt      180
tgttgaagat caattcattg cacaagtcgg ttcaccagat gacgtagaca tcagaggtgc      240
tgaaattata gatgccactg gtatggctgt attaccaggt ttcgttaata cacatcccca      300
```

```
cgttcctcaa attttgttaa gaggtggtgc ttcacatgat agaaatttgt tggaatggtt    360
gcacaacgtc ttatatccag gtttggctgc atacactgat gacgtatca gagttggtac    420 attgttatat tgtgctgaag cattgagatc cggtattact acagttgtcg acaatgaaga   480
tgttagacct aacgattttg ccagagctgg tgccgctggt attggtgcat tcactgatgc   540
cggtatcaga gcaatctatg ccagaatgta ctttgatgct ccaagagcag aattggaaga   600
attagtcgca acaatacatg caaaagcccc tggtgccgta agaatggacg aatctgcttc   660
aaccgatcat gttttggcag acttagatca attgattacc agacatgaca gaactgctga   720
tggtagaatt agagtatggc cagctcctgc aataccattc atggtttctg aaagggtat    780 gaaggcagcc caagaaatag ctgcatccag aactgacggt tggacaatgc atgttagtga   840
agatccaatc gaagccagag tccactctat gaatgctcct gaatatttgc atcacttggg   900
ttgtttagac gatagattgt tagccgctca ttgcgttcac atagactcaa gagatatcag   960
attgtttaga acatgatg ttaagatatc cacacaacct gtctccaata gttacttagc    1020
agccggtata gcaccagttc ctgaaatgtt ggctcatggt gtcacagtag gtattggtac   1080
cgacgatgct aattgtaacg actccgtaaa cttaatcagt gatatgaagg ttttggcatt   1140
gatacataga gctgcacaca gagatgctag tatcattacc ccagaaaaga taatcgaaat   1200
ggccactatt gacggtgcta gatgcattgg tatggctgat caaatcggtt ctttggaagc   1260
tggtaaaaga gcagacataa tcactttgga tttgagacat gcacaaacca ctcctgccca   1320
cgatttggcc gctacaattg tctttcaagc ttatggtaat gaagtaaacg atgttttggt   1380
caacggttct gtagttatga gagatagagt tttgtcattc ttaccaaccc ctcaagaaga   1440
aaaggcttta tacgacgatg catctgaaag atcagcagcc atgttagcca gagctggttt   1500
gactggtaca agaacctggc aaactttggg ttcttaagga aatccattat gatgtcagga   1560
gaacacacgt taaaagcggt acgaggcagt tttattgatg tcacccgtac gatcgataac   1620
ccggaagaga ttgcctctgc gctgcggttt attgaggatg gtttattact cattaaacag   1680
ggaaaagtgg aatggtttgg cgaatgggaa aacggaaagc atcaaattcc tgacaccatt   1740
cgcgtgcgcg actatcgcgg caaactgata gtaccgggct tgtcgatac acatatccat    1800 tatccgcaaa gtgaaatggt gggggcctat ggtgagcaat tgctggagtg gttgaataaa   1860
cacaccttcc ctactgaacg tcgttatgag gatttagagt acgcccgcga aatgtcggcg   1920
ttcttcatca agcagctttt acgtaacgga accaccacgg cgctggtgtt tggcactgtt   1980
catccgcaat ctgttgatgc gctgtttgaa gccgccagtc atatcaatat gcgtatgatt   2040
gccggtaagg tgatgatgga ccgcaacgca ccggattatc tgctcgacac tgccgaaagc   2100
agctatcacc aaagcaaaga actgatcgaa cgctggcaca aaaatggtcg tctgctatat   2160
gcgattacgc cacgcttcgc cccgacctca tctcctgaac agatggcgat ggcgcaacgc   2220
ctgaaagaag aatatccgga tacgtgggta catacccatc tctgtgaaaa caaagatgaa   2280
attgcctggg tgaaatcgct ttatcctgac catgatggtt atctggatgt ttaccatcag   2340
tacggcctga ccggtaaaaa ctgtgtcttt gctcactgcg tccatctcga agaaaaagag   2400
tgggatcgtc tcagcgaaac caaatccagc attgctttct gtccgacctc caacctttac   2460
ctcggcagcg gcttattcaa cttgaaaaaa gcatggcaga agaaagttaa agtgggcatg   2520
ggaacggata tcggtgccgg aaccacttc aacatgctgc aaacgctgaa cgaagcctac   2580
aaagtattgc aattacaagg ctatcgcctc tcggcatatg aagcgtttta cctggccacg   2640
```

```
ctcggcggag cgaaatctct gggccttgac gatttgattg gcaacttttt acctggcaaa    2700
gaggctgatt tcgtggtgat ggaacccacc gccactccgc tacagcagct gcgctatgac    2760
aactctgttt cttagtcga caaattgttc gtgatgatga cgttgggcga tgaccgttcg    2820
atctaccgca cctacgttga tggtcgtctg gtgtacgaac gcaactaagg aacgaccatg    2880
agagaagtcc aattgttaga tggtagaaga gttgatgtcg cctgtgctgg tcctttgatt    2940
agtgaaatag gtgcccactt agatttgact gctccagttg aaattgattg tggtggtggt    3000
ttagcaacta gaccttttac tgaacctcat ttgcacttag acaaagcagg tactgccgat    3060
agattgcctg ccggtgcttc cacaatcggt gacgctattg ctgcaatgca agtgtcaag    3120 gtaaccgaaa gagataatgt cgccgctgta gcagccagaa tgcatagagt tttaaacaga    3180
atcgtcgatg acggttccca cgctattaga gcattggttg atgtcgacga gtttgggt     3240 ttaacagctt ttcatgctgc acaacaagtc caagccgctt tggccccaag agctgttgtc    3300
caaattgtcg cttcccaca acacggttta accctcaag tattggcaat gttagaacaa    3360
gcagccgctg aaggtgcagg tgccttgggt gctcatactg atgttgaccc agatcctgca    3420
gcccacgttg gtgccgtcgc tgcaatagcc gctggtgctt ccttgccatt agaagttcat    3480
actgacgaag gtgctagtcc agataaattt tatttgcctg cagtattgga agttttagat    3540
agattcccag gtttgtctac tacattagct cattgtttgt cattaggtac aattgcacct    3600
aagcaacaac aacattggat cgaagaatta gctcacagag atatcaaagt atgcgttgca    3660
ccatctattt tgggtttcgg tttgccatta gcacctgtta gagccttaat agaagctggt    3720
gtcggtatct tagtaggttc agacaatttg caagatgttt tctttccttt gggtacaggt    3780
agagcaattg aaaacgttag attgttagcc accgcagccc aattaactgc accagaattg    3840
gccggtcctt taattgctgg tgtaaccgac atagcttacg caaccgttac tggtgctgca    3900
gatgccttgg ctgttgaatc tccagctaca ttagtagttc atgatgctac ctcacctgca    3960
gaattgttaa gaggtataga cggtacaaga attaccgtta tagatggttt gttgacatct    4020
ccattgcaat tggataaagg tatcaagtaa gtttaaacta atcccacagc cgccagttcc    4080
gctggcggca tttaacttt ctttaatggg cgcgcctttc cataggctcc gccccctga    4140 cgagcatcac aaaaatcgac gctcaagtca gaggtggcga acccgacag gactataaag    4200 ataccaggcg tttccccctg gaagctccct cgtgcgctct cctgttccga ccctgccgct    4260
taccggatac ctgtccgcct ttctcccttc gggaagcgtg gcgctttctc atagctcacg    4320
ctgtaggtat ctcagttcgg tgtaggtcgt tcgctccaag ctgggctgtg tgcacgaacc    4380
ccccgttcag cccgaccgct gcgccttatc cggtaactat cgtcttgagt ccaacccggt    4440
aagacacgac ttatcgccac tggcagcagc cactggtaac aggattagca gagcgaggta    4500
tgtaggcggt gctacagagt tcttgaagtg gtggcctaac tacggctaca ctagaagaac    4560
agtatttggt atctgcgctc tgctgaagcc agttaccttc ggaaaaagag ttggtagctc    4620
ttgatccggc aaacaaacca ccgctggtag cggtggtttt tttgtttgca agcagcagat    4680
tacgcgcaga aaaaaggat ctcaagaaga tcctttgatc ttttctacgg gtctgacgc    4740 tcagtggaac gaaaactcac gttaagggat tttggtcatg agattatcaa aaggatctt    4800 cacctagatc cttttaaatt aaaaatgaag ttttaaatca atctaaagta tatatgagta    4860
aacttggtct gacagttacc aatgcttaat cagtgaggca cctatctcag cgatctgtct    4920
atttcgttca tccatagttg cctgactccc cgtcgtgtag ataactacga tacgggaggg    4980
cttaccatct ggccccagtg ctgcaatgat accgcgagac ccacgctcac cggctccaga    5040
```

```
tttatcagca ataaaccagc cagccggaag ggccgagcgc agaagtggtc ctgcaacttt    5100
atccgcctcc atccagtcta ttaattgttg ccgggaagct agagtaagta gttcgccagt    5160
taatagtttg cgcaacgttg ttgccattgc tacaggcatc gtggtgtcac gctcgtcgtt    5220
tggtatggct tcattcagct ccggttccca acgatcaagg cgagttacat gatcccccat    5280
gttgtgcaaa aaagcggtta gctccttcgg tcctccgatc gttgtcagaa gtaagttggc    5340
cgcagtgtta tcactcatgg ttatggcagc actgcataat tctcttactg tcatgccatc    5400
cgtaagatgc ttttctgtga ctggtgagta ctcaaccaag tcattctgag aatagtgtat    5460
gcggcgaccg agttgctctt gcccggcgtc aatacgggan aataccgcgc cacatagcag    5520
aactttaaaa gtgctcatca ttggaaaacg ttcttcgggg cgaaaactct caaggatctt    5580
accgctgttg agatccagtt cgatgtaacc cactcgtgca cccaactgat cttcagcatc    5640
ttttactttc accagcgttt ctgggtgagc aaaaacagga aggcaaaatg ccgcaaaaaa    5700
gggaataagg cgacacgga aatgttgaat actcatactc ttccttttc aatattattg    5760 aagcatttat cagggttatt gtctcatgag cggatacata tttgaatgta tttagaaaaa    5820
taaacagcga tcgcgcggcc gcgggtaata actgatataa ttaaattgaa gctctaattt    5880
gtgagtttag tatacatgca tttacttata atacagtttt ttagttttgc tggccgcatc    5940
ttctcaaata tgcttcccag cctgcttttc tgtaacgttc accctctacc ttagcatccc    6000
ttccctttgc aaatagtcct cttccaacaa taataatgtc agatcctgta gagaccacat    6060
catccacggt tctatactgt tgacccaatg cgtctccctt gtcatctaaa cccacaccgg    6120
gtgtcataat caaccaatcg taaccttcat ctcttccacc catgtctctt tgagcaataa    6180
agccgataac aaaatctttg tcgctcttcg caatgtcaac agtaccctta gtatattctc    6240
cagtagctag ggagcccttg catgacaatt ctgctaacat caaaaggcct ctaggttcct    6300
ttgttacttc ttccgccgcc tgcttcaaac cgctaacaat acctgggccc accacaccgt    6360
gtgcattcgt aatgtctgcc cattctgcta ttctgtatac acccgcagag tactgcaatt    6420
tgactgtatt accaatgtca gcaaatttc tgtcttcgaa gagtaaaaaa ttgtacttgg    6480
cggataatgc ctttagcggc ttaactgtgc cctccatgga aaaatcagtc aagatatcca    6540
catgtgtttt tagtaaacaa attttgggac ctaatgcttc aactaactcc agtaattcct    6600
tggtggtacg aacatccaat gaagcacaca agtttgtttg cttttcgtgc atgatattaa    6660
atagcttggc agcaacagga ctaggatgag tagcagcacg ttccttatat gtagctttcg    6720
acatgattta tcttcgtttc ctgcaggttt ttgttctgtg cagttgggtt aagaatactg    6780
ggcaatttca tgtttcttca acaccacata tgcgtatata taccaatcta agtctgtgct    6840
ccttccttcg ttcttccttc tgctcggaga ttaccgaatc aaagctagct tatcgatgat    6900
aagctgtcaa agatgagaat taattccacg gactatagac tatactagat actccgtcta    6960
ctgtacgata cacttccgct caggtccttg tcctttaacg aggccttacc actcttttgt    7020
tactctattg atccagctca gcaaaggcag tgtgatctaa gattctatct tcgcgatgta    7080
gtaaaactag ctagaccgag aaagagacta gaaatgcaaa aggcacttct acaatggctg    7140
ccatcattat tatccgatgt gacgctgcag cttctcaatg atattcgaat acgctttgag    7200
gagatacagc ctaatatccg acaaactgtt ttacagattt acgatcgtac ttgttaccca    7260
tcattgaatt ttgaacatcc gaacctggga gttttccctg aaacagatag tatatttgaa    7320
cctgtataat aatatatagt ctagcgcttt acggaagaca atgtatgtat ttcggttcct    7380
```

```
ggagaaacta ttgcatctat tgcataggta atcttgcacg tcgcatcccc ggttcatttt   7440
ctgcgtttcc atcttgcact tcaatagcat atctttgtta acgaagcatc tgtgcttcat   7500
tttgtagaac aaaaatgcaa cgcgagagcg ctaattttttc aaacaaagaa tctgagctgc   7560 attttttacag aacagaaatg caacgcgaaa gcgctatttt accaacgaag aatctgtgct   7620 tcattttttgt aaaacaaaaa tgcaacgcga cgagagcgct aattttttcaa acaaagaatc   7680 tgagctgcat ttttacagaa cagaaatgca acgcgagagc gctattttac caacaaagaa   7740
tctatacttc ttttttgttc tacaaaaatg catcccgaga gcgctatttt tctaacaaag   7800
catcttagat tacttttttt ctcctttgtg cgctctataa tgcagtctct tgataacttt   7860
ttgcactgta ggtccgttaa ggttagaaga aggctacttt ggtgtctatt ttctcttcca   7920 taaaaaagc ctgactccac ttcccgcgtt tactgattac tagcgaagct gcgggtgcat   7980 ttttttcaaga taaaggcatc cccgattata ttctataccg atgtggattg cgcatacttt   8040
gtgaacagaa agtgatagcg ttgatgattc ttcattggtc agaaaattat gaacggtttc   8100 ttctatttttg tctctatata ctacgtatag gaaatgttta catttttcgta ttgttttcga   8160 ttcactctat gaatagttct tactacaatt ttttttgtcta aagagtaata ctagagataa   8220
acataaaaaa tgtagaggtc gagtttagat gcaagttcaa ggagcgaaag gtggatgggt   8280
aggttatata gggatatagc acagagatat atagcaaaga gatacttttg agcaat         8336

<210> SEQ ID NO 19
<211> LENGTH: 8063
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gtttgtggaa gcggtattcg caatttaatt aaagctggtg acaattaatc atcggctcgt     60
ataatgtgtg gaattgaatc gatataagga ggttaatcat atgtcctcca cagcattata    120
caccgttcct accgcaggtc cagacgatgt tgccgccttg aaagcattag atggtcattc    180
cgcctccgat attttggctg taataggtaa acagagggg aatggttgtg ttaacgactt    240
tagtagaacc ttatctgctg cagttttggca tccattgtta aagagattcag ccattacagt    300 cttttccggt ggtgcagaag gtgtaataag tccacatgta aacatcttcg ttagagatga    360
aagacaatat tctggtcacc ctagaggttt ggtaactgct gttggtagaa caagagttat    420
cggtccagaa gaaattggta gacctgctca agtcgatgca gtacatgaaa ccgttgtcgc    480
attgttaact gaattgggtg ttggtccaga tgacgttcac ttggtcttga ttaaatgccc    540
tttgttatct tcagacgcta tagcaggtgt tcatagaaga ggtttaagac tgtcactac    600 agatacttac gaatctatgt caagatccag agccgcttct gctttgggta tagccatggc    660
tttaaaggaa tgtgatagag acagagcatt gttagccttg gaaggtagag atgacgtttg    720
gtcagcaaga gcctccgctt ccagtggtgc tgaattggat gactgccaca ttttagtagt    780
tgcagaatca gatgcagccg ctaatccatt aagagcagcc catactgcca tgagagatgc    840
tttggacatc caagctttaa cagaagttttt tgacagaatt gctgcagaag gtggtaccgt    900
cagacaaata ttcgcaaagg ccgaagctga tccttcaggt gctatcagag gttataagca    960
taccatgtta actgattccg acgtcaatgc aacaagacac gccagagccg ctgtaggtgg   1020
tttgattgca gccttacatg gtaacggtgc tgtctatgta tcaggtggtg cagaacacca   1080
```

```
aggtccaagt ggtggtggtt ctgttactgt tatatatgat gttcctgcaa cagccaacgc   1140
taccggtgaa gcttctagat aaggaaatcc attatgatat actcaacagt caacgctaat   1200
ccttacgctt ggccttacga tggttcaata gaccctgctc acaccgcttt aatcttaatc   1260
gattggcaaa tagacttttg tggtccaggt ggttatgtcg attccatggg ttacgactta   1320
tccttgacta gaagtggttt agaacctaca gcaagagtat tggctgcagc cagagatact   1380
ggtatgacag ttatccatac tagagaaggt cacagaccag atttggctga cttgccacct   1440
aataagagat ggagatctgc atcagccggt gctgaaatcg gttcagttgg tccatgtggt   1500
agaattttag tcagaggtga acctggttgg gaaatagtac cagaagttgc acctagagaa   1560
ggtgaaccaa ttatagataa acctggtaaa ggtgctttct acgcaacaga tttggacttg   1620
ttgttgagaa caagaggtat cacccatttg attttgaccg gtataactac agatgtttgc   1680
gtccacacca ctatgagaga agccaacgat agaggttacg aatgtttaat tttgtctgat   1740
tgcaccggtg ctactgacag aaagcatcac gaagctgcat tatctatggt caccatgcaa   1800
ggtggtgtat tcggtgcaac tgcccattca gatgactat tggccgcttt gggtacaacc   1860
gttccagcag ccgctggtcc tagagctaga acagaataag gaacgaccat gacagttagt   1920
tccgatacaa ctgctgaaat atcgttaggt tggtcaatcc aagactggat tgatttccac   1980
aagtcatcaa gctcccaggc ttcactaagg cttcttgaat cactactaga ctctcaaaat   2040
gttgcgccag tcgataatgc gtggatatcg ctaatttcaa aggaaatttt actgcaccaa   2100
ttccaaattt taagagcag agaaaataaa gaaactctac ctctctacgg tgtccctatt   2160
gctgttaagg acaacatcga cgttagaggt ctacccacca ccgctgcatg tccatccttt   2220
gcatatgagc cttccaaaga ctctaaagta gtagaactac taagaaatgc aggtgcgata   2280
atcgtgggta agacaaactt ggaccaattt gccacaggat tagtcggcac acggtctcca   2340
tatgggaaaa caccttgcgc ttttagcaaa gagcatgtat ctggtggttc ctccgctggg   2400
tcagcatcgg tggtcgccag aggtatcgta ccaattgcat tgggtactga tacagcaggt   2460
tctggtagag tcccagccgc cttgaacaac ctgattggcc taaagccaac aaagggcgtc   2520
ttttcctgtc aaggtgtagt tcccgcttgt aaatctttag actgcgtctc catctttgca   2580
ttaaacctaa gtgatgctga acgctgcttc cgcatcatgt gccagccaga tcctgataat   2640
gatgaatatt ctagacccta tgtttccaac cctttgaaaa aattttcaag caatgtaacg   2700
attgctattc ctaaaaatat cccatggtat ggtgaaacca agaatcctgt actgttttcc   2760
aatgctgtcg aaaatctatc aagaacgggc gctaacgtca tagaaattga ttttgagcct   2820
cttttagagt tagctcgctg tttatacgaa ggtacttggg tggccgagcg ttatcaagct   2880
attcaatcgt ttttggacag taaaccacca aaggaatctt tggacccta ctgttatttca   2940 attatagaag gggccaagaa atacagtgca gtagactgct tcagttttga atacaaaaga   3000
caaggcatct tgcaaaaagt gagacgactt ctcgaatcag tcgatgtatt gtgtgtgccc   3060
acatgtcctt taaatcctac tatgcaacaa gttgcggatg aaccagtcct agtcaattca   3120
agacaaggca catggactaa ttttgtcaac ttggcagatt tggcagccct tgctgttccc   3180
gcagggttcc gagacgatgg tttgccaaat ggtattactt taatcggtaa aaaattcaca   3240
gattacgcac tattagagtt ggctaaccgc tatttccaaa atatattccc caacggttcc   3300
agaacatacg gtacttttac ctcttcttca gtaaagccag caaacgatca attagtggga   3360
ccagactatg acccatctac gtccataaaa ttggctgttg tcggtgcaca tcttaagggt   3420
ctgcctctac attggcaatt ggaaaaggtc aatgcaacat atttatgtac aacaaaaaca   3480
```

| | |
|---|---|
| tcaaaagctt accagctttt tgctttgccc aaaaatggac cagtttaaa acctggtttg | 3540 |
| agaagagttc aagatagcaa tggctctcaa atcgaattag aagtgtacag tgttccaaaa | 3600 |
| gaactgttcg gtgcttttat ttccatggtt cctgaaccat taggaatagg ttcagtggag | 3660 |
| ttagaatctg tgaatggat caaatccttt atttgtgaag aatctggtta caaagccaaa | 3720 |
| ggtacagttg atatcacaaa gtatggtgga tttagagcat attttgaaat gttgtaagtt | 3780 |
| taaactaatc ccacagccgc cagttccgct ggcggcattt taactttctt taatgggcgc | 3840 |
| gcctttccat aggctccgcc ccctgacga gcatcacaaa atcgacgct caagtcagag | 3900 |
| gtggcgaaac ccgacaggac tataaagata ccaggcgttt ccccctggaa gctccctcgt | 3960 |
| gcgctctcct gttccgaccc tgccgcttac cggatacctg tccgcctttc tcccttcggg | 4020 |
| aagcgtggcg ctttctcata gctcacgctg taggtatctc agttcggtgt aggtcgttcg | 4080 |
| ctccaagctg gctgtgtgc acgaaccccc cgttcagccc gaccgctgcg ccttatccgg | 4140 |
| taactatcgt cttgagtcca acccggtaag cacgactta tcgccactgg cagcagccac | 4200 |
| tggtaacagg attagcagag cgaggtatgt aggcggtgct acagagttct gaagtggtg | 4260 |
| gcctaactac ggctacacta aagaacagt atttggtatc tgcgctctgc tgaagccagt | 4320 |
| taccttcgga aaagagttg gtagctcttg atccggcaaa caaaccaccg ctggtagcgg | 4380 |
| tggttttttt gtttgcaagc agcagattac gcgcagaaaa aaaggatctc aagaagatcc | 4440 |
| tttgatcttt tctacggggt ctgacgctca gtggaacgaa aactcacgtt aagggatttt | 4500 |
| ggtcatgaga ttatcaaaaa ggatcttcac ctagatcctt ttaaattaaa aatgaagttt | 4560 |
| taaatcaatc taaagtatat atgagtaaac ttggtctgac agttaccaat gcttaatcag | 4620 |
| tgaggcacct atctcagcga tctgtctatt tcgttcatcc atagttgcct gactccccgt | 4680 |
| cgtgtagata actacgatac gggagggctt accatctggc cccagtgctg caatgatacc | 4740 |
| gcgagaccca cgctcaccgg ctccagattt atcagcaata aaccagccag ccggaagggc | 4800 |
| cgagcgcaga agtggtcctg caactttatc cgcctccatc cagtctatta attgttgccg | 4860 |
| ggaagctaga gtaagtagtt cgccagttaa tagtttgcgc aacgttgttg ccattgctac | 4920 |
| aggcatcgtg gtgtcacgct cgtcgtttgg tatggcttca ttcagctccg gttcccaacg | 4980 |
| atcaaggcga gttacatgat cccccatgtt gtgcaaaaaa gcggttagct ccttcggtcc | 5040 |
| tccgatcgtt gtcagaagta agttggccgc agtgttatca ctcatggtta tggcagcact | 5100 |
| gcataattct cttactgtca tgccatccgt aagatgcttt tctgtgactg gtgagtactc | 5160 |
| aaccaagtca ttctgagaat agtgtatgcg gcgaccgagt tgctcttgcc cggcgtcaat | 5220 |
| acgggataat accgcgccac atagcagaac tttaaaagtg ctcatcattg gaaaacgttc | 5280 |
| ttcggggcga aaactctcaa ggatcttacc gctgttgaga tccagttcga tgtaacccac | 5340 |
| tcgtgcaccc aactgatctt cagcatcttt tactttcacc agcgtttctg ggtgagcaaa | 5400 |
| aacaggaagg caaaatgccg caaaaaaggg aataagggcg acacggaaat gttgaatact | 5460 |
| catactcttc ctttttcaat attattgaag catttatcag ggttattgtc tcatgagcgg | 5520 |
| atacatattt gaatgtattt agaaaaataa acagcgatcg cgcggccgcg gtaataact | 5580 |
| gatataatta aattgaagct ctaatttgtg agtttagtat acatgcattt acttataata | 5640 |
| cagttttta gttttgctgg ccgcatcttc tcaaatatgc ttcccagcct gcttttctgt | 5700 |
| aacgttcacc ctctacctta gcatccctt cctttgcaaa tagtcctctt ccaacaataa | 5760 |
| taatgtcaga tcctgtagag accacatcat ccacggttct atactgttga cccaatgcgt | 5820 |

| | |
|---|---|
| ctcccttgtc atctaaaccc acaccgggtg tcataatcaa ccaatcgtaa ccttcatctc | 5880 |
| ttccacccat gtctctttga gcaataaagc cgataacaaa atctttgtcg ctcttcgcaa | 5940 |
| tgtcaacagt acccttagta tattctccag tagctaggga gcccttgcat gacaattctg | 6000 |
| ctaacatcaa aaggcctcta ggttcctttg ttacttcttc cgccgcctgc ttcaaaccgc | 6060 |
| taacaatacc tgggcccacc acaccgtgtg cattcgtaat gtctgcccat tctgctattc | 6120 |
| tgtatacacc cgcagagtac tgcaatttga ctgtattacc aatgtcagca aattttctgt | 6180 |
| cttcgaagag taaaaaattg tacttggcgg ataatgcctt tagcggctta actgtgccct | 6240 |
| ccatggaaaa atcagtcaag atatccacat gtgtttttag taaacaaatt ttgggaccta | 6300 |
| atgcttcaac taactccagt aattccttgg tggtacgaac atccaatgaa gcacacaagt | 6360 |
| ttgtttgctt ttcgtgcatg atattaaata gcttggcagc aacaggacta ggatgagtag | 6420 |
| cagcacgttc cttatatgta gctttcgaca tgatttatct tcgtttcctg caggtttttg | 6480 |
| ttctgtgcag ttgggttaag aatactgggc aatttcatgt ttcttcaaca ccacatatgc | 6540 |
| gtatatatac caatctaagt ctgtgctcct tccttcgttc ttccttctgc tcggagatta | 6600 |
| ccgaatcaaa gctagcttat cgatgataag ctgtcaaaga tgagaattaa ttccacggac | 6660 |
| tatagactat actagatact ccgtctactg tacgatacac ttccgctcag gtccttgtcc | 6720 |
| tttaacgagg ccttaccact ctttgttac tctattgatc cagctcagca aaggcagtgt | 6780 |
| gatctaagat tctatcttcg cgatgtagta aaactagcta gaccgagaaa gagactagaa | 6840 |
| atgcaaaagg cacttctaca atggctgcca tcattattat ccgatgtgac gctgcagctt | 6900 |
| ctcaatgata ttcgaatacg ctttgaggag atacagccta atatccgaca aactgttta | 6960 |
| cagatttacg atcgtacttg ttacccatca ttgaattttg aacatccgaa cctgggagtt | 7020 |
| ttccctgaaa cagatagtat atttgaacct gtataataat atatagtcta gcgctttacg | 7080 |
| gaagacaatg tatgtatttc ggttcctgga gaaactattg catctattgc ataggtaatc | 7140 |
| ttgcacgtcg catccccggt tcattttctg cgtttccatc ttgcacttca atagcatatc | 7200 |
| tttgttaacg aagcatctgt gcttcatttt gtagaacaaa aatgcaacgc gagagcgcta | 7260 |
| atttttcaaa caaagaatct gagctgcatt tttacagaac agaaatgcaa cgcgaaagcg | 7320 |
| ctattttacc aacgaagaat ctgtgcttca tttttgtaaa acaaaaatgc aacgcgacga | 7380 |
| gagcgctaat ttttcaaaca agaatctga gctgcatttt tacagaacag aaatgcaacg | 7440 |
| cgagagcgct attttaccaa caaagaatct atacttcttt tttgttctac aaaaatgcat | 7500 |
| cccgagagcg ctattttct aacaaagcat cttagattac ttttttttctc ctttgtgcgc | 7560 |
| tctataatgc agtctcttga taacttttg cactgtaggt ccgttaaggt tagaagaagg | 7620 |
| ctactttggt gtctatttc tcttccataa aaaagcctg actccacttc ccgcgtttac | 7680 |
| tgattactag cgaagctgcg ggtgcatttt ttcaagataa aggcatcccc gattatattc | 7740 |
| tataccgatg tggattgcgc atactttgtg aacagaaagt gatagcgttg atgattcttc | 7800 |
| attggtcaga aaattatgaa cggtttcttc tattttgtct ctatatacta cgtataggaa | 7860 |
| atgtttacat tttcgtattg ttttcgattc actctatgaa tagttcttac tacaattttt | 7920 |
| ttgtctaaag agtaatacta gagataaaca taaaaaatgt agaggtcgag tttagatgca | 7980 |
| agttcaagga gcgaaaggtg gatgggtagg ttatataggg atatagcaca gagatatata | 8040 |
| gcaaagagat acttttgagc aat | 8063 |

<210> SEQ ID NO 20
<211> LENGTH: 6004

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
gatactttg agcaatgttt gtggaagcgg tattcgcaat tataaacggt attttcacaa      60
ttgcacccca gccagaccga tagccggtcg caatccgcca cccacaaccg tctacctccc    120
acagaacccc gtcacttcca cccttttcca ccagatcata tgtcccaact tgccaaatta    180
aaaccgtgcg aattttcaaa ataaactttg gcaaagaggc tgcaaaggag gggctggtga    240
gggcgtctgg aagtcgacca gagaccgggt tggcggcgca tttgtgtccc aaaaaacagc    300
cccaattgcc ccaattgacc ccaaattgac ccagtagcgg gcccaacccc ggcgagagcc    360
cccttctccc cacatatcaa acctcccccg gttcccacac ttgccgttaa gggcgtaggg    420
tactgcagtc tggaatctac gcttgttcag actttgtact agtttctttg tctggccatc    480
cgggtaaccc atgccggacg caaaatagac tactgaaaat ttttttgctt tgtggttggg    540
actttagcca agggtataaa agaccaccgt ccccgaatta cctttcctct tcttttctct    600
ctctccttgt caactcacac ccgaaatcgt taagcatttc cttctgagta taagaatcat    660
tcaaaatgtc atcctcagaa gtaaaagcaa atggttggac cgcagttcct gtttccgcaa    720
aagcaatagt agactccttg ggtaaattag agatgtctc ttcatattcc gtagaagata     780
ttgccttttcc agctgcagac aaattggtag ccgaagctca agcattcgtt aaggctagat    840
tatctcctga aacctacaac cattcaatga gagttttcta ttgggggtact gtcattgcca    900
gaagattgtt accagaacaa gctaaagatt tgtctccttc aacatgggca ttaacctgtt    960
tgttacacga cgttggtact gccgaagctt attttacctc cactagaatg agtttcgata   1020
tctacggtgg tattaaagct atggaagtat tgaaggtttt aggttccagt acagatcaag   1080
cagaagccgt tgctgaagca attataagac atgaagatgt tggtgtcgac ggtaacatca   1140
cattttggg tcaattgatc caattggcaa cattgtacga taacgtcggt gcctacgacg    1200
gtattgatga cttcggttcc tgggttgatg acactacaag aaacagtata aacactgctt   1260
tcccaagaca tggttggtgt tcttggttcg catgcacagt tagaaaagaa gaatcaaaca   1320
agccttggtg ccacaccaca cacataccac aattcgacaa acaaatggaa gcaaacacct   1380
tgatgaaacc ttgggaataa gctgcttgta cctagtgcaa ccccagtttg ttaaaaatta   1440
gtagtcaaaa acttctgagt tagaaatttg tgagtgtagt gagattgtag agtatcatgt   1500
gtgtccgtaa gtgaagtgtt attgactctt agttagttta tctagtactc gtttagttga   1560
cactgatcta gtattttacg aggcgtatga ctttagccaa gtgttgtact tagtcttctc   1620
tccaaacatg agagggctct gtcactcagt cggcctatgg gtgagatggc ttggtgagat   1680
ctttcgatag tctcgtcaag atggtaggat gatgggggaa tacattactg ctctcgtcaa   1740
ggaaaccaca atcagatcac accatcctcc atggtatccg atgactctct tctccacagt   1800
tttccatagg ctccgccccc ctgacgagca tcacaaaaat cgacgctcaa gtcagaggtg   1860
gcgaaacccg acaggactat aaagatacca ggcgtttccc cctggaagct ccctcgtgcg   1920
ctctcctgtt ccgaccctgc cgcttaccgg atacctgtcc gcctttctcc cttcgggaag   1980
cgtggcgctt tctcatagct cacgctgtag gtatctcagt tcggtgtagg tcgttcgctc   2040
caagctgggc tgtgtgcacg aaccccccgt tcagcccgac cgctgcgcct tatccggtaa   2100
ctatcgtctt gagtccaacc cggtaagaca cgacttatcg ccactggcag cagccactgg   2160
```

```
taacaggatt agcagagcga ggtatgtagg cggtgctaca gagttcttga agtggtggcc    2220
taactacggc tacactagaa gaacagtatt tggtatctgc gctctgctga agccagttac    2280
cttcggaaaa agagttggta gctcttgatc cggcaaacaa accaccgctg gtagcggtgg    2340 ttttttgtt tgcaagcagc agattacgcg cagaaaaaaa ggatctcaag aagatccttt    2400
gatcttttct acggggtctg acgctcagtg gaacgaaaac tcacgttaag gattttggt    2460 catgagatta tcaaaaagga tcttcaccta gatcctttta aattaaaaat gaagttttaa    2520
atcaatctaa agtatatatg agtaaacttg gtctgacagt taccaatgct taatcagtga    2580
ggcacctatc tcagcgatct gtctatttcg ttcatccata gttgcctgac tccccgtcgt    2640
gtagataact acgatacggg agggcttacc atctggcccc agtgctgcaa tgataccgcg    2700
agacccacgc tcaccggctc cagatttatc agcaataaac cagccagccg gaagggccga    2760
gcgcagaagt ggtcctgcaa ctttatccgc ctccatccag tctattaatt gttgccggga    2820
agctagagta agtagttcgc cagttaatag tttgcgcaac gttgttgcca ttgctacagg    2880
catcgtggtg tcacgctcgt cgtttggtat ggcttcattc agctccggtt cccaacgatc    2940
aaggcgagtt acatgatccc ccatgttgtg caaaaaagcg gttagctcct tcggtcctcc    3000
gatcgttgtc agaagtaagt tggccgcagt gttatcactc atggttatgg cagcactgca    3060
taattctctt actgtcatgc catccgtaag atgcttttct gtgactggtg agtactcaac    3120
caagtcattc tgagaatagt gtatgcggcg accgagttgc tcttgcccgg cgtcaatacg    3180
ggataatacc gcgccacata gcagaacttt aaaagtgctc atcattggaa aacgttcttc    3240
ggggcgaaaa ctctcaagga tcttaccgct gttgagatcc agttcgatgt aacccactcg    3300
tgcacccaac tgatcttcag catctttac tttcaccagc gtttctgggt gagcaaaaac    3360
aggaaggcaa aatgccgcaa aaaagggaat aagggcgaca cggaaatgtt gaatactcat    3420
actcttcctt tttcaatatt attgaagcat ttatcagggt tattgtctca tgagcggata    3480
catatttgaa tgtatttaga aaaataaaca gcgatcgcgc ggccgcgggt aataactgat    3540
ataattaaat tgaagctcta atttgtgagt ttagtataca tgcatttact tataatacag    3600 tttttagtt ttgctggccg catcttctca aatatgcttc ccagcctgct tttctgtaac    3660
gttcaccctc taccttagca tccccttccct ttgcaaatag tcctcttcca acaataataa    3720
tgtcagatcc tgtagagacc acatcatcca cggttctata ctgttgaccc aatgcgtctc    3780
ccttgtcatc taaacccaca ccgggtgtca taatcaacca atcgtaacct tcatctcttc    3840
cacccatgtc tctttgagca ataaagccga taacaaaatc tttgtcgctc ttcgcaatgt    3900
caacagtacc cttagtatat tctccagtag ctagggagcc cttgcatgac aattctgcta    3960
acatcaaaag gcctctaggt tcctttgtta cttcttccgc cgcctgcttc aaaccgctaa    4020
caatacctgg gcccaccaca ccgtgtgcat tcgtaatgtc tgcccattct gctattctgt    4080
atacacccgc agagtactgc aatttgactg tattaccaat gtcagcaaat tttctgtctt    4140
cgaagagtaa aaaattgtac ttggcggata atgcctttag cggcttaact gtgccctcca    4200
tggaaaaatc agtcaagata tccacatgtg ttttttagtaa acaaattttg ggacctaatg    4260
cttcaactaa ctccagtaat tccttggtgg tacgaacatc caatgaagca cacaagtttg    4320
tttgcttttc gtgcatgata ttaaatagct tggcagcaac aggactagga tgagtagcag    4380
cacgttcctt atatgtagct ttcgacatga tttatcttcg tttcctgcag gttttttgttc    4440 tgtgcagttg ggttaagaat actgggcaat ttcatgtttc ttcaacacca catatgcgta    4500
```

-continued

| | |
|---|---|
| tatataccaa tctaagtctg tgctccttcc ttcgttcttc cttctgctcg agattaccg | 4560 |
| aatcaaagct agcttatcga tgataagctg tcaaagatga gaattaattc cacggactat | 4620 |
| agactatact agatactccg tctactgtac gatacacttc cgctcaggtc cttgtccttt | 4680 |
| aacgaggcct taccactctt ttgttactct attgatccag ctcagcaaag gcagtgtgat | 4740 |
| ctaagattct atcttcgcga tgtagtaaaa ctagctagac cgagaaagag actagaaatg | 4800 |
| caaaaggcac ttctacaatg gctgccatca ttattatccg atgtgacgct gcagcttctc | 4860 |
| aatgatattc gaatacgctt tgaggagata cagcctaata tccgacaaac tgttttacag | 4920 |
| atttacgatc gtacttgtta cccatcattg aattttgaac atccgaacct gggagttttc | 4980 |
| cctgaaacag atagtatatt tgaacctgta taataatata tagtctagcg ctttacggaa | 5040 |
| gacaatgtat gtatttcggt tcctggagaa actattgcat ctattgcata ggtaatcttg | 5100 |
| cacgtcgcat ccccggttca ttttctgcgt ttccatcttg cacttcaata gcatatcttt | 5160 |
| gttaacgaag catctgtgct tcattttgta gaacaaaaat gcaacgcgag agcgctaatt | 5220 |
| tttcaaacaa agaatctgag ctgcattttt acagaacaga aatgcaacgc gaaagcgcta | 5280 |
| ttttaccaac gaagaatctg tgcttcattt ttgtaaaaca aaaatgcaac gcgacgagag | 5340 |
| cgctaatttt tcaaacaaag aatctgagct gcattttttac agaacagaaa tgcaacgcga | 5400 |
| gagcgctatt ttaccaacaa agaatctata cttcttttt gttctacaaa aatgcatccc | 5460 |
| gagagcgcta ttttttctaac aaagcatctt agattacttt ttttctcctt tgtgcgctct | 5520 |
| ataatgcagt ctcttgataa cttttttgcac tgtaggtccg ttaaggttag aagaaggcta | 5580 |
| ctttggtgtc tattttctct tccataaaaa aagcctgact ccactcccg cgtttactga | 5640 |
| ttactagcga agctgcgggt gcatttttc aagataaagg catccccgat tatattctat | 5700 |
| accgatgtgg attgcgcata ctttgtgaac agaaagtgat agcgttgatg attcttcatt | 5760 |
| ggtcagaaaa ttatgaacgg tttcttctat tttgtctcta tatactacgt ataggaaatg | 5820 |
| tttacatttt cgtattgttt tcgattcact ctatgaatag ttcttactac aattttttg | 5880 |
| tctaaagagt aatactagag ataaacataa aaaatgtaga ggtcgagttt agatgcaagt | 5940 |
| tcaaggagcg aaaggtggat gggtaggtta tatagggata tagcacagag atatatagca | 6000 |
| aaga | 6004 |

<210> SEQ ID NO 21
<211> LENGTH: 10640
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

| | |
|---|---|
| gtttgtggaa gcggtattcg caatttaatt aaagctggtg acaattaatc atcggctcgt | 60 |
| ataatgtgtg gaattgaatc gatataagga ggttaatcat atgacagtta gttccgatac | 120 |
| aactgctgaa atatcgttag gttggtcaat ccaagactgg attgatttcc acaagtcatc | 180 |
| aagctcccag gcttcactaa ggcttcttga atcactacta gactctcaaa atgttgcgcc | 240 |
| agtcgataat gcgtggatat cgctaatttc aaaggaaaat ttactgcacc aattccaaat | 300 |
| tttaaagagc agagaaaata agaaactct acctctctac ggtgtcccta ttgctgttaa | 360 |
| ggacaacatc gacgttagag gtctacccac caccgctgca tgtccatcct ttgcatatga | 420 |
| gccttccaaa gactctaaag tagtagaact actaagaaat gcaggtgcga taatcgtggg | 480 |

```
taagacaaac ttggaccaat ttgccacagg attagtcggc acacggtctc catatgggaa      540
aacaccttgc gcttttagca aagagcatgt atctggtggt tcctccgctg ggtcagcatc      600
ggtggtcgcc agaggtatcg taccaattgc attgggtact gatacagcag gttctggtag      660
agtcccagcc gccttgaaca acctgattgg cctaaagcca acaaagggcg tcttttcctg      720
tcaaggtgta gttcccgctt gtaaatcttt agactgcgtc tccatctttg cattaaacct      780
aagtgatgct gaacgctgct tccgcatcat gtgccagcca gatcctgata atgatgaata      840
ttctagaccc tatgtttcca acccttttgaa aaaattttca agcaatgtaa cgattgctat      900
tcctaaaaat atcccatggt atggtgaaac caagaatcct gtactgtttt ccaatgctgt      960
cgaaaatcta tcaagaacgg gcgctaacgt catagaaatt gattttgagc ctcttttaga     1020
gttagctcgc tgtttatacg aaggtacttg ggtggccgag cgttatcaag ctattcaatc     1080 gttttttggac agtaaaccac caaaggaatc tttggaccct actgttattt caattataga     1140
aggggccaag aaatacagtg cagtagactg cttcagtttt gaatacaaaa gacaaggcat     1200
cttgcaaaaa gtgagacgac ttctcgaatc agtcgatgta ttgtgtgtgc ccacatgtcc     1260
tttaaatcct actatgcaac aagttgcgga tgaaccagtc ctagtcaatt caagacaagg     1320
cacatggact aattttgtca acttggcaga tttggcagcc cttgctgttc ccgcagggtt     1380
ccgagacgat ggtttgccaa atggtattac tttaatcggt aaaaaattca cagattacgc     1440
actattagag ttggctaacc gctatttcca aaatatattc cccaacggtt ccagaacata     1500
cggtactttt acctcttctt cagtaaagcc agcaaacgat caattagtgg gaccagacta     1560
tgacccatct acgtccataa aattggctgt gtcggtgca catcttaagg gtctgcctct     1620
acattggcaa ttggaaaagg tcaatgcaac atatttatgt acaacaaaaa catcaaaagc     1680
ttaccagctt tttgctttgc ccaaaaatgg accagttta aaacctggtt tgagaagagt     1740
tcaagatagc aatggctctc aaatcgaatt agaagtgtac agtgttccaa agaactgtt     1800 cggtgctttt atttccatgg ttcctgaacc attaggaata ggttcagtgg agttagaatc     1860
tggtgaatgg atcaaatcct ttatttgtga agaatctggt tacaaagcca aggtacagt     1920 tgatatcaca aagtatggtg gatttagagc atattttgaa atgttgaaga aaaaagagtc     1980
ccaaaagaag aagttatttg ataccgtgtt aattgccaat agaggtgaaa ttgccgttcg     2040
tattatcaag acattaaaaa aattgggtat tagatcagtt gcagtttatt ccgaccctga     2100
taaatattct caacacgtta ctgatgcaga tgtttctgta ccccttcatg gcacaaccgc     2160
agcccaaact tatttagaca tgaataagat catagatgcc gctaagcaaa ctaatgcaca     2220
ggccattatt cctggttatg gtttcttgtc ggaaaatgcg gattttctg atgcgtgcac     2280 cagtgctggc attaccttg ttggtccttc gggagatatt atcagaggtt tagggttaaa     2340
acattctgct agacagattg cacagaaggc tggcgttcct ctagtgccag gctctttgct     2400
tatcacatca gttgaagagg ctaagaaagt cgcagcggaa ttggaatacc cagttatggt     2460
gaagtcaact gctggtggcg gtggtattgg tttcagaaaa gtcgattctg aagaggacat     2520
cgagcatatt tttgagactg tgaaacatca aggtgaaaca ttttcggtg acgctggtgt     2580 atttctggaa cggtttatcg aaaatgccag gcatgttgaa gtccaactta tgggagatgg     2640
ttttggtaag gccattgctt tgggcgaacg tgattgttct ttacagcgtc gtaaccaaaa     2700
agttatcgaa gaactcctg caccaaaattt gccagaaaag acgaggttgg cgttaagaaa     2760
ggcagctgaa agtttgggat ctttattgaa ttacaagtgt gctggtacgg ttgaatttat     2820
ttacgatgag aaaaaggacg agtttttactt tttagaagtt aatacaagat tacaagttga     2880
```

| | |
|---|---|
| acatccaata acagaaatgg ttacagggtt agacttggtc gagtggatga tcaggattgc | 2940 |
| cgctaatgat gcacctgatt ttgattctac aaaggtagaa gtcaatgggg tttcaatgga | 3000 |
| ggcacgttta tatgctgaaa atccattgaa aaatttcaga ccttctccag gtttacttgt | 3060 |
| cgatgtgaaa tttcctgatt gggcaagagt ggatacttgg gttaagaaag gtactaatat | 3120 |
| ttctcccgaa tatgatccaa cattggccaa aattatcgtt catgggaaag accgtgatga | 3180 |
| tgcaatttcc aagttaaatc aagcgttaga agaaacaaaa gtttacggat gtattactaa | 3240 |
| cattgactac ctgaagtcta tcattaccag tgatttcttt gctaaagcaa aagtttctac | 3300 |
| aaacattttg aactcttatc aatatgagcc taccgccatc gaaattactt tgcccggtgc | 3360 |
| acacactagt attcaggatt accccggtag agttgggtac tggagaattg gtgttccgcc | 3420 |
| ctctggtcca atgacgcat attcgtttag attggcgaac agaattgttg gtaatgacta | 3480 |
| caggactcct gccattgaag taacgttgac tggtccatcc atcgttttcc attgtgaaac | 3540 |
| tgtcattgcc attactggtg gtaccgctct atgtacatta gacggccaag aaattcccca | 3600 |
| acacaaaccg gtcgaagtta gaggggatc tactttatcc attggcaagt tgacaagcgg | 3660 |
| ctgtagagca tacttaggta tcaggggtgg cattgatgtg cctaaatact tgggctctta | 3720 |
| ttctactttc actctaggaa atgtcggtgg atacaatgga agggtgctaa aacttggaga | 3780 |
| cgtactattc ttaccaagca atgaagaaaa taaatcagtt gagtgccttc cacagaaatat | 3840 |
| tcctcaatca ttaattcctc aaatttccga aactaaggaa tggagaattg gtgtaacatg | 3900 |
| tggtccccat gggtctccag attttttttaa acctgagtcc atcgaagaat ttttcagtga | 3960 |
| gaagtggaag gttcattaca actccaatag atttggtgtc cgtttgattg gacctaaacc | 4020 |
| taagtgggca agaagtaatg gtggtgaagg tggtatgcat ccttcaaaca ctcacgatta | 4080 |
| cgtttattct ctgggtgcaa ttaatttcac gggtgatgag ccagttatta ttacttgcga | 4140 |
| tggtccttcc ttaggtggtt ttgtgtgtca agctgttgtc ccagaagcag aactgtggaa | 4200 |
| ggttggacag gttaaacccg gtgattccat tcagtttgtg ccactttctt acgaaagctc | 4260 |
| gagatcctta aaggaatctc aggatgttgc aattaaatca ttggatggta ctaagttaag | 4320 |
| gcgcttagac tctgtttcaa ttttaccatc attcgaaacg cctattcttg cacaaatgga | 4380 |
| aaaagtgaat gagcttttcac caaaggttgt atacagacaa gcaggtgatc gttatgttt | 4440 |
| ggtggaatac ggtgataatg aaatgaattt taatatttcc tatagaattg aatgcctgat | 4500 |
| ctcccttgtg aaaagaata agactattgg tattgttgaa atgtcccaag gtgttagatc | 4560 |
| tgtattgata gaatttgatg gttacaaagt cactcaaaaa gaattgctta agtattggt | 4620 |
| ggcatatgaa acagaaatcc agtttgatga aaattggaag ataacttcta atataataag | 4680 |
| attaccgatg gctttcgaag actcgaagac tttggcatgt gttcaaaggt atcaagaaac | 4740 |
| aattcgttcg tctgctccat ggttgccaaa taacgttgat ttcattgcca atgtaaatgg | 4800 |
| aatttcaagg aatgaagttt atgatatgtt gtattctgcc agatttatgg ttttaggttt | 4860 |
| aggtgatgtc ttcctagggt cgccttgtgc tgttccatta gatcctcgtc acagattttt | 4920 |
| gggaagcaag tacaacccaa gtagaacata tacagaaaga ggtgcagtcg gtattggcgg | 4980 |
| tatgtatatg tgcatatatg ctgctaacag tcctggtggg taccaattag tgggtagaac | 5040 |
| aataccaatt tgggacaaac tatgtctggc cgcatcttct gaggttccgt ggttgatgaa | 5100 |
| cccatttgac caagtcgaat tttacccagt ttctgaagaa gatttggata aaatgactga | 5160 |
| agattgtgat aatggtgttt ataaagtcaa tatcgaaaag agtgtttttg atcatcaaga | 5220 |

```
atacttgaga tggatcaacg caaacaaaga ttccatcaca gcattccagg agggccagct   5280
tggtgaaaga gcagaggaat ttgccaaatt gattcaaaat gcaaactctg aactaaaaga   5340
aagtgtcaca gtcaaacctg acgaggaaga agacttccca gaaggtgcag aaattgtata   5400
ttctgagtat tctgggcgtt tttgaaaatc catagcatct gttggagatg ttattgaagc   5460
aggtcaaggg ctactaatta ttgaagccat gaaagcggaa atgattatat ccgctcctaa   5520
atcgggtaag attatcaaga tttgccatgg caatggtgat atggttgatt ctggtgacat   5580
agtggccgtc atagagacat ggcatgagg aaatccatta tgtcatcctc agaagtaaaa    5640
gcaaatggtt ggaccgcagt tcctgttccc gcaaaagcaa tagtagactc cttgggtaaa   5700
ttaggagatg tctcttcata ttccgtagaa gatattgcct ttccagctgc agacaaattg   5760
gtagccgaag ctcaagcatt cgttaaggct agattatctc ctgaaaccta caaccattca   5820
atgagagttt tctattgggg tactgtcatt gccagaagat tgttaccaga acaagctaaa   5880
gatttgtctc cttcaacatg gcattaacc tgtttgttac acgacgttgg tactgccgaa     5940
gcttatttta cctccactag aatgagtttc gatatctacg tggtattaa agctatggaa    6000 gtattgaagg ttttaggttc cagtacagat caagcagaag ccgttgctga agcaattata   6060
agacatgaag atgttggtgt cgacggtaac atcacatttt tgggtcaatt gatccaattg   6120
gcaacattgt acgataacgt cggtgcctac gacggtattg atgacttcgg ttcctgggtt   6180
gatgacacta caagaaacag tataaacact gcttttccaa gacatggttg gtgttcttgg   6240
ttcgcatgca cagttagaaa agaagaatca aacaagcctt ggtgccacac cacacacata   6300
ccacaattcg acaaacaaat ggaagcaaac accttgatga aaccttggga ataagtttaa   6360
actaatccca cagccgccag ttccgctggc ggcattttaa ctttctttaa tgggcgcgcc   6420
tttccatagg ctccgccccc ctgacgagca tcacaaaaat cgacgctcaa gtcagaggtg   6480
gcgaaacccg acaggactat aaagatacca ggcgtttccc cctggaagct ccctcgtgcg   6540
ctctcctgtt ccgaccctgc cgcttaccgg atacctgtcc gcctttctcc cttcgggaag   6600
cgtggcgctt tctcatagct cacgctgtag gtatctcagt tcggtgtagg tcgttcgctc   6660
caagctgggc tgtgtgcacg aaccccccgt tcagcccgac cgctgcgcct tatccggtaa   6720
ctatcgtctt gagtccaacc cggtaagaca cgacttatcg ccactggcag cagccactgg   6780
taacaggatt agcagagcga ggtatgtagg cggtgctaca gagttcttga agtggtggcc   6840
taactacggc tacactagaa gaacagtatt tggtatctgc gctctgctga gccagttac   6900 cttcggaaaa agagttggta gctcttgatc cggcaaacaa accaccgctg gtagcggtgg   6960 ttttttttgtt tgcaagcagc agattacgcg cagaaaaaaa ggatctcaag aagatccttt   7020
gatcttttct acggggtctg acgctcagtg gaacgaaaac tcacgttaag ggattttggt   7080
catgagatta tcaaaaagga tcttcaccta gatccttta aattaaaaat gaagttttaa   7140
atcaatctaa agtatatatg agtaaacttg gtctgacagt taccaatgct taatcagtga   7200
ggcacctatc tcagcgatct gtctatttcg ttcatccata gttgcctgac tccccgtcgt   7260
gtagataact acgatacggg agggcttacc atctggcccc agtgctgcaa tgataccgcg   7320
agacccacgc tcaccggctc cagatttatc agcaataaac cagccagccg aagggccga   7380 gcgcagaagt ggtcctgcaa ctttatccgc ctccatccag tctattaatt gttgccggga   7440
agctagagta agtagttcgc cagttaatag tttgcgcaac gttgttgcca ttgctacagg   7500
catcgtggtg tcacgctcgt cgtttggtat ggcttcattc agctccggtt cccaacgatc   7560
aaggcgagtt acatgatccc ccatgttgtg caaaaaagcg gttagctcct tcggtcctcc   7620
```

```
gatcgttgtc agaagtaagt tggccgcagt gttatcactc atggttatgg cagcactgca    7680
taattctctt actgtcatgc catccgtaag atgcttttct gtgactggtg agtactcaac    7740
caagtcattc tgagaatagt gtatgcggcg accgagttgc tcttgcccgg cgtcaatacg    7800
ggataatacc gcgccacata gcagaacttt aaaagtgctc atcattggaa aacgttcttc    7860
ggggcgaaaa ctctcaagga tcttaccgct gttgagatcc agttcgatgt aacccactcg    7920
tgcacccaac tgatcttcag catcttttac tttcaccagc gtttctgggt gagcaaaaac    7980
aggaaggcaa aatgccgcaa aaagggaat aagggcgaca cggaaatgtt gaatactcat    8040
actcttcctt tttcaatatt attgaagcat ttatcagggt tattgtctca tgagcggata    8100
catatttgaa tgtatttaga aaaataaaca gcgatcgcgc ggccgcgggt aataactgat    8160
ataattaaat tgaagctcta atttgtgagt ttagtataca tgcatttact tataatacag    8220
ttttttagtt ttgctggccg catcttctca aatatgcttc ccagcctgct tttctgtaac    8280
gttcaccctc taccttagca tcccttccct ttgcaaatag tcctcttcca acaataataa    8340
tgtcagatcc tgtagagacc acatcatcca cggttctata ctgttgaccc aatgcgtctc    8400
ccttgtcatc taaacccaca ccgggtgtca taatcaacca atcgtaacct tcatctcttc    8460
cacccatgtc tctttgagca ataaagccga taacaaaatc tttgtcgctc ttcgcaatgt    8520
caacagtacc cttagtatat tctccagtag ctagggagcc cttgcatgac aattctgcta    8580
acatcaaaag gcctctaggt tcctttgtta cttcttccgc cgcctgcttc aaaccgctaa    8640
caatacctgg gcccaccaca ccgtgtgcat tcgtaatgtc tgcccattct gctattctgt    8700
atacacccgc agagtactgc aatttgactg tattaccaat gtcagcaaat tttctgtctt    8760
cgaagagtaa aaaattgtac ttggcggata atgcctttag cggcttaact gtgcccctcca   8820 tggaaaaatc agtcaagata tccacatgtg tttttagtaa acaaattttg ggacctaatg    8880
cttcaactaa ctccagtaat tccttggtgg tacgaacatc caatgaagca cacaagtttg    8940
tttgcttttc gtgcatgata ttaaatagct tggcagcaac aggactagga tgagtagcag    9000
cacgttcctt atatgtagct ttcgacatga tttatcttcg tttcctgcag gttttttgttc   9060 tgtgcagttg ggttaagaat actgggcaat ttcatgtttc ttcaacacca catatgcgta    9120 tataccaa tctaagtctg tgctccttcc ttcgttcttc cttctgctcg gagattaccg      9180
aatcaaagct agcttatcga tgataagctg tcaaagatga gaattaattc cacggactat    9240
agactatact agatactccg tctactgtac gatacacttc cgctcaggtc cttgtccttt    9300
aacgaggcct taccactctt tgttactct attgatccag ctcagcaaag gcagtgtgat     9360
ctaagattct atcttcgcga tgtagtaaaa ctagctagac cgagaaagag actagaaatg    9420
caaaaggcac ttctacaatg gctgccatca ttattatccg atgtgacgct gcagcttctc    9480
aatgatattc gaatacgctt tgaggagata cagcctaata tccgacaaac tgttttacag    9540
atttacgatc gtacttgtta cccatcattg aattttgaac atccgaacct gggagttttc    9600
cctgaaacag atagtatatt tgaacctgta taataatata tagtctagcg ctttacggaa    9660
gacaatgtat gtatttcggt tcctggagaa actattgcat ctattgcata ggtaatcttg    9720
cacgtcgcat ccccggttca ttttctgcgt ttccatcttg cacttcaata gcatatcttt    9780
gttaacgaag catctgtgct tcattttgta gaacaaaaat gcaacgcgag agcgctaatt    9840
tttcaaacaa agaatctgag ctgcattttt acagaacaga aatgcaacgc gaaagcgcta    9900
ttttaccaac gaagaatctg tgcttcattt ttgtaaaaca aaaatgcaac gcgacgagag    9960
```

-continued

```
cgctaatttt tcaaacaaag aatctgagct gcattttttac agaacagaaa tgcaacgcga    10020
gagcgctatt ttaccaacaa agaatctata cttctttttt gttctacaaa aatgcatccc    10080
gagagcgcta ttttctaac aaagcatctt agattacttt ttttctcctt tgtgcgctct    10140
ataatgcagt ctcttgataa ctttttgcac tgtaggtccg ttaaggttag aagaaggcta    10200
ctttggtgtc tattttctct tccataaaaa aagcctgact ccacttcccg cgtttactga    10260
ttactagcga agctgcgggt gcattttttc aagataaagg catccccgat tatattctat    10320
accgatgtgg attgcgcata ctttgtgaac agaaagtgat agcgttgatg attcttcatt    10380
ggtcagaaaa ttatgaacgg tttcttctat tttgtctcta tatactacgt ataggaaatg    10440
tttacatttt cgtattgttt tcgattcact ctatgaatag ttcttactac aatttttttg    10500
tctaaagagt aatactagag ataaacataa aaaatgtaga ggtcgagttt agatgcaagt    10560
tcaaggagcg aaaggtggat gggtaggtta tatagggata tagcacagag atatatagca    10620
aagagatact tttgagcaat                                                10640
```

<210> SEQ ID NO 22
<211> LENGTH: 244
<212> TYPE: PRT
<213> ORGANISM: Fusarium oxysporum

<400> SEQUENCE: 22

```
Met Leu Pro Thr Glu Val Glu Ala Asn Gly Trp Thr Ala Val Pro Val
1               5                   10                  15

Ser Ala Lys Ala Ile Lys Asp Ser Val Gly Gln Leu Val Pro Thr Gln
            20                  25                  30

Thr Tyr Thr Leu Gln Asp Ile Val Phe Pro Ser Glu Asp Lys Leu Val
        35                  40                  45

Ser Glu Ala Gln Ala Phe Val Lys Ala Arg Leu Ser Gln Glu Ala Tyr
    50                  55                  60

Asn His Ser Met Arg Val Phe Tyr Trp Gly Ser Ile Ala Lys Arg
65                  70                  75                  80

Leu Leu Pro Lys His Ala Glu Ala Leu Ser Pro Ser Thr Trp Ala Leu
                85                  90                  95

Thr Cys Leu Leu His Asp Ile Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125

Leu Lys Val Leu Gly Ser Ser Asp Gln Ala Glu Ala Val Ala Glu
    130                 135                 140

Ala Ile Ile Arg His Glu Asp Met Gly Val Asp Gly Ser Ile Thr Phe
145                 150                 155                 160

Leu Gly Gln Leu Ile Gln Leu Ala Thr Leu Tyr Asp Asn Val Gly Thr
                165                 170                 175

Tyr Glu Gly Ile Asp Asp Phe Gly Gly Trp Ile Asp Glu Ala Thr Arg
            180                 185                 190

Asp Asn Val Asn Lys Ala Ile Pro Arg His Gly Trp Cys Ser Trp Phe
        195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240

Lys Gln Trp Glu
```

<210> SEQ ID NO 23
<211> LENGTH: 735
<212> TYPE: DNA
<213> ORGANISM: Fusarium oxysporum

<400> SEQUENCE: 23

```
atgttgccca ccgaagtcga ggccaacggc tggactgccg tgcctgtcag cgccaaggca      60
atcaaggact cggtcggaca gcttgtaccc acgcaaacct acactctcca agacatcgtt     120
ttcccctctg aggacaaact tgtgtctgaa gctcaagcct tgtcaaggc acggctaagt      180
caagaagctt ataaccactc tatgcgagtt ttctactggg gatccattat tgccaagcgt     240
ttgctaccca agcacgcaga ggccctgtcc ccgtccacct gggcgctgac atgtcttttg     300
catgatatcg gtactgctga ggcttacttc acttcaactc gcatgtcttt tgatatctat     360
ggtggaatca aggcaatgga ggtgctcaaa gtcctcggta gcagcgacga tcaggccgag     420
gcagtcgcag aggctatcat ccgtcatgaa gacatgggcg tggacggttc gattactttc     480
ctaggccagt taattcagct tgctacgctg tatgacaacg ttgggacgta cgagggcatt     540
gacgattttg gcggctggat tgacgaagct actcgggata atgtcaacaa agctattcct     600
cgtcacggtt ggtgctcctg gtttgcctgt actgtccgca aggaggaatc caacaagcct     660
tggtgccata ctacccatat tcctcaattt gataagcaga tggaggcaaa cactttgatg     720
aaacagtggg agtag                                                      735
```

<210> SEQ ID NO 24
<211> LENGTH: 245
<212> TYPE: PRT
<213> ORGANISM: Fusarium pseudograminearum

<400> SEQUENCE: 24

Met Ser Ser Pro Glu Val Lys Ile Asn Gly Trp Thr Ala Val Pro Leu
1               5                   10                  15

Asn Ala Lys Asn Ile Leu Asp Ser Val Gly Lys Leu Ala Glu Val Pro
            20                  25                  30

Thr Tyr Lys Ala Glu Asp Ile Lys Phe Pro Ser Asn Asp Lys Leu Val
        35                  40                  45

Ala Glu Ala Gln Ala Phe Val Lys Ala Arg Leu Ser Pro Glu Ala Tyr
    50                  55                  60

Asn His Ser Met Arg Val Phe Tyr Trp Gly Asn Ile Leu Ala Lys Arg
65                  70                  75                  80

Leu Leu Pro Glu His Phe Glu Ala Leu Ser Thr Ser Thr Trp Ala Leu
                85                  90                  95

Thr Cys Leu Leu His Asp Ile Gly Thr Ala Asp Ala Phe Phe Thr Ser
            100                 105                 110

Thr His Met Ser Phe Asp Leu Tyr Gly Gly Ile Lys Ala Met Glu Val
        115                 120                 125

Leu Lys Val Leu Gly Gly Thr Asp Gln Ala Glu Ala Val Ala Glu
    130                 135                 140

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
                165                 170                 175

Tyr Glu Gly Ile Glu Asp Tyr Gly Ser Trp Val Asp Glu Val Thr Arg
            180                 185                 190

Asp Asn Ile Asn Arg Glu Phe Pro Arg His Lys Trp Ala Ser Cys Phe

Ala Ser Val Ile Arg Gln Glu Glu Ser Asn Lys Pro Trp Cys His Ser
            210                 215                 220

Thr His Ile Val Gly Phe Pro Glu Lys Leu Glu Ala Asn Thr Leu Met
225                 230                 235                 240

Lys Pro Trp Glu Glu
                245

<210> SEQ ID NO 25
<211> LENGTH: 738
<212> TYPE: DNA
<213> ORGANISM: Fusarium pseudograminearum

<400> SEQUENCE: 25
atgtcttcac ctgaagtcaa gattaacggt tggactgctg tccccctcaa cgccaagaac      60
attctcgatt ctgtaggaaa actcgcagaa gttccacct acaaggcaga ggatattaaa     120
ttcccatcaa atgacaagct cgtcgccgaa gcccaggcct tgtcaaggc gcgactgagc     180 ccagaagcgt ataatcactc catgagagta ttttactggg aaacattct tgcaaagcgt     240 ttgctgcccg agcattttga agctttgtcc acgtctacct gggcactcac ctgtctctta     300
cacgacatag gaacggccga tgccttcttc acctccacgc acatgtcgtt cgatctctat     360
ggcggcataa aggctatgga agtgctcaag gtgctcggcg gtactaccga ccaagctgaa     420
gctgtcgccg aggccatcat acgtcatcag gatgtgggcg tggacggcac catcactttt     480
cttgggcagc tgattcaact tgccacactt tacgacaacg tcggcgttta tgagggcatt     540
gaggactatg gcagttgggt tgatgaggtc actcgcgata atatcaatag gaatttcct     600 cggcacaagt gggcatcttg ctttgcttct gtcattcgtc aggaggagtc caacaaaccc     660
tggtgccatt ctacacatat tgtaggcttt cctgaaaagc ttgaggccaa cactcttatg     720
aagccttggg aggagtag                                                    738

<210> SEQ ID NO 26
<211> LENGTH: 245
<212> TYPE: PRT
<213> ORGANISM: Fusarium graminearum

<400> SEQUENCE:

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
            165                 170                 175

Tyr Glu Gly Ile Gln Asp Tyr Gly Ser Trp Val Asp Glu Ala Thr Arg
            180                 185                 190

Asp Asn Ile Asn Arg Ala Phe Pro Arg His Lys Trp Thr Ser Cys Phe
            195                 200                 205

Ala Ser Val Ile Arg Gln Glu Glu Ser Asn Lys Pro Trp Cys His Ser
        210                 215                 220

Thr His Ile Val Asp Phe Pro Glu Lys Leu Glu Ala Asn Thr Leu Met
225                 230                 235                 240

Lys Pro Trp Glu Glu
            245

<210> SEQ ID NO 27
<211> LENGTH: 738
<212> TYPE: DNA
<213> ORGANISM: Fusarium graminearum

<400> SEQUENCE: 27
atgtcttcac ctgaagccaa aactaacggt tggactgctg tcccccctcaa cgctaagaat     60 attctcgaca ctgtaggaaa gctcgcagaa gttcccacct acaaggcaga ggatattcaa    120
tttccatcag acgacaagct agtcgccgaa gcccaagcct tgccaaggc acgactaagc     180 cctgaagcct ataatcactc catgcgagta ttttactggg aaacattct tgcaaagcgt     240 ttgctgccag agcattttgg agctttgtcc acgtctacct gggcactcac ctgtctctta    300
cacgacatag gaacggccga tgtcttcttc acatccacac acatgtcgtt cgatctctat    360
ggcggcataa aggctatgga agtgctcaag gtgctcggtg gtaccaccga ccaagctgaa    420
gctgtcgccg aggccatcat acgtcatcag gatgtgggcg tggacggcac catcactttt    480
cttgggcagc tgattcaact tgccacactt tatgataacg tcggcgttta tgagggcatt    540
caagactatg gcagttgggt tgatgaggcc actcgcgata atatcaatag gcatttcct    600 cgacacaagt ggacgtcttg ctttgcttcc gtcattcgtc aggaggagtc caacaaaccc    660
tggtgccatt ctacacatat tgtggacttt cctgaaaagc ttgaggccaa cactcttatg    720
aagccttggg aggagtag                                                    738

<210> SEQ ID NO 28
<211> LENGTH: 244
<212> TYPE: PRT
<213> ORGANISM: Aspergillus kawachii

<400> SEQUENCE: 28

Met Cys Asn Asp Glu Ile Lys Ala Asn Gly Trp Ser Ser Met Pro Ala
1               5                   10                  15

Asn Ala Gly Ala Ile Phe Thr Asp Gln Ser Phe Ile Glu Arg Ala Glu
            20                  25                  30

Ala Met Gln Leu Asp Thr Ile Ile Phe Pro Phe Asp Asp Pro Val Val
        35                  40                  45

Ser Lys Thr Trp Glu Tyr Ala Arg Ala Val Leu His Pro Gln Thr Leu
    50                  55                  60

Asn His Ser Met Arg Val Tyr Phe Tyr Gly Met Val Ile Thr Thr Gln
65                  70                  75                  80

```
Gln Phe Pro Glu Ile Ala Ala Ser Leu Asn Pro Val Thr Trp Ala Leu
                85                  90                  95

Thr Cys Leu Leu His Asp Ile Gly Thr Ala Glu Glu Asn Leu Thr Ala
            100                 105                 110

Thr Arg Met Ser Phe Asp Ile Tyr Gly Gly Ile Lys Ala Leu His Val
            115                 120                 125

Leu Lys Glu Phe Gly Ala Thr Ala Asp Gln Ala Glu Ala Val Ala Glu
        130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Val
                165                 170                 175

His Pro His Val Lys Ser Phe Glu Gly Leu Val His Gln Thr Thr Arg
            180                 185                 190

Lys Gln Ile Asn Glu Ala Tyr Pro Arg Leu Lys Trp Cys Glu Phe Phe
        195                 200                 205

Ser Gly Met Ile Arg Lys Glu Thr Ile Lys Pro Trp Cys His Ser
210                 215                 220

Thr His Leu Val Asp Phe Asp Arg Glu Ile Glu Glu Asn Thr Leu Met
225                 230                 235                 240

Arg Glu Trp Glu

<210> SEQ ID NO 29
<211> LENGTH: 735
<212> TYPE: DNA
<213> ORGANISM: Aspergillus kawachii

<400> SEQUENCE: 29
atgtgcaacg acgaaataaa agccaacggc tggtccagca tgcccgccaa tgccggtgcc      60
atatttacgg accaatcctt catcgaaagg gcagaagcca tgcagctcga tacaatcata     120
ttccccttcg acgatcctgt cgtttcaaag acctgggaat acgccagggc tgttcttcac     180
ccccagacat tgaaccattc catgagggtc tacttctacg gaatggtaat caccacccag     240
caattccctg aaatagcagc atccctcaac ccagtcacct gggctctgac ctgcctcctc     300
cacgacatcg gtactgcgga ggagaaccta actgcaacgc gcatgtcatt cgatatctat     360
ggcggtatca aggccctcca tgtgctgaag gagtttggtg ccactgcgga ccaggccgag     420
gccgttgctg aggcgatcat tcgacatgag gatatgggcg tcgatggaac tattacatat     480
ttcggtcagc ttattcagtt ggctactaca tatgataata ccggagttca tccgcatgtg     540
aagagttttg agggcttggt gcatcagaca actcgcaaac agatcaatga ggcgtatccg     600
cggttgaagt ggtgtgaatt tttctcgggg atgattagga aggaagagac gatcaagcct     660
tggtgtcatt cgacccattt ggtggacttt gacagggaga tagaagagaa tacgcttatg     720
agggagtggg agtaa                                                      735

<210> SEQ ID NO 30
<211> LENGTH: 244
<212> TYPE: PRT
<213> ORGANISM: Aspergillus niger

<400> SEQUENCE: 30

Met Cys His Asp Glu Ile Lys Ala Asn Gly Trp Ser Ser Thr Pro Ala
1               5                   10                  15

Asn Ala Gly Ala Ile Phe Thr Asp Gln Ser Phe Ile Glu Arg Ala Glu
            20                  25                  30
```

```
Ala Val Glu Leu Asp Thr Ile Gln Phe Pro Phe Asp Asp Pro Val Val
            35                  40                  45

Ser Lys Thr Leu Glu Tyr Val Lys Ala Val Leu His Pro Glu Thr Leu
 50                  55                  60

Asn His Ser Met Arg Val Tyr Tyr Gly Met Val Ile Thr Thr Gln
 65                  70                  75                  80

Gln Phe Pro Glu Gln Ala Ala Ser Ile Asn Pro Val Thr Trp Ala Leu
                 85                  90                  95

Thr Cys Leu Leu His Asp Leu Gly Thr Ala Glu Glu Asn Leu Thr Ala
                100                 105                 110

Thr Arg Met Ser Phe Asp Ile Tyr Gly Gly Ile Lys Ala Leu His Val
                115                 120                 125

Leu Lys Glu Phe Gly Ala Thr Ala Asp Gln Ala Glu Ala Ala Ala Glu
            130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Ile
                165                 170                 175

His Pro His Val Lys Gly Phe Glu Gly Leu Val His Arg Thr Thr Arg
            180                 185                 190

Lys Gln Ile Asn Glu Ala Tyr Pro Arg Leu Lys Trp Cys Ala Phe Phe
            195                 200                 205

Ser Gly Leu Ile Arg Lys Glu Glu Thr Ile Lys Pro Trp Cys His Ser
        210                 215                 220

Thr His Leu Val Asp Phe Asp Lys Glu Ile Glu Asn Thr Leu Met
225                 230                 235                 240

Arg Glu Trp Glu

<210> SEQ ID NO 31
<211> LENGTH: 735
<212> TYPE: DNA
<213> ORGANISM: Aspergillus niger

<400> SEQUENCE: 31
atgtgccacg acgaaatcaa agccaacggc tggtccagca ctcccgccaa tgccggtgcc      60
atatttacgg accaatcctt cattgaaagg gcagaagccg tggagctcga tacgatccag     120 ttccccttg acgaccctgt agtctcgaag acattggaat atgtcaaggc tgttcttcac     180
cccgagactt tgaatcattc catgagggtt tactattacg gaatggtaat caccacccaa     240
caattccccg aacaagcagc atccataaac ccagtgacct gggctctgac ttgtctcctc     300
cacgacctcg gaaccgcgga ggagaacctc accgcaacgc gcatgtcatt cgatatctac     360
ggcggcatca aagccctcca tgtgctgaag gagtttggtg ccactgcgga ccaggccgaa     420
gcagcagctg aggcaatcat tcgacatgaa gatatgggag tcgatggaac gattacctac     480
ttcggtcagc ttattcagct ggctacgacg tatgataata ccggattca tccgcatgtg     540 aagggctttg agggggttggt ccatcgcacg actcgcaagc agattaatga ggcgtatccg     600
cggttgaagt ggtgtgcgtt tttctccggg ttgattagaa aggaggagac gattaagcct     660
tggtgtcatt cgactcattt ggtggattt gataaggaga tcgaggagaa tacgcttatg     720
agggagtggg agtaa                                                     735

<210> SEQ ID NO 32
<211> LENGTH: 241
```

<212> TYPE: PRT
<213> ORGANISM: Aspergillus niger

<400> SEQUENCE: 32

```
Met Cys His Asp Lys Ile Pro Leu Asn Gly Trp Thr Ser Thr Pro Ala
1               5                   10                  15

Asn Ala Gly Ala Ile Phe Pro Asp Lys Pro Phe Ile His Pro Pro Thr
            20                  25                  30

Pro Ile Ser Ile Thr Asp Ile Pro Phe Pro Ser Thr Asp Pro Leu Val
        35                  40                  45

Ala Lys Thr Leu Glu Tyr Val Gln Ser Leu Leu Pro Arg Glu Thr Val
    50                  55                  60

Asn His Ser Met Arg Val Tyr Ser Tyr Gly Met Ile Leu Leu Thr Gln
65                  70                  75                  80

Gln Phe Pro Ser His His Leu Ser Pro Thr Thr Trp Ala Leu Thr Cys
                85                  90                  95

Leu Leu His Asp Ile Gly Thr Ala Pro Ser Leu Leu Thr Ser Thr Asn
            100                 105                 110

Met Ser Phe Asp Leu Tyr Gly Gly Ile Lys Ala His Ser Val Leu Thr
        115                 120                 125

Ser Phe Asp Cys Pro Ala Asp Val Ala Asp Ala Val Ala Glu Ala Ile
    130                 135                 140

Ile Arg His Gln Asp Leu Gly Val Asp Gly Asn Ile Thr Phe Leu Gly
145                 150                 155                 160

Gln Leu Ile Gln Leu Ala Thr Ile Tyr Asp Asn Val Gly Glu His Pro
                165                 170                 175

His Val Lys Asp Phe Gly Gly Leu Ile His Glu Asp Ala Arg Arg Glu
            180                 185                 190

Val Asn Glu Arg Trp Arg Arg Gly Trp Cys Gly Val Phe Ala Asp
        195                 200                 205

Val Val Lys Leu Glu Val Gly Arg Lys Pro Trp Cys His Ser Thr His
    210                 215                 220

Ile Val Gly Phe Glu Gly Lys Val Arg Gly Asn Ala Leu Phe Gly Glu
225                 230                 235                 240

Lys
```

<210> SEQ ID NO 33
<211> LENGTH: 726
<212> TYPE: DNA
<213> ORGANISM: Aspergillus niger

<400> SEQUENCE: 33

```
atgtgccacg acaagatccc cctcaacggc tggaccagca ccccccgccaa cgctggtgcc      60
atcttccccg acaagcccttt catccaccca cccacgccca tctccatcac cgacatcccc    120
ttcccctcca ccgatcccct cgtcgccaag accctcgaat acgtccaatc cctcctcccc    180
cgcgagaccg tcaaccactc catgcgcgta tactcctacg gaatgatcct cctcacccag    240
caattccctt cccaccatct atctccaaca acctgggccc taacctgcct tctgcatgac    300
atcggcaccg cccctccct cctcacctca acaaacatgt cctttgacct ctacggcggc    360
atcaaagccc actccgtact tacttccttc gactgtcccg ctgatgttgc tgacgccgta    420
gcggaagcta ttatccggca tcaggatcta ggcgtggatg gaatatcac gttcctggga    480
cagttgatcc agctggctac catttatgat aatgtggggg aacatccgca cgtcaaggac    540
tttggagggt tgattcatga ggatgcgagg agggaggtta tgagcgctg gagaagggag    600
```

```
ggatggtgtg gggtgtttgc tgatgtggtg aagttggagg tggggaggaa gccgtggtgt    660
cattcgacgc atattgtggg gtttgagggg aaggttaggg ggaatgcgct ttttggggag    720
aaatag                                                               726
```

<210> SEQ ID NO 34
<211> LENGTH: 242
<212> TYPE: PRT
<213> ORGANISM: Aspergillus oryzae

<400> SEQUENCE: 34

```
Met Ser Pro Thr Arg Ala Ala Gln Val Glu Glu Tyr Gly Trp Thr Ala
1               5                   10                  15

Val Ser Cys Asp Pro Gln Gln Arg Ala Ala Thr Asn Pro Pro Thr Lys
            20                  25                  30

Pro Ser Val Pro Gln Leu Val Lys Asp Thr Thr Leu Pro Asp Thr Pro
        35                  40                  45

Leu Val Lys Asp Ala Met Glu Tyr Val Lys Ala Glu Leu Pro Ala His
    50                  55                  60

Thr Phe Asn His Ser Met Arg Val Tyr Tyr Gly Leu Ala Ile Ala
65                  70                  75                  80

Arg Gln His Phe Pro Glu Trp Lys Phe Ser Asp Glu Thr Trp Leu Leu
                85                  90                  95

Thr Cys Leu Phe His Asp Ile Gly Thr Ile Asp Lys Tyr Thr Gln Asp
            100                 105                 110

Val Phe Met Ser Phe Asp Ile Tyr Gly Gly Ile Val Ala Leu Asn Val
        115                 120                 125

Leu Thr Glu Lys Gly Ala Pro Ala Pro Gln Ala Glu Ser Val Ala Glu
    130                 135                 140

Ala Ile Ile Arg His Gln Asp Pro Val Lys Val Gly Thr Ile His Ser
145                 150                 155                 160

Val Gly Leu Leu Ile Gln Leu Ala Thr Gln Phe Asp Asn Leu Gly Ala
                165                 170                 175

His Lys Glu Tyr Val His Pro Asp Thr Val Glu Asp Val Asn Gln His
            180                 185                 190

Tyr Pro Arg Arg Gln Trp Ser Lys Cys Phe Ser Lys Leu Arg Glu
        195                 200                 205

Glu Ile Gly Leu Lys Pro Trp Cys His Thr Thr Ala Glu Gly Glu Gly
    210                 215                 220

Phe Pro Val Gly Ile Glu Asn Asn Thr Leu Met Glu Pro Tyr Asp Gly
225                 230                 235                 240

Arg Phe
```

<210> SEQ ID NO 35
<211> LENGTH: 729
<212> TYPE: DNA
<213> ORGANISM: Aspergillus oryzae

<400> SEQUENCE: 35

```
atgtcaccca ccagagcagc tcaagtcgaa gaatacggtt ggacagcggt gtcctgcgat     60
cctcagcagc gagctgctac aaacccacct accaagcctt ctgttcccca gttggtcaaa    120
gatacaactc ttcccgatac tcctctagtc aaagatgcca tggaatatgt taaggcagag    180
ctacccgctc acacttttaa ccacagcatg cgtgtctact attatggcct tgcaatcgcc    240
agacaacact tcccagaatg gaagttcagc gatgaaacct ggcttctcac ctgcctcttc    300
```

```
cacgacatcg gcactatcga caagtacacc caagacgtct ttatgtcctt cgatatctac    360
ggtggaattg tcgctctgaa cgtcctcacg gagaaaggtg cgccagcacc ccaggctgaa    420
agtgtcgcag aagccatcat ccgtcatcag gatccggtga agttgggac tattcattct    480 gtcggtttac ttattcagct tgctacgcag tttgacaacc ttggtgccca caaggagtat    540
gtccaccctg atactgtgga agatgtgaac cagcattatc cgcgtcgtca gtggtcgaag    600
tgcttctcga gtaagctgag ggaggaaatt gggctcaagc cttggtgcca tactactgcg    660
gagggcgagg ggttccctgt tgggatcgag aacaacactt tgatggagcc ttatgatgga    720
cgcttctag                                                             729
```

```
<210> SEQ ID NO 36
<211> LENGTH: 243
<212> TYPE: PRT
<213> ORGANISM: Saccharomyces cerevisiae

<400> SEQUENCE: 36
```

Met Lys Leu Leu Arg Thr Val Phe Leu Pro Cys Ser Ser Ser Lys Glu
1               5                   10                  15

Ser Ile Met Ser Gln Tyr Gly Phe Val Arg Val Pro Arg Glu Val Glu
            20                  25                  30

Lys Ala Ile Pro Val Val Asn Ala Ser Arg Pro Arg Ala Val Val Pro
        35                  40                  45

Pro Pro Asn Ser Glu Thr Ala Arg Leu Val Arg Glu Tyr Ala Ala Lys
    50                  55                  60

Glu Leu Thr Ala Pro Val Leu Asn His Ser Leu Arg Val Phe Gln Tyr
65                  70                  75                  80

Ser Leu Ala Ile Ile Arg Asp Gln Phe Pro Ala Trp Asp Leu Asp Gln
                85                  90                  95

Glu Val Leu Tyr Val Thr Cys Leu Leu His Asp Ile Ala Thr Thr Asp
            100                 105                 110

Lys Asn Met Arg Ala Thr Lys Met Ser Phe Glu Tyr Tyr Gly Gly Ile
        115                 120                 125

Leu Ser Arg Glu Leu Val Phe Asn Ala Thr Gly Gly Asn Gln Asp Tyr
    130                 135                 140

Ala Asp Ala Val Thr Glu Ala Ile Ile Arg His Gln Asp Leu Thr Gly
145                 150                 155                 160

Thr Gly Tyr Ile Thr Thr Leu Gly Leu Ile Leu Gln Ile Ala Thr Thr
                165                 170                 175

Leu Asp Asn Val Gly Ser Asn Thr Asp Leu Ile His Ile Asp Thr Val
            180                 185                 190

Arg Ala Ile Asn Glu Gln Phe Pro Arg Leu His Trp Leu Ser Cys Phe
        195                 200                 205

Ala Thr Val Val Asn Thr Glu Asn Ser Arg Lys Pro Trp Gly His Thr
    210                 215                 220

Ser Ser Leu Gly Asp Asp Phe Ser Lys Lys Val Ile Cys Asn Thr Phe
225                 230                 235                 240

Gly Tyr Asn

```
<210> SEQ ID NO 37
<211> LENGTH: 732
<212> TYPE: DNA
<213> ORGANISM: Saccharomyces cerevisiae

<400> SEQUENCE: 37
```

-continued

```
ttagttatac ccaaatgtat tgcatatgac tttctttgaa aaatcatcac ccaaagaact        60
ggtgtggccc cacggttttc tcgagttttc agtgttcacc accgtagcaa acatgataa        120
ccagtgcagt cttggaaatt gctcattaat ggctctaact gtatcgatat gaatcagatc       180
ggtattggat ccgacattgt caagcgtagt agcaatctgc agaatgagcc caaggtggt        240
aatgtagcca gtcccagtca atcctggtg acgaatgatg ccctcagtta ctgcatctgc       300
atagtcctga tttccacctg tcgcattaaa tacaagctcc cttgaaagta tgccaccata      360
atactcaaat gacatcttcg tggctctcat attcttatct gttgttgcaa tatcatgaag      420
taagcaggtg acgtacaaaa cttcctgatc caagtcccat gctggaaatt ggtctcttat      480
gatagctaaa ctatattgaa aaacacgcaa agagtggttt agaacggggg cagtcaattc      540
tttagcggca tattcccgaa caagcctagc agtttcactg tttggaggcg aacaacggc      600
ccgtggtcta gatgcattca ccactggaat ggccttttct acctctctag gaactcttac      660
aaatccgtac tgtgacatga ttgattcttt tgaagaggag caaggcaaaa aaacagtacg      720
aagcaacttc at                                                          732
```

<210> SEQ ID NO 38
<211> LENGTH: 390
<212> TYPE: PRT
<213> ORGANISM: Rhodococcus sp.

<400> SEQUENCE: 38

```
Met Arg Glu Val Gln Leu Leu Asp Gly Arg Val Asp Val Ala Cys
1               5                   10                  15

Ala Gly Pro Leu Ile Ser Glu Ile Gly Ala His Leu Asp Leu Thr Ala
                20                  25                  30

Pro Val Glu Ile Asp Cys Gly Gly Gly Leu Ala Thr Arg Pro Phe Thr
            35                  40                  45

Glu Pro His Leu His Leu Asp Lys Ala Gly Thr Ala Asp Arg Leu Pro
        50                  55                  60

Ala Gly Ala Ser Thr Ile Gly Asp Ala Ile Ala Met Gln Ser Val
65                  70                  75                  80

Lys Val Thr Glu Arg Asp Asn Val Ala Ala Val Ala Arg Met His
                85                  90                  95

Arg Val Leu Asn Arg Ile Val Asp Asp Gly Ser His Ala Ile Arg Ala
            100                 105                 110

Leu Val Asp Val Asp Glu Val Trp Gly Leu Thr Ala Phe His Ala Ala
        115                 120                 125

Gln Gln Val Gln Ala Ala Leu Ala Pro Arg Ala Val Val Gln Ile Val
    130                 135                 140

Ala Phe Pro Gln His Gly Leu Thr Pro Gln Val Leu Ala Met Leu Glu
145                 150                 155                 160

Gln Ala Ala Ala Glu Gly Ala Gly Ala Leu Gly Ala His Thr Asp Val
                165                 170                 175

Asp Pro Asp Pro Ala Ala His Val Gly Ala Val Ala Ala Ile Ala Ala
            180                 185                 190

Gly Ala Ser Leu Pro Leu Glu Val His Thr Asp Glu Gly Ala Ser Pro
        195                 200                 205

Asp Lys Phe Tyr Leu Pro Ala Val Leu Glu Val Leu Asp Arg Phe Pro
    210                 215                 220

Gly Leu Ser Thr Thr Leu Ala His Cys Leu Ser Leu Gly Thr Ile Ala
225                 230                 235                 240
```

-continued

Pro Lys Gln Gln Gln His Trp Ile Glu Glu Leu Ala His Arg Asp Ile
    245                 250                 255

Lys Val Cys Val Ala Pro Ser Ile Leu Gly Phe Gly Leu Pro Leu Ala
            260                 265                 270

Pro Val Arg Ala Leu Ile Glu Ala Gly Val Gly Ile Leu Val Gly Ser
        275                 280                 285

Asp Asn Leu Gln Asp Val Phe Phe Pro Leu Gly Thr Gly Arg Ala Ile
    290                 295                 300

Glu Asn Val Arg Leu Leu Ala Thr Ala Ala Gln Leu Thr Ala Pro Glu
305                 310                 315                 320

Leu Ala Gly Pro Leu Ile Ala Gly Val Thr Asp Ile Ala Tyr Ala Thr
            325                 330                 335

Val Thr Gly Ala Ala Asp Ala Leu Ala Val Glu Ser Pro Ala Thr Leu
        340                 345                 350

Val Val His Asp Ala Thr Ser Pro Ala Glu Leu Leu Arg Gly Ile Asp
    355                 360                 365

Gly Thr Arg Ile Thr Val Ile Asp Gly Leu Leu Thr Ser Pro Leu Gln
370                 375                 380

Leu Asp Lys Gly Ile Lys
385                 390

<210> SEQ ID NO 39
<211> LENGTH: 412
<212> TYPE: PRT
<213> ORGANISM: Pseudomonas sp.

<400> SEQUENCE: 39

Met Ser Met Glu Thr His Ser Tyr Val Asp Val Ala Ile Arg Asn Ala
1               5                   10                  15

Arg Leu Ala Asp Thr Glu Gly Ile Val Asp Ile Leu Ile His Asp Gly
            20                  25                  30

Arg Ile Ala Ser Ile Val Lys Ser Thr Lys Thr Lys Gly Ser Val Glu
        35                  40                  45

Ile Asp Ala His Glu Gly Leu Val Thr Ser Gly Leu Val Glu Pro His
    50                  55                  60

Ile His Leu Asp Lys Ala Leu Thr Ala Asp Arg Val Pro Ala Gly Ser
65                  70                  75                  80

Ile Gly Asp Leu Arg Thr Arg Arg Gly Leu Glu Met Ala Ile Arg Ala
                85                  90                  95

Thr Arg Asp Ile Lys Arg Thr Phe Thr Val Glu Asp Val Arg Glu Arg
            100                 105                 110

Ala Ile Arg Ala Ala Leu Met Ala Ser Arg Ala Gly Thr Thr Ala Leu
        115                 120                 125

Arg Thr His Val Asp Val Asp Pro Ile Val Gly Leu Ala Gly Ile Arg
    130                 135                 140

Gly Val Leu Glu Ala Arg Glu Val Cys Ala Gly Leu Ile Asp Ile Gln
145                 150                 155                 160

Ile Val Ala Phe Pro Gln Glu Gly Leu Phe Cys Ser Ala Gly Ala Val
                165                 170                 175

Asp Leu Met Arg Glu Ala Ile Lys Leu Gly Ala Asp Ala Val Gly Gly
            180                 185                 190

Ala Pro Ala Leu Asp Asp Arg Pro Gln Asp His Val Arg Ala Val Phe
        195                 200                 205

Asp Leu Ala Ala Glu Phe Gly Leu Pro Val Asp Met His Val Asp Glu

```
                210                 215                 220
Ser Asp Arg Arg Glu Asp Phe Thr Leu Pro Phe Val Ile Glu Ala Ala
225                 230                 235                 240

Arg Glu Arg Arg Val Pro Asn Val Thr Val Ala His Ile Ser Ser Leu
                245                 250                 255

Ser Val Gln Thr Asp Asp Val Ala Arg Ser Thr Ile Ala Ala Leu Ala
            260                 265                 270

Asp Ala Asp Val Asn Val Val Asn Pro Ile Ile Val Lys Ile Thr
            275                 280                 285

Arg Leu Ser Glu Leu Leu Asp Ala Gly Val Ser Val Met Phe Gly Ser
            290                 295                 300

Asp Asn Leu Arg Asp Pro Phe Tyr Pro Leu Gly Ala Ala Asn Pro Leu
305                 310                 315                 320

Gly Ser Ala Ile Phe Ala Cys Gln Ile Ala Ala Leu Gly Thr Pro Gln
                325                 330                 335

Asp Leu Arg Arg Val Phe Asp Ala Val Thr Ile Asn Ala Ala Arg Met
            340                 345                 350

Leu Gly Phe Pro Ser Leu Leu Gly Val Val Glu Gly Ala Val Ala Asp
            355                 360                 365

Leu Ala Val Phe Pro Ser Ala Thr Pro Glu Glu Val Val Leu Asp Gln
            370                 375                 380

Gln Ser Pro Leu Phe Val Leu Lys Gly Gly Arg Val Val Ala Met Arg
385                 390                 395                 400

Leu Ala Ala Gly Ser Thr Ser Phe Arg Asp Tyr Ser
                405                 410

<210> SEQ ID NO 40
<211> LENGTH: 241
<212> TYPE: PRT
<213> ORGANISM: Rhodococcus sp.

<400> SEQUENCE: 40

Met Ile Tyr Ser Thr Val Asn Ala Asn Pro Tyr Ala Trp Pro Tyr Asp
1               5                   10                  15

Gly Ser Ile Asp Pro Ala His Thr Ala Leu Ile Leu Ile Asp Trp Gln
                20                  25                  30

Ile Asp Phe Cys Gly Pro Gly Gly Tyr Val Asp Ser Met Gly Tyr Asp
            35                  40                  45

Leu Ser Leu Thr Arg Ser Gly Leu Glu Pro Thr Ala Arg Val Leu Ala
50              55                  60

Ala Ala Arg Asp Thr Gly Met Thr Val Ile His Thr Arg Glu Gly His
65                  70                  75                  80

Arg Pro Asp Leu Ala Asp Leu Pro Pro Asn Lys Arg Trp Arg Ser Ala
                85                  90                  95

Ser Ala Gly Ala Glu Ile Gly Ser Val Gly Pro Cys Gly Arg Ile Leu
            100                 105                 110

Val Arg Gly Glu Pro Gly Trp Glu Ile Val Pro Glu Val Ala Pro Arg
            115                 120                 125

Glu Gly Glu Pro Ile Ile Asp Lys Pro Gly Lys Gly Ala Phe Tyr Ala
            130                 135                 140

Thr Asp Leu Asp Leu Leu Leu Arg Thr Arg Gly Ile Thr His Leu Ile
145                 150                 155                 160

Leu Thr Gly Ile Thr Thr Asp Val Cys Val His Thr Thr Met Arg Glu
                165                 170                 175
```

Ala Asn Asp Arg Gly Tyr Glu Cys Leu Ile Leu Ser Asp Cys Thr Gly
            180                 185                 190

Ala Thr Asp Arg Lys His His Glu Ala Ala Leu Ser Met Val Thr Met
        195                 200                 205

Gln Gly Gly Val Phe Gly Ala Thr Ala His Ser Asp Asp Leu Leu Ala
    210                 215                 220

Ala Leu Gly Thr Thr Val Pro Ala Ala Ala Gly Pro Arg Ala Arg Thr
225                 230                 235                 240

Glu

<210> SEQ ID NO 41
<211> LENGTH: 233
<212> TYPE: PRT
<213> ORGANISM: Rhizobium leguminosarum

<400> SEQUENCE: 41

Met Asp Ala Met Val Glu Thr Asn Arg His Phe Ile Asp Ala Asp Pro
1               5                   10                  15

Tyr Pro Trp Pro Tyr Asn Gly Ala Leu Arg Pro Asp Asn Thr Ala Leu
            20                  25                  30

Ile Ile Ile Asp Met Gln Thr Asp Phe Cys Gly Lys Gly Gly Tyr Val
        35                  40                  45

Asp His Met Gly Tyr Asp Leu Ser Leu Val Gln Ala Pro Ile Glu Pro
    50                  55                  60

Ile Lys Arg Val Leu Ala Ala Met Arg Ala Lys Gly Tyr His Ile Ile
65                  70                  75                  80

His Thr Arg Glu Gly His Arg Pro Asp Leu Ala Asp Leu Pro Ala Asn
                85                  90                  95

Lys Arg Trp Arg Ser Gln Arg Ile Gly Ala Gly Ile Gly Asp Pro Gly
            100                 105                 110

Pro Cys Gly Arg Ile Leu Thr Arg Gly Glu Pro Gly Trp Asp Ile Ile
        115                 120                 125

Pro Glu Leu Tyr Pro Ile Glu Gly Glu Thr Ile Ile Asp Lys Pro Gly
    130                 135                 140

Lys Gly Ser Phe Cys Ala Thr Asp Leu Glu Leu Val Leu Asn Gln Lys
145                 150                 155                 160

Arg Ile Glu Asn Ile Ile Leu Thr Gly Ile Thr Thr Asp Val Cys Val
                165                 170                 175

Ser Thr Thr Met Arg Glu Ala Asn Asp Arg Gly Tyr Glu Cys Leu Leu
            180                 185                 190

Leu Glu Asp Cys Cys Gly Ala Thr Asp Tyr Gly Asn His Leu Ala Ala
        195                 200                 205

Ile Lys Met Val Lys Met Gln Gly Gly Val Phe Gly Ser Val Ser Asn
    210                 215                 220

Ser Ala Ala Leu Val Glu Ala Leu Pro
225                 230

<210> SEQ ID NO 42
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gtttgtggaa gcggtattcg caatttaatt aagtttaaac ggcgcgcctt tccataggct      60

```
ccgccccct  dacgagcatc  acaaaaatcg  acgctcaagt  cagaggtggc  gaaacccgac   120
aggactataa  agataccagg  cgtttccccc  tggaagctcc  ctcgtgcgct  ctcctgttcc   180
gaccctgccg  cttaccggat  acctgtccgc  ctttctccct  tcgggaagcg  tggcgctttc   240
tcatagctca  cgctgtaggt  atctcagttc  ggtgtaggtc  gttcgctcca  agctgggctg   300
tgtgcacgaa  ccccccgttc  agcccgaccg  ctgcgcctta  tccggtaact  atcgtcttga   360
gtccaacccg  gtaagacacg  acttatcgcc  actggcagca  gccactggta  acaggattag   420
cagagcgagg  tatgtaggcg  gtgctacaga  gttcttgaag  tggtggccta  actacggcta   480
cactagaaga  acagtatttg  gtatctgcgc  tctgctgaag  ccagttacct  tcggaaaaag   540
agttggtagc  tcttgatccg  gcaaacaaac  caccgctggt  agcggtggtt  ttttgtttg   600 caagcagcag  attacgcgca  gaaaaaaagg  atctcaagaa  gatcctttga  tcttttctac   660
ggggtctgac  gctcagtgga  acgaaaactc  acgttaaggg  attttggtca  tgagattatc   720
aaaaaggatc  ttcacctaga  tccttttaaa  ttaaaaatga  agttttaaat  caatctaaag   780
tatatatgag  taaacttggt  ctgacagtta  ccaatgctta  atcagtgagg  cacctatctc   840
agcgatctgt  ctatttcgtt  catccatagt  tgcctgactc  cccgtcgtgt  agataactac   900
gatacgggag  ggcttaccat  ctggccccag  tgctgcaatg  ataccgcgag  acccacgctc   960
accggctcca  gatttatcag  caataaacca  gccagccgga  agggccgagc  gcagaagtgg  1020
tcctgcaact  ttatccgcct  ccatccagtc  tattaattgt  tgccgggaag  ctagagtaag  1080
tagttcgcca  gttaatagtt  tgcgcaacgt  tgttgccatt  gctacaggca  tcgtggtgtc  1140
acgctcgtcg  tttggtatgg  cttcattcag  ctccggttcc  caacgatcaa  ggcgagttac  1200
atgatccccc  atgttgtgca  aaaaagcggt  tagctccttc  ggtcctccga  tcgttgtcag  1260
aagtaagttg  gccgcagtgt  tatcactcat  ggttatggca  gcactgcata  attctcttac  1320
tgtcatgcca  tccgtaagat  gcttttctgt  gactggtgag  tactcaacca  agtcattctg  1380
agaatagtgt  atgcggcgac  cgagttgctc  ttgcccggcg  tcaatacggg  ataataccgc  1440
gccacatagc  agaactttaa  aagtgctcat  cattggaaaa  cgttcttcgg  ggcgaaaact  1500
ctcaaggatc  ttaccgctgt  tgagatccag  ttcgatgtaa  cccactcgtg  cacccaactg  1560
atcttcagca  tcttttactt  tcaccagcgt  ttctgggtga  gcaaaaacag  gaaggcaaaa  1620
tgccgcaaaa  aagggaataa  gggcgacacg  gaaatgttga  atactcatac  tcttcctttt  1680
tcaatattat  tgaagcattt  atcagggtta  ttgtctcatg  agcggataca  tatttgaatg  1740
tatttagaaa  aataaacagc  gatcgcgcgg  ccgcgggtaa  taactgatat  aattaaattg  1800
aagctctaat  ttgtgagttt  agtatacatg  catttactta  taatacagtt  ttttagtttt  1860
gctggccgca  tcttctcaaa  tatgcttccc  agcctgcttt  tctgtaacgt  tcaccctcta  1920
ccttagcatc  ccttcccttt  gcaaatagtc  ctcttccaac  aataataatg  tcagatcctg  1980
tagagaccac  atcatccacg  gttctatact  gttgacccaa  tgcgtctccc  ttgtcatcta  2040
aacccacacc  gggtgtcata  atcaaccaat  cgtaaccttc  atctcttcca  cccatgtctc  2100
tttgagcaat  aaagccgata  acaaaatctt  tgtcgctctt  cgcaatgtca  acagtaccct  2160
tagtatattc  tccagtagct  agggagccct  tgcatgacaa  ttctgctaac  atcaaaaggc  2220
ctctaggttc  ctttgttact  tcttccgccg  cctgcttcaa  accgctaaca  ataccggc   2280 ccaccacacc  gtgtgcattc  gtaatgtctg  cccattctgc  tattctgtat  acacccgcag  2340
agtactgcaa  tttgactgta  ttaccaatgt  cagcaaattt  tctgtcttcg  aagagtaaaa  2400
```

```
aattgtactt ggcggataat gcctttagcg gcttaactgt gccctccatg gaaaaatcag    2460
tcaagatatc cacatgtgtt tttagtaaac aaattttggg acctaatgct tcaactaact    2520
ccagtaattc cttggtggta cgaacatcca atgaagcaca caagtttgtt tgcttttcgt    2580
gcatgatatt aaatagcttg gcagcaacag gactaggatg agtagcagca cgttccttat    2640
atgtagcttt cgacatgatt tatcttcgtt tcctgcaggt ttttgttctg tgcagttggg    2700
ttaagaatac tgggcaattt catgtttctt caacaccaca tatgcgtata tataccaatc    2760
taagtctgtg ctccttcctt cgttcttcct tctgctcgga gattaccgaa tcaaagctag    2820
cttatcgatg ataagctgtc aaagatgaga attaattcca cggactatag actatactag    2880
atactccgtc tactgtacga tacacttccg ctcaggtcct tgtcctttaa cgaggcctta    2940
ccactctttt gttactctat tgatccagct cagcaaaggc agtgtgatct aagattctat    3000
cttcgcgatg tagtaaaact agctagaccg agaaagagac tagaaatgca aaaggcactt    3060
ctacaatggc tgccatcatt attatccgat gtgacgctgc agcttctcaa tgatattcga    3120
atacgctttg aggagataca gcctaatatc cgacaaactg ttttacagat ttacgatcgt    3180
acttgttacc catcattgaa ttttgaacat ccgaacctgg gagttttccc tgaaacagat    3240
agtatatttg aacctgtata ataatatata gtctagcgct ttacggaaga caatgtatgt    3300
atttcggttc ctggagaaac tattgcatct attgcatagg taatcttgca cgtcgcatcc    3360
ccggttcatt ttctgcgttt ccatcttgca cttaatagc atatctttgt taacgaagca    3420
tctgtgcttc attttgtaga acaaaaatgc aacgcgagag cgctaatttt tcaaacaaag    3480
aatctgagct gcattttac agaacagaaa tgcaacgcga aagcgctatt ttaccaacga    3540
agaatctgtg cttcattttt gtaaaacaaa aatgcaacgc gacgagagcg ctaatttttc    3600
aaacaaagaa tctgagctgc attttacag aacagaaatg caacgcgaga gcgctatttt    3660
accaacaaag aatctatact tcttttttgt tctacaaaaa tgcatcccga gagcgctatt    3720
tttctaacaa agcatcttag attactttt ttctcctttg tgcgctctat aatgcagtct    3780
cttgataact ttttgcactg taggtccgtt aaggttagaa gaaggctact ttggtgtcta    3840 tttttctcttc cataaaaaaa gcctgactcc acttcccgcg tttactgatt actagcgaag    3900
ctgcgggtgc attttttcaa gataaaggca tccccgatta tattctatac cgatgtggat    3960
tgcgcatact tgtgaacag aaagtgatag cgttgatgat tcttcattgg tcagaaaatt    4020
atgaacggtt tcttctattt tgtctctata tactacgtat aggaaatgtt tacattttcg    4080
tattgttttc gattcactct atgaatagtt cttactacaa ttttttttgtc taaagagtaa    4140 tactagagat aaacataaaa aatgtagagg tcgagtttag atgcaagttc aaggagcgaa    4200
aggtggatgg gtaggttata tagggatata gcacagagat atatagcaaa gagatacttt    4260
tgagcaat                                                             4268
```

<210> SEQ ID NO 43
<211> LENGTH: 4399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
gtttgtggaa gcggtattcg caatttaatt aaagctggtg acaattaatc atcggctcgt      60
ataatgtgtg gaattgaatc gatataagga ggttaatcat gtttaaaccc tcaaaatata     120
```

```
ttttccctct atcttctcgt tgcgcttaat ttgactaatt ctcattagcg aggcgcgcct      180
ttccataggc tccgccccc tgacgagcat cacaaaaatc gacgctcaag tcagaggtgg      240
cgaaacccga caggactata aagataccag gcgtttcccc ctggaagctc cctcgtgcgc      300
tctcctgttc cgaccctgcc gcttaccgga tacctgtccg cctttctccc ttcgggaagc      360
gtggcgcttt ctcatagctc acgctgtagg tatctcagtt cggtgtaggt cgttcgctcc      420
aagctgggct gtgtgcacga accccccgtt cagcccgacc gctgcgcctt atccggtaac      480
tatcgtcttg agtccaaccc ggtaagacac gacttatcgc cactggcagc agccactggt      540
aacaggatta gcagagcgag gtatgtaggc ggtgctacag agttcttgaa gtggtggcct      600
aactacggct acactagaag aacagtattt ggtatctgcg ctctgctgaa gccagttacc      660
ttcggaaaaa gagttggtag ctcttgatcc ggcaaacaaa ccaccgctgg tagcggtggt      720 tttttttgttt gcaagcagca gattacgcgc agaaaaaaag gatctcaaga agatcctttg      780
atcttttcta cggggtctga cgctcagtgg aacgaaaact cacgttaagg gattttggtc      840
atgagattat caaaaaggat cttcacctag atccttttaa attaaaaatg aagttttaaa      900
tcaatctaaa gtatatatga gtaaacttgg tctgacagtt accaatgctt aatcagtgag      960
gcacctatct cagcgatctg tctatttcgt tcatccatag ttgcctgact ccccgtcgtg     1020
tagataacta cgatacggga gggcttacca tctggcccca gtgctgcaat gataccgcga     1080
gacccacgct caccggctcc agatttatca gcaataaacc agccagccgg aagggccgag     1140
cgcagaagtg gtcctgcaac tttatccgcc tccatccagt ctattaattg ttgccgggaa     1200
gctagagtaa gtagttcgcc agttaatagt ttgcgcaacg ttgttgccat tgctacaggc     1260
atcgtggtgt cacgctcgtc gtttggtatg gcttcattca gctccggttc ccaacgatca     1320
aggcgagtta catgatcccc catgttgtgc aaaaaagcgg ttagctcctt cggtcctccg     1380
atcgttgtca gaagtaagtt ggccgcagtg ttatcactca tggttatggc agcactgcat     1440
aattctctta ctgtcatgcc atccgtaaga tgcttttctg tgactggtga gtactcaacc     1500
aagtcattct gagaatagtg tatgcggcga ccgagttgct cttgcccggc gtcaatacgg     1560
gataataccg cgccacatag cagaacttta aaagtgctca tcattggaaa acgttcttcg     1620
gggcgaaaac tctcaaggat cttaccgctg ttgagatcca gttcgatgta acccactcgt     1680
gcacccaact gatcttcagc atcttttact ttcaccagcg tttctgggtg agcaaaaaca     1740
ggaaggcaaa atgccgcaaa aaagggaata agggcgacac ggaaatgttg aatactcata     1800
ctcttccttt ttcaatatta ttgaagcatt tatcagggtt attgtctcat gagcggatac     1860
atatttgaat gtatttagaa aaataaacag cgatcgcgcg gccgcgggta ataactgata     1920
taattaaatt gaagctctaa tttgtgagtt tagtatacat gcatttactt ataatacagt     1980
tttttagttt tgctggccgc atcttctcaa atatgcttcc cagcctgctt ttctgtaacg     2040
ttcaccctct accttagcat cccttccctt tgcaaatagt cctcttccaa caataataat     2100
gtcagatcct gtagagacca catcatccac ggttctatac tgttgaccca atgcgtctcc     2160
cttgtcatct aaacccacac cgggtgtcat aatcaaccaa tcgtaacctt catctcttcc     2220
acccatgtct ctttgagcaa taaagccgat aacaaaatct tgtcgctct tcgcaatgtc     2280 aacagtaccc ttagtatatt ctccagtagc tagggagccc ttgcatgaca attctgctaa     2340
catcaaaagg cctctaggtt cctttgttac ttcttccgcc gcctgcttca aaccgctaac     2400
aatacctggg cccaccacac cgtgtgcatt cgtaatgtct gcccattctg ctattctgta     2460
tacacccgca gagtactgca atttgactgt attaccaatg tcagcaaatt ttctgtcttc     2520
```

```
gaagagtaaa aaattgtact tggcggataa tgcctttagc ggcttaactg tgccctccat    2580
ggaaaaatca gtcaagatat ccacatgtgt ttttagtaaa caaattttgg gacctaatgc    2640
ttcaactaac tccagtaatt ccttggtggt acgaacatcc aatgaagcac acaagtttgt    2700
ttgcttttcg tgcatgatat taaatagctt ggcagcaaca ggactaggat gagtagcagc    2760
acgttcctta tatgtagctt tcgacatgat ttatcttcgt ttcctgcagg ttttttgttct   2820 gtgcagttgg gttaagaata ctgggcaatt tcatgtttct tcaacaccac atatgcgtat    2880
atataccaat ctaagtctgt gctccttcct tcgttcttcc ttctgctcgg agattaccga    2940
atcaaagcta gctatcgat gataagctgt caaagatgag aattaattcc acggactata    3000
gactatacta gatactccgt ctactgtacg atacacttcc gctcaggtcc ttgtcccttta   3060 acgaggcctt accactcttt tgttactcta ttgatccagc tcagcaaagg cagtgtgatc    3120
taagattcta tcttcgcgat gtagtaaaac tagctagacc gagaaagaga ctagaaatgc    3180
aaaaggcact tctacaatgg ctgccatcat tattatccga tgtgacgctg cagcttctca    3240
atgatattcg aatacgcttt gaggagatac agcctaatat ccgacaaact gttttacaga    3300
tttacgatcg tacttgttac ccatcattga attttgaaca tccgaacctg ggagttttcc    3360
ctgaaacaga tagtatattt gaacctgtat aataatatat agtctagcgc tttacggaag    3420
acaatgtatg tatttcggtt cctggagaaa ctattgcatc tattgcatag gtaatcttgc    3480
acgtcgcatc cccggttcat tttctgcgtt tccatcttgc acttcaatag catatctttg    3540
ttaacgaagc atctgtgctt cattttgtag aacaaaaatg caacgcgaga gcgctaattt    3600
ttcaaacaaa gaatctgagc tgcatttta cagaacagaa atgcaacgcg aaagcgctat    3660
tttaccaacg aagaatctgt gcttcatttt tgtaaaacaa aaatgcaacg cgacgagagc    3720
gctaattttt caaacaaaga atctgagctg catttttaca gaacagaaat gcaacgcgag    3780
agcgctattt taccaacaaa gaatctatac ttcttttttg ttctacaaaa atgcatcccg    3840
agagcgctat ttttctaaca aagcatctta gattactttt tttctccttt gtgcgctcta    3900
taatgcagtc tcttgataac tttttgcact gtaggtccgt taaggttaga agaaggctac    3960
tttggtgtct attttctctt ccataaaaaa agcctgactc cacttcccgc gtttactgat    4020
tactagcgaa gctgcgggtg cattttttca agataaaggc atccccgatt atattctata    4080
ccgatgtgga ttgcgcatac tttgtgaaca gaaagtgata gcgttgatga ttcttcattg    4140
gtcagaaaat tatgaacggt ttcttctatt ttgtctctat atactacgta taggaaatgt    4200 ttacatttc gtattgtttt cgattcactc tatgaatagt tcttactaca attttttttgt    4260 ctaaagagta atactagaga taaacataaa aaatgtagag gtcgagttta gatgcaagtt    4320
caaggagcga aggtggatg ggtaggttat atagggatat agcacagaga tatatagcaa    4380
agagatactt ttgagcaat                                                 4399

<210> SEQ ID NO 44
<211> LENGTH: 8762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gtttgtggaa gcggtattcg caatcattta gtcgtgcaat gtatgacttt aagatttgtg    60
agcaggaaga aaagggagaa tcttctaacg ataaacccttt gaaaaactgg gtagactacg    120
```

```
ctatgttgag ttgctacgca ggctgcacaa ttacacgaga atgctcccgc ctaggattta    180
aggctaaggg acgtgcaatg cagacgacag atctaaatga ccgtgtcggt gaagtgttcg    240
ccaaactttt cggttaacac atgcagtgat gcacgcgcga tggtgctaag ttacatatat    300
atatatatat atatatatat atatatatag ccatagtgat gtctaagtaa cctttatggt    360
atatttctta atgtggaaag atactagcgc gcgcacccac acacaagctt cgtcttttct    420
tgaagaaaag aggaagctcg ctaaatggga ttccactttc cgttccctgc cagctgatgg    480
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt ataataacaaa   660 gaagaaataa tgaactgatt ctcttcctcc ttcttgtcct ttcttaattc tgttgtaatt    720
accttccttt gtaattttttt ttgtaattat tcttcttaat aatccaaaca aacacacata   780
ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta cttttttccat aggctccgcc ccctgacga gcatcacaaa aatcgacgct   2280
caagtcagag gtggcgaaac ccgacaggac tataaagata ccaggcgttt cccctggaa    2340 gctcctcgt gcgctctcct gttccgaccc tgccgcttac cggatacctg tccgcctttc   2400
tcccttcggg aagcgtggcg ctttctcata gctcacgctg taggtatctc agttcggtgt   2460
```

```
aggtcgttcg ctccaagctg gctgtgtgc acgaacccc cgttcagccc gaccgctgcg      2520
ccttatccgg taactatcgt cttgagtcca acccggtaag acacgactta tcgccactgg      2580
cagcagccac tggtaacagg attagcagag cgaggtatgt aggcggtgct acagagttct      2640
tgaagtggtg gcctaactac ggctacacta gaagaacagt atttggtatc tgcgctctgc      2700
tgaagccagt taccttcgga aaaagagttg gtagctcttg atccggcaaa caaccaccg      2760 ctggtagcgg tggttttttt gtttgcaagc agcagattac gcgcagaaaa aaggatctc      2820 aagaagatcc tttgatcttt tctacggggt ctgacgctca gtggaacgaa aactcacgtt      2880
aagggatttt ggtcatgaga ttatcaaaaa ggatcttcac ctagatcctt ttaaattaaa      2940
aatgaagttt taaatcaatc taaagtatat atgagtaaac ttggtctgac agttaccaat      3000
gcttaatcag tgaggcacct atctcagcga tctgtctatt tcgttcatcc atagttgcct      3060
gactccccgt cgtgtagata actacgatac gggagggctt accatctggc cccagtgctg      3120
caatgatacc gcgagaccca cgctcaccgg ctccagattt atcagcaata aaccagccag      3180
ccggaagggc cgagcgcaga agtggtcctg caactttatc cgcctccatc cagtctatta      3240
attgttgccg ggaagctaga gtaagtagtt cgccagttaa tagtttgcgc aacgttgttg      3300
ccattgctac aggcatcgtg gtgtcacgct cgtcgtttgg tatggcttca ttcagctccg      3360
gttcccaacg atcaaggcga gttacatgat cccccatgtt gtgcaaaaaa gcggttagct      3420
ccttcggtcc tccgatcgtt gtcagaagta agttggccgc agtgttatca ctcatggtta      3480
tggcagcact gcataattct cttactgtca tgccatccgt aagatgcttt tctgtgactg      3540
gtgagtactc aaccaagtca ttctgagaat agtgtatgcg gcgaccgagt tgctcttgcc      3600
cggcgtcaat acgggataat accgcgccac atagcagaac tttaaaagtg ctcatcattg      3660
gaaaacgttc ttcggggcga aaactctcaa ggatcttacc gctgttgaga tccagttcga      3720
tgtaacccac tcgtgcaccc aactgatctt cagcatcttt tactttcacc agcgtttctg      3780
ggtgagcaaa aacaggaagg caaaatgccg caaaaaaggg aataagggcg acacggaaat      3840
gttgaatact catactcttc ctttttcaat attattgaag catttatcag ggttattgtc      3900
tcatgagcgg atacatattt gaatgtattt agaaaaataa acagcgatcg cagctagctc      3960
gtcgtgttca ggaactgttc gatggttcgg agagagtcgc cgcccagaac atacgcgcac      4020
cgatgtcagc agacagcctt attacaagta tattcaagca agtatatccg tagggtgcgg      4080
gtgatttgga tctaaggttc gtactcaaca ctcacgagca gcttgccat gttacatcct      4140 tttatcagac ataacataat tggagtttac ttacacacgg ggtgtacctg tatgagcacc      4200
acctacaatt gtagcactgg tacttgtaca aagaatttat tcgtacgaat cacagggacg      4260
gccgccctca ccgaaccagc gaatacctca gcggtcccct gcagtgactc aacaaagcga      4320
tatgaacatc ttgcgatggt atcctgctga tagttttac tgtacaaaca cctgtgtagc      4380
tccttctagc attttaagt tattcacacc tcaggggag ggataaatta ataaattcc       4440 aaaagcgaag atcgagaaac taaattaaaa ttccaaaaac gaagttggaa cacaccccc       4500 cgaaaaaaaa caacaaacaa aaacccaac aaaataaaca aaaacaaaat aaatatataa       4560
ctaccagtat ctgactaaaa gttcaaatac tcgtacttac aacaaataga aatgagccgg      4620
ccaaaattct gcagaaaaaa atttcaaaca agtactggta taattaaatt aaaaaacaca      4680
tcaaagtatc ataacgttag ttatttttatt ttatttaata aagaaaaca acaagatggg      4740 ctcaaaactt tcaacttata cgatacatac caaataacaa tttagtattt atctaagtgc      4800
ttttcgtaga taatggaata caaatggata tccagagtat acacatggat agtatacact      4860
```

```
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaagag accgcctcgt ttcttttct tcgtcgaaaa aggcaataaa    5220
aatttttatc acgtttcttt ttcttgaaaa ttttttttt tgatttttt ctctttcgat    5280 gacctcccat tgatatttaa gttaataaac ggtcttcaat ttctcaagtt tcagtttcat   5340
ttttcttgtt ctattacaac ttttttact tcttgctcat tagaaagaaa gcatagcaat    5400
ctaatctaag ttttaattac aaaatgacca ctctggatga caccgcttac cgataccgaa   5460
cttccgttcc tggcgatgcc gaggctattg aggctctgga tggatctttc accactgaca   5520
ccgttttccg agtgaccgct actggcgacg gcttcaccct gcgagaggtg cctgtcgacc   5580
ctcctctcac caaggttttc cctgacgatg agtcggacga tgagtctgac gctggagagg   5640
acggcgaccc tgactctcga actttcgtgg cttacggcga cgatggagac ctggccggct   5700 tgtggtcgt ttcttactcc ggatggaacc gacgactgac cgtggaggac atcgaggtcg    5760
ctcctgagca ccgaggtcat ggtgtcggac gagctctgat gggtctcgct actgagttcg   5820
ctcgagagcg aggtgctggc cacctgtggc tcgaggtcac caacgttaac gcccctgcta   5880
ttcatgccta ccgacgaatg ggttttaccc tgtgtggcct cgatactgcc ctgtacgacg   5940
gaaccgcttc cgatggagag caggccctct acatgtcgat gccctgccct taaacaggcc   6000
ccttttcctt tgtcgatatc atgtaattag ttatgtcacg cttacattca cgccctcctc   6060
ccacatccgc tctaaccgaa aaggaaggag ttagacaacc tgaagtctag gtccctattt   6120 attttttta atagttatgt tagtattaag aacgttattt atatttcaaa ttttctttt    6180 ttttctgtac aaacgcgtgt acgcatgtaa cattatactg aaaaccttgc ttgagaaggt   6240
tttgggacgc tcgaaggctt taatttgcgg gtaataactg atataattaa attgaagctc   6300
taatttgtga gtttagtata catgcattta cttataatac agttttttag ttttgctggc   6360
cgcatcttct caaatatgct tcccagcctg ctttttctgta acgttcaccc tctaccttag   6420
catcccttcc ctttgcaaat agtcctcttc caacaataat aatgtcagat cctgtagaga   6480
ccacatcatc cacggttcta tactgttgac ccaatgcgtc tcccttgtca tctaaaccca   6540
caccgggtgt cataatcaac caatcgtaac cttcatctct tccacccatg tctctttgag   6600
caataaagcc gataacaaaa tctttgtcgc tcttcgcaat gtcaacagta cccttagtat   6660
attctccagt agctagggag cccttgcatg acaattctgc taacatcaaa aggcctctag   6720 gttccttttgt tacttcttcc gccgcctgct tcaaaccgct aacaatacct gggcccacca   6780
caccgtgtgc attcgtaatg tctgcccatt ctgctattct gtatacaccc gcagagtact   6840
gcaatttgac tgtattacca atgtcagcaa attttctgtc ttcgaagagt aaaaaattgt   6900
acttggcgga taatgccttt agcggcttaa ctgtgccctc catggaaaaa tcagtcaaga   6960
tatccacatg tgttttagt aaacaaattt tgggacctaa tgcttcaact aactccagta    7020
attccttggt ggtacgaaca tccaatgaag cacacaagtt tgtttgcttt tcgtgcatga   7080
tattaaatag cttggcagca acaggactag gatgagtagc agcacgttcc ttatatgtag   7140
ctttcgacat gatttatctt cgtttcctgc aggttttgt tctgtgcagt tgggttaaga    7200
```

```
atactgggca atttcatgtt tcttcaacac cacatatgcg tatatatacc aatctaagtc    7260
tgtgctcctt ccttcgttct tccttctgct cggagattac cgaatcaaag ctagcttatc    7320
gatgataagc tgtcaaagat gagaattaat tccacggact atagactata ctagatactc    7380
cgtctactgt acgatacact tccgctcagg tccttgtcct ttaacgaggc cttaccactc    7440
ttttgttact ctattgatcc agctcagcaa aggcagtgtg atctaagatt ctatcttcgc    7500
gatgtagtaa aactagctag accgagaaag agactagaaa tgcaaaaggc acttctacaa    7560
tggctgccat cattattatc cgatgtgacg ctgcagcttc tcaatgatat tcgaatacgc    7620
tttgaggaga tacagcctaa tatccgacaa actgttttac agatttacga tcgtacttgt    7680
tacccatcat tgaattttga acatccgaac ctgggagttt tccctgaaac agatagtata    7740
tttgaacctg tataataata tatagtctag cgctttacgg aagacaatgt atgtatttcg    7800
gttcctggag aaactattgc atctattgca taggtaatct tgcacgtcgc atccccggtt    7860
cattttctgc gtttccatct tgcacttcaa tagcatatct ttgttaacga agcatctgtg    7920
cttcattttg tagaacaaaa atgcaacgcg agagcgctaa ttttttcaaac aaagaatctg    7980 agctgcattt ttacagaaca gaaatgcaac gcgaaagcgc tattttacca acgaagaatc    8040
tgtgcttcat ttttgtaaaa caaaaatgca acgcgacgag agcgctaatt tttcaaacaa    8100
agaatctgag ctgcattttt acagaacaga atgcaacgc gagagcgcta ttttaccaac    8160
aaagaatcta tacttctttt ttgttctaca aaaatgcatc ccgagagcgc tattttttcta    8220 acaaagcatc ttagattact tttttttctcc tttgtgcgct ctataatgca gtctcttgat    8280 aacttttgc actgtaggtc cgttaaggtt agaagaaggc tactttggtg tctatttttct    8340 cttccataaa aaaagcctga ctccacttcc cgcgtttact gattactagc gaagctgcgg    8400
gtgcattttt tcaagataaa ggcatccccg attatattct ataccgatgt ggattgcgca    8460
tactttgtga acagaaagtg atagcgttga tgattcttca ttggtcagaa aattatgaac    8520
ggtttcttct attttgtctc tatatactac gtataggaaa tgtttacatt ttcgtattgt    8580
tttcgattca ctctatgaat agttcttact acaattttttt tgtctaaaga gtaatactag    8640
agataaacat aaaaaatgta gaggtcgagt ttagatgcaa gttcaaggag cgaaaggtgg    8700
atgggtaggt tatataggga tatagcacag agatatatag caaagagata cttttgagca    8760
at                                                                   8762
```

<210> SEQ ID NO 45
<211> LENGTH: 5824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
gtttgtggaa gcggtattcg caatttaatt aaagctggtg acaattaatc atcggctcgt      60
ataatgtgtg gaattgaatc gatataagga ggttaatcat atgcaaacgc tcagcatcca     120
gcacggtacc ctcgtcacga tggatcagta ccgcagagtc cttggggata gctgggttca     180
cgtgcaggat ggacggatcg tcgcgctcgg agtgcacgcc gagtcggtgc ctccgccagc     240
ggatcgggtg atcgatgcac gcggcaaggt cgtgttaccc ggtttcatca atgcccacac     300
ccatgtgaac cagatcctcc tgcgcggagg gccctcgcac gggcgtcaac tctatgactg     360
gctgttcaac gttttgtatc cgggacaaaa ggcgatgaga ccggaggacg tagcggtggc     420
```

```
ggtgaggttg tattgtgcgg aagctgtgcg cagcgggatt acgacgatca acgacaacgc    480
cgattcggcc atctacccag gcaacatcga ggccgcgatg gcggtctatg gtgaggtggg    540
tgtgagggtc gtctacgccc gcatgttctt tgatcggatg gacgggcgca ttcaagggta    600
tgtgacgcgc ttgaaggctc gctctcccca agtcgaactg tgctcgatca tggaggaaac    660
ggctgtggcc aaagatcgga tcacagccct gtcagatcag tatcatggca cggcaggagg    720
tcgtatatca gtttggcccg ctcctgccat taccccggcg gtgacagttg aaggaatgcg    780
atgggcacaa gccttcgccc gtgatcgggc ggtaatgtgg acgcttcaca tggcggagag    840
cgatcatgat gagcggcttc attggatgag tcccgccgag tacatggagt gttacggact    900
cttggatgag cgtctgcagg tcgcgcattg cgtgtacttt gaccggaagg atgttcggct    960
gctgcaccgc cacaatgtga aggtcgcgtc gcaggttgtg agcaatgcct acctcggctc   1020
aggggtggcc cccgtgccag agatggtgga gcgcggcatg gccgtgggca ttggaacaga   1080
tgacgggaat tgtaatgact ccgtaaacat gatcggagac atgaagtttta tggcccatat   1140 tcaccgcgcg gtgcatcggg atgcggacgt gctgaccccca gagaagattc ttgaaatggc   1200
gacgatcgat ggggcgcgtt cgttgggaat ggaccacgag attggttcca tcgaaaccgg   1260
caagcgcgcg gaccttatcc tgcttgacct gcgtcaccct cagacgactc ctcaccatca   1320
tttggcggcc acgatcgtgt ttcaggctta cggcaatgag gtggacactg tcctgattga   1380
cggaaacgtt gtgatggaga accgccgctt gagctttctt cccccctgaac gtgagttggc   1440 gttccttgag gaagcgcaga gccgcgccac agctattttg cagcgggcga acatggtggc   1500
taacccagct tggcgcagcc tctaggttta acccctcaaa atatattttc cctctatctt   1560
ctcgttgcgc ttaatttgac taattctcat tagcgaggcg cgccttttcca taggctccgc   1620 ccccctgacg agcatcacaa aaatcgacgc tcaagtcaga ggtggcgaaa cccgacagga   1680
ctataaagat accaggcgtt tccccctgga agctccctcg tgcgctctcc tgttccgacc   1740
ctgccgctta ccggatacct gtccgccttt ctcccttcgg gaagcgtggc gctttctcat   1800
agctcacgct gtaggtatct cagttcggtg taggtcgttc gctccaagct gggctgtgtg   1860 cacgaaccccc ccgttcagcc cgaccgctgc gccttatccg gtaactatcg tcttgagtcc   1920
aacccggtaa gacacgactt atcgccactg gcagcagcca ctggtaacag gattagcaga   1980
gcgaggtatg taggcggtgc tacagagttc ttgaagtggt ggcctaacta cggctacact   2040
agaagaacag tatttggtat ctgcgctctg ctgaagccag ttaccttcgg aaaaagagtt   2100
ggtagctctt gatccggcaa acaaaccacc gctggtagcg gtggtttttt tgtttgcaag   2160
cagcagatta cgcgcagaaa aaaggatctc aagaagatcc tttgatcttt tctacggggg   2220
tctgacgctc agtggaacga aaactcacgt taagggattt tggtcatgag attatcaaaa   2280
aggatcttca cctagatcct tttaaattaa aaatgaagtt ttaaatcaat ctaaagtata   2340
tatgagtaaa cttggtctga cagttaccaa tgcttaatca gtgaggcacc tatctcagcg   2400
atctgtctat ttcgttcatc catagttgcc tgactccccg tcgtgtagat aactacgata   2460
cgggagggct taccatctgg ccccagtgct gcaatgatac cgcgagaccc acgctcaccg   2520
gctccagatt tatcagcaat aaaccagcca gccgaaggg ccgagcgcag aagtggtcct   2580
gcaactttat ccgcctccat ccagtctatt aattgttgcc gggaagctag agtaagtagt   2640
tcgccagtta atagtttgcg caacgttgtt gccattgcta caggcatcgt ggtgtcacgc   2700
tcgtcgtttg gtatggcttc attcagctcc ggttcccaac gatcaaggcg agttacatga   2760
tcccccatgt tgtgcaaaaa agcggttagc tccttcggtc ctccgatcgt tgtcagaagt   2820
```

```
aagttggccg cagtgttatc actcatggtt atggcagcac tgcataattc tcttactgtc   2880
atgccatccg taagatgctt ttctgtgact ggtgagtact caaccaagtc attctgagaa   2940
tagtgtatgc ggcgaccgag ttgctcttgc ccggcgtcaa tacgggataa taccgcgcca   3000
catagcagaa ctttaaaagt gctcatcatt ggaaaacgtt cttcggggcg aaaactctca   3060
aggatcttac cgctgttgag atccagttcg atgtaaccca ctcgtgcacc caactgatct   3120
tcagcatctt ttactttcac cagcgtttct gggtgagcaa aaacaggaag caaaatgcc    3180
gcaaaaaagg gaataagggc gacacggaaa tgttgaatac tcatactctt cctttttcaa   3240
tattattgaa gcatttatca gggttattgt ctcatgagcg gatacatatt tgaatgtatt   3300
tagaaaaata aacagcgatc gcgcggccgc gggtaataac tgatataatt aaattgaagc   3360
tctaatttgt gagtttagta tacatgcatt tacttataat acagtttttt agttttgctg   3420
gccgcatctt ctcaaatatg cttcccagcc tgcttttctg taacgttcac cctctacctt   3480
agcatccctt cccttttgcaa atagtcctct tccaacaata ataatgtcag atcctgtaga   3540
gaccacatca tccacggttc tatactgttg acccaatgcg tctcccttgt catctaaacc   3600
cacaccgggt gtcataatca accaatcgta accttcatct cttccaccca tgtctctttg   3660
agcaataaag ccgataacaa atctttgtc gctcttcgca atgtcaacag tacccttagt    3720
atattctcca gtagctaggg agcccttgca tgacaattct gctaacatca aaaggcctct   3780
aggttccttt gttacttctt ccgccgcctg cttcaaaccg ctaacaatac ctgggcccac   3840
cacaccgtgt gcattcgtaa tgtctgccca ttctgctatt ctgtatacac ccgcagagta   3900
ctgcaatttg actgtattac caatgtcagc aaattttctg tcttcgaaga gtaaaaaatt   3960
gtacttggcg gataatgcct ttagcggctt aactgtgccc tccatggaaa aatcagtcaa   4020
gatatccaca tgtgttttta gtaaacaaat tttgggacct aatgcttcaa ctaactccag   4080
taattccttg gtggtacgaa catccaatga agcacacaag tttgtttgct tttcgtgcat   4140
gatattaaat agcttggcag caacaggact aggatgagta gcagcacgtt ccttatatgt   4200
agctttcgac atgatttatc ttcgtttcct gcaggttttt gttctgtgca gttgggttaa   4260
gaatactggg caatttcatg tttcttcaac accacatatg cgtatatata ccaatctaag   4320
tctgtgctcc ttccttcgtt cttccttctg ctcggagatt accgaatcaa agctagctta   4380
tcgatgataa gctgtcaaag atgagaatta attccacgga ctatagacta tactagatac   4440
tccgtctact gtacgataca cttccgctca ggtccttgtc ctttaacgag gccttaccac   4500
tcttttgtta ctctattgat ccagctcagc aaaggcagtg tgatctaaga ttctatcttc   4560
gcgatgtagt aaaactagct agaccgagaa agagactaga atgcaaaag gcacttctac    4620
aatggctgcc atcattatta tccgatgtga cgctgcagct tctcaatgat attcgaatac   4680
gctttgagga gatacagcct aatatccgac aaactgtttt acagatttac gatcgtactt   4740
gttacccatc attgaatttt gaacatccga acctgggagt tttccctgaa acagatagta   4800
tatttgaacc tgtataataa tatatagtct agcgctttac ggaagacaat gtatgtattt   4860
cggttcctgg agaaactatt gcatctattg cataggtaat cttgcacgtc gcatccccgg   4920
ttcattttct gcgtttccat cttgcacttc aatagcatat ctttgttaac gaagcatctg   4980
tgcttcattt tgtagaacaa aaatgcaacg cgagagcgct aattttccaa acaaagaatc   5040
tgagctgcat tttacagaa cagaaatgca acgcgaaagc gctattttac caacgaagaa    5100
tctgtgcttc attttgtaa aacaaaaatg caacgcgacg agagcgctaa ttttttcaaac   5160
```

-continued

```
aaagaatctg agctgcattt ttacagaaca gaaatgcaac gcgagagcgc tattttacca    5220
acaaagaatc tatacttctt ttttgttcta caaaaatgca tcccgagagc gctattttc     5280 taacaaagca tcttagatta ctttttttct cctttgtgcg ctctataatg cagtctcttg    5340
ataacttttt gcactgtagg tccgttaagg ttagaagaag gctactttgg tgtctatttt    5400
ctcttccata aaaaagcct  gactccactt cccgcgttta ctgattacta gcgaagctgc    5460
gggtgcattt tttcaagata aaggcatccc cgattatatt ctataccgat gtggattgcg    5520
catactttgt gaacagaaag tgatagcgtt gatgattctt cattggtcag aaaattatga    5580
acggtttctt ctattttgtc tctatatact acgtatagga aatgtttaca ttttcgtatt    5640
gttttcgatt cactctatga atagttctta ctacaattt  tttgtctaaa gagtaatact    5700
agagataaac ataaaaaatg tagaggtcga gtttagatgc aagttcaagg agcgaaaggt    5760
ggatgggtag gttatatagg gatatagcac agagatatat agcaaagaga acttttgag    5820 caat                                                                5824
```

<210> SEQ ID NO 46
<211> LENGTH: 8336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
gtttgtggaa gcggtattcg caatttaatt aaagctggtg acaattaatc atcggctcgt    60
ataatgtgtg gaattgaatc gatataagga ggttaatcat atgactagaa tcgctatcac    120
aggtggtaga gttttgacta tggacccaga aagaagagta ttagaaccag gtacagttgt    180
tgttgaagat caattcattg cacaagtcgg ttcaccagat gacgtagaca tcagaggtgc    240
tgaaattata gatgccactg gtatggctgt attaccaggt tcgttaata  cacatacccca   300 cgttcctcaa attttgttaa gaggtggtgc ttcacatgat agaaatttgt tggaatggtt    360
gcacaacgtc ttatatccag gtttggctgc atacactgat gacgatatca gagttggtac    420
attgttatat tgtgctgaag cattgagatc cggtattact acagttgtcg acaatgaaga    480
tgttagacct aacgattttg ccagagctgg tgccgctggt attggtgcat tcactgatgc    540
cggtatcaga gcaatctatg ccagaatgta ctttgatgct ccaagagcag aattggaaga    600
attagtcgca acaatacatg caaaagcccc tggtgccgta agaatggacg aatctgcttc    660
aaccgatcat gttttggcag acttagatca attgattacc agacatgaca gaactgctga    720
tggtagaatt agagtatggc cagctcctgc aataccattc atggtttctg aaaagggtat    780
gaaggcagcc caagaaatag ctgcatccag aactgacggt tggacaatgc atgttagtga    840
agatccaatc gaagccagag tccactctat gaatgctcct gaatatttgc atcacttggg    900
ttgtttagac gatagattgt tagccgctca ttgcgttcac atagactcaa gagatatcag    960
attgtttaga caacatgatg ttaagatatc cacacaacct gtctccaata gttacttagc    1020
agccggtata gcaccagttc ctgaaatgtt ggctcatggt gtcacagtag gtattggtac    1080
cgacgatgct aattgtaacg actccgtaaa cttaatcagt gatatgaagg ttttggcatt    1140
gatacataga gctgcacaca gagatgctag tatcattacc ccagaaaaga taatcgaaat    1200
ggccactatt gacggtgcta gatgcattgg tatggctgat caaatcggtt ctttggaagc    1260
tggtaaaaga gcagacataa tcactttgga tttgagacat gcacaaacca ctcctgccca    1320
```

```
cgatttggcc gctacaattg tctttcaagc ttatggtaat gaagtaaacg atgttttggt   1380
caacggttct gtagttatga gagatagagt tttgtcattc ttaccaaccc ctcaagaaga   1440
aaaggcttta tacgacgatg catctgaaag atcagcagcc atgttagcca gagctggttt   1500
gactggtaca agaacctggc aaactttggg ttcttaagga atccattat gatgtcagga    1560
gaacacacgt taaaagcggt acgaggcagt tttattgatg tcacccgtac gatcgataac   1620
ccggaagaga ttgcctctgc gctgcggttt attgaggatg gtttattact cattaaacag   1680
ggaaaagtgg aatggtttgg cgaatgggaa aacggaaagc atcaaattcc tgacaccatt   1740
cgcgtgcgcg actatcgcgg caaactgata gtacccggct tgtcgatac acatatccat    1800
tatccgcaaa gtgaaatggt gggggcctat ggtgagcaat tgctggagtg gttgaataaa   1860
cacaccttcc ctactgaacg tcgttatgag gatttagagt acgcccgcga atgtcggcg    1920
ttcttcatca agcagctttt acgtaacgga accaccacgg cgctggtgtt tggcactgtt   1980
catccgcaat ctgttgatgc gctgtttgaa gccgccagtc atatcaatat gcgtatgatt   2040
gccggtaagg tgatgatgga ccgcaacgca ccggattatc tgctcgacac tgccgaaagc   2100
agctatcacc aaagcaaaga actgatcgaa cgctggcaca aaaatggtcg tctgctatat   2160
gcgattacgc cacgcttcgc cccgacctca tctcctgaac agatggcgat ggcgcaacgc   2220
ctgaaagaag aatatccgga tacgtgggta catacccatc tctgtgaaaa caaagatgaa   2280
attgcctggg tgaaatcgct ttatcctgac catgatggtt atctgatgt ttaccatcag    2340
tacggcctga ccggtaaaaa ctgtgtcttt gctcactgcg tccatctcga agaaaagag    2400
tgggatcgtc tcagcgaaac caaatccagc attgctttct gtccgacctc caaccttac   2460
ctcggcagcg gcttattcaa cttgaaaaaa gcatggcaga agaaagttaa agtgggcatg   2520
ggaacggata tcggtgccgg aaccactttc aacatgctgc aaacgctgaa cgaagcctac   2580
aaagtattgc aattacaagg ctatcgcctc tcggcatatg aagcgtttta cctggccacg   2640
ctcggcggag cgaaatctct gggccttgac gatttgattg caacttttt acctggcaaa    2700
gaggctgatt tcgtggtgat ggaacccacc gccactccgc tacagcagct gcgctatgac   2760
aactctgttt ctttagtcga caaattgttc gtgatgatga cgttgggcga tgaccgttcg   2820
atctaccgca cctacgttga tggtcgtctg gtgtacgaac gcaactaagg aacgaccatg   2880
agagaagtcc aattgttaga tggtagaaga gttgatgtcg cctgtgctgg tccttttgatt   2940
agtgaaatag gtgcccactt agatttgact gctccagttg aaattgattg tggtggtggt   3000
ttagcaacta gacctttttac tgaacctcat ttgcacttag acaaagcagg tactgccgat   3060
agattgcctg ccggtgcttc cacaatcggt gacgctattg ctgcaatgca aagtgtcaag   3120
gtaaccgaaa gagataatgt cgccgctgta gcagccagaa tgcatagagt tttaaacaga   3180
atcgtcgatg acggttccca cgctattaga gcattggttg atgtcgacga gtttggggt    3240
ttaacagctt ttcatgctgc acaacaagtc caagccgctt tggccccaag agctgttgtc   3300
caaattgtcg ctttcccaca acacggttta acccctcaag tattggcaat gttagaacaa   3360
gcagccgctg aaggtgcagg tgccttgggt gctcatactg atgttgaccc agatcctgca   3420
gcccacgttg gtgccgtcgc tgcaatagcc gctggtgctt ccttgccatt agaagttcat   3480
actgacgaag gtgctagtcc agataaattt tatttgcctg cagtattgga gtttagat   3540
agattcccag gtttgtctac tacattagct cattgtttgt cattaggtac aattgcacct   3600
aagcaacaac aacattggat cgaagaatta gctcacagag atatcaaagt atgcgttgca   3660
ccatctatt tggggtttcgg tttgccatta gcacctgtta gagccttaat agaagctggt   3720
```

```
gtcggtatct tagtaggttc agacaatttg caagatgttt tctttccttt gggtacaggt    3780
agagcaattg aaaacgttag attgttagcc accgcagccc aattaactgc accagaattg    3840
gccggtcctt taattgctgg tgtaaccgac atagcttacg caaccgttac tggtgctgca    3900
gatgccttgg ctgttgaatc tccagctaca ttagtagttc atgatgctac ctcacctgca    3960
gaattgttaa gaggtataga cggtacaaga attaccgtta tagatggttt gttgacatct    4020
ccattgcaat tggataaagg tatcaagtaa gtttaaacta atcccacagc cgccagttcc    4080
gctggcggca ttttaacttt ctttaatggg cgcgcctttc cataggctcc gccccctga    4140
cgagcatcac aaaaatcgac gctcaagtca gaggtggcga acccgacag gactataaag    4200
ataccaggcg tttccccctg gaagctccct cgtgcgctct cctgttccga ccctgccgct    4260
taccggatac ctgtccgcct ttctcccttc gggaagcgtg gcgctttctc atagctcacg    4320
ctgtaggtat ctcagttcgg tgtaggtcgt tcgctccaag ctgggctgtg tgcacgaacc    4380
ccccgttcag cccgaccgct gcgccttatc cggtaactat cgtcttgagt ccaacccggt    4440
aagacacgac ttatcgccac tggcagcagc cactggtaac aggattagca gagcgaggta    4500
tgtaggcggt gctacagagt tcttgaagtg gtggcctaac tacggctaca ctagaagaac    4560
agtatttggt atctgcgctc tgctgaagcc agttaccttc ggaaaaagag ttggtagctc    4620
ttgatccggc aaacaaacca ccgctggtag cggtggtttt tttgtttgca agcagcagat    4680
tacgcgcaga aaaaaggat ctcaagaaga tcctttgatc ttttctacgg ggtctgacgc    4740
tcagtggaac gaaaactcac gttaagggat tttggtcatg agattatcaa aaaggatctt    4800
cacctagatc cttttaaatt aaaaatgaag ttttaaatca atctaaagta tatatgagta    4860
aacttggtct gacagttacc aatgcttaat cagtgaggca cctatctcag cgatctgtct    4920
atttcgttca tccatagttg cctgactccc cgtcgtgtag ataactacga tacgggaggg    4980
cttaccatct ggccccagtg ctgcaatgat accgcgagac ccacgctcac cggctccaga    5040
tttatcagca ataaaccagc cagccggaag ggccgagcgc agaagtggtc ctgcaacttt    5100
atccgcctcc atccagtcta ttaattgttg ccgggaagct agagtaagta gttcgccagt    5160
taatagtttg cgcaacgttg ttgccattgc tacaggcatc gtggtgtcac gctcgtcgtt    5220
tggtatggct tcattcagct ccggttccca acgatcaagg cgagttacat gatcccccat    5280
gttgtgcaaa aaagcggtta gctccttcgg tcctccgatc gttgtcagaa gtaagttggc    5340
cgcagtgtta tcactcatgg ttatggcagc actgcataat tctcttactg tcatgccatc    5400
cgtaagatgc ttttctgtga ctggtgagta ctcaaccaag tcattctgag aatagtgtat    5460
gcggcgaccg agttgctctt gcccggcgtc aatacgggat aataccgcgc cacatagcag    5520
aactttaaaa gtgctcatca ttggaaaacg ttcttcgggg cgaaaactct caaggatctt    5580
accgctgttg agatccagtt cgatgtaacc cactcgtgca cccaactgat cttcagcatc    5640
ttttactttc accagcgttt ctgggtgagc aaaaacagga aggcaaaatg ccgcaaaaaa    5700
gggaataagg gcgacacgga aatgttgaat actcatactc ttcctttttc aatattattg    5760
aagcatttat cagggttatt gtctcatgag cggatacata tttgaatgta tttagaaaaa    5820
taaacagcga tcgcgcggcc gcgggtaata actgatataa ttaaattgaa gctctaattt    5880
gtgagtttag tatacatgca tttacttata atacagtttt ttagttttgc tggccgcatc    5940
ttctcaaata tgcttcccag cctgcttttc tgtaacgttc accctctacc ttagcatccc    6000
ttccctttgc aaatagtcct cttccaacaa taataatgtc agatcctgta gagaccacat    6060
```

```
catccacggt tctatactgt tgacccaatg cgtctccctt gtcatctaaa cccacaccgg   6120
gtgtcataat caaccaatcg taaccttcat ctcttccacc catgtctctt tgagcaataa   6180
agccgataac aaaatctttg tcgctcttcg caatgtcaac agtacccctta gtatattctc   6240 cagtagctag ggagcccttg catgacaatt ctgctaacat caaaaggcct ctaggttcct   6300
ttgttacttc ttccgccgcc tgcttcaaac cgctaacaat acctgggccc accacaccgt   6360
gtgcattcgt aatgtctgcc cattctgcta ttctgtatac acccgcagag tactgcaatt   6420
tgactgtatt accaatgtca gcaaattttc tgtcttcgaa gagtaaaaaa ttgtacttgg   6480
cggataatgc ctttagcggc ttaactgtgc cctccatgga aaaatcagtc aagatatcca   6540
catgtgtttt tagtaaacaa attttgggac ctaatgcttc aactaactcc agtaattcct   6600
tggtggtacg aacatccaat gaagcacaca agtttgtttg cttttcgtgc atgatattaa   6660
atagcttggc agcaacagga ctaggatgag tagcagcacg ttccttatat gtagctttcg   6720
acatgattta tcttcgtttc ctgcaggttt tgttctgtg cagttgggtt aagaatactg   6780
ggcaatttca tgtttcttca acaccacata tgcgtatata taccaatcta agtctgtgct   6840
ccttccttcg ttcttccttc tgctcggaga ttaccgaatc aaagctagct tatcgatgat   6900
aagctgtcaa agatgagaat taattccacg gactatagac tatactagat actccgtcta   6960
ctgtacgata cacttccgct caggtccttg tcctttaacg aggccttacc actcttttgt   7020
tactctattg atccagctca gcaaaggcag tgtgatctaa gattctatct tcgcgatgta   7080
gtaaaactag ctagaccgag aaagagacta gaaatgcaaa aggcacttct acaatggctg   7140
ccatcattat tatccgatgt gacgctgcag cttctcaatg atattcgaat acgctttgag   7200
gagatacagc ctaatatccg acaaactgtt ttacagattt acgatcgtac ttgttaccca   7260
tcattgaatt ttgaacatcc gaacctggga gttttccctg aaacagatag tatatttgaa   7320
cctgtataat aatatatagt ctagcgcttt acggaagaca atgtatgtat ttcggttcct   7380
ggagaaacta ttgcatctat tgcataggta atccttgcacg tcgcatcccc ggttcatttt   7440
ctgcgtttcc atcttgcact tcaatagcat atctttgtta acgaagcatc tgtgcttcat   7500
tttgtagaac aaaaatgcaa cgcgagagcg ctaattttc aaacaaagaa tctgagctgc   7560 attttttacag aacagaaatg caacgcgaaa gcgctatttt accaacgaag aatctgtgct   7620
tcatttttgt aaaacaaaaa tgcaacgcga cgagagcgct aatttttcaa acaaagaatc   7680
tgagctgcat tttacagaa cagaaatgca acgcgagagc gctattttac caacaaagaa   7740
tctatacttc ttttttgttc tacaaaaatg catcccgaga gcgctatttt tctaacaaag   7800
catcttagat tactttttt ctcctttgtg cgctctataa tgcagtctct tgataacttt   7860
ttgcactgta ggtccgttaa ggttagaaga aggctacttt ggtgtctatt ttctcttcca   7920 taaaaaagc ctgactccac ttcccgcgtt tactgattac tagcgaagct gcgggtgcat   7980 ttttttcaaga taaaggcatc cccgattata ttctataccg atgtggattg cgcatacttt   8040
gtgaacagaa agtgatagcg ttgatgattc ttcattggtc agaaaattat gaacggtttc   8100
ttctattttg tctctatata ctacgtatag gaaatgttta cattttcgta ttgttttcga   8160
ttcactctat gaatagttct tactacaatt ttttgtcta aagagtaata ctagagataa   8220
acataaaaaa tgtagaggtc gagtttagat gcaagttcaa ggagcgaaag gtggatgggt   8280
aggttatata gggatatagc acagagatat atagcaaaga gatacttttg agcaat        8336
```

<210> SEQ ID NO 47
<211> LENGTH: 8063

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

| | |
|---|---|
| gtttgtggaa gcggtattcg caatttaatt aaagctggtg acaattaatc atcggctcgt | 60 |
| ataatgtgtg gaattgaatc gatataagga ggttaatcat atgtcctcca cagcattata | 120 |
| caccgttcct accgcaggtc cagacgatgt tgccgccttg aaagcattag atggtcattc | 180 |
| cgcctccgat attttggctg taataggtaa acagagggt aatggttgtg ttaacgactt | 240 |
| tagtagaacc ttatctgctg cagtttggca tccattgtta aagattcag ccattacagt | 300 |
| cttttccggt ggtgcagaag gtgtaataag tccacatgta aacatcttcg ttagagatga | 360 |
| aagacaatat tctggtcacc ctagaggttt ggtaactgct gttggtagaa caagagttat | 420 |
| cggtccagaa gaaattggta gacctgctca agtcgatgca gtacatgaaa ccgttgtcgc | 480 |
| attgttaact gaattgggtg ttggtccaga tgacgttcac ttggtcttga ttaaatgccc | 540 |
| tttgttatct tcagacgcta tagcaggtgt tcatagaaga ggtttaagac ctgtcactac | 600 |
| agatacttac aatctatgt caagatccag agccgcttct gctttgggta tagccatggc | 660 |
| tttaaaggaa tgtgatagag acagagcatt gttagccttg gaaggtagag atgacgtttg | 720 |
| gtcagcaaga gcctccgctt ccagtggtgc tgaattggat gactgccaca ttttagtagt | 780 |
| tgcagaatca gatgcagccg ctaatccatt aagagcagcc catactgcca tgagagatgc | 840 |
| tttggacatc caagctttaa cagaagtttt tgacagaatt gctgcagaag gtggtaccgt | 900 |
| cagacaaata ttcgcaaagg ccgaagctga tccttcaggt gctatcagag gttatagaca | 960 |
| taccatgtta actgattccg acgtcaatgc aacaagacac gccagagccg ctgtaggtgg | 1020 |
| tttgattgca gccttacatg gtaacggtgc tgtctatgta tcaggtggtg cagaacacca | 1080 |
| aggtccaagt ggtggtggtt ctgttactgt tatatatgat gttcctgcaa cagccaacgc | 1140 |
| taccggtgaa gcttctagat aaggaaatcc attatgatat actcaacagt caacgctaat | 1200 |
| ccttacgctt ggccttacga tggttcaata gaccctgctc acaccgcttt aatcttaatc | 1260 |
| gattggcaaa tagacttttg tggtccaggt ggttatgtcg attccatggg ttacgactta | 1320 |
| tccttgacta gaagtggttt agaacctaca gcaagagtat tggctgcagc cagagatact | 1380 |
| ggtatgacag ttatccatac tagagaaggt cacagaccag atttggctga cttgccacct | 1440 |
| aataagagat ggagatctgc atcagccggt gctgaaatcg ttcagttgg tccatgtggt | 1500 |
| agaattttag tcagaggtga acctggttgg gaaatagtac cagaagttgc acctagagaa | 1560 |
| ggtgaaccaa ttatagataa acctggtaaa ggtgctttct acgcaacaga tttggacttg | 1620 |
| ttgttgagaa caagaggtat cacccatttg attttgaccg gtataactac agatgtttgc | 1680 |
| gtccacacca ctatgagaga agccaacgat agaggttacg aatgtttaat tttgtctgat | 1740 |
| tgcaccggtg ctactgacag aaagcatcac gaagctgcat tatctatggt caccatgcaa | 1800 |
| ggtggtgtat tcggtgcaac tgcccattca gatgacttat tggccgcttt gggtacaacc | 1860 |
| gttccagcag ccgctggtcc tagagctaga acagaataag gaacgaccat gacagttagt | 1920 |
| tccgatacaa ctgctgaaat atcgttaggt tggtcaatcc aagactggat tgatttccac | 1980 |
| aagtcatcaa gctcccaggc ttcactaagg cttcttgaat cactactaga ctctcaaaat | 2040 |
| gttgcgccaa tcgataatgc gtggatatcg ctaatttcaa aggaaaattt actgcaccaa | 2100 |
| ttccaaattt taagagcag agaaaataaa gaaactctac ctctctacgg tgtccctatt | 2160 |

```
gctgttaagg acaacatcga cgttagaggt ctacccacca ccgctgcatg tccatccttt    2220
gcatatgagc cttccaaaga ctctaaagta gtagaactac taagaaatgc aggtgcgata    2280
atcgtgggta agacaaactt ggaccaattt gccacaggat tagtcggcac acggtctcca    2340
tatgggaaaa caccttgcgc ttttagcaaa gagcatgtat ctggtggttc ctccgctggg    2400
tcagcatcgg tggtcgccag aggtatcgta ccaattgcat tgggtactga tacagcaggt    2460
tctggtagag tcccagccgc cttgaacaac ctgattggcc taaagccaac aaagggcgtc    2520
ttttcctgtc aaggtgtagt tcccgcttgt aaatctttag actgcgtctc catctttgca    2580
ttaaacctaa gtgatgctga acgctgcttc cgcatcatgt gccagccaga tcctgataat    2640
gatgaatatt ctagacccta tgtttccaac cctttgaaaa aattttcaag caatgtaacg    2700
attgctattc ctaaaaatat cccatggtat ggtgaaacca agaatcctgt actgttttcc    2760
aatgctgtcg aaaatctatc aagaacgggc gctaacgtca tagaaattga ttttgagcct    2820
cttttagagt tagctcgctg tttatacgaa ggtacttggg tggccgagcg ttatcaagct    2880
attcaatcgt ttttggacag taaaccacca aaggaatctt tggaccctac tgttatttca    2940
attatagaag gggccaagaa atacagtgca gtagactgct tcagttttga atacaaaaga    3000
caaggcatct tgcaaaaagt gagacgactt ctcgaatcag tcgatgtatt gtgtgtgccc    3060
acatgtcctt taaatcctac tatgcaacaa gttgcggatg aaccagtcct agtcaattca    3120
agacaaggca catggactaa ttttgtcaac ttggcagatt tggcagccct tgctgttccc    3180
gcagggttcc gagacgatgg tttgccaaat ggtattactt taatcggtaa aaaattcaca    3240
gattacgcac tattagagtt ggctaaccgc tatttccaaa atatattccc caacggttcc    3300
agaacatacg gtacttttac ctcttcttca gtaaagccag caaacgatca attagtggga    3360
ccagactatg acccatctac gtccataaaa ttggctgttg tcggtgcaca tcttaagggt    3420
ctgcctctac attggcaatt ggaaaaggtc aatgcaacat atttatgtac aacaaaaaca    3480
tcaaaagctt accagctttt tgctttgccc aaaaatggac cagttttaaa acctggtttg    3540
agaagagttc aagatagcaa tggctctcaa atcgaattag aagtgtacag tgttccaaaa    3600
gaactgttcg gtgcttttat ttccatggtt cctgaaccat taggaatagg ttcagtggag    3660
ttagaatctg gtgaatggat caaatccttt atttgtgaag aatctggtta caaagccaaa    3720
ggtacagttg atatcacaaa gtatggtgga tttagagcat attttgaaat gttgtaagtt    3780
taaactaatc ccacagccgc cagttccgct ggcggcattt taactttctt taatgggcgc    3840 gccttttccat aggctccgcc ccctgacga gcatcacaaa atcgacgct caagtcagag    3900 gtggcgaaac ccgacaggac tataaagata ccaggcgttt ccccctggaa gctccctcgt    3960
gcgctctcct gttccgaccc tgccgcttac cggatacctg tccgcctttc tcccttcggg    4020
aagcgtggcg ctttctcata gctcacgctg taggtatctc agttcggtgt aggtcgttcg    4080
ctccaagctg ggctgtgtgc acgaaccccc cgttcagccc gaccgctgcg ccttatccgg    4140
taactatcgt cttgagtcca acccggtaag acacgactta tcgccactgg cagcagccac    4200
tggtaacagg attagcagag cgaggtatgt aggcggtgct acagagttct tgaagtggtg    4260
gcctaactac ggctacacta agaacagt atttggtatc tgcgctctgc tgaagccagt    4320
taccttcgga aaagagttg gtagctcttg atccggcaaa caaaccaccg ctggtagcgg    4380
tggttttttt gtttgcaagc agcagattac gcgcagaaaa aaaggatctc aagaagatcc    4440
tttgatcttt tctacggggt ctgacgctca gtggaacgaa aactcacgtt aagggatttt    4500
```

```
ggtcatgaga ttatcaaaaa ggatcttcac ctagatcctt ttaaattaaa aatgaagttt    4560
taaatcaatc taaagtatat atgagtaaac ttggtctgac agttaccaat gcttaatcag    4620
tgaggcacct atctcagcga tctgtctatt tcgttcatcc atagttgcct gactccccgt    4680
cgtgtagata actacgatac gggagggctt accatctggc cccagtgctg caatgatacc    4740
gcgagaccca cgctcaccgg ctccagattt atcagcaata aaccagccag ccggaagggc    4800
cgagcgcaga agtggtcctg caactttatc cgcctccatc cagtctatta attgttgccg    4860
ggaagctaga gtaagtagtt cgccagttaa tagtttgcgc aacgttgttg ccattgctac    4920
aggcatcgtg gtgtcacgct cgtcgtttgg tatggcttca ttcagctccg gttcccaacg    4980
atcaaggcga gttacatgat cccccatgtt gtgcaaaaaa gcggttagct ccttcggtcc    5040
tccgatcgtt gtcagaagta agttggccgc agtgttatca ctcatggtta tggcagcact    5100
gcataattct cttactgtca tgccatccgt aagatgcttt tctgtgactg gtgagtactc    5160
aaccaagtca ttctgagaat agtgtatgcg gcgaccgagt tgctcttgcc cggcgtcaat    5220
acgggataat accgcgccac atagcagaac tttaaaagtg ctcatcattg gaaaacgttc    5280
ttcggggcga aaactctcaa ggatcttacc gctgttgaga tccagttcga tgtaacccac    5340
tcgtgcaccc aactgatctt cagcatcttt tactttcacc agcgtttctg ggtgagcaaa    5400
aacaggaagg caaaatgccg caaaaaaggg aataagggcg acacggaaat gttgaatact    5460
catactcttc ctttttcaat attattgaag catttatcag ggttattgtc tcatgagcgg    5520
atacatattt gaatgtattt agaaaaataa acagcgatcg cgcggccgcg ggtaataact    5580
gatataatta aattgaagct ctaatttgtg agtttagtat acatgcattt acttataata    5640 cagttttta gttttgctgg ccgcatcttc tcaaatatgc ttcccagcct gcttttctgt    5700
aacgttcacc ctctaccta gcatcccttc cctttgcaaa tagtcctctt ccaacaataa    5760
taatgtcaga tcctgtagag accacatcat ccacggttct atactgttga cccaatgcgt    5820
ctcccttgtc atctaaaccc acaccggggtg tcataatcaa ccaatcgtaa ccttcatctc    5880
ttccacccat gtctctttga gcaataaagc cgataacaaa atctttgtcg ctcttcgcaa    5940
tgtcaacagt acccttagta tattctccag tagctaggga gcccttgcat gacaattctg    6000
ctaacatcaa aaggcctcta ggttcctttg ttacttcttc cgccgcctgc ttcaaaccgc    6060
taacaatacc tgggcccacc acaccgtgtg cattcgtaat gtctgcccat tctgctattc    6120
tgtatacacc cgcagagtac tgcaatttga ctgtattacc aatgtcagca aattttctgt    6180
cttcgaagag taaaaaattg tacttggcgg ataatgcctt tagcggctta actgtgccct    6240
ccatggaaaa atcagtcaag atatccacat gtgttttag taaacaaatt ttgggaccta    6300
atgcttcaac taactccagt aattccttgg tggtacgaac atccaatgaa gcacacaagt    6360
ttgtttgctt ttcgtgcatg atattaaata gcttggcagc aacaggacta ggatgagtag    6420
cagcacgttc cttatatgta gctttcgaca tgatttatct tcgtttcctg caggtttttg    6480
ttctgtgcag ttgggttaag aatactgggc aatttcatgt tcttcaaca ccacatatgc    6540 gtatatatac caatctaagt ctgtgctcct tccttcgttc ttccttctgc tcggagatta    6600
ccgaatcaaa gctagcttat cgatgataag ctgtcaaaga tgagaattaa ttccacggac    6660
tatagactat actagatact ccgtctactg tacgatacac ttccgctcag gtccttgtcc    6720
tttaacgagg ccttaccact cttttgttac tctattgatc cagctcagca aaggcagtgt    6780
gatctaagat tctatcttcg cgatgtagta aaactagcta gaccgagaaa gagactagaa    6840
atgcaaaagg cacttctaca atggctgcca tcattattat ccgatgtgac gctgcagctt    6900
```

```
ctcaatgata ttcgaatacg ctttgaggag atacagccta atatccgaca aactgtttta    6960
cagatttacg atcgtacttg ttacccatca ttgaattttg aacatccgaa cctgggagtt    7020
ttccctgaaa cagatagtat atttgaacct gtataataat atatagtcta gcgctttacg    7080
gaagacaatg tatgtatttc ggttcctgga gaaactattg catctattgc ataggtaatc    7140
ttgcacgtcg catccccggt tcattttctg cgtttccatc ttgcacttca atagcatatc    7200
tttgttaacg aagcatctgt gcttcatttt gtagaacaaa aatgcaacgc gagagcgcta    7260 attttcaaa caaagaatct gagctgcatt tttacagaac agaaatgcaa cgcgaaagcg    7320
ctattttacc aacgaagaat ctgtgcttca tttttgtaaa acaaaaatgc aacgcgacga    7380
gagcgctaat ttttcaaaca agaatctga gctgcatttt tacagaacag aaatgcaacg    7440
cgagagcgct attttaccaa caaagaatct atacttcttt tttgttctac aaaaatgcat    7500
cccgagagcg ctatttttct aacaaagcat cttagattac tttttttctc ctttgtgcgc    7560
tctataatgc agtctcttga taacttttg cactgtaggt ccgttaaggt tagaagaagg    7620
ctactttggt gtctattttc tcttccataa aaaaagcctg actccacttc ccgcgtttac    7680
tgattactag cgaagctgcg ggtgcatttt ttcaagataa aggcatcccc gattatattc    7740
tataccgatg tggattgcgc atactttgtg aacagaaagt gatagcgttg atgattcttc    7800
attggtcaga aaattatgaa cggtttcttc tattttgtct ctatatacta cgtataggaa    7860
atgtttacat tttcgtattg ttttcgattc actctatgaa tagttcttac tacaattttt    7920
ttgtctaaag agtaatacta gagataaaca taaaaaatgt agaggtcgag tttagatgca    7980
agttcaagga gcgaaaggtg gatgggtagg ttatataggg atatagcaca gagatatata    8040
gcaaagagat acttttgagc aat                                            8063

<210> SEQ ID NO 48
<211> LENGTH: 8927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gtttgtggaa gcggtattcg caatcattta gtcgtgcaat gtatgacttt aagatttgtg      60
agcaggaaga aaagggagaa tcttctaacg ataaacccct gaaaaactgg gtagactacg     120
ctatgttgag ttgctacgca ggctgcacaa ttacacgaga atgctcccgc ctaggattta     180
aggctaaggg acgtgcaatg cagacgacag atctaaatga ccgtgtcggt gaagtgttcg     240
ccaaactttt cggttaacac atgcagtgat gcacgcgcga tggtgctaag ttacatatat     300
atatatatat atatatatat atatatatag ccatagtgat gtctaagtaa cctttatggt     360
atatttctta atgtggaaag atactagcgc gcgcacccac acacaagctt cgtcttttct     420
tgaagaaaag aggaagctcg ctaaatggga ttccactttc cgttccctgc cagctgatgg     480
aaaaaggtta gtggaacgat gaagaataaa agagagatc cactgaggtg aaatttcagc     540
tgacagcgag tttcatgatc gtgatgaaca atggtaacga gttgtggctg ttgccaggga     600 ggtggttct caacttttaa tgtatggcca atcgctact tgggtttgtt atataacaaa     660
gaagaaataa tgaactgatt ctcttcctcc ttcttgtcct ttcttaattc tgttgtaatt     720
accttccttt gtaattttt ttgtaattat tcttcttaat aatccaaaca acacacata     780 ttacaataat gaagaagccc gagctgaccg ctacctctgt tgagaagttc ctgattgaga     840
```

```
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc cccttttggac  1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatctttt tcagcctgtc gtggtagcaa tttgaggagt attattaatt gaataggttc    2040
atttttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta cttttttccat aggctccgcc ccctgacga gcatcacaaa atcgacgct    2280
caagtcagag gtggcgaaac ccgacaggac tataaagata ccaggcgttt ccccctggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaacccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta agaacagt atttggtatc tgcgctctgc    2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taagtatat atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
```

```
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa aacaggaagg caaaatgccg caaaaaaggg aataagggcg acacggaaat    3840
gttgaatact catactcttc ctttttcaat attattgaag catttatcag ggttattgtc    3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca agaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagttttttac tgtacaaaca cctgtgtagc    4380
tccttctagc attttttaagt tattcacacc tcaaggggag ggataaatta aataaattcc    4440
aaaagcgaag atcgagaaac taaattaaaa ttccaaaaac gaagttggaa cacaaccccc    4500
cgaaaaaaaa caacaaacaa aaacccaac aaaatatatca aaaacaaaat aaatatataa    4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttatttttatt ttatttaata aagaaaaca acaagatggg    4740 ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttacatttca cagtctgaac ttttgcagat tacctaattt ggtaagatat    4980
taattatgaa ctgaaagttg atggcggccg catagcttca aaatgtttct actccttttt    5040
tactcttcca gattttctcg gactccgcgc atcgccgtac cacttcaaaa cacccaagca    5100
cagcatacta aatttcccct cttctcttcct ctagggtgtc gttaattacc cgtactaaag    5160
gtttggaaaa gaaaaagag accgcctcgt ttcttttct tcgtcgaaaa aggcaataaa    5220
aatttttatc acgtttctt ttcttgaaaa ttttttttt tgatttttt ctctttcgat    5280 gacctcccat tgatatttaa gttaataaac ggtcttcaat ttctcaagtt tcagtttcat    5340
ttttcttgtt ctattacaac ttttttttact tcttgctcat tagaaagaaa gcatagcaat    5400
ctaatctaag ttttaattac aaaatgtcat cctcagaagt aaaagcaaat ggttggaccg    5460
cagttcctgt ttccgcaaaa gcaatagtag actccttggg taaattagga gatgtctctt    5520
catattccgt agaagatatt gcctttccag ctgcagacaa attggtagcc gaagctcaag    5580
```

```
cattcgttaa ggctagatta tctcctgaaa cctacaacca ttcaatgaga gttttctatt    5640
ggggtactgt cattgccaga agattgttac cagaacaagc taaagatttg tctccttcaa    5700
catgggcatt aacctgtttg ttacacgacg ttggtactgc cgaagcttat tttacctcca    5760
ctagaatgag tttcgatatc tacggtggta ttaaagctat ggaagtattg aaggttttag    5820
gttccagtac agatcaagca gaagccgttg ctgaagcaat tataagacat gaagatgttg    5880
gtgtcgacgg taacatcaca ttttgggtc aattgatcca attggcaaca ttgtacgata    5940
acgtcggtgc ctacgacggt attgatgact tcggttcctg ggttgatgac actacaagaa    6000
acagtataaa cactgctttc ccaagacatg gttggtgttc ttggttcgca tgcacagtta    6060
gaaaagaaga atcaaacaag ccttggtgcc acaccacaca cataccacaa ttcgacaaac    6120
aaatggaagc aaacaccttg atgaaacctt gggaataaac aggccccttt cctttgtcg    6180 atatcatgta attagttatg tcacgcttac attcacgccc tcctcccaca tccgctctaa    6240
ccgaaaagga aggagttaga caacctgaag tctaggtccc tatttatttt ttttaatagt    6300
tatgttagta ttaagaacgt tatttatatt tcaaattttt ctttttttc tgtacaaacg    6360 cgtgtacgca tgtaacatta tactgaaaac cttgcttgag aaggttttgg gacgctcgaa    6420
ggctttaatt tgcgggtaat aactgatata attaaattga agctctaatt tgtgagttta    6480
gtatacatgc atttacttat aatacagttt tttagttttg ctggccgcat cttctcaaat    6540
atgcttccca gcctgctttt ctgtaacgtt caccctctac cttagcatcc cttccctttg    6600
caaatagtcc tcttccaaca ataataatgt cagatcctgt agagaccaca tcatccacgg    6660
ttctatactg ttgacccaat gcgtctccct tgtcatctaa acccacaccg ggtgtcataa    6720
tcaaccaatc gtaaccttca tctcttccac ccatgtctct tgagcaata aagccgataa    6780 caaaatcttt gtcgctcttc gcaatgtcaa cagtacccctt agtatattct ccagtagcta    6840 gggagcccctt gcatgacaat tctgctaaca tcaaaaggcc tctaggttcc tttgttactt    6900
cttccgccgc ctgcttcaaa ccgctaacaa tacctgggcc caccacaccg tgtgcattcg    6960
taatgtctgc ccattctgct attctgtata cacccgcaga gtactgcaat ttgactgtat    7020
taccaatgtc agcaaatttt ctgtcttcga agagtaaaaa attgtacttg gcggataatg    7080
cctttagcgg cttaactgtg ccctccatgg aaaaatcagt caagatatcc acatgtgttt    7140
ttagtaaaca aattttggga cctaatgctt caactaactc cagtaattcc ttggtggtac    7200
gaacatccaa tgaagcacac aagtttgttt gcttttcgtg catgatatta aatagcttgg    7260
cagcaacagc actaggatga gtagcagcac gttcctata tgtagctttc gacatgatt    7320 atcttcgttt cctgcaggtt tttgttctgt gcagttgggt taagaatact gggcaatttc    7380
atgtttcttc aacaccacat atgcgtatat ataccaatct aagtctgtgc tccttccttc    7440
gttcttcctt ctgctcggag attaccgaat caaagctagc ttatcgatga taagctgtca    7500
aagatgagaa ttaattccac ggactataga ctatactaga tactccgtct actgtacgat    7560
acacttccgc tcaggtcctt gtcctttaac gaggccttac cactcttttg ttactctatt    7620
gatccagctc agcaaaggca gtgtgatcta agattctatc ttcgcgatgt agtaaaacta    7680
gctagaccga gaaagagact agaaatgcaa aaggcacttc tacaatggct gccatcatta    7740
ttatccgatg tgacgctgca gcttctcaat gatattcgaa tacgctttga ggagatacag    7800
cctaatatcc gacaaactgt tttacagatt tacgatcgta cttgttaccc atcattgaat    7860
tttgaacatc cgaacctggg agttttccct gaaacagata gtatatttga acctgtataa    7920
```

| | | |
|---|---|---|
| taatatatag tctagcgctt tacggaagac aatgtatgta tttcggttcc tggagaaact | 7980 |
| attgcatcta ttgcataggt aatcttgcac gtcgcatccc cggttcattt tctgcgtttc | 8040 |
| catcttgcac ttcaatagca tatctttgtt aacgaagcat ctgtgcttca ttttgtagaa | 8100 |
| caaaaatgca acgcgagagc gctaattttt caaacaaaga atctgagctg cattttaca | 8160 |
| gaacagaaat gcaacgcgaa agcgctattt taccaacgaa gaatctgtgc ttcatttttg | 8220 |
| taaaacaaaa atgcaacgcg acgagagcgc taattttttca aacaaagaat ctgagctgca | 8280 |
| ttttttacaga acagaaatgc aacgcgagag cgctatttta ccaacaaaga atctatactt | 8340 |
| cttttttgtt ctacaaaaat gcatcccgag agcgctattt ttctaacaaa gcatcttaga | 8400 |
| ttactttttt tctcctttgt gcgctctata atgcagtctc ttgataactt tttgcactgt | 8460 |
| aggtccgtta aggttagaag aaggctactt tggtgtctat tttctcttcc ataaaaaaag | 8520 |
| cctgactcca cttcccgcgt ttactgatta ctagcgaagc tgcgggtgca tttttttcaag | 8580 |
| ataaaggcat ccccgattat attctatacc gatgtggatt gcgcatactt tgtgaacaga | 8640 |
| aagtgatagc gttgatgatt cttcattggt cagaaaatta tgaacggttt cttctatttt | 8700 |
| gtctctatat actacgtata ggaaatgttt acattttcgt attgttttcg attcactcta | 8760 |
| tgaatagttc ttactacaat ttttttgtct aaagagtaat actagagata aacataaaaa | 8820 |
| atgtagaggt cgagtttaga tgcaagttca aggagcgaaa ggtggatggg taggttatat | 8880 |
| agggatatag cacagagata tatagcaaag agatactttt gagcaat | 8927 |

<210> SEQ ID NO 49
<211> LENGTH: 8918
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

| | | |
|---|---|---|
| gtttgtggaa gcggtattcg caatcattta gtcgtgcaat gtatgacttt aagatttgtg | 60 |
| agcaggaaga aaagggagaa tcttctaacg ataaaccctt gaaaaactgg gtagactacg | 120 |
| ctatgttgag ttgctacgca ggctgcacaa ttacacgaga atgctcccgc ctaggattta | 180 |
| aggctaaggg acgtgcaatg cagacgacag atctaaatga ccgtgtcggt gaagtgttcg | 240 |
| ccaaactttt cggttaacac atgcagtgat gcacgcgcga tggtgctaag ttacatatat | 300 |
| atatatatat atatatatat atatatatag ccatagtgat gtctaagtaa cctttatggt | 360 |
| atatttctta atgtggaaag atactagcgc gcgcacccac acacaagctt cgtcttttct | 420 |
| tgaagaaaag aggaagctcg ctaaatggga ttccactttc cgttccctgc cagctgatgg | 480 |
| aaaaaggtta gtggaacgat gaagaataaa aagagagatc cactgaggtg aaatttcagc | 540 |
| tgacagcgag tttcatgatc gtgatgaaca atggtaacga gttgtggctg ttgccaggga | 600 |
| gggtggttct caacttttaa tgtatggcca aatcgctact tgggtttgtt atataacaaa | 660 |
| gaagaaataa tgaactgatt ctcttcctcc ttcttgtcct ttcttaattc tgttgtaatt | 720 |
| accttccttt gtaattttttt ttgtaattat tcttcttaat aatccaaaca aacacacata | 780 |
| ttacaataat gaagaagccc gagctgaccg ctacctctgt tgagaagttc ctgattgaga | 840 |
| agtttgattc cgtttccgac ctgatgcagc tgtccgaggg cgaggagtct cgagccttct | 900 |
| cctttgacgt gggcggacga ggttacgttc tgcgagtgaa ctcgtgtgcc gacggcttct | 960 |
| acaaggatcg atacgtctac cgacactttg cttctgccgc tctgcccatc cctgaggttc | 1020 |

```
tcgacattgg cgagttctct gagtccctca cctactgcat ctctcgacga gctcagggag    1080
tcaccctgca ggacctccct gagactgagc tgcctgctgt cctccagcct gttgctgagg    1140
ccatggacgc tatcgctgct gctgatctgt cccagacctc gggtttcggc ccctttggac    1200
ctcagggaat tggacagtac accacttggc gagacttcat ctgtgctatt gccgatcctc    1260
acgtctacca ttggcagacc gttatggacg atactgtgtc ggcttctgtc gctcaggctc    1320
tggacgagct gatgctctgg gccgaggatt gccccgaggt tcgacacctg gtgcatgctg    1380
acttcggttc caacaacgtt ctcaccgaca acggccgaat cactgccgtg attgactggt    1440
ccgaggctat gtttgcgac tcgcagtacg aggtggccaa catcttcttt tggcgaccct    1500
ggctggcttg tatggagcag cagacccgat acttcgagcg acgacatcct gagctcgctg    1560
gatcccctcg actgcgagct acatgctcc gaattggtct ggaccagctc taccagtcgc    1620
tggtggatgg caactttgac gatgctgcct gggctcaggg acgatgtgac gccatcgtgc    1680
gatctggcgc tggaaccgtc ggacgaactc agattgcccg acgatccgct gctgtctgga    1740
ccgacggatg cgtggaggtc ctggctgatt cgggtaaccg acgaccctct actcgacctc    1800
gagctaagga gtaataaacg gcgcgccgtc tgaagaatga atgatttgat gatttctttt    1860
tccctccatt tttcttactg aatatatcaa tgatatagac ttgtatagtt tattatttca    1920
aattaagtag ctatatatag tcaagataac gtttgtttga cacgattaca ttattcgtcg    1980
acatctttt tcagcctgtc gtggtagcaa tttgaggagt attattaatt gataggttc    2040
attttgcgct cgcataaaca gttttcgtca gggacagtat gttggaatga gtggtaatta    2100
atggtgacat gacatgttat agcaataacc ttgatgttta catcgtagtt taatgtacac    2160
cccgcgaatt cgttcaagta ggagtgcacc aattgcaaag ggaaaagctg aatgggcagt    2220
tcgaatagta cttttccat aggctccgcc cccctgacga gcatcacaaa aatcgacgct    2280
caagtcagag gtggcgaaac ccgacaggac tataaagata ccaggcgttt ccccctggaa    2340
gctcccgt cgcgctctcct gttccgaccc tgccgcttac cggatacctg tccgcctttc    2400
tccctttcggg aagcgtggcg ctttctcata gctcacgctg taggtatctc agttcggtgt    2460
aggtcgttcg ctccaagctg ggctgtgtgc acgaaccccc cgttcagccc gaccgctgcg    2520
ccttatccgg taactatcgt cttgagtcca acccggtaag acacgactta tcgccactgg    2580
cagcagccac tggtaacagg attagcagag cgaggtatgt aggcggtgct acagagttct    2640
tgaagtggtg gcctaactac ggctacacta agaacagt atttggtatc tgcgctctgc    2700
tgaagccagt taccttcgga aaagagttg gtagctcttg atccggcaaa caaaccaccg    2760
ctggtagcgg tggtttttttt gtttgcaagc agcagattac gcgcagaaaa aaaggatctc    2820
aagaagatcc tttgatcttt tctacggggt ctgacgctca gtggaacgaa actcacgtt    2880
aagggatttt ggtcatgaga ttatcaaaaa ggatcttcac ctagatcctt ttaaattaaa    2940
aatgaagttt taaatcaatc taagtatat atgagtaaac ttggtctgac agttaccaat    3000
gcttaatcag tgaggcacct atctcagcga tctgtctatt tcgttcatcc atagttgcct    3060
gactccccgt cgtgtagata actacgatac gggagggctt accatctggc cccagtgctg    3120
caatgatacc gcgagaccca cgctcaccgg ctccagattt atcagcaata aaccagccag    3180
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
```

```
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa acaggaagg caaaatgccg caaaaaggg ataagggcg acacggaaat   3840 gttgaatact catactcttc cttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
tatgaacatc ttgcgatggt atcctgctga tagttttta cgtacaaaca cctgtgtagc   4380
tccttctagc atttttaagt tattcacacc tcaaggggag ggataaatta aataaattcc   4440
aaaagcgaag atcgagaaac taaattaaaa ttccaaaaac gaagttggaa cacaaccccc   4500
cgaaaaaaaa caacaaacaa aaacccaac aaaataaaca aaaacaaaat aaatatataa   4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gatttctcg gactccgcgc atcgccgtac cacttcaaaa cacccaagca   5100
cagcatacta aatttccct ctttcttcct ctagggtgtc gttaattacc cgtactaaag   5160
gtttggaaaa gaaaaagag accgcctcgt ttcttttct tcgtcgaaaa aggcaataaa   5220 aattttatc acgtttcttt ttcttgaaaa ttttttttt tgatttttt ctctttcgat   5280 gacctcccat tgatatttaa gttaataaac ggtcttcaat ttctcaagtt tcagtttcat   5340
ttttcttgtt ctattacaac ttttttact tcttgctcat tagaaagaaa gcatagcaat   5400
ctaatctaag ttttaattac aaaatgatat actcaacagt caacgctaat ccttacgctt   5460
ggccttacga tggttcaata gaccctgctc acaccgcttt aatcttaatc gattggcaaa   5520
tagacttttg tggtccaggt ggttatgtcg attccatggg ttacgactta tccttgacta   5580
gaagtggttt agaacctaca gcaagagtat tggctgcagc cagagatact ggtatgacag   5640
ttatccatac tagagaaggt cacagaccag atttggctga cttgccacct aataagagat   5700
ggagatctgc atcagccggt gctgaaatcg gttcagttgg tccatgtggt agaattttag   5760
```

```
tcagaggtga acctggttgg gaaatagtac cagaagttgc acctagagaa ggtgaaccaa       5820
ttatagataa acctggtaaa ggtgctttct acgcaacaga tttggacttg ttgttgagaa       5880
caagaggtat cacccatttg attttgaccg gtataactac agatgtttgc gtccacacca       5940
ctatgagaga agccaacgat agaggttacg aatgtttaat tttgtctgat tgcaccggtg       6000
ctactgacag aaagcatcac gaagctgcat tatctatggt caccatgcaa ggtggtgtat       6060
tcggtgcaac tgcccattca gatgactat tggccgcttt gggtacaacc gttccagcag       6120
ccgctggtcc tagagctaga acagaataaa caggcccctt ttcctttgtc gatatcatgt       6180
aattagttat gtcacgctta cattcacgcc ctcctcccac atccgctcta accgaaaagg       6240
aaggagttag acaacctgaa gtctaggtcc ctatttattt tttttaatag ttatgttagt       6300
attaagaacg ttatttatat ttcaaatttt tctttttttt ctgtacaaac gcgtgtacgc       6360
atgtaacatt atactgaaaa ccttgcttga gaaggttttg ggacgctcga aggctttaat       6420
ttgcgggtaa taactgatat aattaaattg aagctctaat ttgtgagttt agtatacatg       6480
catttactta taatacagtt ttttagtttt gctggccgca tcttctcaaa tatgcttccc       6540
agcctgcttt tctgtaacgt tcaccctcta ccttagcatc ccttcccttt gcaaatagtc       6600
ctcttccaac aataataatg tcagatcctg tagagaccac atcatccacg gttctatact       6660
gttgacccaa tgcgtctccc ttgtcatcta aacccacacc gggtgtcata atcaaccaat       6720
cgtaaccttc atctcttcca cccatgtctc tttgagcaat aaagccgata acaaaatctt       6780
tgtcgctctt cgcaatgtca acagtaccct tagtatattc tccagtagct agggagccct       6840
tgcatgacaa ttctgctaac atcaaaaggc ctctaggttc cttgttact tcttccgccg       6900 cctgcttcaa accgctaaca atacctgggc ccaccacacc gtgtgcattc gtaatgtctg       6960
cccattctgc tattctgtat acacccgcag agtactgcaa tttgactgta ttaccaatgt       7020
cagcaaattt tctgtcttcg aagagtaaaa aattgtactt ggcggataat gcctttagcg       7080
gcttaactgt gccctccatg gaaaaatcag tcaagatatc cacatgtgtt tttagtaaac       7140
aaattttggg acctaatgct tcaactaact ccagtaattc cttggtggta cgaacatcca       7200
atgaagcaca caagttttgtt tgcttttcgt gcatgatatt aaatagcttg gcagcaacag       7260
gactaggatg agtagcagca cgttccttat atgtagcttt cgacatgatt tatcttcgtt       7320
tcctgcaggt ttttgttctg tgcagttggg ttaagaatac tgggcaattt catgtttctt       7380
caacaccaca tatgcgtata tataccaatc taagtctgtg ctccttcctt cgttcttcct       7440
tctgctcgga gattaccgaa tcaaagctag cttatcgatg ataagctgtc aaagatgaga       7500
attaattcca cggactatag actatactag atactccgtc tactgtacga tacacttccg       7560
ctcaggtcct tgtcctttaa cgaggcctta ccactctttt gttactctat tgatccagct       7620
cagcaaaggc agtgtgatct aagattctat cttcgcgatg tagtaaaact agctagaccg       7680
agaaagagac tagaaatgca aaaggcactt ctacaatggc tgccatcatt attatccgat       7740
gtgacgctgc agcttctcaa tgatattcga atacgctttg aggagataca gcctaatatc       7800
cgacaaactg ttttacagat ttacgatcgt acttgttacc catcattgaa ttttgaacat       7860
ccgaacctgg gagttttccc tgaaacagat agtatatttg aacctgtata ataatatata       7920
gtctagcgct ttacggaaga caatgtatgt atttcggttc ctggagaaac tattgcatct       7980
attgcatagg taatccttgca cgtcgcatcc ccggttcatt ttctgcgttt ccatcttgca       8040
cttcaatagc atatctttgt taacgaagca tctgtgcttc attttgtaga acaaaaatgc       8100
aacgcgagag cgctaatttt tcaaacaaag aatctgagct gcatttttac agaacagaaa       8160
```

```
tgcaacgcga aagcgctatt ttaccaacga agaatctgtg cttcattttt gtaaaacaaa    8220
aatgcaacgc gacgagagcg ctaattttc aaacaaagaa tctgagctgc attttacag     8280 aacagaaatg caacgcgaga gcgctatttt accaacaaag aatctatact tctttttgt    8340 tctacaaaaa tgcatcccga gagcgctatt tttctaacaa agcatcttag attacttttt    8400
ttctcctttg tgcgctctat aatgcagtct cttgataact ttttgcactg taggtccgtt    8460
aaggttagaa gaaggctact ttggtgtcta ttttctcttc cataaaaaaa gcctgactcc    8520
acttcccgcg tttactgatt actagcgaag ctgcgggtgc attttttcaa gataaaggca    8580
tccccgatta tattctatac cgatgtggat tgcgcatact ttgtgaacag aaagtgatag    8640
cgttgatgat tcttcattgg tcagaaaatt atgaacggtt tcttctatt tgtctctata    8700 tactacgtat aggaaatgtt tacattttcg tattgttttc gattcactct atgaatagtt    8760
cttactacaa ttttttgtc taaagagtaa tactagagat aaacataaaa aatgtagagg     8820
tcgagtttag atgcaagttc aaggagcgaa aggtggatgg gtaggttata tagggatata    8880
gcacagagat atatagcaaa gagatacttt tgagcaat                            8918
```

<210> SEQ ID NO 50
<211> LENGTH: 8894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
gtttgtggaa gcggtattcg caatcattta gtcgtgcaat gtatgacttt aagatttgtg      60
agcaggaaga aaagggagaa tcttctaacg ataaaccctt gaaaaactgg gtagactacg     120
ctatgttgag ttgctacgca ggctgcacaa ttacacgaga atgctcccgc ctaggattta     180
aggctaaggg acgtgcaatg cagacgcacg atctaaatga ccgtgtcggt gaagtgttcg     240
ccaaactttt cggttaacac atgcagtgat gcacgcgcga tggtgctaag ttacatatat     300
atatatatat atatatatat atatatatag ccatagtgat gtctaagtaa cctttatggt     360
atatttctta atgtggaaag atactagcgc gcgcacccac acacaagctt cgtcttttct     420
tgaagaaaag aggaagctcg ctaaatggga ttccactttc cgttccctgc cagctgatgg     480
aaaaaggtta gtggaacgat gaagaataaa aagagagatc cactgaggtg aaatttcagc     540
tgacagcgag tttcatgatc gtgatgaaca atggtaacga gttgtggctg ttgccaggga     600
gggtggttct caacttttaa tgtatggcca aatcgctact tgggtttgtt atataacaaa     660
gaagaaataa tgaactgatt ctcttcctcc ttcttgtcct ttcttaattc tgttgtaatt     720
accttccttt gtaattttt ttgtaattat tcttcttaat aatccaaaca aacacacata     780
ttacaataat gaagaagccc gagctgaccg ctacctctgt tgagaagttc ctgattgaga     840
agtttgattc cgtttccgac ctgatgcagc tgtccgaggg cgaggagtct cgagccttct     900
cctttgacgt gggcggacga ggttacgttc tgcgagtgaa ctcgtgtgcc gacggcttct     960
acaaggatcg atacgtctac cgacactttg cttctgccgc tctgcccatc cctgaggttc    1020
tcgacattgg cgagttctct gagtccctca cctactgcat ctctcgacga gctcagggag    1080
tcaccctgca ggacctccct gagactgagc tgcctgctgt cctccagcct gttgctgagg    1140
ccatggacgc tatcgctgct gctgatcgtg cccagaccgc gggtttcggc ccctttggac    1200
ctcagggaat tggacagtac accaccttggc gagacttcat ctgtgctatt gccgatcctc    1260
```

```
acgtctacca ttggcagacc gttatggacg atactgtgtc ggcttctgtc gctcaggctc    1320
tggacgagct gatgctctgg gccgaggatt gccccgaggt tcgacacctg gtgcatgctg    1380
acttcggttc caacaacgtt ctcaccgaca acggccgaat cactgccgtg attgactggt    1440
ccgaggctat gtttggcgac tcgcagtacg aggtggccaa catcttcttt tggcgaccct    1500
ggctggcttg tatggagcag cagacccgat acttcgagcg acgacatcct gagctcgctg    1560
gatcccctcg actgcgagct tacatgctcc gaattggtct ggaccagctc taccagtcgc    1620
tggtggatgg caactttgac gatgctgcct gggctcaggg acgatgtgac gccatcgtgc    1680
gatctggcgc tggaaccgtc ggacgaactc agattgcccg acgatccgct gctgtctgga    1740
ccgacggatg cgtggaggtc ctggctgatt cgggtaaccg acgaccctct actcgacctc    1800
gagctaagga gtaataaacg gcgcgccgtc tgaagaatga atgatttgat gatttctttt    1860
tccctccatt tttcttactg aatatatcaa tgatatagac ttgtatagtt tattatttca    1920
aattaagtag ctatatatag tcaagataac gtttgtttga cacgattaca ttattcgtcg    1980
acatcttttt tcagcctgtc gtggtagcaa tttgaggagt attattaatt gaataggttc    2040
attttgcgct cgcataaaca gttttcgtca gggacagtat gttggaatga gtggtaatta    2100
atggtgacat gacatgttat agcaataacc ttgatgttta catcgtagtt taatgtacac    2160
cccgcgaatt cgttcaagta ggagtgcacc aattgcaaag ggaaaagctg aatgggcagt    2220
tcgaatagta cttttccat aggctccgcc ccctgacga gcatcacaaa aatcgacgct    2280
caagtcagag gtggcgaaac ccgacaggac tataaagata ccaggcgttt ccccctggaa    2340
gctccctcgt gcgctctcct gttccgaccc tgccgcttac cggatacctg tccgcctttc    2400
tcccttcggg aagcgtggcg ctttctcata gctcacgctg taggtatctc agttcggtgt    2460
aggtcgttcg ctccaagctg gctgtgtgc acgaaccccc cgttcagccc gaccgctgcg    2520
ccttatccgg taactatcgt cttgagtcca acccggtaag acacgactta tcgccactgg    2580
cagcagccac tggtaacagg attagcagag cgaggtatgt aggcggtgct acagagttct    2640
tgaagtggtg gcctaactac ggctacacta agaacagt atttggtatc tgcgctctgc    2700
tgaagccagt taccttcgga aaaagagttg gtagctcttg atccggcaaa caaccaccg    2760 ctggtagcgg tggttttttt gtttgcaagc agcagattac gcgcagaaaa aaaggatctc    2820
aagaagatcc tttgatcttt tctacggggt ctgacgctca gtggaacgaa aactcacgtt    2880
aagggatttt ggtcatgaga ttatcaaaaa ggatcttcac ctagatcctt ttaaattaaa    2940
aatgaagttt taaatcaatc taagtatat atgagtaaac ttggtctgac agttaccaat    3000
gcttaatcag tgaggcacct atctcagcga tctgtctatt tcgttcatcc atagttgcct    3060
gactccccgt cgtgtagata actacgatac gggagggctt accatctggc cccagtgctg    3120
caatgatacc gcgagaccca cgctcaccgg ctccagattt atcagcaata aaccagccag    3180
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
```

```
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa acaggaagg caaaatgccg caaaaaggg aataagggcg acacggaaat    3840
gttgaatact catactcttc cttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
tatgaacatc ttgcgatggt atcctgctga tagttttac tgtacaaaca cctgtgtagc    4380
tccttctagc attttaagt tattcacacc tcaagggag ggataaatta ataaaattcc    4440
aaaagcgaag atcgagaaac taaattaaaa ttccaaaaac gaagttggaa cacaaccccc   4500
cgaaaaaaaa caacaaacaa aaacccaac aaaataaaca aaaacaaaat aaatatataa    4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttatttatt ttatttaata aaagaaaaca acaagatggg    4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttcatttca cagtctgaac ttttgcagat tacctaattt ggtaagatat    4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttcccct ctttcttcct ctagggtgtc gttaattacc cgtactaaag   5160
gtttggaaaa gaaaaagag accgcctcgt ttcttttct tcgtcgaaaa aggcaataaa    5220
aattttatc acgtttcttt ttcttgaaaa ttttttttt tgatttttt ctctttcgat     5280
gacctcccat tgatatttaa gttaataaac ggtcttcaat ttctcaagtt tcagtttcat   5340
ttttcttgtt ctattacaac ttttttact tcttgctcat tagaaagaaa gcatagcaat    5400
ctaatctaag ttttaattac aaaatggacg caatggtaga aacaaataga cacttcatag   5460
atgccgaccc ttacccttgg ccttacaacg gtgccttgag acctgataac acagccttga   5520
ttataatcga tatgcaaacc gactttgtg gtaaaggtgg ttatgtcgat catatgggtt    5580
acgacttatc attggtacaa gccccaatcg aacctattaa aagagttta gctgcaatga    5640
gagctaaggg ttatcatatt atacacacaa gagaaggtca cagaccagat ttggctgact   5700
tacctgcaaa caagagatgg agatctcaaa gaataggtgc tggtatcggt gacccaggtc   5760
cttgtggtag aattttgacc agaggtgaac caggttggga tatcattcca gaattgtacc   5820
ctatagaagg tgaaactatc atcgataaac ctggtaaagg tagttttgc gcaacagact    5880
tagaattggt tttgaaccaa aagagaatcg aaaacatcat cttgaccggt atcactacag   5940
atgtttgtgt ctctaccact atgagagaag caaacgatag aggttacgaa tgcttgttgt   6000
```

```
tggaagattg ttgcggtgcc actgactacg gtaaccattt ggccgctatt aaaatggtca    6060
agatgcaagg tggtgtattc ggttctgttt caaattccgc agccttggtt gaagcattac    6120
cataaacagg ccccttttcc tttgtcgata tcatgtaatt agttatgtca cgcttacatt    6180
cacgccctcc tcccacatcc gctctaaccg aaaaggaagg agttagacaa cctgaagtct    6240
aggtccctat ttatttttt taatagttat gttagtatta agaacgttat ttatatttca    6300
aatttttctt tttttctgt acaaacgcgt gtacgcatgt aacattatac tgaaaacctt    6360
gcttgagaag gttttgggac gctcgaaggc tttaatttgc gggtaataac tgatataatt    6420
aaattgaagc tctaatttgt gagtttagta tacatgcatt tacttataat acagtttttt    6480
agttttgctg gccgcatctt ctcaaatatg cttcccagcc tgcttttctg taacgttcac    6540
cctctacctt agcatccctt ccctttgcaa atagtcctct tccaacaata ataatgtcag    6600
atcctgtaga gaccacatca tccacggttc tatactgttg acccaatgcg tctcccttgt    6660
catctaaacc cacaccgggt gtcataatca accaatcgta accttcatct cttccaccca    6720
tgtctctttg agcaataaag ccgataacaa atctttgtc gctcttcgca atgtcaacag    6780
tacccttagt atattctcca gtagctaggg agccctgca tgacaattct gctaacatca    6840
aaaggcctct aggttccttt gttacttctt ccgccgcctg cttcaaaccg ctaacaatac    6900
ctgggcccac cacccgtgt gcattcgtaa tgtctgccca ttctgctatt ctgtatacac    6960
ccgcagagta ctgcaatttg actgtattac caatgtcagc aaatttctg tcttcgaaga    7020 gtaaaaaatt gtacttggcg gataatgcct ttagcggctt aactgtgccc tccatggaaa    7080
aatcagtcaa gatatccaca tgtgttttta gtaaacaaat tttgggacct aatgcttcaa    7140
ctaactccag taattccttg gtggtacgaa catccaatga agcacacaag tttgtttgct    7200
tttcgtgcat gatattaaat agcttggcag caacaggact aggatgagta gcagcacgtt    7260
ccttatatgt agctttcgac atgatttatc ttcgtttcct gcaggttttt gttctgtgca    7320
gttgggttaa gaatactggg caatttcatg tttcttcaac accacatatg cgtatatata    7380
ccaatctaag tctgtgctcc ttccttcgtt cttccttctg ctcggagatt accgaatcaa    7440
agctagctta tcgatgataa gctgtcaaag atgagaatta attccacgga ctatagacta    7500
tactagatac tccgtctact gtacgataca cttccgctca ggtccttgtc ctttaacgag    7560
gccttaccac tcttttgtta ctctattgat ccagctcagc aaaggcagtg tgatctaaga    7620
ttctatcttc gcgatgtagt aaaactagct agaccgagaa agagactaga atgcaaaag    7680 gcacttctac aatggctgcc atcattatta tccgatgtga cgctgcagct tctcaatgat    7740
attcgaatac gctttgagga gatacagcct aatatccgac aaactgtttt acagatttac    7800
gatcgtactt gttacccatc attgaattt gaacatccga acctgggagt tttccctgaa    7860
acagatagta tatttgaacc tgtataataa tatatagtct agcgctttac ggaagacaat    7920
gtatgtattt cggttcctgg agaaactatt gcatctattg cataggtaat cttgcacgtc    7980
gcatccccgg ttcatttct gcgtttccat cttgcacttc aatagcatat ctttgttaac    8040
gaagcatctg tgcttcattt tgtagaacaa aaatgcaacg cgagagcgct aattttcaa    8100 acaaagaatc tgagctgcat ttttacagaa cagaaatgca acgcgaaagc gctattttac    8160
caacgaagaa tctgtgcttc attttttgtaa aacaaaaatg caacgcgacg agagcgctaa    8220
tttttcaaac aaagaatctg agctgcattt ttacagaaca gaaatgcaac gcgagagcgc    8280 tatttttacca acaaagaatc tatacttctt ttttgttcta caaaaatgca tcccgagagc    8340
```

| | |
|---|---|
| gctattttc taacaaagca tcttagatta ctttttttct cctttgtgcg ctctataatg | 8400 |
| cagtctcttg ataactttt gcactgtagg tccgttaagg ttagaagaag gctactttgg | 8460 |
| tgtctatttt ctcttccata aaaaaagcct gactccactt cccgcgttta ctgattacta | 8520 |
| gcgaagctgc gggtgcattt tttcaagata aaggcatccc cgattatatt ctataccgat | 8580 |
| gtggattgcg catactttgt gaacagaaag tgatagcgtt gatgattctt cattggtcag | 8640 |
| aaaattatga acggtttctt ctattttgtc tctatatact acgtatagga aatgtttaca | 8700 |
| ttttcgtatt gttttcgatt cactctatga atagttctta ctacaatttt tttgtctaaa | 8760 |
| gagtaatact agagataaac ataaaaaatg tagaggtcga gtttagatgc aagttcaagg | 8820 |
| agcgaaaggt ggatgggtag gttatatagg gatatagcac agagatatat agcaaagaga | 8880 |
| tacttttgag caat | 8894 |

<210> SEQ ID NO 51
<211> LENGTH: 8395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

| | |
|---|---|
| gtttgtggaa gcggtattcg caatttaatt aaagctggtg acaattaatc atcggctcgt | 60 |
| ataatgtgtg gaattgaatc gatataagga ggttaatcat atgtcaatgg aaacccatag | 120 |
| ttatgtagac gtcgcaattc gtaacgcgcg tcttgccgat acggagggaa ttgtcgatat | 180 |
| tcttattcac gatgggcgca ttgcgtccat cgtgaagtcg acaaaaacaa aaggatcggt | 240 |
| ggagatcgat gctcatgagg gtctggtcac ttccggcctg gtagagcctc acatccatct | 300 |
| cgataaggcc ctgacggcag atcgggttcc cgcaggaagc attggcgacc ttcgaacgcg | 360 |
| acgaggcctt gagatggcaa ttcgggccac ccgtgatatc aagcgtacgt tcacggttga | 420 |
| agatgttcga gaacgggcca tacgtgcggc cctgatggca tcccgtgcgg gaaccaccgc | 480 |
| attgcggaca cacgtcgatg tcgacccgat tgtcggcctc gcaggtatcc gtggtgtcct | 540 |
| tgaggcgcgt gaagtctgcg cgggattgat cgatatccag atcgtcgcct ccctcagga | 600 |
| gggactcttc tgctctgcgg gggccgtgga cctcatgcgg gaggcgatca aactgggcgc | 660 |
| ggatgccgtc ggcggcgcac ccgcgctgga tgatcgcccg caggaccatg tccgagccgt | 720 |
| ttttgacctt gctgctgagt tcggcctgcc cgtagacatg cacgtcgatg agtccgaccg | 780 |
| gcgggaagac tttacgcttc cctttgtgat tgaagctgcc cgtgaacggc gtgtgcccaa | 840 |
| tgtgaccgtc gcgcacatca gctcgctgtc cgtacagacg gatgacgtag cacggtcgac | 900 |
| cattgccgcc cttgcggacg ccgatgttaa tgtcgtggtt aatccgatca ttgtcaaaat | 960 |
| tacgcggctg agtgaattac tcgatgccgg agtctccgta atgtttggct cggacaacct | 1020 |
| gcgggatccg ttctataccgc tcggagcggc gaatcccctt ggatcagcca tttttgcctg | 1080 |
| tcaaattgcc gcgctgggaa caccgcaaga tctcagacgg gtattcgatg cggtcaccat | 1140 |
| caacgctgcc cgcatgctgg gattcccctc acttttaggc gtcgtggaag gggcagtcgc | 1200 |
| ggatctcgca gtattcccat cggcgacgcc cgaggaggtt gttctggatc aacagtctcc | 1260 |
| gctcttcgta ctcaagggcg gacgtgtcgt tgccatgcga ttggccgctg atcaacgtc | 1320 |
| gttccgcgac tactcatgag gaaatccatt atgatgtcag gagaacacac gttaaaagcg | 1380 |
| gtacgaggca gttttattga tgtcacccgt acgatcgata acccggaaga gattgcctct | 1440 |

```
gcgctgcggt ttattgagga tggtttatta ctcattaaac agggaaaagt ggaatggttt    1500
ggcgaatggg aaaacggaaa gcatcaaatt cctgacacca ttcgcgtgcg cgactatcgc    1560
ggcaaactga tagtaccggg cttttgtcgat acacatatcc attatccgca aagtgaaatg   1620
gtgggggcct atggtgagca attgctggag tggttgaata acacaccctt ccctactgaa    1680
cgtcgttatg aggatttaga gtacgcccgc gaaatgtcgg cgttcttcat caagcagctt    1740
ttacgtaacg gaaccaccac ggcgctggtg tttggcactg ttcatccgca atctgttgat    1800
gcgctgtttg aagccgccag tcatatcaat atgcgtatga ttgccggtaa ggtgatgatg    1860
gaccgcaacg caccggatta tctgctcgac actgccgaaa gcagctatca ccaaagcaaa    1920
gaactgatcg aacgctggca caaaaatggt cgtctgctat atgcgattac gccacgcttc    1980
gccccgacct catctcctga acagatggcg atggcgcaac gcctgaaaga gaatatccg    2040 gatacgtggg tacatacccca tctctgtgaa acaaagatg aaattgcctg ggtgaaatcg    2100
ctttatcctg accatgatgg ttatctggat gtttaccatc agtacggcct gaccggtaaa    2160
aactgtgtct ttgctcactg cgtccatctc gaagaaaaag agtgggatcg tctcagcgaa    2220
accaaatcca gcattgcttt ctgtccgacc tccaaccttt acctcggcag cggcttattc    2280
aacttgaaaa aagcatggca gaagaaagtt aaagtgggca tgggaacgga tatcggtgcc    2340
ggaaccactt tcaacatgct gcaaacgctg aacgaagcct acaaagtatt gcaattacaa    2400
ggctatcgcc tctcggcata tgaagcgttt tacctggcca cgctcggcgg agcgaaatct    2460
ctgggccttg acgatttgat tggcaacttt ttacctggca agaggctga tttcgtggtg    2520 atggaaccca ccgccactcc gctacagcag ctgcgctatg acaactctgt ttctttagtc    2580
gacaaattgt tcgtgatgat gacgttgggc gatgaccgtt cgatctaccg cacctacgtt    2640
gatggtcgtc tggtgtacga acgcaactaa ggaacgacca tgcaaacgct cagcatccag    2700
cacggtaccc tcgtcacgat ggatcagtac cgcagagtcc ttggggatag ctgggttcac    2760
gtgcaggatg gacggatcgt cgcgctcgga gtgcacgccg agtcggtgcc tccgccagcg    2820
gatcgggtga tcgatgcacg cggcaaggtc gtgttacccg gtttcatcaa tgcccacacc    2880
catgtgaacc agatcctcct gcgcggaggg ccctcgcacg ggcgtcaact ctatgactgg    2940
ctgttcaacg ttttgtatcc gggacaaaag gcgatgagac cggaggacgt agcggtggcg    3000
gtgaggttgt attgtgcgga agctgtgcgc agcgggatta cgacgatcaa cgacaacgcc    3060
gattcggcca tctacccagg caacatcgag gccgcgatgg cggtctatgg tgaggtgggt    3120
gtgagggtcg tctacgcccg catgttcttt gatcggatgg acgggcgcat tcaagggtat    3180
gtggacgcct tgaaggctcg ctctccccaa gtcgaactgt gctcgatcat ggaggaaacg    3240
gctgtggcca aagatcggat cacagccctg tcagatcagt atcatggcac ggcaggaggt    3300
cgtatatcag tttggcccgc tcctgccatt accccggcgg tgacagttga aggaatgcga    3360
tgggcacaag ccttcgcccg tgatcggcg gtaatgtgga cgcttcacat ggcggagagc    3420
gatcatgatg agcggcttca ttggatgagt cccgccgagt acatggagtg ttacggactc    3480
ttggatgagc gtctgcaggt cgcgcattgc gtgtactttg accggaagga tgttcggctg    3540
ctgcaccgcc acaatgtgaa ggtcgcgtcg caggttgtga gcaatgccta cctcggctca    3600
ggggtggccc ccgtgccaga gatggtggag cgcggcatgg ccgtgggcat tggaacagat    3660
gacgggaatt gtaatgactc cgtaaacatg atcggagaca tgaagtttat ggcccatatt    3720 caccgcgcg tgcatcggga tgcggacgtg ctgaccccag agaagattct tgaaatggcg    3780
acgatcgatg gggcgcgttc gttgggaatg gaccacgaga ttggttccat cgaaaccggc    3840
```

```
aagcgcgcgg accttatcct gcttgacctg cgtcaccctc agacgactcc tcaccatcat   3900
ttggcggcca cgatcgtgtt tcaggcttac ggcaatgagg tggacactgt cctgattgac   3960
ggaaacgttg tgatggagaa ccgccgcttg agctttcttc ccctgaacg tgagttggcg    4020 ttccttgagg aagcgcagag ccgcgccaca gctattttgc agcgggcgaa catggtggct   4080
aacccagctt ggcgcagcct ctagcctcaa aatatatttt ccctctatct tctcgttgcg   4140
cttaatttga ctaattctca ttagcgaggc gcgcctttcc ataggctccg ccccctgac    4200 gagcatcaca aaatcgacg ctcaagtcag aggtggcgaa acccgacagg actataaaga    4260
taccaggcgt ttccccctgg aagctccctc gtgcgctctc ctgttccgac cctgccgctt   4320
accggatacc tgtccgcctt tctcccttcg ggaagcgtgg cgctttctca tagctcacgc   4380
tgtaggtatc tcagttcggt gtaggtcgtt cgctccaagc tgggctgtgt gcacgaaccc   4440
cccgttcagc ccgaccgctg cgccttatcc ggtaactatc gtcttgagtc caacccggta   4500
agacacgact tatcgccact ggcagcagcc actggtaaca ggattagcag agcgaggtat   4560
gtaggcggtg ctacagagtt cttgaagtgg tggcctaact acggctacac tagaagaaca   4620
gtatttggta tctgcgctct gctgaagcca gttaccttcg gaaaaagagt tggtagctct   4680
tgatccggca aacaaaccac cgctggtagc ggtggttttt ttgtttgcaa gcagcagatt   4740
acgcgcagaa aaaaggatc tcaagaagat cctttgatct tttctacggg gtctgacgct    4800
cagtggaacg aaaactcacg ttaagggatt ttggtcatga gattatcaaa aaggatcttc   4860
acctagatcc ttttaaatta aaaatgaagt tttaaatcaa tctaaagtat atatgagtaa   4920
acttggtctg acagttacca atgcttaatc agtgaggcac ctatctcagc gatctgtcta   4980
tttcgttcat ccatagttgc ctgactcccc gtcgtgtaga taactacgat acgggagggc   5040
ttaccatctg gccccagtgc tgcaatgata ccgcgagacc cacgctcacc ggctccagat   5100
ttatcagcaa taaccagcc agccggaagg gccgagcgca gaagtggtcc tgcaacttta    5160
tccgcctcca tccagtctat taattgttgc cgggaagcta gagtaagtag ttcgccagtt   5220
aatagtttgc gcaacgttgt tgccattgct acaggcatcg tggtgtcacg ctcgtcgttt   5280
ggtatggctt cattcagctc cggttcccaa cgatcaaggc gagttacatg atcccccatg   5340
ttgtgcaaaa aagcggttag ctccttcggt cctccgatcg ttgtcagaag taagttggcc   5400
gcagtgttat cactcatggt tatggcagca ctgcataatt ctcttactgt catgccatcc   5460
gtaagatgct tttctgtgac tggtgagtac tcaaccaagt cattctgaga atagtgtatg   5520
cggcgaccga gttgctcttg cccggcgtca atacgggata taccgcgcc acatagcaga    5580 actttaaaag tgctcatcat tggaaaacgt tcttcggggc gaaaactctc aaggatctta   5640
ccgctgttga gatccagttc gatgtaaccc actcgtgcac ccaactgatc ttcagcatct   5700
tttactttca ccagcgtttc tgggtgagca aaaacaggaa ggcaaaatgc cgcaaaaaag   5760
ggaataaggg cgacacggaa atgttgaata ctcatactct tccttttca atattattga    5820 agcatttatc agggttattg tctcatgagc ggatacatat ttgaatgtat ttagaaaaat   5880
aaacagcgat cgcgcggccg cgggtaataa ctgatataat taattgaag ctctaatttg    5940 tgagtttagt atacatgcat ttacttataa tacagttttt tagttttgct ggccgcatct   6000
tctcaaatat gcttcccagc ctgcttttct gtaacgttca ccctctacct tagcatccct   6060 tcccttttgca aatagtcctc ttccaacaat aataatgtca gatcctgtag agaccacatc   6120
atccacggtt ctatactgtt gacccaatgc gtctcccttg tcatctaaac ccacaccggg   6180
```

```
tgtcataatc aaccaatcgt aaccttcatc tcttccaccc atgtctcttt gagcaataaa   6240
gccgataaca aaatctttgt cgctcttcgc aatgtcaaca gtaccctag tatattctcc    6300 agtagctagg gagcccttgc atgacaattc tgctaacatc aaaaggcctc taggttcctt   6360
tgttacttct tccgccgcct gcttcaaacc gctaacaata cctgggccca ccacaccgtg   6420
tgcattcgta atgtctgccc attctgctat tctgtataca cccgcagagt actgcaattt   6480
gactgtatta ccaatgtcag caaatttct gtcttcgaag agtaaaaaat tgtacttggc     6540
ggataatgcc tttagcggct taactgtgcc ctccatggaa aaatcagtca agatatccac   6600
atgtgttttt agtaaacaaa ttttgggacc taatgcttca actaactcca gtaattcctt   6660
ggtggtacga acatccaatg aagcacacaa gtttgtttgc ttttcgtgca tgatattaaa   6720
tagcttggca gcaacaggac taggatgagt agcagcacgt tccttatatg tagctttcga   6780
catgatttat cttcgtttcc tgcaggtttt tgttctgtgc agttgggtta agaatactgg   6840
gcaatttcat gtttcttcaa caccacatat gcgtatatat accaatctaa gtctgtgctc   6900
cttccttcgt tcttccttct gctcggagat taccgaatca aagctagctt atcgatgata   6960
agctgtcaaa gatgagaatt aattccacgg actatagact atactagata ctccgtctac   7020
tgtacgatac acttccgctc aggtccttgt cctttaacga ggccttacca ctcttttgtt   7080
actctattga tccagctcag caaaggcagt gtgatctaag attctatctt cgcgatgtag   7140
taaaactagc tagaccgaga aagagactag aaatgcaaaa ggcacttcta caatggctgc   7200
catcattatt atccgatgtg acgctgcagc ttctcaatga tattcgaata cgctttgagg   7260
agatacagcc taatatccga caaactgttt tacagattta cgatcgtact tgttacccat   7320 cattgaatt tgaacatccg aacctgggag ttttccctga aacagatagt atatttgaac   7380
ctgtataata atatatagtc tagcgcttta cggaagacaa tgtatgtatt tcggttcctg   7440
gagaaactat tgcatctatt gcataggtaa tcttgcacgt cgcatccccg gttcattttc   7500
tgcgtttcca tcttgcactt caatagcata tcttgttaa cgaagcatct gtgcttcatt    7560
ttgtagaaca aaaatgcaac gcgagagcgc taattttca aacaaagaat ctgagctgca    7620
tttttacaga acagaaatgc aacgcgaaag cgctatttta ccaacgaaga atctgtgctt   7680 cattttgta aaacaaaaat gcaacgcgac gagagcgcta attttcaaa caaagaatct     7740 gagctgcatt tttacagaac agaaatgcaa cgcgagagcg ctattttacc aacaaagaat   7800
ctatacttct tttttgttct acaaaaatgc atcccgagag cgctattttt ctaacaaagc   7860
atcttagatt acttttttc tcctttgtgc gctctataat gcagtctctt gataactttt    7920
tgcactgtag gtccgttaag gttagaagaa ggctactttg gtgtctattt tctcttccat   7980
aaaaaaagcc tgactccact tcccgcgttt actgattact agcgaagctg cgggtgcatt   8040
ttttcaagat aaaggcatcc ccgattatat tctataccga tgtggattgc gcatactttg   8100
tgaacagaaa gtgatagcgt tgatgattct tcattggtca gaaaattatg aacggtttct   8160
tctattttgt ctctatatac tacgtatagg aaatgtttac attttcgtat tgttttcgat   8220
tcactctatg aatagttctt actacaattt ttttgtctaa agagtaatac tagagataaa   8280
cataaaaaat gtagaggtcg agtttagatg caagttcaag gagcgaaagg tggatgggta   8340
ggttatatag ggatatagca cagagatata tagcaaagag atactttga gcaat         8395
```

<210> SEQ ID NO 52
<211> LENGTH: 12133
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gtttgtggaa gcggtattcg caatttaatt aaagctggtg acaattaatc atcggctcgt      60
ataatgtgtg gaattgaatc gatataagga ggttaatcat atgcaagcgc aagtttttcg     120
agttccaatg agtaatccag ccgatgttag tggcgtagcc aagctcatcg atgagggagt     180
gatccgtgcc gaagaggtcg tctgcgttct cggcaagacc gaaggcaacg gctgtgtcaa     240
tgacttcacg cgtggctaca ccaccctcgc gttcaaggtc tacttctccg agaaactggg     300
cgtgtcccgg caagaggtcg gcgagcgcat cgctttcatc atgtccggcg gtaccgaagg     360
cgtcatggcg cctcactgca ccatcttcac cgtgcagaag acggacaaca agcagaagac     420
cgccgctgaa ggcaagcgac ttgccgttca gcagatcttt acccgcgagt tcctgccgga     480
ggagatcggc cgcatgccgc aggtcacgga aacagccgac gctgttcgcc gcgccatgcg     540
cgaagccggc atcgcggatg catccgatgt ccacttcgtt caggtcaagt gcccactgct     600
cactgccggc cgcatgcatg acgctgtcga gcgcgggcat acggttgcca ccgaagatac     660
ctatgagtcc atgggctact cccgcggcgc atccgcgctt ggtatcgccc tggccctcgg     720
ggaagtcgag aaggccaacc tcagtgatga agttattacc gcagactaca gtctctactc     780
ctcggttgcc tcaacttcgg cgggtatcga gttgatgaac aacgagatca tcgtcatggg     840
caacagccgc gcatggggtg gtgaccctcgt catcggccac gccgagatga aggacgccat     900
cgacggtgca gcggtccggc aggccctgcg cgacgtcggg tgctgcgaga cgacctgcc     960
gaccgtcgac gagctcggcc gcgtggtcaa tgtatttgcc aaggctgaag cctccccgga    1020
cggtgaggtt cgtaaccgcc gccacacgat gctggacgat tcggacatta acagcacgcg    1080
ccatgcgcga gcggtcgtca atgcagttat cgcttcgatc gtgggagatc ccatggttta    1140
tgtctccggc ggctccgagc atcagggccc cgccggtggc ggtcccgttg cagttatcgc    1200
gcgcacagct taaggaaatc cattatgata tactcaacag tcaacgctaa tccttacgct    1260
tggccttacg atggttcaat agaccctgct cacaccgctt taatcttaat cgattggcaa    1320
atagactttt gtggtccagg tggttatgtc gattccatgg gttacgactt atccttgact    1380
agaagtggtt tagaacctac agcaagagta ttggctgcag ccagagatac tggtatgaca    1440
gttatccata ctagagaagg tcacagacca gatttggctg acttgccacc taataagaga    1500
tggagatctg catcagccgg tgctgaaatc ggttcagttg gtccatgtgg tagaatttta    1560
gtcagaggtg aacctggttg ggaaatagta ccagaagttg cacctagaga aggtgaacca    1620
attatagata aacctggtaa aggtgctttc tacgcaacag atttggactt gttgttgaga    1680
acaagaggta tcacccattt gattttgacc ggtataacta cagatgtttg cgtccacacc    1740
actatgagag aagccaacga tagaggttac gaatgtttaa ttttgtctga ttgcaccggt    1800
gctactgaca gaaagcatca cgaagctgca ttatctatgg tcaccatgca aggtggtgta    1860
ttcggtgcaa ctgcccattc agatgactta ttggccgctt tgggtacaac cgttccagca    1920
gccgctggtc ctagagctag aacagaataa ggaacgacca tgacagttag ttccgataca    1980
actgctgaaa tatcgttagg ttggtcaatc caagactgga ttgatttcca caagtcatca    2040
agctcccagg cttcactaag gcttcttgaa tcactactag actctcaaaa tgttgcgcca    2100
gtcgataatg cgtggatatc gctaatttca aaggaaaatt tactgcacca attccaaatt    2160
ttaaagagca gagaaaataa agaaactcta cctctctacg gtgtccctat tgctgttaag    2220
```

```
gacaacatcg acgttagagg tctacccacc accgctgcat gtccatcctt tgcatatgag    2280
ccttccaaag actctaaagt agtagaacta ctaagaaatg caggtgcgat aatcgtgggt    2340
aagacaaact tggaccaatt tgccacagga ttagtcggca cacggtctcc atatgggaaa    2400
acaccttgcg cttttagcaa agagcatgta tctggtggtt cctccgctgg gtcagcatcg    2460
gtggtcgcca gaggtatcgt accaattgca ttgggtactg atacagcagg ttctggtaga    2520
gtcccagccg ccttgaacaa cctgattggc ctaaagccaa caaagggcgt cttttcctgt    2580
caaggtgtag ttcccgcttg taaatcttta gactgcgtct ccatctttgc attaaaccta    2640
agtgatgctg aacgctgctt ccgcatcatg tgccagccag atcctgataa tgatgaatat    2700
tctagaccct atgtttccaa ccctttgaaa aaattttcaa gcaatgtaac gattgctatt    2760
cctaaaaata tcccatggta tggtgaaacc aagaatcctg tactgttttc caatgctgtc    2820
gaaaatctat caagaacggg cgctaacgtc atagaaattg attttgagcc tcttttagag    2880
ttagctcgct gtttatacga aggtacttgg gtggccgagc gttatcaagc tattcaatcg    2940
tttttggaca gtaaaccacc aaaggaatct ttggacccta ctgttatttc aattatagaa    3000
ggggccaaga aatacagtgc agtagactgc ttcagttttg aatacaaaag acaaggcatc    3060
ttgcaaaaag tgagacgact tctcgaatca gtcgatgtat tgtgtgtgcc cacatgtcct    3120
ttaaatccta ctatgcaaca agttgcggat gaaccagtcc tagtcaattc aagacaaggc    3180
acatggacta attttgtcaa cttggcagat ttggcagccc ttgctgttcc cgcagggttc    3240
cgagacgatg gtttgccaaa tggtattact ttaatcggta aaaaattcac agattacgca    3300
ctattagagt tggctaaccg ctatttccaa aatatattcc ccaacggttc cagaacatac    3360
ggtactttta cctcttcttc agtaaagcca gcaaacgatc aattagtggg accagactat    3420
gacccatcta cgtccataaa attggctgtt gtcggtgcac atcttaaggg tctgcctcta    3480
cattggcaat tggaaaaggt caatgcaaca tatttatgta caacaaaaac atcaaaagct    3540
taccagcttt ttgctttgcc caaaaatgga ccagttttaa aacctggttt gagaagagtt    3600
caagatagca atggctctca aatcgaatta gaagtgtaca gtgttccaaa agaactgttc    3660
ggtgctttta tttccatggt tcctgaacca ttaggaatag gttcagtgga gttagaatct    3720
ggtgaatgga tcaaatcctt tatttgtgaa gaatctggtt acaaagccaa aggtacagtt    3780
gatatcacaa agtatggtgg atttagagca tattttgaaa tgttgtaagg acacgataat    3840
gtcaatggaa acccatagtt atgtagacgt cgcaattcgt aacgcgcgtc ttgccgatac    3900
ggagggaatt gtcgatattc ttattcacga tgggcgcatt gcgtccatcg tgaagtcgac    3960
aaaaacaaaa ggatcggtgg agatcgatgc tcatgagggt ctggtcactt ccggcctggt    4020
agagcctcac atccatctcg ataaggccct gacggcagat cgggttcccg caggaagcat    4080
tggcgacctt cgaacgcgac gaggccttga gatggcaatt cgggccaccc gtgatatcaa    4140
gcgtacgttc acggttgaag atgttcgaga acgggccata cgtgcggccc tgatggcatc    4200
ccgtgcggga accaccgcat tgcggacaca cgtcgatgtc gacccgattg tcggcctcgc    4260
aggtatccgt ggtgtccttg aggcgcgtga agtctgcgcg ggattgatcg atatccagat    4320
cgtcgccttc cctcaggagg gactcttctg ctctgcgggg gccgtggacc tcatgcggga    4380
ggcgatcaaa ctgggcgcgg atgccgtcgg cggcgcaccc gcgctggatg atcgcccgca    4440
ggaccatgtc cgagccgttt ttgacccttgc tgctgagttc ggcctgcccg tagacatgca    4500
cgtcgatgag tccgaccggc gggaagactt tacgcttccc tttgtgattg aagctgcccg    4560
```

```
tgaacggcgt gtgcccaatg tgaccgtcgc gcacatcagc tcgctgtccg tacagacgga    4620
tgacgtagca cggtcgacca ttgccgccct tgcggacgcc gatgttaatg tcgtggttaa    4680
tccgatcatt gtcaaaatta cgcggctgag tgaattactc gatgccggag tctccgtaat    4740
gtttggctcg gacaacctgc gggatccgtt ctatccgctc ggagcggcga atccccttgg    4800
atcagccatt tttgcctgtc aaattgccgc gctgggaaca ccgcaagatc tcagacgggt    4860
attcgatgcg gtcaccatca acgctgcccg catgctggga ttcccctcac ttttaggcgt    4920
cgtggaaggg gcagtcgcgg atctcgcagt attcccatcg gcgacgcccg aggaggttgt    4980
tctggatcaa cagtctccgc tcttcgtact caagggcgga cgtgtcgttg ccatgcgatt    5040
ggccgctgga tcaacgtcgt tccgcgacta ctcatgagga aatccattat gatgtcagga    5100
gaacacacgt taaagcggt acgaggcagt tttattgatg tcacccgtac gatcgataac     5160
ccggaagaga ttgcctctgc gctgcggttt attgaggatg gtttattact cattaaacag    5220
ggaaaagtgg aatggtttgg cgaatgggaa aacggaaagc atcaaattcc tgacaccatt    5280
cgcgtgcgcg actatcgcgg caaactgata gtaccgggct tgtcgatac acatatccat     5340 tatccgcaaa gtgaaatggt gggggcctat ggtgagcaat tgctggagtg gttgaataaa    5400
cacaccttcc ctactgaacg tcgttatgag gatttagagt acgcccgcga aatgtcggcg    5460
ttcttcatca agcagctttt acgtaacgga accaccacgg cgctggtgtt tggcactgtt    5520
catccgcaat ctgttgatgc gctgtttgaa gccgccagtc atatcaatat gcgtatgatt    5580
gccggtaagg tgatgatgga ccgcaacgca ccggattatc tgctcgacac tgccgaaagc    5640
agctatcacc aaagcaaaga actgatcgaa cgctggcaca aaaatggtcg tctgctatat    5700
gcgattacgc cacgcttcgc cccgacctca tctcctgaac agatggcgat ggcgcaacgc    5760
ctgaaagaag aatatccgga tacgtgggta catacccatc tctgtgaaaa caaagatgaa    5820
attgcctggg tgaaatcgct ttatcctgac catgatggtt atctggatgt ttaccatcag    5880 tacgcctga ccgtaaaaa ctgtgtcttt gctcactgcg tccatctcga agaaaaagag     5940
tgggatcgtc tcagcgaaac caaatccagc attgctttct gtccgacctc caacctttac    6000
ctcggcagcg gcttattcaa cttgaaaaaa gcatggcaga agaaagttaa agtgggcatg    6060
ggaacggata tcggtgccgg aaccactttc aacatgctgc aaacgctgaa cgaagcctac    6120
aaagtattgc aattacaagg ctatcgcctc tcggcatatg aagcgtttta cctgccacg     6180 ctcggcggag cgaaatctct gggccttgac gatttgattg gcaactttt acctggcaaa     6240 gaggctgatt tcgtggtgat ggaacccacc gccactccgc tacagcagct gcgctatgac    6300
aactctgttt ctttagtcga caaattgttc gtgatgatga cgttgggcga tgaccgttcg    6360
atctaccgca cctacgttga tggtcgtctg gtgtacgaac gcaactaagg aacgaccatg    6420
caaacgctca gcatccagca cggtaccctc gtcacgatgg atcagtaccg cagagtcctt    6480
ggggatagct gggttcacgt gcaggatgga cggatcgtcg cgctcggagt gcacgccgag    6540
tcggtgcctc cgccagcgga tcgggtgatc gatgcacgcg gcaaggtcgt gttacccggt    6600
ttcatcaatg cccacaccca tgtgaaccag atcctcctgc gcggagggcc ctcgcacggg    6660
cgtcaactct atgactggct gttcaacgtt ttgtatccgg acaaaaggc gatgagaccg     6720 gaggacgtag cggtggcggt gaggttgtat tgtgcggaag ctgtgcgcag cgggattacg    6780
acgatcaacg acaacgccga ttcggccatc tacccaggca acatcgaggc cgcgatggcg    6840
gtctatggtg aggtgggtgt gagggtcgtc tacgcccgca tgttctttga tcggatggac    6900
gggcgcattc aagggtatgt ggacgccttg aaggctcgct ctccccaagt cgaactgtgc    6960
```

```
tcgatcatgg aggaaacggc tgtggccaaa gatcggatca cagccctgtc agatcagtat   7020
catggcacgg caggaggtcg tatatcagtt tggcccgctc ctgccattac cccggcggtg   7080
acagttgaag gaatgcgatg ggcacaagcc ttcgcccgtg atcgggcggt aatgtggacg   7140
cttcacatgg cggagagcga tcatgatgag cggcttcatt ggatgagtcc cgccgagtac   7200
atggagtgtt acggactctt ggatgagcgt ctgcaggtcg cgcattgcgt gtactttgac   7260
cggaaggatg ttcggctgct gcaccgccac aatgtgaagg tcgcgtcgca ggttgtgagc   7320
aatgcctacc tcggctcagg ggtggccccc gtgccagaga tggtggagcg cggcatggcc   7380
gtgggcattg gaacagatga cgggaattgt aatgactccg taaacatgat cggagacatg   7440
aagtttatgg cccatattca ccgcgcggtg catcgggatg cggacgtgct gaccccagag   7500
aagattcttg aaatggcgac gatcgatggg gcgcgttcgt tgggaatgga ccacgagatt   7560
ggttccatcg aaaccggcaa gcgcgcggac cttatcctgc ttgacctgcg tcaccctcag   7620
acgactcctc accatcattt ggcggccacg atcgtgtttc aggcttacgg caatgaggtg   7680
gacactgtcc tgattgacgg aaacgttgtg atggagaacc gccgcttgag ctttcttccc   7740
cctgaacgtg agttggcgtt ccttgaggaa gcgcagagcc gcgccacagc tattttgcag   7800
cgggcgaaca tggtggctaa cccagcttgg cgcagcctct agcctcaaaa tatattttcc   7860
ctctatcttc tcgttgcgct taatttgact aattctcatt agcgaggcgc gcctttccat   7920
aggctccgcc cccctgacga gcatcacaaa aatcgacgct caagtcagag gtggcgaaac   7980
ccgacaggac tataaagata ccaggcgttt ccccctggaa gctccctcgt gcgctctcct   8040
gttccgaccc tgccgcttac cggatacctg tccgcctttc tcccttcggg aagcgtggcg   8100
ctttctcata gctcacgctg taggtatctc agttcggtgt aggtcgttcg ctccaagctg   8160
ggctgtgtgc acgaaccccc cgttcagccc gaccgctgcg ccttatccgg taactatcgt   8220
cttgagtcca acccggtaag acacgactta tcgccactgg cagcagccac tggtaacagg   8280
attagcagag cgaggtatgt aggcggtgct acagagttct tgaagtggtg gcctaactac   8340
ggctacacta gaagaacagt atttggtatc tgcgctctgc tgaagccagt taccttcgga   8400
aaaagagttg gtagctcttg atccggcaaa caaaccaccg ctggtagcgg tggtttttt   8460 gtttgcaagc agcagattac gcgcagaaaa aaaggatctc aagaagatcc tttgatcttt   8520
tctacggggt ctgacgctca gtggaacgaa aactcacgtt aagggatttt ggtcatgaga   8580
ttatcaaaaa ggatcttcac ctagatcctt ttaaattaaa aatgaagttt taaatcaatc   8640
taaagtatat atgagtaaac ttggtctgac agttaccaat gcttaatcag tgaggcacct   8700
atctcagcga tctgtctatt tcgttcatcc atagttgcct gactccccgt cgtgtagata   8760
actacgatac gggagggctt accatctggc cccagtgctg caatgatacc gcgagaccca   8820
cgctcaccgg ctccagattt atcagcaata aaccagccag ccggaagggc cgagcgcaga   8880
agtggtcctg caactttatc cgcctccatc cagtctatta attgttgccg ggaagctaga   8940
gtaagtagtt cgccagttaa tagtttgcgc aacgttgttg ccattgctac aggcatcgtg   9000
gtgtcacgct cgtcgtttgg tatggcttca ttcagctccg gttcccaacg atcaaggcga   9060
gttacatgat cccccatgtt gtgcaaaaaa gcggttagct ccttcggtcc tccgatcgtt   9120
gtcagaagta agttggccgc agtgttatca ctcatggtta tggcagcact gcataattct   9180
cttactgtca tgccatccgt aagatgcttt tctgtgactg gtgagtactc aaccaagtca   9240
ttctgagaat agtgtatgcg gcgaccgagt tgctcttgcc cggcgtcaat acgggataat   9300
```

```
accgcgccac atagcagaac tttaaaagtg ctcatcattg gaaaacgttc ttcggggcga   9360
aaactctcaa ggatcttacc gctgttgaga tccagttcga tgtaacccac tcgtgcaccc   9420
aactgatctt cagcatcttt tactttcacc agcgtttctg ggtgagcaaa acaggaagg    9480 caaaatgccg caaaaaggg aataagggcg cacggaaat gttgaatact catactcttc     9540 cttttcaat attattgaag catttatcag ggttattgtc tcatgagcgg atacatattt    9600
gaatgtattt agaaaaataa acagcgatcg cgcggccgcg ggtaataact gatataatta   9660
aattgaagct ctaatttgtg agtttagtat acatgcattt acttataata cagttttta    9720 gttttgctgg ccgcatcttc tcaaatatgc ttcccagcct gcttttctgt aacgttcacc   9780 ctctaccta gcatcccttc cctttgcaaa tagtcctctt ccaacaataa taatgtcaga    9840
tcctgtagag accacatcat ccacggttct atactgttga cccaatgcgt ctcccttgtc   9900
atctaaaccc acaccgggtg tcataatcaa ccaatcgtaa ccttcatctc ttccacccat   9960
gtctctttga gcaataaagc cgataacaaa atctttgtcg ctcttcgcaa tgtcaacagt  10020
acccttagta tattctccag tagctaggga gcccttgcat gacaattctg ctaacatcaa  10080
aaggcctcta ggttcctttg ttacttcttc cgccgcctgc ttcaaaccgc taacaatacc  10140
tgggcccacc acaccgtgtg cattcgtaat gtctgcccat tctgctattc tgtatacacc  10200
cgcagagtac tgcaatttga ctgtattacc aatgtcagca aattttctgt cttcgaagag  10260
taaaaaattg tacttggcgg ataatgcctt tagcggctta actgtgccct ccatggaaaa  10320
atcagtcaag atatccacat gtgtttttag taaacaaatt ttgggaccta atgcttcaac  10380
taactccagt aattccttgg tggtacgaac atccaatgaa gcacacaagt ttgtttgctt  10440
ttcgtgcatg atattaaata gcttggcagc aacaggacta ggatgagtag cagcacgttc  10500
cttatatgta gctttcgaca tgatttatct tcgtttcctg caggttttg ttctgtgcag   10560 ttgggttaag aatactgggc aatttcatgt ttcttcaaca ccacatatgc gtatatatac  10620
caatctaagt ctgtgctcct tccttcgttc ttccttctgc tcggagatta ccgaatcaaa  10680
gctagcttat cgatgataag ctgtcaaaga tgagaattaa ttccacggac tatagactat  10740
actagatact ccgtctactg tacgatacac ttccgctcag gtccttgtcc tttaacgagg  10800
ccttaccact cttttgttac tctattgatc cagctcagca aaggcagtgt gatctaagat  10860
tctatcttcg cgatgtagta aaactagcta gaccgagaaa gagactagaa atgcaaaagg  10920
cacttctaca atggctgcca tcattattat ccgatgtgac gctgcagctt ctcaatgata  10980
ttcgaatacg ctttgaggag atacagccta atatccgaca aactgtttta cagatttacg  11040
atcgtacttg ttacccatca ttgaattttg aacatccgaa cctgggagtt ttccctgaaa  11100
cagatagtat atttgaacct gtataataat atatagtcta gcgctttacg aagacaatg   11160 tatgtatttc ggttcctgga gaaactattg catctattgc ataggtaatc ttgcacgtcg  11220
catccccggt tcattttctg cgtttccatc ttgcacttca atagcatatc tttgttaacg  11280
aagcatctgt gcttcatttt gtagaacaaa aatgcaacgc gagagcgcta atttttcaaa  11340
caaagaatct gagctgcatt tttacagaac agaaatgcaa cgcgaaagcg ctattttacc  11400
aacgaagaat ctgtgcttca tttttgtaaa acaaaaatgc aacgcgacga gagcgctaat  11460
ttttcaaaca aagaatctga gctgcatttt tacagaacag aaatgcaacg cgagagcgct  11520
attttaccaa caaagaatct atacttcttt tttgttctac aaaaatgcat cccgagagcg  11580
ctatttttct aacaaagcat cttagattac ttttttttctc ctttgtgcgc tctataatgc  11640
agtctcttga taactttttg cactgtaggt ccgttaaggt tagaagaagg ctactttggt  11700
```

```
gtctattttc tcttccataa aaaaagcctg actccacttc ccgcgtttac tgattactag   11760
cgaagctgcg ggtgcatttt ttcaagataa aggcatcccc gattatattc tataccgatg   11820
tggattgcgc atactttgtg aacagaaagt gatagcgttg atgattcttc attggtcaga   11880
aaattatgaa cggtttcttc tattttgtct ctatatacta cgtataggaa atgtttacat   11940
tttcgtattg ttttcgattc actctatgaa tagttcttac tacaattttt ttgtctaaag   12000
agtaatacta gagataaaca taaaaaatgt agaggtcgag tttagatgca agttcaagga   12060
gcgaaaggtg gatgggtagg ttatataggg atatagcaca gagatatata gcaaagagat   12120
acttttgagc aat                                                       12133

<210> SEQ ID NO 53
<211> LENGTH: 12112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gtttgtggaa gcggtattcg caatttaatt aaagctggtg acaattaatc atcggctcgt     60
ataatgtgtg gaattgaatc gatataagga ggttaatcat atgtaccata tagatgtatt    120
cagaatccct tgccatagtc caggtgacac ttcaggttta aagatttga tagaaacagg     180 tagagtcgct ccagcagata ttgttgctgt catgggtaaa acagagggta atggttgtgt    240
taacgactat acaagagaat acgccaccgc tatgttggct gcatgcttag gtagacattt    300
gcaattacca cctcacgaag ttgaaaagag agtagctttt gttatgtccg gtggtacaga    360
aggtgtattg tctccacatc acaccgtttt cgctagaaga ccagcaatag atgcccatag    420
acctgcaggt aaaagattga ctttaggtat cgcttttaca agagatttct tgcctgaaga    480
aattggtaga catgcacaaa taaccgaaac tgcaggtgcc gttaagagag ctatgagaga    540
tgctggtatc gcatcaatag atgacttaca tttcgtacag gttaagtgtc cattgttgac    600
tcctgcaaag atcgcttcag caagatccag aggttgcgct ccagtcacta cagatacata    660
tgaaagtatg ggttactcta gaggtgcctc agctttgggt attgcattag ccaccgaaga    720
agttccttct tcaatgttgg tcgatgaatc cgtattaaat gactgagttt tgtccagttc    780
tttagcttca gcatccgccg gtatagaatt ggaacataac gttgtcattg ccataggcat    840
gtccgaacaa gctacaagtg aattagttat cgcacacggt gtcatgtctg atgccattga    900
cgccgcttca gttagaagaa ctatagaatc tttgggtatc agatcagatg acgaaatgga    960
tagaatagtc aacgtattcg ctaaagcaga agcctctcca gacggtgtag ttagaggcat   1020
gagacatact atgttgagtg attctgacat caactctacc agacacgcta gagcagttac   1080
tggtgcagcc atagcttctg tcgtaggtca tggtatggtt tatgtctcag gtggtgccga   1140
acaccaaggt ccagctggtg gtggtccttt cgcagttatt gccagagctt aaggaaatcc   1200
attatgatat actcaacagt caacgctaat ccttacgctt ggccttacga tggttcaata   1260
gaccctgctc acaccgcttt aatcttaatc gattggcaaa tagacttttg tggtccaggt   1320
ggttatgtcg attccatggg ttacgactta tccttgacta gaagtggttt agaacctaca   1380
gcaagagtat tggctgcagc cagagatact ggtatgacag ttatccatac tagagaaggt   1440
cacagaccag atttggctga cttgccacct aataagagat ggagatctgc atcagccggt   1500
gctgaaatcg gttcagttgg tccatgtggt agaatttttag tcagaggtga acctggttgg   1560
```

```
gaaatagtac cagaagttgc acctagagaa ggtgaaccaa ttatagataa acctggtaaa    1620
ggtgctttct acgcaacaga tttggacttg ttgttgagaa caagaggtat cacccatttg    1680
attttgaccg gtataactac agatgtttgc gtccacacca ctatgagaga agccaacgat    1740
agaggttacg aatgtttaat tttgtctgat tgcaccggtg ctactgacag aaagcatcac    1800
gaagctgcat tatctatggt caccatgcaa ggtggtgtat tcggtgcaac tgcccattca    1860
gatgacttat tggccgcttt gggtacaacc gttccagcag ccgctggtcc tagagctaga    1920
acagaataag gaacgaccat gacagttagt tccgatacaa ctgctgaaat atcgttaggt    1980
tggtcaatcc aagactggat tgatttccac aagtcatcaa gctcccaggc ttcactaagg    2040
cttcttgaat cactactaga ctctcaaaat gttgcgccag tcgataatgc gtggatatcg    2100
ctaatttcaa aggaaaattt actgcaccaa ttccaaattt taaagagcag agaaaataaa    2160
gaaactctac ctctctacgg tgtccctatt gctgttaagg acaacatcga cgttagaggt    2220
ctacccacca ccgctgcatg tccatccttt gcatatgagc cttccaaaga ctctaaagta    2280
gtagaactac taagaaatgc aggtgcgata atcgtgggta agacaaactt ggaccaattt    2340
gccacaggat tagtcggcac acggtctcca tatgggaaaa caccttgcgc ttttagcaaa    2400
gagcatgtat ctggtggttc ctccgctggg tcagcatcgg tggtcgccag aggtatcgta    2460
ccaattgcat tgggtactga tacagcaggt tctggtagag tcccagccgc cttgaacaac    2520
ctgattggcc taaagccaac aaagggcgtc ttttcctgtc aaggtgtagt tcccgcttgt    2580
aaatctttag actgcgtctc catctttgca ttaaacctaa gtgatgctga acgctgcttc    2640
cgcatcatgt gccagccaga tcctgataat gatgaatatt ctagaccccta tgtttccaac    2700 cctttgaaaa aattttcaag caatgtaacg attgctattc ctaaaaatat cccatggtat    2760
ggtgaaacca agaatcctgt actgttttcc aatgctgtcg aaaatctatc aagaacgggc    2820
gctaacgtca tagaaattga ttttgagcct ctttttagagt tagctcgctg tttatacgaa    2880
ggtacttggg tggccgagcg ttatcaagct attcaatcgt ttttggacag taaaccacca    2940
aaggaatctt tggaccctac tgttatttca attatagaag gggccaagaa atacagtgca    3000
gtagactgct tcagttttga atacaaaaga caaggcatct tgcaaaaagt gagacgactt    3060
ctcgaatcag tcgatgtatt gtgtgtgccc acatgtcctt taaatcctac tatgcaacaa    3120
gttgcggatg aaccagtcct agtcaattca agacaaggca catggactaa ttttgtcaac    3180
ttggcagatt tggcagccct tgctgttccc gcagggttcc gagacgatgg tttgccaaat    3240
ggtattactt taatcggtaa aaaattcaca gattacgcac tattagagtt ggctaaccgc    3300
tatttccaaa atatattccc caacggttcc agaacatacg gtactttac ctcttcttca    3360 gtaaagccag caaacgatca attagtggga ccagactatg acccatctac gtccataaaa    3420
ttggctgttg tcggtgcaca tcttaagggt ctgcctctac attggcaatt ggaaaaggtc    3480
aatgcaacat atttatgtac aacaaaaaca tcaaaagctt accagctttt tgctttgccc    3540
aaaaatggac cagttttaaa acctggtttg agaagagttc aagatagcaa tggctctcaa    3600
atcgaattag aagtgtacag tgttccaaaa gaactgttcg gtgcttttat ttccatggtt    3660
cctgaaccat taggaatagg ttcagtggag ttagaatctg gtgaatggat caaatccttt    3720
atttgtgaag aatctggtta caaagccaaa ggtacagttg atatcacaaa gtatggtgga    3780
tttagagcat attttgaaat gttgtaagga cacgataatg tcaatggaaa cccatagtta    3840
tgtagacgtc gcaattcgta acgcgcgtct tgccgatacg gagggaattg tcgatattct    3900
```

```
tattcacgat gggcgcattg cgtccatcgt gaagtcgaca aaaacaaaag gatcggtgga   3960
gatcgatgct catgagggtc tggtcacttc cggcctggta gagcctcaca tccatctcga   4020
taaggccctg acggcagatc gggttcccgc aggaagcatt ggcgaccttc gaacgcgacg   4080
aggccttgag atggcaattc gggccacccg tgatatcaag cgtacgttca cggttgaaga   4140
tgttcgagaa cgggccatac gtgcggccct gatggcatcc cgtgcgggaa ccaccgcatt   4200
gcggacacac gtcgatgtcg acccgattgt cggcctcgca ggtatccgtg gtgtccttga   4260
ggcgcgtgaa gtctgcgcgg gattgatcga tatccagatc gtcgccttcc ctcaggaggg   4320
actcttctgc tctgcggggg ccgtggacct catgcgggag gcgatcaaac tgggcgcgga   4380
tgccgtcggc ggcgcacccg cgctggatga tcgcccgcag gaccatgtcc gagccgtttt   4440
tgaccttgct gctgagttcg gcctgcccgt agacatgcac gtcgatgagt ccgaccggcg   4500
ggaagacttt acgcttccct tgtgattga agctgcccgt gaacggcgtg tgcccaatgt   4560
gaccgtcgcg cacatcagct cgctgtccgt acagacggat gacgtagcac ggtcgaccat   4620
tgccgcccTT gcggacgccg atgttaatgt cgtggttaat ccgatcattg tcaaaattac   4680
gcggctgagt gaattactcg atgccggagt ctccgtaatg tttggctcgg acaacctgcg   4740
ggatccgttc tatccgctcg gagcggcgaa tccccttgga tcagccattt ttgcctgtca   4800
aattgccgcg ctgggaacac cgcaagatct cagacgggta ttcgatgcgg tcaccatcaa   4860
cgctgcccgc atgctgggat ccccctcact tttaggcgtc gtggaagggg cagtcgcgga   4920
tctcgcagta ttcccatcgg cgacgcccga ggaggttgtt ctggatcaac agtctccgct   4980
cttcgtactc aagggcggac gtgtcgttgc catgcgattg gccgctggat caacgtcgtt   5040
ccgcgactac tcatgaggaa atccattatg atgtcaggag aacacacgtt aaaagcggta   5100
cgaggcagtt ttattgatgt cacccgtacg atcgataacc cggaagagat tgcctctgcg   5160
ctgcggttta ttgaggatgg tttattactc attaaacagg gaaaagtgga atggtttggc   5220
gaatgggaaa acgaaagca tcaaattcct gacaccattc gcgtgcgcga ctatcgcggc   5280
aaactgatag taccgggctt tgtcgataca catatccatt atccgcaaag tgaaatggtg   5340
ggggcctatg gtgagcaatt gctggagtgg ttgaataaac acaccttccc tactgaacgt   5400
cgttatgagg atttagagta cgcccgcgaa atgtcggcgt tcttcatcaa gcagctttta   5460
cgtaacggaa ccaccacggc gctggtgttt ggcactgttc atccgcaatc tgttgatgcg   5520
ctgtttgaag ccgccagtca tatcaatatg cgtatgattg ccggtaaggt gatgatggac   5580
cgcaacgcac cggattatct gctcgacact gccgaaagca gctatcacca aagcaaagaa   5640
ctgatcgaac gctggcacaa aaatggtcgt ctgctatatg cgattacgcc acgcttcgcc   5700
ccgacctcat ctcctgaaca gatggcgatg gcgcaacgcc tgaaagaaga atatccggat   5760
acgtgggtac ataccatct ctgtgaaaac aaagatgaaa ttgcctgggt gaaatcgctt   5820
tatcctgacc atgatggtta tctggatgtt taccatcagt acggcctgac cggtaaaaac   5880
tgtgtctttg ctcactgcgt ccatctcgaa gaaaaagagt gggatcgtct cagcgaaacc   5940
aaatccagca ttgctttctg tccgacctcc aacctttacc tcggcagcgg cttattcaac   6000
ttgaaaaaag catggcagaa gaaagttaaa gtgggcatgg gaacggatat cggtgccgga   6060
accactttca acatgctgca aacgctgaac gaagcctaca agtattgcga attacaaggc   6120
tatcgcctct cggcatatga agcgttttac ctggccacgc tcggcggagc gaaatctctg   6180
ggccttgaca atttgattgg caacttttta cctggcaaag aggctgattt cgtggtgatg   6240
gaacccaccg ccactccgct acagcagctg cgctatgaca actctgtttc tttagtcgac   6300
```

```
aaattgttcg tgatgatgac gttgggcgat gaccgttcga tctaccgcac ctacgttgat    6360
ggtcgtctgg tgtacgaacg caactaagga acgaccatgc aaacgctcag catccagcac    6420
ggtaccctcg tcacgatgga tcagtaccgc agagtccttg gggatagctg ggttcacgtg    6480
caggatggac ggatcgtcgc gctcggagtg cacgccgagt cggtgcctcc gccagcggat    6540
cgggtgatcg atgcacgcgg caaggtcgtg ttacccggtt tcatcaatgc ccacacccat    6600
gtgaaccaga tcctcctgcg cggagggccc tcgcacgggc gtcaactcta tgactggctg    6660
ttcaacgttt tgtatccggg acaaaaggcg atgagaccgg aggacgtagc ggtggcggtg    6720
aggttgtatt gtgcggaagc tgtgcgcagc gggattacga cgatcaacga caacgccgat    6780
tcggccatct acccaggcaa catcgaggcc gcgatggcgg tctatggtga ggtgggtgtg    6840
agggtcgtct acgcccgcat gttctttgat cggatggacg ggcgcattca agggtatgtg    6900
gacgccttga aggctcgctc tccccaagtc gaactgtgct cgatcatgga ggaaacggct    6960
gtggccaaag atcggatcac agccctgtca gatcagtatc atggcacggc aggaggtcgt    7020
atatcagttt ggcccgctcc tgccattacc ccggcggtga cagttgaagg aatgcgatgg    7080
gcacaagcct tcgcccgtga tcgggcggta atgtggacgc ttcacatggc ggagagcgat    7140
catgatgagc ggcttcattg gatgagtccc gccgagtaca tggagtgtta cggactcttg    7200
gatgagcgtc tgcaggtcgc gcattgcgtg tactttgacc ggaaggatgt tcggctgctg    7260
caccgccaca atgtgaaggt cgcgtcgcag gttgtgagca atgcctacct cggctcaggg    7320
gtggcccccg tgccagagat ggtggagcgc ggcatggccg tgggcattgg aacagatgac    7380
gggaattgta atgactccgt aaacatgatc ggagacatga agtttatggc ccatattcac    7440
cgcgcggtgc atcgggatgc ggacgtgctg accccagaga agattcttga aatggcgacg    7500
atcgatgggg cgcgttcgtt gggaatggac cacgagattg gttccatcga aaccggcaag    7560
cgcgcggacc ttatcctgct tgacctgcgt caccctcaga cgactcctca ccatcatttg    7620
gcggccacga tcgtgtttca ggcttacggc aatgaggtgg acactgtcct gattgacgga    7680
aacgttgtga tggagaaccg ccgcttgagc tttcttcccc ctgaacgtga gttggcgttc    7740
cttgaggaag cgcagagccg cgccacagct attttgcagc gggcgaacat ggtggctaac    7800
ccagcttggc gcagcctcta gcctcaaaat atattttccc tctatcttct cgttgcgctt    7860
aatttgacta attctcatta gcgaggcgcg ccttttccata ggctccgccc ccctgacgag    7920
catcacaaaa atcgacgctc aagtcagagg tggcgaaacc cgacaggact ataaagatac    7980
caggcgtttc cccctggaag ctccctcgtg cgctctcctg ttccgaccct gccgcttacc    8040
ggatacctgt ccgcctttct cccttcggga agcgtggcgc tttctcatag ctcacgctgt    8100
aggtatctca gttcggtgta ggtcgttcgc tccaagctgg gctgtgtgca cgaaccccc     8160
gttcagcccg accgctgcgc cttatccggt aactatcgtc ttgagtccaa cccggtaaga    8220
cacgacttat cgccactggc agcagccact ggtaacagga ttagcagagc gaggtatgta    8280
ggcggtgcta cagagttctt gaagtggtgg cctaactacg gctacactag aagaacagta    8340
tttggtatct gcgctctgct gaagccagtt accttcggaa aaagagttgg tagctcttga    8400
tccggcaaac aaaccaccgc tggtagcggt ggtttttttg tttgcaagca gcagattacg    8460
cgcagaaaaa aaggatctca agaagatcct ttgatctttt ctacggggtc tgacgctcag    8520
tggaacgaaa actcacgtta agggattttg gtcatgagat tatcaaaaag gatcttcacc    8580
tagatccttt taaattaaaa atgaagtttt aaatcaatct aaagtatata tgagtaaact    8640
```

-continued

```
tggtctgaca gttaccaatg cttaatcagt gaggcaccta tctcagcgat ctgtctattt    8700
cgttcatcca tagttgcctg actcccgtc gtgtagataa ctacgatacg ggagggctta     8760
ccatctggcc ccagtgctgc aatgataccg cgagacccac gctcaccggc tccagattta    8820
tcagcaataa accagccagc cggaagggcc gagcgcagaa gtggtcctgc aactttatcc    8880
gcctccatcc agtctattaa ttgttgccgg gaagctagag taagtagttc gccagttaat    8940
agtttgcgca acgttgttgc cattgctaca ggcatcgtgg tgtcacgctc gtcgtttggt    9000
atggcttcat tcagctccgg ttcccaacga tcaaggcgag ttacatgatc ccccatgttg    9060
tgcaaaaaag cggttagctc cttcggtcct ccgatcgttg tcagaagtaa gttggccgca    9120
gtgttatcac tcatggttat ggcagcactg cataattctc ttactgtcat gccatccgta    9180
agatgctttt ctgtgactgg tgagtactca accaagtcat tctgagaata gtgtatgcgg    9240
cgaccgagtt gctcttgccc ggcgtcaata cgggataata ccgcgccaca tagcagaact    9300
ttaaaagtgc tcatcattgg aaaacgttct cggggcgaaa actctcaag gatcttaccg     9360
ctgttgagat ccagttcgat gtaacccact cgtgcaccca actgatcttc agcatctttt    9420
actttcacca cgtttctgg gtgagcaaaa acaggaaggc aaaatgccgc aaaaaaggga     9480
ataagggcga cacggaaatg ttgaatactc atactcttcc ttttcaata ttattgaagc     9540
atttatcagg gttattgtct catgagcgga tacatatttg aatgtattta gaaaaataaa    9600
cagcgatcgc gcggccgcgg gtaataactg atataattaa attgaagctc taatttgtga    9660
gtttagtata catgcattta cttataatac agttttttag ttttgctggc cgcatcttct    9720
caaatatgct tcccagcctg ctttttctgta acgttcaccc tctaccttag catcccttcc   9780
ctttgcaaat agtcctcttc caacaataat aatgtcagat cctgtagaga ccacatcatc    9840
cacggttcta tactgttgac ccaatgcgtc tcccttgtca tctaaaccca caccgggtgt    9900
cataatcaac caatcgtaac cttcatctct tccacccatg tctctttgag caataaagcc    9960
gataacaaaa tctttgtcgc tcttcgcaat gtcaacagta cccttagtat attctccagt   10020
agctagggag cccttgcatg acaattctgc taacatcaaa aggcctctag gttcctttgt   10080
tacttcttcc gccgcctgct tcaaaccgct aacaatacct gggcccacca caccgtgtgc   10140
attcgtaatg tctgcccatt ctgctattct gtatacaccc gcagagtact gcaatttgac   10200
tgtattacca atgtcagcaa attttctgtc ttcgaagagt aaaaaattgt acttggcgga   10260
taatgccttt agcggcttaa ctgtgccctc catggaaaaa tcagtcaaga tatccacatg   10320
tgtttttagt aaacaaattt tgggacctaa tgcttcaact aactccagta attccttggt   10380
ggtacgaaca tccaatgaag cacacaagtt tgtttgcttt tcgtgcatga tattaaatag   10440
cttggcagca acaggactag gatgagtagc agcacgttcc ttatatgtag ctttcgacat   10500
gatttatctt cgtttcctgc aggttttgt tctgtgcagt tgggttaaga atactgggca    10560
atttcatgtt tcttcaacac cacatatgcg tatatatacc aatctaagtc tgtgctcctt   10620
ccttcgttct tccttctgct cggagattac cgaatcaaag ctagcttatc gatgataagc   10680
tgtcaaagat gagaattaat tccacggact atagactata ctagatactc cgtctactgt   10740
acgatacact tccgctcagg tccttgtcct ttaacgaggc cttaccactc ttttgttact   10800
ctattgatcc agctcagcaa aggcagtgtg atctaagatt ctatcttcgc gatgtagtaa   10860
aactagctag accgagaaag agactagaaa tgcaaaaggc acttctacaa tggctgccat   10920
cattattatc cgatgtgacg ctgcagcttc tcaatgatat tcgaatacgc tttgaggaga   10980
tacagcctaa tatccgacaa actgttttac agatttacga tcgtacttgt tacccatcat   11040
```

```
tgaattttga acatccgaac ctgggagttt tccctgaaac agatagtata tttgaacctg   11100
tataataata tatagtctag cgctttacgg aagacaatgt atgtatttcg gttcctggag   11160
aaactattgc atctattgca taggtaatct tgcacgtcgc atccccggtt cattttctgc   11220
gtttccatct tgcacttcaa tagcatatct ttgttaacga agcatctgtg cttcattttg   11280
tagaacaaaa atgcaacgcg agagcgctaa tttttcaaac aaagaatctg agctgcattt   11340
ttacagaaca gaaatgcaac gcgaaagcgc tattttacca acgaagaatc tgtgcttcat   11400
ttttgtaaaa caaaaatgca acgcgacgag agcgctaatt tttcaaacaa agaatctgag   11460
ctgcattttt acagaacaga aatgcaacgc gagagcgcta ttttaccaac aaagaatcta   11520
tacttctttt ttgttctaca aaatgcatc ccgagagcgc tattttttcta caaagcatc    11580 ttagattact ttttttctcc tttgtgcgct ctataatgca gtctcttgat aacttttttgc  11640 actgtaggtc cgttaaggtt agaagaaggc tactttggtg tctatttttct cttccataaa  11700 aaaagcctga ctccacttcc cgcgtttact gattactagc gaagctgcgg gtgcattttt   11760
tcaagataaa ggcatccccg attatattct ataccgatgt ggattgcgca actttgtga    11820 acagaaagtg atagcgttga tgattcttca ttggtcagaa aattatgaac ggtttcttct   11880
attttgtctc tatatactac gtataggaaa tgtttacatt ttcgtattgt tttcgattca   11940
ctctatgaat agttcttact acaattttt tgtctaaaga gtaatactag agataaacat    12000
aaaaaatgta gaggtcgagt ttagatgcaa gttcaaggag cgaaaggtgg atgggtaggt   12060 tatatagggga tatagcacag agatatatag caaagagata ctttttgagca at         12112

<210> SEQ ID NO 54
<211> LENGTH: 1173
<212> TYPE: DNA
<213> ORGANISM: Rhodococcus sp.

<400> SEQUENCE: 54
ttgcgggaag tccaactgct cgacggccgc cgagttgatg ttgcatgcgc cggaccgttg     60
atctccgaaa tcggcgccca tctcgacctc accgctccag tggagatcga ctgtggcggc   120
ggcctggcga cgcgaccgtt caccgaaccc catttgcacc tcgacaaggc ggggaccgcc   180
gatcgtctac cggcaggcgc cagcaccatc ggtgatgcga tcgccgccat gcaatcggtg   240
aaagtcactg agcgcgacaa tgtggcggcg tcgccgcac gaatgcaccg cgtcctgaac    300
cgcattgtcg acgatggttc ccacgccatt cgcgctctcg tcgacgtcga tgaggtctgg   360
ggattgaccg cttttcatgc agcccaacaa gtccaagctg ctctcgcgcc gcgcgcggta   420
gtacaaatcg tggccttccc acaacatggc ctcaccccgc aggtacttgc catgctcgag   480
caagcggccg cagaaggtgc aggagcactc ggcgcccaca ccgacgtcga ccctgaccca   540
gcggcgcacg tcggtgctgt ggccgccatt gccgccgggg catcgctacc gctcgaagtc   600
cacactgatg aaggcgccag tcccgacaag ttctacttgc ctgcagtact ggaggtcctc   660
gaccggtttc ctggactctc gacgaccctc gcacactgtc tgtcactcgg aacgatcgcg   720
ccgaaacaac agcagcactg gattgaggaa ctggcccatc gggacatcaa agtctgtgtc   780
gcgcctagca ttttaggttt cggcctgccc ttggcgccag tccgggcact catcgaggcc   840
ggcgtcggaa tacttgtcgg atcagacaac ctgcaggacg ttttctttcc gctcggtacg   900
ggccgcgcca tcgaaaacgt gcgtctgctg gcgaccgcag cacagctcac cgcacctgag   960
ctcgctggcc cgctcatcgc aggtgtcacc gacatccgcgt acgccaccgt gaccggcgca  1020
```

| | |
|---|---|
| gcagatgcac tggcggtgga atcccccgca accctcgtcg tccacgacgc gacctcgccg | 1080 |
| gcggagctgc ttcgcggcat cgacggtact cgaatcaccg ttatcgacgg cctgttgaca | 1140 |
| tccccgctcc aactcgacaa aggaatcaag tga | 1173 |

<210> SEQ ID NO 55
<211> LENGTH: 1239
<212> TYPE: DNA
<213> ORGANISM: Pseudomonas sp.

<400> SEQUENCE: 55

| | |
|---|---|
| atgtcaatgg aaacccatag ttatgtagac gtcgcaattc gtaacgcgcg tcttgccgat | 60 |
| acggagggaa ttgtcgatat tcttattcac gatgggcgca ttgcgtccat cgtgaagtcg | 120 |
| acaaaaacaa aaggatcggt ggagatcgat gctcatgagg gtctggtcac ttccggcctg | 180 |
| gtagagcctc acatccatct cgataaggcc ctgacggcag atcgggttcc cgcaggaagc | 240 |
| attggcgacc ttcgaacgcg acgaggcctt gagatggcaa ttcgggccac ccgtgatatc | 300 |
| aagcgtacgt tcacggttga agatgttcga gaacgggcca tacgtgcggc cctgatggca | 360 |
| tcccgtgcgg gaaccaccgc attgcggaca cacgtcgatg tcgacccgat tgtcggcctc | 420 |
| gcaggtatcc gtggtgtcct tgaggcgcgt gaagtctgcg cgggattgat cgatatccag | 480 |
| atcgtcgcct tccctcagga gggactcttc tgctctgcgg gggccgtgga cctcatgcgg | 540 |
| gaggcgatca aactgggcgc ggatgccgtc ggcggcgcac ccgcgctgga tgatcgcccg | 600 |
| caggaccatg tccgagccgt ttttgacctt gctgctgagt tcggcctgcc cgtagacatg | 660 |
| cacgtcgatg agtccgaccg gcgggaagac tttacgcttc cctttgtgat tgaagctgcc | 720 |
| cgtgaacggc gtgtgcccaa tgtgaccgtc gcgcacatca gctcgctgtc cgtacagacg | 780 |
| gatgacgtag cacggtcgac cattgccgcc cttgcggacg ccgatgttaa tgtcgtggtt | 840 |
| aatccgatca ttgtcaaaat tacgcggctg agtgaattac tcgatgccgg agtctccgta | 900 |
| atgtttggct cggacaacct gcgggatccg ttctatccgc tcggagcggc gaatcccctt | 960 |
| ggatcagcca ttttttgcctg tcaaattgcc gcgctgggaa caccgcaaga tctcagacgg | 1020 |
| gtattcgatg cggtcaccat caacgctgcc cgcatgctgg gattcccctc acttttaggc | 1080 |
| gtcgtggaag gggcagtcgc ggatctcgca gtattcccat cggcgacgcc cgaggaggtt | 1140 |
| gttctggatc aacagtctcc gctcttcgta ctcaagggcg gacgtgtcgt tgccatgcga | 1200 |
| ttggccgctg gatcaacgtc gttccgcgac tactcatga | 1239 |

<210> SEQ ID NO 56
<211> LENGTH: 726
<212> TYPE: DNA
<213> ORGANISM: Rhodococcus sp.

<400> SEQUENCE: 56

| | |
|---|---|
| atgatatact caacagtcaa cgctaatcct tacgcttggc cttacgatgg ttcaatagac | 60 |
| cctgctcaca ccgctttaat cttaatcgat tggcaaatag acttttgtgg tccaggtggt | 120 |
| tatgtcgatt ccatgggtta cgacttatcc ttgactagaa gtggtttaga acctacagca | 180 |
| agagtattgg ctgcagccag agatactggt atgacagtta tccatactag agaaggtcac | 240 |
| agaccagatt tggctgactt gccacctaat aagagatgga gatctgcatc agccggtgct | 300 |
| gaaatcggtt cagttggtcc atgtggtaga attttagtca gaggtgaacc tggttgggaa | 360 |
| atagtaccag aagttgcacc tagagaaggt gaaccaatta tagataaacc tggtaaaggt | 420 |
| gctttctacg caacagattt ggacttgttg ttgagaacaa gaggtatcac ccatttgatt | 480 |

```
ttgaccggta taactacaga tgtttgcgtc cacaccacta tgagagaagc caacgataga    540
ggttacgaat gtttaattt gtctgattgc accggtgcta ctgacagaaa gcatcacgaa     600
gctgcattat ctatggtcac catgcaaggt ggtgtattcg gtgcaactgc ccattcagat    660
gacttattgg ccgctttggg tacaaccgtt ccagcagccg ctggtcctag agctagaaca    720
gaataa                                                              726
```

<210> SEQ ID NO 57
<211> LENGTH: 702
<212> TYPE: DNA
<213> ORGANISM: Rhizobium leguminosarum

<400> SEQUENCE: 57

```
atggacgcga tggtcgaaac caaccggcat tttatcgacg ccgatccgta tccgtggccc     60
tataacggag ctctgaggcc tgacaatacc gccctcatca tcatcgacat gcagacggat    120
ttctgcggca agggcggtta tgtcgaccac atgggctacg acctgtcgct ggtgcaggcg    180
ccgatcgaac ccatcaaacg cgtgcttgcc gccatgcggg ccaagggtta tcacatcatc    240
cacacccgcg agggccaccg ccccgacctc gccgatctgc cagcaaacaa cgctggcgc    300 tcgcaacgga tcggggccgg catcggtgat cccggcccct gcggccgaat cctgacgcgt    360
ggcgaacccg ctgggacat catccccgaa ctctacccga tcgaaggcga cgatcatc     420 gacaagcccg gcaagggttc gttctgcgcc accgacctcg aactcgtcct caaccagaaa    480
cgcatcgaga acattatcct caccgggatc accaccgatg tctgcgtctc gacgacgatg    540
cgcgaggcga acgaccgcgg ctacgaatgc ctgctgctgg aggactgctg tggtgcgacc    600
gactacggaa accacctcgc cgccatcaag atggtgaaga tgcagggcgg cgtcttcggc    660
tcggtctcca attccgcggc tctagtcgag gcgctgccct ga                       702
```

<210> SEQ ID NO 58
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Leu Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Asp Asn Ala Asp
        115                 120                 125

Ser Ala Ile Tyr Pro Gly Asn Ile Glu Ala Ala Met Ala Val Tyr Gly
```

130                 135                 140
Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                    165                 170                 175

Gln Val Glu Leu Cys Ser Ile Met Glu Thr Ala Val Ala Lys Asp
                180                 185                 190

Arg Ile Thr Ala Leu Ser Asp Gln Tyr His Gly Thr Ala Gly Gly Arg
                    195                 200                 205

Ile Ser Val Trp Pro Ala Pro Ala Ile Thr Pro Ala Val Thr Val Glu
210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                    245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
                    275                 280                 285

His Arg His Asn Val Lys Val Ala Ser Gln Val Val Ser Asn Ala Tyr
290                 295                 300

Leu Gly Ser Gly Val Ala Pro Val Pro Glu Met Val Glu Arg Gly Met
305                 310                 315                 320

Ala Val Gly Ile Gly Thr Asp Asp Gly Asn Cys Asn Asp Ser Val Asn
                    325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
                    355                 360                 365

Ile Asp Gly Ala Arg Ser Leu Gly Met Asp His Glu Ile Gly Ser Ile
                    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                    405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
                435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu
465                 470

<210> SEQ ID NO 59
<211> LENGTH: 423
<212> TYPE: DNA
<213> ORGANISM: Saccharomyces cerevisiae

<400> SEQUENCE: 59
aggaacccat caggttggtg aagattacc cgttctaaga cttttcagct tcctctattg    60
atgttacacc tggacacccc tttctggca tccagttttt aatcttcagt ggcatgtgag   120
attctccgaa attaattaaa gcaatcacac aattctctcg gataccacct cggttgaaac   180

```
tgacaggtgg tttgttacgc atgctaatgc aaaggagcct atataccttt ggctcggctg    240
ctgtaacagg gaatataaag ggcagcataa tttaggagtt tagtgaactt gcaacattta    300 ctatttccc ttcttacgta aatattttc tttttaattc taaatcaatc tttttcaatt     360
ttttgtttgt attcttttct tgcttaaatc tataactaca aaaacacat acataaacta    420 aaa                                                                 423

<210> SEQ ID NO 60
<211> LENGTH: 658
<212> TYPE: DNA
<213> ORGANISM: Saccharomyces cerevisiae

<400> SEQUENCE: 60
ttgctacgca ggctgcacaa ttacacgaga atgctcccgc ctaggattta aggctaaggg     60
acgtgcaatg cagacgacag atctaaatga ccgtgtcggt gaagtgttcg ccaaactttt    120
cggttaacac atgcagtgat gcacgcgcga tggtgctaag ttacatatat atatatatat    180
atatatatat atatatatag ccatagtgat gtctaagtaa cctttatggt atatttctta    240
atgtggaaag atactagcgc gcgcacccac acacaagctt cgtcttttct tgaagaaaag    300
aggaagctcg ctaaatggga ttccactttc cgttccctgc cagctgatgg aaaaaggtta    360
gtggaacgat gaagaataaa agagagatc cactgaggtg aaatttcagc tgacagcgag    420
tttcatgatc gtgatgaaca atggtaacga gttgtggctg ttgccaggga gggtggttct    480 caactttta tgtatggcca aatcgctact tgggtttgtt ataacaaa gaagaaataa    540 tgaactgatt ctcttcctcc ttcttgtcct ttccttaattc tgttgtaatt accttccttt   600
gtaatttttt ttgtaattat tcttcttaat aatccaaaca aacacacata ttacaata     658

<210> SEQ ID NO 61
<211> LENGTH: 573
<212> TYPE: DNA
<213> ORGANISM: Saccharomyces cerevisiae

<400> SEQUENCE: 61
tgctgtaacc cgtacatgcc caaaataggg ggcgggttac acagaatata taacatcgta     60
ggtgtctggg tgaacagttt attcctggca tccactaaat ataatggagc ccgcttttta    120
agctggcatc cagaaaaaaa aagaatccca gcaccaaaat attgttttct tcaccaacca    180
tcagttcata ggtccattct cttagcgcaa ctacagagaa caggggcaca aacaggcaaa    240
aaacgggcac aacctcaatg gagtgatgca acctgcctgg agtaaatgat gacacaaggc    300
aattgaccca cgcatgtatc tatctcattt tcttacacct tctattacct tctgctctct    360
ctgatttgga aaaagctgaa aaaaaaggtt gaaaccagtt ccctgaaatt attcccctac    420
ttgactaata agtatataaa gacggtaggt attgattgta attctgtaaa tctatttctt    480
aaacttctta aattctactt ttatagttag tctttttttt agttttaaaa caccaagaac    540
ttagtttcga ataaacacac ataaacaaac aaa                                573

<210> SEQ ID NO 62
<211> LENGTH: 812
<212> TYPE: DNA
<213> ORGANISM: Saccharomyces cerevisiae

<400> SEQUENCE: 62
gcaccgctgg cttgaacaac aataccagcc ttccaacttc tgtaaataac ggcggtacgc     60
cagtgccacc agtaccgtta cctttcggta tacctccttt ccccatgttt ccaatgccct    120
```

```
tcatgcctcc aacggctact atcacaaatc ctcatcaagc tgacgcaagc cctaagaaat      180
gaataacaat actgacagta ctaaataatt gcctacttgg cttcacatac gttgcatacg      240
tcgatataga taataatgat aatgacagca ggattatcgt aatacgtaat agttgaaaat      300
ctcaaaaatg tgtgggtcat tacgtaaata atgataggaa tgggattctt ctattttttcc    360 ttttccatt ctagcagccg tcgggaaaac gtggcatcct ctctttcggg ctcaattgga       420
gtcacgctgc cgtgagcatc ctctcttttcc atatctaaca actgagcacg taaccaatgg    480
aaaagcatga gcttagcgtt gctccaaaaa agtattggat ggttaatacc atttgtctgt     540
tctcttctga ctttgactcc tcaaaaaaaa aaaatctaca atcaacagat cgcttcaatt     600
acgccctcac aaaaactttt ttccttcttc ttcgcccacg ttaaatttta tccctcatgt     660
tgtctaacgg atttctgcac ttgatttatt ataaaaagac aaagacataa tacttctcta    720
tcaatttcag ttattgttct tccttgcgtt attcttctgt tcttcttttt cttttgtcat    780
atataaccat aaccaagtaa tacatattca aa                                    812

<210> SEQ ID NO 63
<211> LENGTH: 625
<212> TYPE: DNA
<213> ORGANISM: Yarrowia lipolytica

<400> SEQUENCE: 63
tataaacggt attttcacaa ttgcacccca gccagaccga tagccggtcg caatccgcca      60
cccacaaccg tctacctccc acagaaccccc gtcacttcca cccttttcca ccagatcata    120
tgtcccaact tgccaaatta aaaccgtgcg aattttcaaa ataaactttg gcaaagaggc     180
tgcaaaggag gggctggtga gggcgtctgg aagtcgacca gagaccgggt tggcggcgca     240
tttgtgtccc aaaaaacagc cccaattgcc ccaattgacc caaattgac ccagtagcgg      300 gcccaacccc ggcgagagcc ccttctccc cacatatcaa acctccccg gttcccacac      360 ttgccgttaa gggcgtaggg tactgcagtc tggaatctac gcttgttcag actttgtact    420
agtttctttg tctggccatc cgggtaaccc atgccggacg caaatagac tactgaaaat     480 ttttttgctt tgtggttggg actttagcca agggtataaa agaccaccgt ccccgaatta    540
cctttcctct tcttttctct ctctccttgt caactcacac ccgaaatcgt taagcatttc    600
cttctgagta taagaatcat tcaaa                                            625

<210> SEQ ID NO 64
<211> LENGTH: 318
<212> TYPE: DNA
<213> ORGANISM: Saccharomyces cerevisiae

<400> SEQUENCE: 64
gcataatatt gtccgctgcc cgttttctg ttagacggtg tcttgatcta cttgctatcg       60
ttcaacacca cctattttc taactatttt ttttttagct catttgaatc agcttatggt     120
gatggcacat ttttgcataa acctagctgt cctcgttgaa cataggaaaa aaaaatatat     180
aaacaaggct ctttcactct ccttggaatc agatttgggt tgttcccctt tattttcata    240
tttcttgtca tattctttc tcaattatta tcttctactc ataacctcac gcaaaataac    300
acagtcaaat caatcaaa                                                    318

<210> SEQ ID NO 65
<211> LENGTH: 413
<212> TYPE: DNA
```

<213> ORGANISM: Saccharomyces cerevisiae

<400> SEQUENCE: 65

```
catagcttca aaatgtttct actccttttt tactcttcca gattttctcg gactccgcgc      60
atcgccgtac cacttcaaaa cacccaagca cagcatacta aatttcccct ctttcttcct     120
ctagggtgtc gttaattacc cgtactaaag gtttggaaaa gaaaaagag accgcctcgt     180
ttctttttct tcgtcgaaaa aggcaataaa aattttatc acgttctttt ttcttgaaaa     240
tttttttttt tgattttttt ctctttcgat gacctcccat tgatatttaa gttaataaac     300
ggtcttcaat ttctcaagtt tcagtttcat ttttcttgtt ctattacaac ttttttttact    360
tcttgctcat tagaaagaaa gcatagcaat ctaatctaag ttttaattac aaa            413
```

<210> SEQ ID NO 66
<211> LENGTH: 330
<212> TYPE: DNA
<213> ORGANISM: Saccharomyces cerevisiae

<400> SEQUENCE: 66

```
taagattaat ataattatat aaaaatatta tcttcttttc tttatatcta gtgttatgta      60
aaataaattg atgactacgg aaagcttttt tatattgttt ctttttcatt ctgagccact     120
taaatttcgt gaatgttctt gtaagggacg gtagatttac aagtgataca acaaaaagca     180
aggcgctttt tctaataaaa agaagaaaag catttaacaa ttgaacacct ctatatcaac     240
gaagaatatt actttgtctc taaatccttg taaaatgtgt acgatctcta tatgggttac     300
tcataagtgt accgaagact gcattgaaag                                       330
```

<210> SEQ ID NO 67
<211> LENGTH: 377
<212> TYPE: DNA
<213> ORGANISM: Saccharomyces cerevisiae

<400> SEQUENCE: 67

```
gtctgaagaa tgaatgattt gatgatttct ttttccctcc attttcttta ctgaatatat      60
caatgatata gacttgtata gtttattatt tcaaattaag tagctatata tagtcaagat     120
aacgtttgtt tgacacgatt acattattcg tcgacatctt ttttcagcct gtcgtggtag     180
caatttgagg agtattatta attgaatagg ttcattttgc gctcgcataa acagttttcg     240
tcagggacag tatgttggaa tgagtggtaa ttaatggtga catgacatgt tatagcaata     300
accttgatgt ttacatcgta gtttaatgta caccccgcga attcgttcaa gtaggagtgc     360
accaattgca aagggaa                                                     377
```

<210> SEQ ID NO 68
<211> LENGTH: 506
<212> TYPE: DNA
<213> ORGANISM: Saccharomyces cerevisiae

<400> SEQUENCE: 68

```
gtgaatttac tttaaatctt gcatttaaat aaattttctt tttatagctt tatgacttag      60
tttcaattta tatactattt taatgacatt ttcgattcat tgattgaaag ctttgtgttt     120
tttcttgatg cgctattgca ttgttcttgt cttttcgcc acatgtaata tctgtagtag     180
atacctgata cattgtggat gctgagtgaa attttagtta ataatggagg cgctcttaat     240
aattttgggg atattggctt tttttttttaa agttacaaa tgaattttttt ccgccaggat     300
aacgattctg aagttactct tagcgttcct atcggtacag ccatcaaatc atgcctataa     360
```

```
atcatgccta tatttgcgtg cagtcagtat catctacatg aaaaaaactc ccgcaatttc    420
ttatagaata cgttgaaaat taaatgtacg cgccaagata agataacata tatctagatg    480
cagtaatata cacagattcc cgcgga                                         506
```

<210> SEQ ID NO 69
<211> LENGTH: 199
<212> TYPE: DNA
<213> ORGANISM: Saccharomyces cerevisiae

<400> SEQUENCE: 69

```
gttaattcaa attaattgat atagtttttt aatgagtatt gaatctgttt agaaataatg     60
gaatattatt tttatttatt tatttatatt attggtcggc tctttcttc tgaaggtcaa    120 tgacaaaatg atatgaagga ataatgatt tctaaaattt tacaacgtaa gatattttta    180
caaaagccta gctcatctt                                                 199
```

<210> SEQ ID NO 70
<211> LENGTH: 400
<212> TYPE: DNA
<213> ORGANISM: Yarrowia lipolytica

<400> SEQUENCE: 70

```
gctgcttgta cctagtgcaa ccccagtttg ttaaaaatta gtagtcaaaa acttctgagt     60
tagaaatttg tgagtgtagt gagattgtag agtatcatgt gtgtccgtaa gtgaagtgtt    120
attgactctt agttagttta tctagtactc gttagttga cactgatcta gtattttacg    180
aggcgtatga ctttagccaa gtgttgtact tagtcttctc tccaaacatg agagggctct    240
gtcactcagt cggcctatgg gtgagatggc ttggtgagat ctttcgatag tctcgtcaag    300
atggtaggat gatgggggaa tacattactg ctctcgtcaa ggaaaccaca atcagatcac    360
accatcctcc atggtatccg atgactctct tctccacagt                          400
```

<210> SEQ ID NO 71
<211> LENGTH: 203
<212> TYPE: DNA
<213> ORGANISM: Saccharomyces cerevisiae

<400> SEQUENCE: 71

```
acaagctaag ttgactgctg ctaccaacgc taagcaataa gcgatttaat ctctaattat     60
tagttaaagt tttataagca tttttatgta acgaaaaata aattggttca tattattact    120
gcactgtcac ttaccatgga aagaccagac aagaagttgc cgacacgaca gtctgttgaa    180
ttggcttaag tctgggtccg ctt                                            203
```

<210> SEQ ID NO 72
<211> LENGTH: 274
<212> TYPE: DNA
<213> ORGANISM: Saccharomyces cerevisiae

<400> SEQUENCE: 72

```
caggcccctt ttcctttgtc gatatcatgt aattagttat gtcacgctta cattcacgcc     60
ctcctcccac atccgctcta accgaaaagg aaggagttag acaacctgaa gtctaggtcc    120
ctatttattt tttttaatag ttatgttagt attaagaacg ttatttatat ttcaaatttt    180
tctttttttt ctgtacaaac gcgtgtacgc atgtaacatt atactgaaaa ccttgcttga    240
gaaggttttg ggacgctcga aggctttaat ttgc                                274
```

```
<210> SEQ ID NO 73
<211> LENGTH: 67
<212> TYPE: DNA
<213> ORGANISM: Escherichia coli

<400> SEQUENCE: 73
agctggtgac aattaatcat cggctcgtat aatgtgtgga attgaatcga tataaggagg     60
ttaatca                                                               67

<210> SEQ ID NO 74
<211> LENGTH: 89
<212> TYPE: DNA
<213> ORGANISM: Escherichia coli

<400> SEQUENCE: 74
ctcaaaatat attttccctc tatcttctcg ttgcgcttaa tttgactaat tctcattagc     60
gaggcgcgcc tttccatagg ctccgcccc                                       89

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaaatccat t                                                          11

<210> SEQ ID NO 76
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76 ggaacgacc                                                             9
```

MICROORGANISMS ENGINEERED TO USE UNCONVENTIONAL SOURCES OF NITROGEN

RELATED APPLICATIONS

This application is the U.S. National Stage filed under 35 U.S.C. §371 of PCT Patent Application serial number PCT/US2014/010332, filed Jan. 6, 2014, which claims the benefit of priority to U.S. Provisional Patent Application Ser. No. 61/748,901, filed Jan. 4, 2013, and 61/782,351, filed Mar. 14, 2013.

SEQUENCE LISTING

The instant application contains a Sequence Listing which has been submitted electronically in ASCII format and is hereby incorporated by reference in its entirety. Said ASCII copy, created on Feb. 14, 2014, is named NGX-016.25_SL.txt and is 284,885 bytes in size.

BACKGROUND

In the fermentation industry, cell culture media is typically formulated to provide all nutrients necessary for the growth of a host cell line, with particular emphasis on meeting the cell line's requirements for carbon, nitrogen, phosphorus, sulfur, and other major nutrients. Some cell lines require additional components, including amino acids, trace minerals and metals, and complex growth factors. The presence of these nutrients provides a suitable growth environment for the organism of choice and, unfortunately, for any potential contaminating organisms. In this environment the production organism is required to compete directly with any contaminant organism in the cell culture.

Even in robust hosts, the combination of opportunistic infections of the culture and the metabolic burden resulting from the demands of product manufacture is a major concern in monoculture operations. Industrial robustness is typically considered a multigenic trait specific to the host strain and thus difficult to engineer predictably into organisms late in the development process. Addition of selective growth inhibitors, such as bacterial antibiotics, is one method used to create a more robust fermentation environment for host organisms that are resistant to the growth inhibitor. However, antibiotic addition is often undesirable or unfeasible, and spontaneously resistant contaminations frequently result.

Accordingly, there exists a need for rationally engineered traits that, when engineered into a host organism, create a robust monoculture fermentation environment.

SUMMARY OF THE INVENTION

In certain embodiments, the invention relates to a genetically engineered organism, wherein the genetically engineered organism has been transformed by a nucleic acid molecule comprising any one or more of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of allophanate hydrolase, biuret amidohydrolase, cyanuric acid amidohydrolase, guanine deaminase, melamine deaminase, isopropylammelide isopropylaminohydrolase, cyanamide hydratase, urease, and urea carboxylase.

In certain embodiments, the invention relates to a method, comprising the step of
contacting any one of the aforementioned genetically engineered organisms with a substrate,
wherein
the substrate comprises a nitrogen-containing fraction and a non-nitrogen-containing fraction;
the nitrogen-containing fraction comprises, in an amount from about 10% by weight to about 100% by weight, a nitrogen-containing compound of any one of Formulas I-III, or a salt thereof;
a native organism of the same species as the genetically engineered organism could not metabolize (i.e., use as a source of nitrogen) the nitrogen-containing compound;
the genetically engineered organism converts the substrate to a product; and
the compound of formula I is

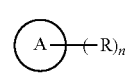

wherein, independently for each occurrence,
Ⓐ is a five-, six, nine-, or ten-membered aryl or heteroaryl group;
R is —OH, —CO$_2$H, —NO$_2$, —CN, substituted or unsubstituted amino, or substituted or unsubstituted alkyl; and
n is 0, 1, 2, 3, 4, or 5;
the compound of formula II is

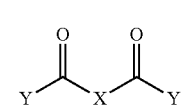

wherein, independently for each occurrence,
X is —NH—, —N(alkyl)-, —O—, —C(R$^1$)$_2$—, —S—, or absent;
Y is —H, —NH$_2$, —N(H)(alkyl), —N(alkyl)$_2$, —CO$_2$H, —CN, or substituted or unsubstituted alkyl; and
R$^1$ is —H, —OH, —CO$_2$H, —NO$_2$, —CN, substituted or unsubstituted amino, or substituted or unsubstituted alkyl; and
the compound of formula III is

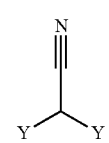

wherein, independently for each occurrence,
Y is —H, —NH$_2$, —N(H)(alkyl), —N(alkyl)$_2$, —CO$_2$H, —CN, or substituted or unsubstituted alkyl.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen containing fraction consists essentially of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a method comprising the step of contacting any one of the aforementioned genetically engineered organisms with a substrate, wherein the substrate consists of a nitrogen-containing fraction and a non-nitrogen-containing fraction;

the nitrogen containing fraction consists of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and the genetically engineered organism converts the substrate to a product.

In certain embodiments, the invention relates to a product made by any one of the aforementioned methods.

In certain embodiments, the invention relates to a recombinant vector comprising a gene operably linked to a promoter, wherein the gene encodes an enzyme; and the enzyme is allophanate hydrolase, biuret amidohydrolase, cyanuric acid amidohydrolase, guanine deaminase, melamine deaminase, isopropylammelide isopropylaminohydrolase, cyanamide hydratase, urease, or urea carboxylase.

BRIEF DESCRIPTION OF THE FIGURES

FIG. 2 tabulates exemplary compounds capable of delivering nitrogen that could be accessed by an engineered organism.

FIG. 3 tabulates DNA and protein sequences encoding the melamine degradation pathway.

FIG. 11 tabulates the concentrations of the components in the MOPS medium used in Example 9.

Because ammeline has five nitrogen atoms, organisms having the ability to utilize melamine should be approximately five times more efficient (see, for example, NS110 on 0.25 mM ammeline, as compared to a native organism on 1.25 mM $NH_4Cl$).

Figure 26:
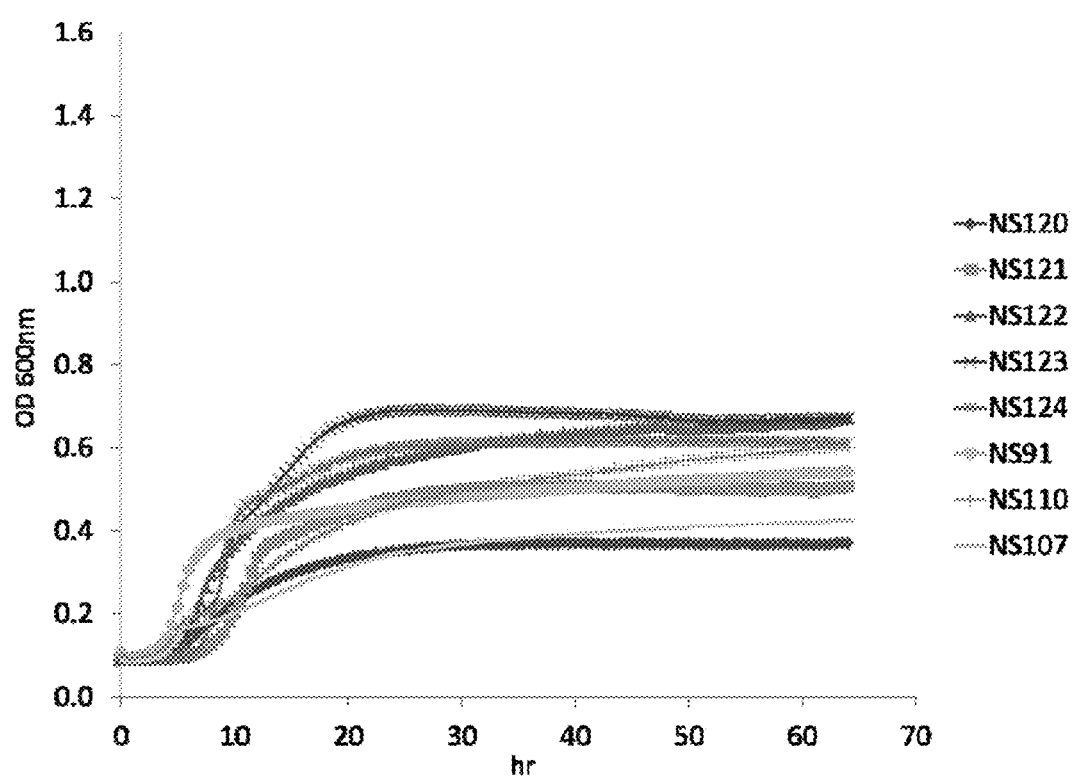

FIG. 26 depicts the growth of various organisms of the invention on 0.5 mM $NH_4Cl$. Importantly, the organisms described in FIGS. 26-28, for example NS120, NS91, NS107, and NS123, are *E. coli* strains derived from *E. coli* K12, *E. coli* B, *E. coli* Crooks, and *E. coli* MG1655 and are intended to show the breadth of the invention across various strains of *E. coli*.

Figure 27:
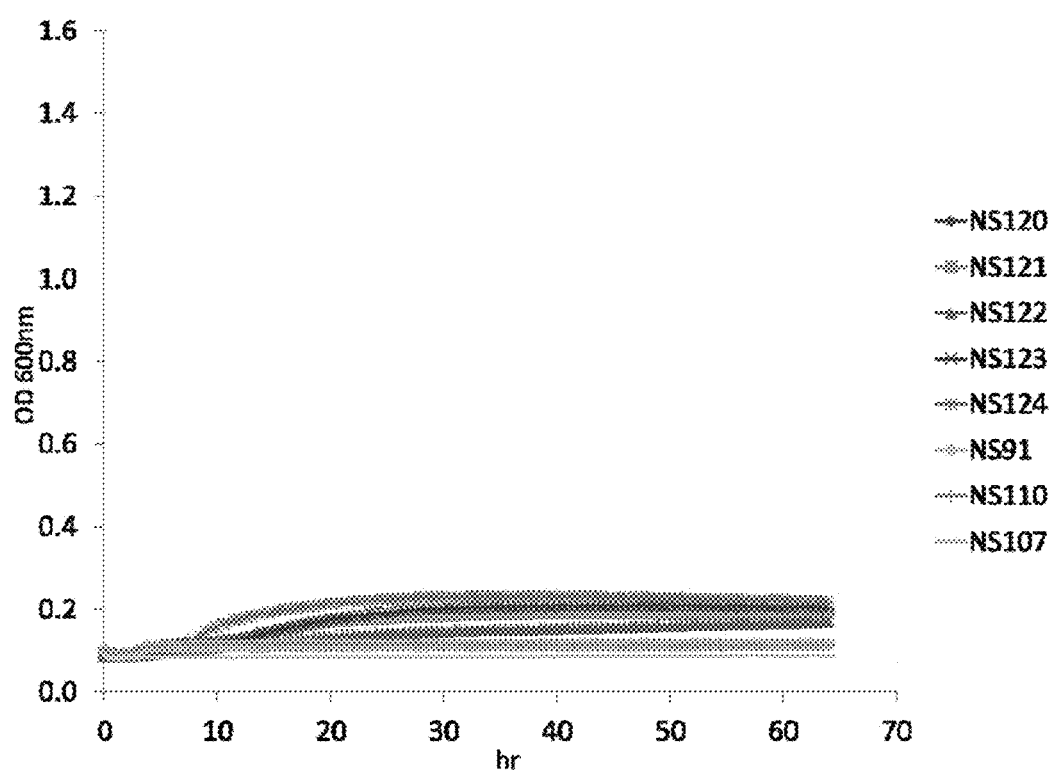

FIG. 27 depicts the growth of various organisms of the invention on a medium containing no nitrogen.

Figure 28:
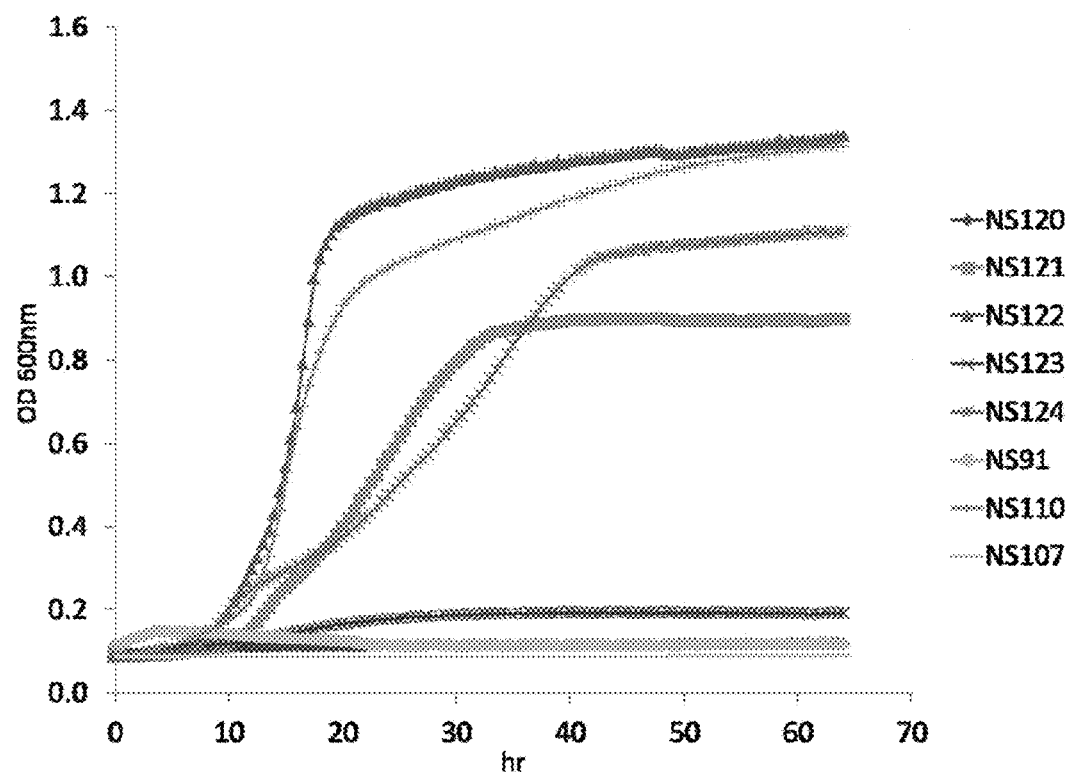

FIG. 28 depicts the growth of various organisms of the invention on a medium containing 0.5 mM melamine.

FIG. 29 tabulates a summary of various plasmids of the invention.

FIG. 30 tabulates a summary of various organisms of the invention.

FIG. 31 tabulates the components and molar concentrations of each component in a MOPS defined medium, which is used, for example, with *E. coli*.

FIG. 32 tabulates the components and weight concentrations of each component in a YNB medium, which is used, for example, with *S. cerevisiae*.

FIG. 33 tabulates the components and weight concentrations of each component in a SC amino acid medium.

DETAILED DESCRIPTION OF THE INVENTION

Overview

In certain embodiments, the invention relates to a genetically engineered host organism, wherein the genetically engineered host organism has a non-native ability to obtain a growth-limiting nutrient from a complex substrate; and the complex substrate could not have been metabolized or used as a nutrient by the native host organism. In certain embodiments, the non-native ability will provide the organism with a significant competitive advantage, and provide a major barrier to the success of contaminants in a fermentation. In certain embodiments, the genetically engineered host organism is a bacterium, a yeast, a fungus, a mammalian cell, or an insect cell. In certain embodiments, the genetically engineered host organism is a bacterium or a yeast.

In certain embodiments, the invention relates to a method of using the above-mentioned genetically engineered host organism, comprising contacting the genetically engineered host organism with a modified cell culture medium. In certain embodiments, the invention relates to a method of using the above-mentioned genetically engineered host organism, comprising contacting the genetically engineered host organism with a modified cell culture medium, wherein the genetically engineered host organism converts the cell culture medium to a product. In certain embodiments, using this approach provides a unique and targeted manner to promote the growth of the desired genetically engineered host organism. In certain embodiments, the above-mentioned methods minimize the growth of contaminant organisms, provide a valuable competitive advantage, and allow management of production of a range of valuable products.

In certain embodiments, the inventive methods decrease or eliminate the need for use of prophylactic antibiotics in large scale yeast cultures. Avoiding unnecessary antibiotics is an important benefit due to emerging environmental considerations and societal pressures. Additionally, in certain embodiments, the technique can be applied to bacterial systems in which antibiotics may not be added.

In certain embodiments, the genetically engineered host organism is a yeast; and the product is ethanol, isobutanol, lactic acid, an isoprenoid, a lipid, and enzyme product, or a high value specialty chemical.

In certain embodiments, the genetically engineered host organism is a bacterium; and the product is butanol, ethanol, isopropanol, 1,3-propanediol (PDO), 1,4-butanediol (BDO), succinic acid, itaconic acid, an enzyme product, a polyol, a protein product, or a high value specialty chemical.

In certain embodiments, the inventive technology is applicable in the production of one or more commodities, fine chemicals, and pharmaceuticals.

Definitions

"Dry weight" and "dry cell weight" mean weight determined in the relative absence of water. For example, reference to oleaginous cells as comprising a specified percentage of a particular component by dry weight means that the percentage is calculated based on the weight of the cell after substantially all water has been removed.

"Exogenous gene" is a nucleic acid that codes for the expression of an RNA and/or protein that has been introduced into a cell (e.g., by transformation/transfection), and is also referred to as a "transgene." A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell as an insertion into the genome (nuclear or plastid) or as an episomal molecule.

"Expression vector" or "expression construct" or "plasmid" or "recombinant DNA construct" is a vehicle for introducing a nucleic acid into a host cell. The nucleic acid can be one that has been generated via human intervention, including by recombinant means or direct chemical synthesis, with a series of specified nucleic acid elements that permit transcription and/or translation of a particular nucleic acid. The expression vector can be part of a plasmid, virus, or nucleic acid fragment, or other suitable vehicle. Typically, the expression vector includes a nucleic acid to be transcribed operably linked to a promoter.

"Inducible promoter" is a promoter that mediates transcription of an operably linked gene in response to a particular stimulus.

"In operable linkage" is a functional linkage between two nucleic acid sequences, such a control sequence (typically a promoter) and the linked sequence (typically a sequence that encodes a protein, also called a coding sequence). A promoter is in operable linkage with an exogenous gene if it can mediate transcription of the gene.

"Lysate" is a solution containing the contents of lysed cells.

"Lysis" is the breakage of the plasma membrane and optionally the cell wall of a biological organism sufficient to release at least some intracellular content, often by mechanical, viral or osmotic mechanisms that compromise its integrity.

"Lysing" is disrupting the cellular membrane and optionally the cell wall of a biological organism or cell sufficient to release at least some intracellular content.

"Osmotic shock" is the rupture of cells in a solution following a sudden reduction in osmotic pressure. Osmotic shock is sometimes induced to release cellular components of such cells into a solution.

The terms "plasmid", "vector" and "cassette" refer to an extra chromosomal element often carrying genes that are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements, in addition to the foreign gene, that facilitate transformation of a particular host cell. "Expression cassette" refers to a specific vector containing a foreign gene and having elements in addition to the foreign gene that allow for enhanced expression of that gene in a foreign host.

"Promoter" is a nucleic acid control sequence that directs transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

"Recombinant" is a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

"Sonication" is a process of disrupting biological materials, such as a cell, by use of sound wave energy.

"Transformation" refers to the transfer of a nucleic acid fragment into a host organism or the genome of a host organism, resulting in genetically stable inheritance. Host organisms containing the transformed nucleic acid fragments are referred to as "recombinant", "transgenic" or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

Microbe Engineering

A. Overview

In certain embodiments of the invention, a microorganism is genetically modified to improve or provide de novo growth characteristics on a variety of feedstock materials.

Genes and gene products may be introduced into microbial host cells. Suitable host cells for expression of the genes and nucleic acid molecules are microbial hosts that can be found broadly within the fungal or bacterial families and which grow over a wide range of temperature, pH values, and solvent tolerances. Examples of suitable host strains include but are not limited to fungal or yeast species, such as *Aspergillus, Trichoderma, Saccharomyces, Pichia, Candida, Hansenula, Kluyveromyces*, or bacterial species, such as member of the proteobacteria and actinomycetes as well as the specific genera *Acinetobacter, Arthrobacter, Brevibacterium, Acidovorax, Bacillus, Clostridia, Streptomyces, Escherichia, Salmonella, Pseudomonas*, and *Cornyebacterium*.

*E. coli* is well suited to use as the host microorganism in the invention fermentative processes.

Microbial expression systems and expression vectors containing regulatory sequences that direct high level expression of foreign proteins are well known to those skilled in the art. Any of these could be used to construct chimeric genes to produce the any one of the gene products of the instant sequences. These chimeric genes could then be introduced into appropriate microorganisms via transformation techniques to provide high-level expression of the enzymes.

For example, a gene encoding an enzyme can be cloned in a suitable plasmid, and the aforementioned starting parent strain as a host can be transformed with the resulting plasmid. This approach can increase the copy number of each of the genes encoding the enzymes and, as a result, the activities of these enzymes can be increased. The plasmid is not particularly limited so long as it can autonomously replicate in the microorganism.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (see, for example, Molecular Cloning: A Laboratory Manual, Sambrook et al. (3d edition, 2001, Cold Spring Harbor Press; and U.S. Pat. No. 4,683,202 (incorporated by reference)). Alternatively, elements can be generated synthetically using known methods (see, for example, Gene. 1995 Oct. 16; 164(1):49-53).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding genomic homologous sequences.

The ability to carry out homologous recombination in a host organism has many practical implications for what can be carried out at the molecular genetic level and is useful in the generation of an oleaginous microbe that can produced tailored oils. By its very nature homologous recombination is a precise gene targeting event, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from heterologous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements such as promoters/UTRs to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, and thus affecting the desired change in metabolism of the host cell. Homologous recombination provides a powerful means to manipulate the host genome resulting in gene targeting, gene conversion, gene deletion, gene duplication, gene inversion and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

C. Vectors and Vector Components

Vectors for transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

This subsection is divided into subsections. Subsection 1 describes control sequences typically contained on vectors as well as novel control sequences provided by the present invention. Subsection 2 describes genes typically contained in vectors as well as novel codon optimization methods and genes prepared using them provided by the invention.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of an exogenous gene in a microbe contains a coding sequence for a desired gene product (for example, a selectable marker, or an enzyme) in operable linkage with a promoter active in microalgae. Alternatively, if the vector does not contain a promoter in operable linkage with the coding sequence of interest, the coding sequence can be transformed into the cells such that it becomes operably linked to an endogenous promoter at the point of vector integration.

The promoter used to express an exogenous gene can be the promoter naturally linked to that gene or can be a heterologous promoter.

A promoter can generally be characterized as either constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, preferably substantially, transcription of an operably linked gene that is transcribed at a low level.

Inclusion of termination region control sequence is optional, and if employed, then the choice is be primarily one of convenience, as the termination region is relatively interchangeable. The termination region may be native to the transcriptional initiation region (the promoter), may be native to the DNA sequence of interest, or may be obtainable from another source. See, for example, Chen and Orozco, Nucleic Acids Res. (1988) 16:8411.

2. Genes and Codon Optimization

Typically, a gene includes a promoter, coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the heterologous vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the heterologous mRNA resulting in ribosomal stalling and termination and possible instability of the transgenic mRNA.

D. Expression of Two or More Exogenous Genes

Further, a genetically engineered microorganism may comprise and express more than one exogenous gene. One or more genes can be expressed using an inducible promoter, which allows the relative timing of expression of these genes to be controlled. Expression of the two or more exogenous genes may be under control of the same inducible promoter or under control of different inducible promoters. In the latter situation, expression of a first exogenous gene can be induced for a first period of time (during which expression of a second exogenous gene may or may not be induced) and expression of a second or further exogenous gene can be induced for a second period of time (during which expression of a first exogenous gene may or may not be induced). Provided herein are vectors and methods for engineering microbes to grow on non-traditional growth media.

E. Transformation

Cells can be transformed by any suitable technique including, e.g., biolistics, electroporation, glass bead transformation and silicon carbide whisker transformation. Any convenient technique for introducing a transgene into a microorganism can be employed in the present invention. Transformation can be achieved by, for example, the method of D. M. Morrison (Methods in Enzymology 68, 326 (1979)), the method by increasing permeability of recipient cells for DNA with calcium chloride (Mandel, M. and Higa, A., J. Mol. Biol., 53, 159 (1970)), or the like.

Examples of expression of transgenes in oleaginous yeast (e.g., *Yarrowia lipolytica*) can be found in the literature (see, for example, Bordes et al., J Microbiol Methods, Jun. 27 (2007)). Examples of expression of exogenous genes in bacteria such as *E. coli* are well known; see, for example, Molecular Cloning: A Laboratory Manual, Sambrook et al. (3d edition, 2001, Cold Spring Harbor Press).

Vectors for transformation of microorganisms in accordance with the present invention can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to an endogenous promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (see, for example, Protist 2004 December; 155(4):381-93). The transformed cells can be optionally selected based upon the ability to grow in the presence of the antibiotic or other selectable marker under conditions in which cells lacking the resistance cassette would not grow.

Nitrogen-Containing Compounds in Feedstocks

In certain embodiments, the invention relates to use of an atypical nitrogen-containing feedstock comprising, consisting essentially of, or consisting of a nitrogen-containing compound of any one of Formulas I-III. In certain embodiments, a non-genetically engineered organism, i.e., a native organism, could not metabolize (i.e., use as a source of nitrogen) the nitrogen-containing compounds in the feedstock.

In certain embodiments, the invention relates to any one of the aforementioned nitrogen-containing feedstocks, wherein the nitrogen-containing compound is a compound of formula I or a salt thereof:

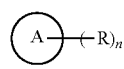

I wherein, independently for each occurrence,

Ⓐ is a five-, six-, nine-, or ten-membered aryl or heteroaryl group;

R is —OH, —CO$_2$H, —NO$_2$, —CN, substituted or unsubstituted amino, or substituted or unsubstituted alkyl; and n is 0, 1, 2, 3, 4, or 5.

In certain embodiments, the invention relates to any one of the aforementioned nitrogen-containing feedstocks, wherein the nitrogen-containing compound is a compound of formula II or a salt thereof:

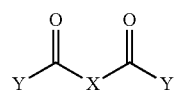

II wherein, independently for each occurrence,

X is —NH—, —N(alkyl)-, —O—, —C(R$^1$)$_2$—, —S—, or absent;

Y is —H, —NH$_2$, —N(H)(alkyl), —N(alkyl)$_2$, —CO$_2$H, —CN, or substituted or unsubstituted alkyl; and R$^1$ is —H, —OH, —CO$_2$H, —NO$_2$, —CN, substituted or unsubstituted amino, or substituted or unsubstituted alkyl.

In certain embodiments, the invention relates to any one of the aforementioned nitrogen-containing feedstocks, wherein the nitrogen-containing compound is a compound of formula III or a salt thereof:

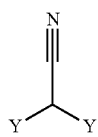

III wherein, independently for each occurrence,

Y is —H, —NH$_2$, —N(H)(alkyl), —N(alkyl)$_2$, —CO$_2$H, —CN, or substituted or unsubstituted alkyl.

In certain embodiments, the invention relates to any one of the aforementioned nitrogen-containing feedstocks, wherein the nitrogen-containing compound is selected from the group consisting of:

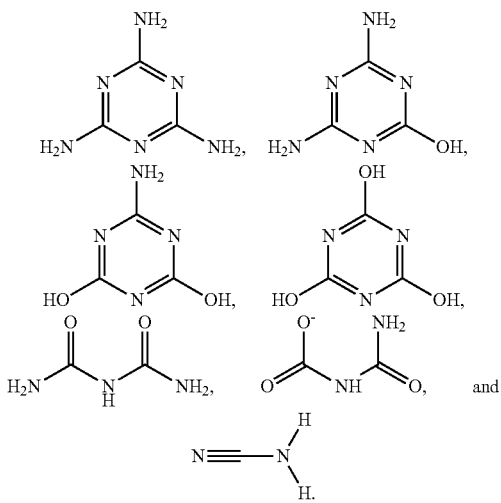

In certain embodiments, the invention relates to any one of the aforementioned nitrogen-containing feedstocks, wherein the nitrogen-containing compound is selected from the group consisting of Hydrazine, 5-Aminotetrazole, Tetrazole, Melamine, Cyanamide, 2-Cyanoguanidine, Sodium azide, Carbohydrazide, 1,2,3-Triazole, 1,2,4-Triazole, 1,3-Diaminoguanidine HCl, Ammeline, 1,3,5-triazine, Aminoacetonitrile, Cyanoethylhydrazine, Azodicarbonamide, Biurea, Formamidoxime, 1,2-Dimethylhydrazine, 1,1-Dimethylhydrazine, ethylhydrazine, Ethylenediamine, Sodium dicyanamide, Guanidine carbonate, Methylamine, Ammelide, Hydroxylamine, Malononitrile, Biuret, Diethyltriamine, Hexamethylenetetramine, Triethylenetetramine, 1,3-Diaminopropane, Triethylenetetramine, 1,3-Diaminopropane, Hydroxyurea, Tetraethylenepentamine, Thiourea, Succinonitrile, Calcium cyanamide, Cyanuric acid, Aminoethylpiperazine, Piperazine, Dimethylamine, Ethylamine, dalfampridine, Tetranitromethane, Imidazolidinyl urea, Trinitromethane, malonamide, Chloramine, Allophanate, Trimethylamine, Nitromethane, Acetaldoxime, Diazolidinyl urea, 1,2-Cyclohexanedione dioxime, Acetone oxime, Thioacetamide, Sodium thiocyanate, Isothiazole, Thiazole, Dimethylacetamide, Isothiazolinone, Methylene blue, Diethanolamine, Aspartame, Benzisothiazolinone, and Acesulfame potassium.

Exemplary Isolated Nucleic Acid Molecules and Vectors

In certain embodiments, the invention relates to an isolated nucleic acid molecule, wherein the nucleic acid molecule encodes an enzyme that provides the organism with the ability to assimilate a nitrogen source that otherwise would not have been accessible to the native organism; and the enzyme is allophanate hydrolase, biuret amidohydrolase, cyanuric acid amidohydrolase, guanine deaminase, ammeline hydrolase, ammelide hydrolyase, melamine deaminase, isopropylammelide isopropylaminohydrolase, cyanamide hydratase, urease, or urea carboxylase.

In certain embodiments, the invention relates to an isolated nucleic acid molecule, wherein the nucleic acid molecule is selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CU B122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from *Bradyrhizobium japonicum* USDA 110, GUD1/Y DL238C from *S. cerevisiae*, YAL10E2 5740p from *Y. lipolytica* CUM 122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to an isolated nucleic acid molecule comprising any one of the sequences disclosed herein. In certain embodiments, the invention relates to an isolated nucleic acid molecule having at least 85% sequence homology with any one of the sequences disclosed herein. In certain embodiments, the invention relates to an isolated nucleic acid molecule having at least 90% sequence homology with any one of the sequences disclosed herein. In certain embodiments, the invention relates to an isolated nucleic acid molecule having at least 95% sequence homology with any one of the sequences disclosed herein. In certain embodiments, the invention relates to an isolated nucleic acid molecule having at least 99% sequence homology with any one of the sequences disclosed herein. In certain embodiments, the invention relates to an isolated nucleic acid molecule having any one of the sequences disclosed herein.

A recombinant vector comprising any one of the aforementioned nucleic acid molecules operably linked to a promoter.

In certain embodiments, the invention relates to a recombinant vector comprising any one of the sequences disclosed herein. In certain embodiments, the invention relates to a recombinant vector having at least 85% sequence homology with any one of the sequences disclosed herein. In certain embodiments, the invention relates to a recombinant vector having at least 90% sequence homology with any one of the sequences disclosed herein. In certain embodiments, the invention relates to a recombinant vector having at least 95% sequence homology with any one of the sequences disclosed herein. In certain embodiments, the invention relates to a recombinant vector having at least 99% sequence homology with any one of the sequences disclosed herein.
Exemplary Genetically Engineered Organisms of the Invention In certain embodiments, the invention relates to a genetically engineered organism, wherein the genetically engineered organism has been transformed by a nucleic acid molecule or a recombinant vector comprising any one of the sequences disclosed herein. In certain embodiments, the nucleic acid molecule or recombinant vector has at least 85% sequence homology with any one of the sequences disclosed herein. In certain embodiments, the nucleic acid molecule or recombinant vector has at least 90% sequence homology with any one of the sequences disclosed herein. In certain embodiments, the nucleic acid molecule or recombinant vector has at least 95% sequence homology with any one of the sequences disclosed herein. In certain embodiments, the nucleic acid molecule or recombinant vector has at least 99% sequence homology with any one of the sequences disclosed herein. In certain embodiments, the invention relates to a genetically engineered organism, wherein the genetically engineered organism has been transformed by a nucleic acid molecule or a recombinant vector having any one of the sequences disclosed herein.

In certain embodiments, the invention relates to a genetically engineered organism, wherein the genetically engineered organism has been transformed by a nucleic acid molecule; the nucleic acid molecule comprises a non-native gene; and the non-native gene encodes for a non-native enzyme selected from the group consisting of allophanate hydrolase, biuret amidohydrolase, cyanuric acid amidohydrolase, guanine deaminase, ammeline hydrolase, ammelide hydrolyase, melamine deaminase, and isopropylammelide isopropylaminohydrolase, cyanamide hydratase, urease, or urea carboxylase.

In certain embodiments, the invention relates to any one of the aforementioned genetically engineered organisms, wherein the non-native gene is selected from the group consisting of atzF, DUR1,2 YALI0E 07271g, atzE, atzD, trzC, trzD, trzE, atzD, guaD, blr3880, GUD1/Y DL238C, YAL10E2 5740p, trzA, triA, atzC, and cah. In certain embodiments, the invention relates to any one of the aforementioned genetically engineered organisms, wherein the non-native gene is selected from the group consisting of atzF, DUR1,2 YALI0E 07271g, atzE, atzD, trzD, atzD, guaD, blr3880, GUD1/Y DL238C, YAL10E2 5740p, trzA, triA, atzC, and cah. Any organism may be used as a source of the non-native gene, as long as the organisms has the desired enzymatic activity The non-native gene can each be obtained from chromosomal DNA of any one of the aforementioned microorganisms by isolating a DNA fragment complementing auxotrophy of a variant strain lacking the enzymatic activity. Alternatively, if the nucleotide sequence of these gene of the organism has already been elucidated (Biochemistry, Vol. 22, pp. 5243-5249, 1983; J. Biochem. Vol. 95, pp. 909-916, 1984; Gene, Vol. 27, pp. 193-199, 1984; Microbiology, Vol. 140, pp. 1817-1828, 1994; Mol. Gene Genet. Vol. 218, pp. 330-339, 1989; and Molecular Microbiology, Vol. 6, pp. 317-326, 1992), the genes can be obtained by PCR using primers synthesized based on each of the elucidated nucleotide sequences, and the chromosome DNA as a template.

In certain embodiments, the invention relates to any one of the aforementioned genetically engineered organisms, wherein the non-native gene is selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CLIB122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from *Bradyrhizobium japonicum* USDA 110, GUD1/Y DL238C from *S. cerevisiae*, YAL10E2 5740p from *Y. lipolytica* CLIB122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to any one of the aforementioned genetically engineered organisms, wherein the genetically engineered organism is a species of the genus *Yarrowia, Saccharomyces, Ogataea, Pichia*, or *Escherichia*.

In certain embodiments, the invention relates to any one of the aforementioned genetically engineered organisms, wherein the genetically engineered organism is selected from the group consisting of *Yarrowia lipolytica, Saccharomyces cerevisiae, Ogataea polymorpha, Pichia pastoris*, and *Escherichia coli*.

In certain embodiments, the genetically engineered organism is not *Rhodococcus* sp. Strain Mel.

Exemplary Methods of the Invention

In certain embodiments, the invention relates to a method, comprising the step of contacting any one of the aforementioned genetically engineered organisms with a substrate, wherein the substrate comprises a nitrogen-containing fraction and a non-nitrogen-containing fraction;

the nitrogen-containing fraction comprises, in an amount from about 10% by weight to about 100% by weight, a nitrogen-containing compound of any one of Formulas I-III;

a native organism of the same species as the genetically engineered organism could not metabolize (i.e., use as a source of nitrogen) the nitrogen-containing compound; and the genetically engineered organism converts the substrate to a product.

In certain embodiments, the invention relates to any one of the aforementioned methods, wherein the nitrogen-containing compounds have a low molecular weight. In certain embodiments, the invention relates to any one of the aforementioned methods, wherein the nitrogen-containing compounds have a molecular weight between about 30 Da and about 800 Da. In certain embodiments, the invention relates to any one of the aforementioned methods, wherein the nitrogen-containing compounds have a molecular weight between about 40 Da and about 600 Da. In certain embodiments, the invention relates to any one of the aforementioned methods, wherein the nitrogen-containing compounds have a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, bout 560 Da, about 580 Da, or about 600 Da.

In certain embodiments, the invention relates to any one of the aforementioned methods, wherein the nitrogen-containing compounds have less than 12 carbon atoms. In certain embodiments, the invention relates to any one of the aforementioned methods, wherein the nitrogen-containing compounds have less than 8 carbon atoms. In certain embodiments, the invention relates to any one of the aforementioned methods, wherein the nitrogen-containing compounds have 1, 2, 3, 4, 5, 6, or 7 carbon atoms.

In certain embodiments, the invention relates to any one of the aforementioned methods, wherein the nitrogen-containing compounds have 1, 2, 3, 4, 5, 6, 7, 8, 9, or 10 nitrogen atoms.

In certain embodiments, the invention relates to any one of the aforementioned methods, wherein the nitrogen-containing compounds have 0, 1, 2, 3, 4, 5, 6, 7, or 8 oxygen atoms.

In certain embodiments, the invention relates to any one of the aforementioned methods, wherein the nitrogen-containing compounds have an octanol-water partition coefficient (log P) less than about 5. In certain embodiments, the invention relates to any one of the aforementioned methods, wherein the nitrogen-containing compounds have an octanol-water partition coefficient (log P) from about −0.5 to about 5. In certain embodiments, the invention relates to any one of the aforementioned methods, wherein the nitrogen-containing compounds have an octanol-water partition coefficient (log P) of about −0.5, about 0, about 0.5, about 1, about 1.5, about 2, about 2.5, about 3, about 3.5, about 4, or about 4.5.

In certain embodiments, the invention relates to any one of the aforementioned methods, wherein the nitrogen-containing compounds are soluble in water at about 20° C. at a concentration of between about 0.01 g/L to about 1000 g/L. In certain embodiments, the invention relates to any one of the aforementioned methods, wherein the nitrogen-containing compounds are soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In certain embodiments, the invention relates to any one of the aforementioned methods, wherein the nitrogen-containing compounds move through the cell membrane by passive transport. Passive transport includes diffusion, facilitated diffusion, and filtration.

In certain embodiments, the invention relates to any one of the aforementioned methods, wherein the nitrogen-containing compounds move through the cell membrane by active transport, such as, for example, via an ATP-Binding Cassette (ABC) transporter or other known transmembrane transporter.

In certain embodiments, the invention relates to any one of the aforementioned methods, wherein the nitrogen-containing compounds are transported through the cell membrane.

In certain embodiments, the invention relates to any one of the aforementioned methods, wherein the nitrogen-containing compounds are substantially non-biocidal.

In certain embodiments, the invention relates to any one of the aforementioned methods, wherein the nitrogen-containing compounds are substantially biodegradable.

In certain embodiments, the invention relates to any one of the aforementioned methods, wherein the nitrogen-containing fraction comprises the nitrogen-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of
  contacting any one of the aforementioned genetically engineered organisms with a substrate,
  wherein
  the substrate comprises a nitrogen-containing fraction and a non-nitrogen-containing fraction;
  the nitrogen-containing fraction comprises, in an amount from about 10% by weight to about 100% by weight, a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
  the genetically engineered organism converts the substrate to a product.'

In certain embodiments, the invention relates to any one of the aforementioned methods, wherein the nitrogen-containing fraction comprises the nitrogen-containing compound in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the invention relates to a method, comprising the step of
  contacting any one of the aforementioned genetically engineered organisms with a substrate,
  wherein
  the substrate comprises a nitrogen-containing fraction and a non-nitrogen-containing fraction;
  the nitrogen containing fraction consists essentially of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
  the genetically engineered organism converts the substrate to a product.

In certain embodiments, the invention relates to a method, comprising the step of
  contacting any one of the aforementioned genetically engineered organisms with a substrate,
  wherein
  the substrate consists of a nitrogen-containing fraction and a non-nitrogen-containing fraction;
  the nitrogen containing fraction consists of a nitrogen-containing compound selected from the group consisting of triazine, urea, melamine, cyanamide, 2-cyanoguanidine, ammeline, guanidine carbonate, ethylenediamine, ammelide, biuret, diethylenetriamine, triethylenetetramine, 1,3-diaminopropane, calcium cyanamide, cyanuric acid, aminoethylpiperazine, piperazine, and allophante; and
  the genetically engineered organism converts the substrate to a product.

In certain embodiments, the invention relates to any one of the aforementioned methods, wherein the genetically engineered organism sequesters the product.

In certain embodiments, the invention relates to any one of the aforementioned methods, wherein a plurality of genetically engineered organisms is used.

In certain embodiments, the invention relates to any one of the aforementioned methods, wherein the substrate does not comprise an antibiotic.

In certain embodiments, the invention relates to any one of the aforementioned methods, wherein the substrate does not comprise ammonium sulfate.

In certain embodiments, the invention relates to any one of the aforementioned methods, wherein the substrate does not comprise urea.

In certain embodiments, the invention relates to any one of the aforementioned methods, wherein a non-genetically engineered organism, i.e., a native organism, could not metabolize (i.e., use as a source of nitrogen) the nitrogen-containing compound. In certain embodiments, the genetically engineered organism is not *Rhodococcus* sp. Strain Mel.

In certain embodiments, the invention relates to any one of the aforementioned methods, wherein the substrate comprises lignocellulosic material, glucose, xylose, sucrose, acetic acid, formic acid, lactic acid, butyric acid, a free fatty acid, dextrose, glycerol, fructose, lactose, galactose, mannose, rhamnose, or arabinose, or a combination thereof In certain embodiments, the invention relates to any one of the aforementioned methods, wherein the pH of the substrate is from about 2.5 to about 10.

In certain embodiments, the invention relates to any one of the aforementioned methods, wherein the genetically engineered organism is contacted with the substrate at a temperature of from about 15° C. to about 80° C.

In certain embodiments, the invention relates to any one of the aforementioned methods, wherein the genetically engineered organism is contacted with the substrate over a time period of from about 6 h to about 10 d.

In certain embodiments, the invention relates to any one of the aforementioned methods, wherein the genetically engineered organism is contacted with the substrate in a fermentor.

In certain embodiments, the invention relates to any one of the aforementioned methods, wherein the genetically engineered organism is contacted with the substrate in an industrial-size fermentor.

In certain embodiments, the invention relates to any one of the aforementioned methods, wherein a plurality of genetically engineered organisms is contacted with a plurality of substrates in a plurality of fermentors, wherein the plurality of fermentors are arranged in parallel.

In certain embodiments, the invention relates to any one of the aforementioned methods, wherein the product is ethanol, isopropanol, lactic acid, an isoprenoid, a lipid, a high-value specialty chemical, butanol, 1,3-propanediol, 1,4-butanediol, succinic acid, an expressed protein product, an enzyme product, a polyol, a pharmaceutical product, itaconic acid, or a high value specialty chemical.

Exemplary Products

In certain embodiments, the invention relates to a product made by any one of the aforementioned methods.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1

The oleaginous yeast *Yarrowia lipolytica* may be engineered to convert melamine into ammonia. Melamine ($C_3N_6H_6$) is a highly nitrogenous compound that can only be degraded by a very limited number of organisms including *Rhodococcus* sp. Strain Mel. Incorporating the pathway for melamine degradation into *Yarrowia*, accompanied with a modification in the media composition to use melamine as the predominant nitrogen source, will generate a more robust industrial production solution applicable to a number of applications. The advantage confirmed by this modification is significant enough to provide advantage in multiple applications including situations where the core technology may be significant genetic burden on the organism.

Example 2

Genes from FIG. 3, or suitable homologs, will be cloned into a host strain such as *Yarrowia lipolytica*, *Saccharomyces cerevisiae*, or *Escherichia coli*. Enzymes native to the host organism, such as allophante hydrolase or guanine deaminase may be overexpressed with a heterologous promoter. Functional expression will be assayed by enzymatic activity and the ability to confer nitrogen limited growth on the appropriate pathway intermediate. Ultimately, strains able to degrade melamine will be selected for improved utilization of the pathway via melamine limited continuous culturing or other selective methods. Similar strategies can be devised for nitrogen compounds listed in FIG. 2.

Example 3

Vector Construction Via Yeast Mediated Ligation

Base Vector

Vector pNC10 contains an *E. coli* pMB1 origin of replication and ampicillin resistance gene, a *S. cerevisiae* 2 μm origin of replication and URA3 gene, and a multiple cloning site containing the 8-bp recognition sequences for PacI, PmeI, and AscI. DNA of interest is inserted in the multiple cloning site via yeast mediated homologous recombination (YML) cloning. (Shanks et al. 2006; Shanks et al. 2009). Briefly, target DNA sequences are amplified by PCR using primers with 20-40 bp overhang homology to adjacent DNA segments in the final vector. pNC10 or another suitable base vector is then restriction digested, creating a linearized plasmid. PCR products and linear plasmid are transformed in *S. cerevisiae*, and the native *S. cerevisiae* gap repair mechanism assembles an intact plasmid based on homology overhangs.

Figure 1:
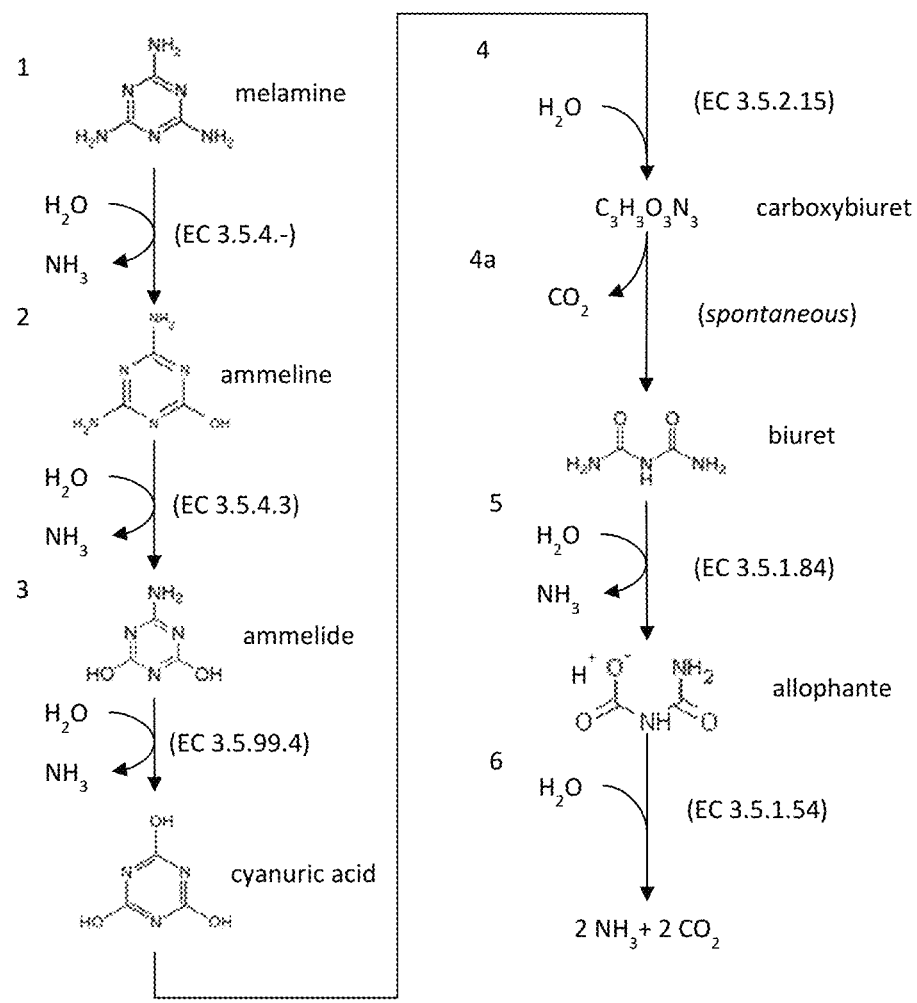
FIG. 1 depicts a schematic representation of the melamine degradation pathway. 1—Melamine deaminase (tzrA) (EC 3.5.4.-); 2—Ammeline deaminase (guanine deaminase) (EC 3.5.4.3); 3—N-isopropylammelide isopropylamino (Ammelide) hydrolyase (EC 3.5.99.4); 4—Cyanuric acid hydrolyase (EC 3.5.2.15); 4a—Carboxybiuret decarboxylase, spontaneous reaction; 5—Biuret amidohydrolase (EC 3.5.1.84); 6—Allophanate hydrolyase (EC 3.5.1.54). Nitrogen can be assimilated (as $NH_3$) by the action of the complete pathway acting on melamine, liberating 6 mol $NH_3$ per mol melamine, or via a subset of enzymes acting on pathway intermediates (e.g., steps 4, 4a, 5, and 6 acting on cyanuric acid releasing 3 mol $NH_3$ per mol cyanuric acid).
Figure 4:
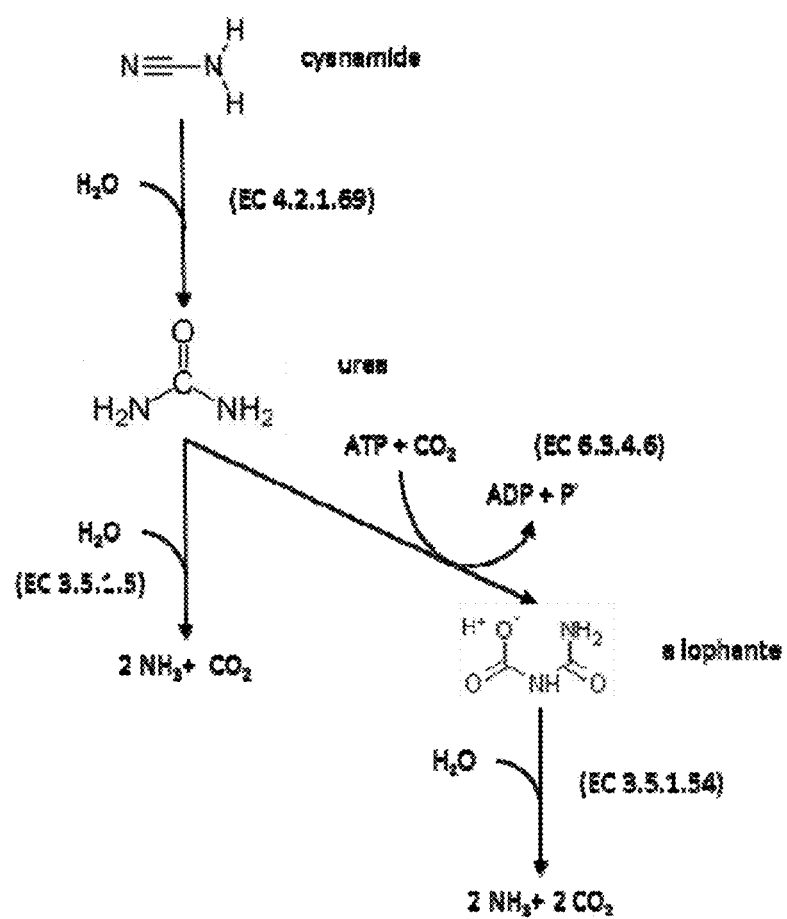
FIG. 4 depicts a schematic representation of the cyanamide assimilation pathway. After conversion of cyanamide to urea by cyanamide hydratase (EC 4.2.1.69), urea can be degraded either via urease (EC 3.5.1.5) or by urea carboxylase (EC 6.3.4.6) and allophante hydrolyase (EC 3.5.1.54).
Figure 5:
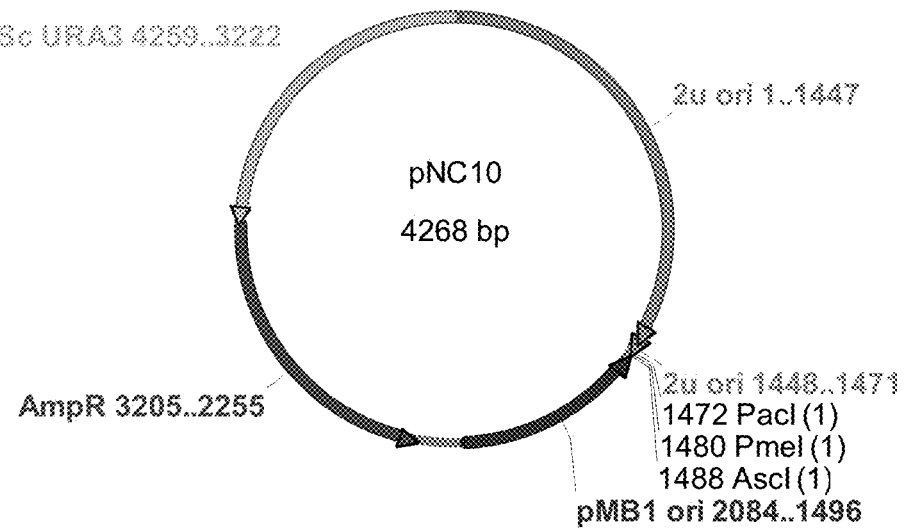
FIGS. 5-10 depict various plasmids of the invention.

The complete vector can then be isolated from *S. cerevisiae* via a DNA extraction protocol and used to transform *E. coli*. Concentrated vector can then be recovered from *E. coli* via DNA plasmid mini-prep or other suitable standard molecular biology protocols. See FIG. 5.

Example 4

*S. cerevisiae* Transformation

Grow overnight a 5 mL culture of a *S. cerevisiae* ura3 auxotroph strain in YPD at 30 C.

Transfer 1.5 mL of overnight culture to 50 mL fresh YPD (OD ~0.3) and shake at 200 rpm, 30° C. in a flask. Allow to grow for approx. 4-5 hrs to an OD of 1.0.

Centrifuge cells at >5,000 rpm for 1 min, resuspend in 50 mL sterile water and repeat.

Add 1 mL of 100 mM Lithium acetate to cell pellet and transfer cells to a 1.5 mL tube.

Spin cells for 10 sec at >12,000 rpm, remove supernatant, and resuspend in 400-800 µL of 100 mM LiAc (each transformation uses 50 µL of this cell suspension).

Prepare a transformation master mix of the following, per sample

X number of transformations+1

| | |
|---|---|
| 50% PEG 3350 | 240 µL |
| 1M LiAc | 36 µL |
| Salmon sperm DNA* (2 mg/mL) | 50 µL |

*SS DNA should be first boiled for 10 min and rapidly cooled to 4° C.

Prepare one 1.5 mL tube for each transformation. Per tube, add: 5 µL of digested vector, 5 µL of each PCR insert (assuming a good PCR amplification, approx. 100-200 ng DNA), and water to bring the final volume to 34 µL. Add 326 µL master mix, and then 50 µL of cell suspension. Vortex tubes to completely mix contents.

Incubate for 30 min at 30° C., then mix by inverting and place in 42° C. water bath for 30 min. (Note optimal time at 42° C. varies strain to strain).

Spin down cells for 10 sec at >12,000 rpm, remove PEG mixture and resuspend in 1 mL sterile water. Spin down again, remove 800 µL, and use final 200 µL to resuspend and spread on SD-URA plates. Incubate at 30° C. for 2-4 days.

Example 5

Expression of Melamine Assimilation Enzymes in *S. cerevisiae*

Melamine assimilation genes, or a subset of them, can be expressed in *S. cerevisiae* by construction of a vector using the yeast mediated ligation described above. Expression vectors consist of an *S. cerevisiae* functional promoter, a gene encoding an enzyme of the melamine assimilation pathway, and an *S. cerevisiae* functional terminator. Assemblies of the promoter-gene-terminator motif can be incorporated into a single strain, either on a replicating plasmid or integrated into a chromosome. Possible promoters and terminators are listed below, see also Sun et al. 2012. A representative plasmid, expressing the trzA melamine hydratase under control of the *Y. lipolytica* TEF1 promoter and terminator is shown below.

Figure 6:
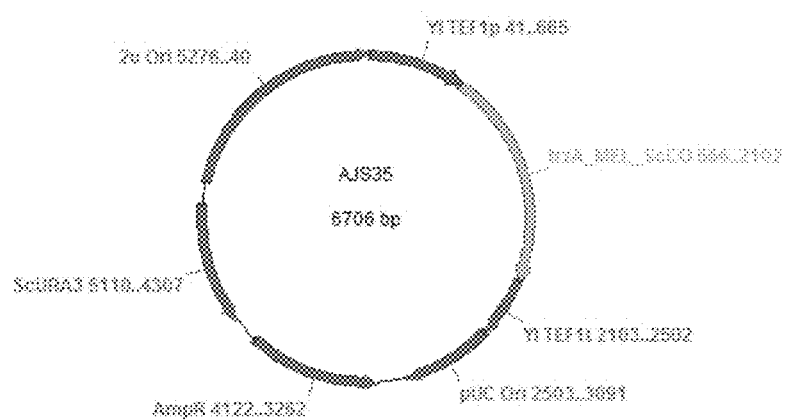

Plasmid AJS35 is an example of the melamine dehydratase trzA transcribed via the *Y. lipolytica* TEF1 promoter and terminator. See FIG. 6.

Strains NS98 and NS99 are industrial *S. cereviaie* strains carrying plasmids pNC96 (hyg$^R$, and a codon optimized trzE from *Rhodococcus* sp. MEL and pNC97 (hyg$^R$, and a codon optimized trzE from *Rhizobium leguminosarum*), respectively. Strain NS100 is the same industrial *S. cerevisiae* stain carrying plasmid pNC67 (hyg$^R$, nat$^R$) which serves as a control strain.

Figures 23, 24:
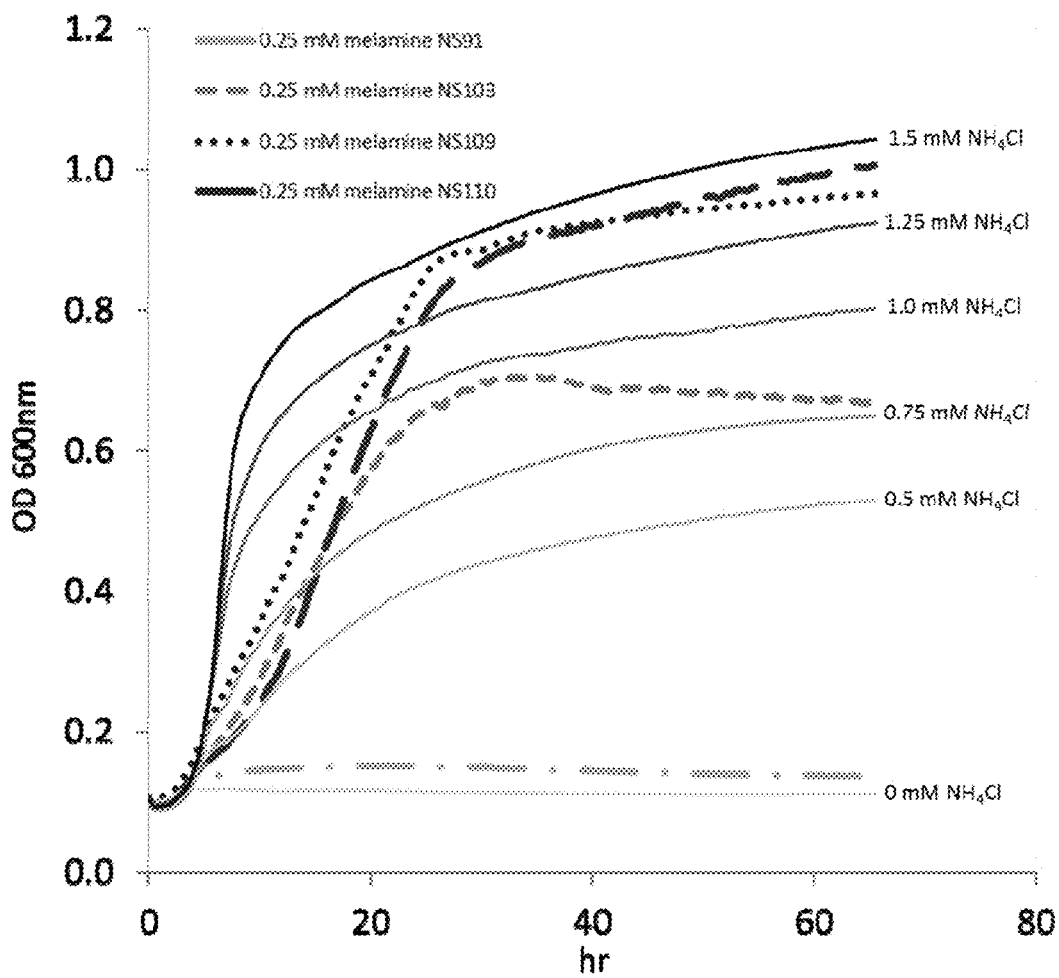
FIG. 23 tabulates the optical density at 600 nm after growth of three organisms of the invention on various media.
FIG. 24 depicts the growth of four organisms of the invention (NS91=control) on 0.25 mM melamine, as compared to the standard curves for a native organism on $NH_4Cl$. Because melamine has six nitrogen atoms, organisms having the ability to utilize melamine should be approximately six times more efficient (see, for example, NS110 on 0.25 mM melamine, as compared to a native organism on 1.5 mM $NH_4Cl$).

Strains NS98, NS99, and NS100 were grown in defined YNB medium with 10 mM urea and 100 µg/mL hygromycin to stationary phase aerobically at 30° C. 1/1000 v/v inoculations were then made into the same defined medium with either 10 mM urea, 10 mM biuret, or no additional nitrogen and grown under the same conditions. Optical density was measured after 72 hours, as shown in FIG. 23. Strains NS98 and NS99 were able to grow to an optical density approximately double that of NS100 in medium containing biuret, and also approximately double that with medium with no nitrogen supply. This shows that *S. cerevisiae* strains expressing trzE genes are advantaged in their utilization of biuret.

DNA that can be used as promoters for gene transcription in *S. cerevisiae*

S. cerevisiae TPI promoter
aggaacccatcaggttggtggaaGATTACCCGTTCTAAGACTTTTCAGCT

TCCTCTATTGATGTTACACCTGGACACCCCTTTTCTGGCATCCAGTTTTT

AATCTTCAGTGGCATGTGAGATTCTCCGAAATTAATTAAAGCAATCACAC

AATTCTCTCGGATACCACCTCGGTTGAAACTGACAGGTGGTTTGTTACGC

ATGCTAATGCAAAGGAGCCTATATACCTTTGGCTCGGCTGCTGTAACAGG

GAATATAAAGGGCAGCATAATTTAGGAGTTTAGTGAACTTGCAACATTTA

CTATTTTCCCTTCTTACGTAAATATTTTTCTTTTTAATTCTAAATCAATC

TTTTTCAATTTTTTGTTTGTATTCTTTTCTTGCTTAAAtctataactaca aaaaacacatacataaactaaaa (SEQ ID NO: 59)

S. cerevisiae GPM1 promoter
ttgctacgcaggctgcacaattacACGAGAATGCTCCCGCCTAGGATTTA

AGGCTAAGGGACGTGCAATGCAGACGACAGATCTAAATGACCGTGTCGGT

GAAGTGTTCGCCAAACTTTTCGGTTAACACATGCAGTGATGCACGCGCGA

TGGTGCTAAGTTACATATATATATATATATATATATATATATATATATAG

CCATAGTGATGTCTAAGTAACCTTTATGGTATATTTCTTAATGTGGAAAG

ATACTAGCGCGCGCACCCACACACAAGCTTCGTCTTTTCTTGAAGAAAAG

AGGAAGCTCGCTAAATGGGATTCCACTTTCCGTTCCCTGCCAGCTGATGG

AAAAAGGTTAGTGGAACGATGAAGAATAAAAAGAGAGATCCACTGAGGTG

AAATTTCAGCTGACAGCGAGTTTCATGATCGTGATGAACAATGGTAACGA

GTTGTGGCTGTTGCCAGGGAGGGTGGTTCTCAACTTTTAATGTATGGCCA

AATCGCTACTTGGGTTTGTTATATAACAAAGAAGAAATAATGAACTGATT

CTCTTCCTCCTTCTTGTCCTTTCTTAATTCTGTTGTAATTACCTTCCTTT

GTAATTTTTTTGTAATTATTCTtcttaataatccaaacaaacacacata ttacaata (SEQ ID NO: 60)

S. cerevisiae TDH3 promoter
tgctgtaacccgtacatgcccaaaATAGGGGGCGGGTTACACAGAATATA

TAACATCGTAGGTGTCTGGGTGAACAGTTTATTCCTGGCATCCACTAAAT

ATAATGGAGCCCGCTTTTTAAGCTGGCATCCAGAAAAAAAAAGAATCCCA

GCACCAAAATATTGTTTTCTTCACCAACCATCAGTTCATAGGTCCATTCT

CTTAGCGCAACTACAGAGAACAGGGGCACAAACAGGCAAAAAACGGGCAC

AACCTCAATGGAGTGATGCAACCTGCCTGGAGTAAATGATGACACAAGGC

AATTGACCCACGCATGTATCTATCTCATTTTCTTACACCTTCTATTACCT

-continued

TCTGCTCTCTCTGATTTGGAAAAAGCTGAAAAAAAAGGTTGAAACCAGTT

CCCTGAAATTATTCCCCTACTTGACTAATAAGTATATAAAGACGGTAGGT

ATTGATTGTAATTCTGTAAATCTATTTCTTAAACTTCTTAAATTCTACTT

TTATAGTTAGTCTTTTTTTTAGTTTTAAAACACCAAGAacttagtttcga ataaacacacataaacaaacaaa (SEQ ID NO: 61)

Y. lipolytica TEF1 promoter
tataaacggtattttcacaattgcACCCCAGCCAGACCGATAGCCGGTCG

CAATCCGCCACCCACAACCGTCTACCTCCCACAGAACCCCGTCACTTCCA

CCCTTTTCCACCAGATCATATGTCCCAACTTGCCAAATTAAAACCGTGCG

AATTTTCAAAATAAACTTTGGCAAAGAGGCTGCAAAGGAGGGGCTGGTGA

GGGCGTCTGGAAGTCGACCAGAGACCGGGTTGGCGGCGCATTTGTGTCCC

AAAAAACAGCCCCAATTGCCCCAATTGACCCCAAATTGACCCAGTAGCGG

GCCCAACCCCGGCGAGAGCCCCCTTCTCCCCACATATCAAACCTCCCCCG

GTTCCCACACTTGCCGTTAAGGGCGTAGGGTACTGCAGTCTGGAATCTAC

GCTTGTTCAGACTTTGTACTAGTTTCTTTGTCTGGCCATCCGGGTAACCC

ATGCCGGACGCAAAATAGACTACTGAAAATTTTTTGCTTTGTGGTTGGG

ACTTTAGCCAAGGGTATAAAAGACCACCGTCCCCGAATTACCTTTCCTCT

TCTTTTCTCTCTCCTTGTCAACTCACACCCGAAATCGTtaagcatttc cttctgagtataagaatcattcaaa (SEQ ID NO: 63)

S. cerevisiae FBA1 promoter
gcaccgctggcttgaacaacaataCCAGCCTTCCAACTTCTGTAAATAAC

GGCGGTACGCCAGTGCCACCAGTACCGTTACCTTTCGGTATACCTCCTTT

CCCCATGTTTCCAATGCCCTTCATGCCTCCAACGGCTACTATCACAAATC

CTCATCAAGCTGACGCAAGCCCTAAGAAATGAATAACAATACTGACAGTA

CTAAATAATTGCCTACTTGGCTTCACATACGTTGCATACGTCGATATAGA

TAATAATGATAATGACAGCAGGATTATCGTAATACGTAATAGTTGAAAAT

CTCAAAAATGTGTGGGTCATTACGTAAATAATGATAGGAATGGGATTCTT

CTATTTTTCCTTTTTCCATTCTAGCAGCCGTCGGGAAAACGTGGCATCCT

CTCTTTCGGGCTCAATTGGAGTCACGCTGCCGTGAGCATCCTCTCTTTCC

ATATCTAACAACTGAGCACGTAACCAATGGAAAAGCATGAGCTTAGCGTT

GCTCCAAAAAAGTATTGGATGGTTAATACCATTTGTCTGTTCTCTTCTGA

CTTTGACTCCTCAAAAAAAAAAATCTACAATCAACAGATGCTTCAATT

ACGCCCTCACAAAAACTTTTTTCCTTCTTCTTCGCCCACGTTAAATTTTA

TCCCTCATGTTGTCTAACGGATTTCTGCACTTGATTTATTATAAAAGAC

AAAGACATAATACTTCTCTATCAATTTCAGTTATTGTTCTTCCTTGCGTT

ATTCTTCTGTTCTTCTTTTTCTTTTGTcatatataaccataaccaagtaa tacatattcaaa (SEQ ID NO: 62)

S. cerevisiae PDC1 promoter
gcataatattgtccgctgcccgttTTTCTGTTAGACGGTGTCTTGATCTA

CTTGCTATCGTTCAACACCACCTTATTTTCTAACTATTTTTTTTTAGCT

CATTTGAATCAGCTTATGGTGATGGCACATTTTTGCATAAACCTAGCTGT

CCTCGTTGAACATAGGAAAAAAAAATATATAAACAAGGCTCTTTCACTCT

CCTTGGAATCAGATTTGGGTTTGTTCCCTTTATTTTCATATTTCTTGTCA

TATTCTTTTCTCAATTATTATCTTCTACTCATAacctcacgcaaaataac acagtcaaatcaatcaaa (SEQ ID NO: 64)

S. cerevisiae TEF1 promoter
CATAGCTTCAAAATGTTTCTACTCCTTTTTTACTCTTCCAGATTTTCTCG

GACTCCGCGCATCGCCGTACCACTTCAAAACACCCAAGCACAGCATACTA

AATTTCCCCTCTTTCTTCCTCTAGGGTGTCGTTAATTACCCGTACTAAAG

GTTTGGAAAAGAAAAAGAGACCGCCTCGTTTCTTTTTCTTCGTCGAAAA

AGGCAATAAAAATTTTTATCACGTTTCTTTTTCTTGAAAATTTTTTTTT

TGATTTTTTTCTCTTTCGATGACCTCCCATTGATATTTAAGTTAATAAAC

GGTCTTCAATTTCTCAAGTTTCAGTTTCATTTTTCTTGTTCTATTACAAC

TTTTTTTACTTCTTGCTCATTAGAAAGAaagcatagcaatctaatctaag ttttaattacaaa (SEQ ID NO: 65)

DNA Sequences that can be Used as Terminators of Gene Transcription

S. cerevisiae TP1 terminator
taagattaatataattatataaAAATATTATCTTCTTTTCTTTATATCTA

GTGTTATGTAAAATAAATTGATGACTACGGAAAGCTTTTTTATATTGTTT

CTTTTTCATTCTGAGCCACTTAAATTTCGTGAATGTTCTTGTAAGGGACG

GTAGATTTACAAGTGATACAACAAAAAGCAAGGCGCTTTTTCTAATAAAA

AGAAGAAAAGCATTTAACAATTGAACACCTCTATATCAACGAAGAATATT

ACTTTGTCTCTAAATCCTTGTAAAATGTGTACGATCTCTATATGGGTTAC

TCATAAgtgtaccgaagactgcattgaaag (SEQ ID NO: 66)

S. cerevisiae GPM1 terminator
gtagaagaatgaatgatttgaTGATTTCTTTTTCCCTCCATTTTCTTAC

TGAATATATCAATGATATAGACTTGTATAGTTTATTATTTCAAATTAAGT

AGCTATATATAGTCAAGATAACGTTTGTTTGACACGATTACATTATTCGT

CGACATCTTTTTTCAGCCTGTCGTGGTAGCAATTTGAGGAGTATTATTAA

TTGAATAGGTTCATTTGCGCTCGCATAAACAGTTTTCGTCAGGGACAGT

ATGTTGGAATGAGTGGTAATTAATGGTGACATGACATGTTATAGCAATAA

CCTTGATGTTTACATCGTAGTTTAATGTACACCCCGCGAATTCGTTCAAG

TAggagtgcaccaattgcaaagggaa (SEQ ID NO: 67)

```
                           S. cerevisiae TDH3 terminator
gtgaatttactttaaatcttgcATTTAAATAAATTTTCTTTTTATAGCTT

TATGACTTAGTTTCAATTTATATACTATTTTAATGACATTTTCGATTCAT

TGATTGAAAGCTTTGTGTTTTTCTTGATGCGCTATTGCATTGTTCTTGT

CTTTTTCGCCACATGTAATATCTGTAGTAGATACCTGATACATTGTGGAT

GCTGAGTGAAATTTTAGTTAATAATGGAGGCGCTCTTAATAATTTTGGGG

ATATTGGCTTTTTTTTTAAAGTTTACAAATGAATTTTTTCCGCCAGGAT

AACGATTCTGAAGTTACTCTTAGCGTTCCTATCGGTACAGCCATCAAATC

ATGCCTATAAATCATGCCTATATTTGCGTGCAGTCAGTATCATCTACATG

AAAAAAACTCCCGCAATTTCTTATAGAATACGTTGAAAATTAAATGTACG

CGCCAAGATAAGATAACATATATCTAGATGCAGTAATATACACAGATTCC

CGCGGA (SEQ ID NO: 68)

S. cerevisiae FBA1 terminator
gttaattcaaattaattgatatAGTTTTTTAATGAGTATTGAATCTGTTT

AGAAATAATGGAATATTATTTTTATTTATTTATTTATATTATTGGTCGGC

TCTTTTCTTCTGAAGGTCAATGACAAAATGATATGAAGGAAATAATGATT

TCTAAAATTTTACAACGTAAGATATTTTTACAaaagcctagctcatctt (SEQ ID NO: 69)

Y. lipolytica TEF1 terminator
gctgcttgtacctagtgcaacccagtttgttaaaAATTAGTAGTCAAAA

ACTTCTGAGTTAGAAATTTGTGAGTGTAGTGAGATTGTAGAGTATCATGT

GTGTCCGTAAGTGAAGTGTTATTGACTCTTAGTTAGTTTATCTAGTACTC

GTTTAGTTGACACTGATCTAGTATTTTACGAGGCGTATGACTTTAGCCAA

GTGTTGTACTTAGTCTTCTCTCCAAACATGAGAGGGCTCTGTCACTCAGT

CGGCCTATGGGTGAGATGGCTTGGTGAGATCTTTCGATAGTCTCGTCAAG

ATGGTAGGATGATGGGGAATACATTACTGCTCTCGTCAAGGAAACCACA

ATCAGATCACACCATCCTCCATGGTAtccgatgactctcttctccacagt (SEQ ID NO: 70)

S. cerevisiae PDC1 terminator
acaagctaagttgactgctgctACCAACGCTAAGCAATAAGCGATTTAAT

CTCTAATTATTAGTTAAAGTTTTATAAGCATTTTTATGTAACGAAAAATA

AATTGGTTCATATTATTACTGCACTGTCACTTACCATGGAAAGACCAGAC

AAGAAGTTGCCGACACGACAGTCTGTTGAattggcttaagtctgggtccg ctt (SEQ ID NO: 71)

S. cerevisiae CYC1 terminator
caggcccatttcctttgtcgaTATCATGTAATTAGTTATGTCACGCTTAC

ATTCACGCCCTCCTCCCACATCCGCTCTAACCGAAAAGGAAGGAGTTAGA

CAACCTGAAGTCTAGGTCCCTATTTATTTTTTTTAATAGTTATGTTAGTA

TTAAGAACGTTATTTATATTTCAAATTTTTCTTTTTTTCTGTACAAACG

CGTGTACGCATGTAACATTATACTGAAAACCTTGCTTGAGAAGGTTTTGG

GACGCTCGAAGGCTTTAATTTGC (SEQ ID NO: 72)
```

Example 6

Expression of Melamine Assimilation Enzymes in E. coli

Melamine assimilation genes, or a subset of them, can be expressed in E. coli by construction of a vector using the yeast mediated ligation described above. Expression vectors consist of an E. coli functional promoter, a gene encoding an enzyme of the melamine assimilation pathway, and an E. coli functional terminator. Alternatively, several genes can be expressed from a single promoter as part of a gene operon; in this case inter-gene linker sequences are placed between genes. Sequences that can act as promoters, terminators, and linkers are listed below, as well as two representative E. coli expression plasmids, AJS67 (expressing genes for degradation of melamine to cyanuric acid with release of 3 $NH_3$ per melamine) and AJS68 (expressing genes for degradation of cyanuric acid to $NH_3$ and $CO_2$ with release of 3 $NH_3$ per cyanuric acid)

```
                                  E. coli Ptach promoter
agctggtgacaattaatcatcggctgtataatgtgtggaattgaatcgat
aaggaggttaatca (SEQ ID NO: 73)

E. coli trpT' promoter
ctcaaaatatattttccctctatcttctcgttgcgcttaatttgactaatt
ctcattagcgaggcgcgcctttccataggctccgcccc
(SEQ ID NO: 74)
```

Inter-gene Operon Linkers

```
                                         lacZ-lacY linker
            ggaaatccatt (SEQ ID NO: 75)

galT-galK linker
              ggaacgacc(SEQ ID NO: 76)
```

Figure 7:
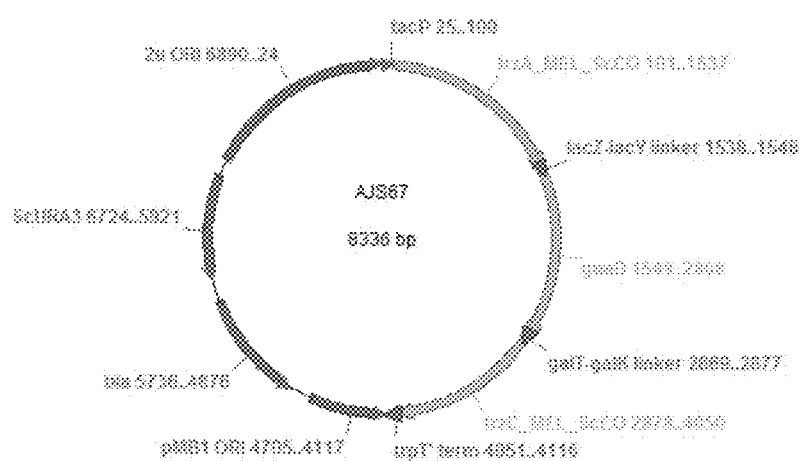
Figure 8:
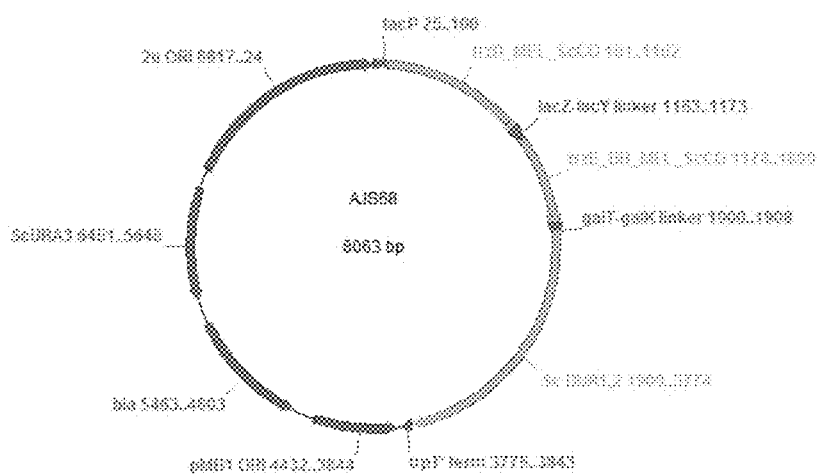

See FIG. 7 and FIG. 8.

Example 7

Expression of Cyanamide Assimilation Enzyme in S. cerevisiae

Figure 9:
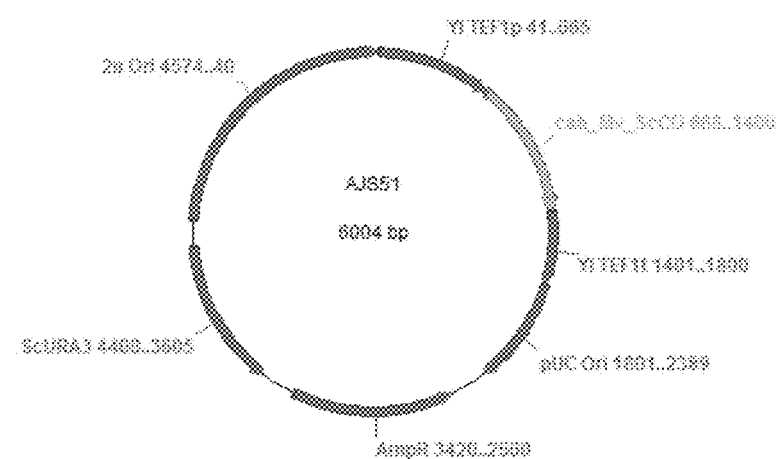

The gene expression methods described in example 5 can also be used in example 7. S. cerevisiae has the native ability to convert urea to $NH_3$ and $CO_2$ via the actions of urea carboxylase and allophante hydrolase, encoded in the fusion gene DUR1,2. Therefore, functional expression of cyanamide hydrolase is sufficient to convert cyanamide to $NH_3$. A representative cyanamide hydratase expression vector is shown below, with Y. lipolytica TEF1 promoter and terminator and a S. cerevisiae codon-optimized cyanamide hydratase (cah) from Myrothecium verrucaria. See FIG. 9.

Example 8

Expression of Cyanamide Assimilation Enzymes in E. coli

Figure 10:
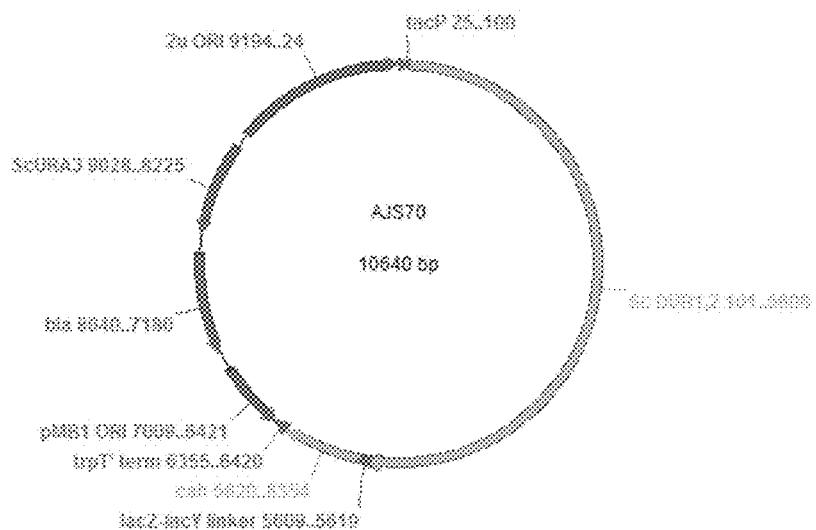

The gene expression methods described in Example 6 can also be used in example 8. Unlike S. cerevisiae, most E. coli strains are unable to utilize urea as a nitrogen source, so these additional conversion steps must also be engineered. Either a urea carboxylase/allophante hydrolase system or a urease enzyme with appropriate accessory enzymes must be expressed in addition to a cyanamide hydrolase. Urease can be found in some *E. coli* isolates (Collins and Falkow 1990) or heterologously expressed (Cussac et al. 1992). Alternatively, the DUR1,2 genes from *S. cerevisiae* could be expressed, as shown below in plasmid AJS70, along with a cyanamide hydratase. See FIG. 10.

Example 9

Expression of Melamine Assimilation Enzymes in *E. coli*

Figure 12:
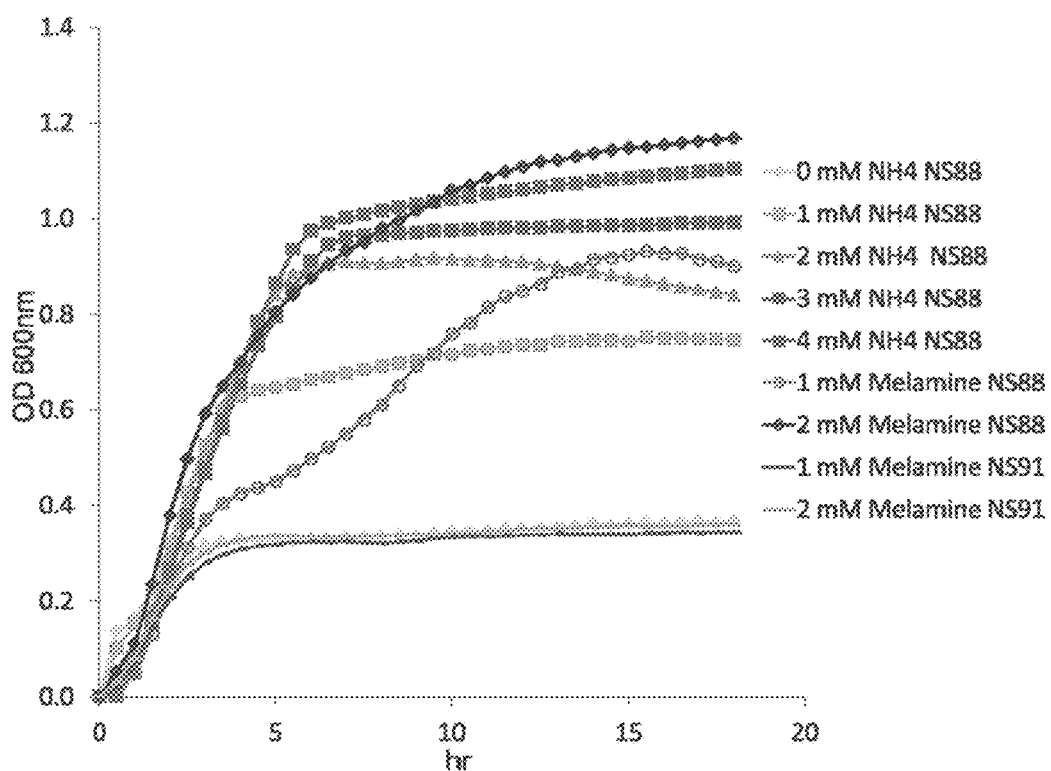
FIG. 12 depicts the growth progress of NS88 and NS91 (control) in media containing various concentrations of ammonium ion or melamine.

Several *E. coli* strains containing partial or complete melamine utilization pathways were constructed, as shown in FIGS. 29 and 30. Vector and strain construction was as described in example 6. All vectors contain the ampicillin resistance gene, and 100 ug/mL ampicillin was added to all culture medium. These strains were grown in MOPS defined medium with different nitrogen sources.
*E. coli* strains and melamine utilization genes
NS88—triA (step 1)
NS89—trzA, guaD, trzC (steps 1, 2, 3)
NS90—trzD, trzE, DUR1,2 (steps 4, 5, 6)
NS91—none (control strain)
NS93—triA, native guaD selected for improved ammeline utilization (steps 1, 2)
NS103—triA, guaD, trzC (steps 1, 2, 3)
NS109—triA, guaD, trzC, trzD 12227, trzE, DUR1,2 (steps 1-6)
NS110—triA, guaD, trzC, atzD ADP, trzE, DUR1,2 (steps 1-6)
FIG. 12 shows the growth progress of NS88 and NS91 (control) in media containing various concentrations of ammonium chloride or melamine NS88 grown on 1 mM melamine reaches an optical density comparable to that of the equivalent use of 2 mM ammonium chloride, suggesting that 2 mM ammonia are liberated from melamine by triA and the natively encoded guaD genes. The control strain NS91 does not grow with melamine as nitrogen source.

Figure 13:
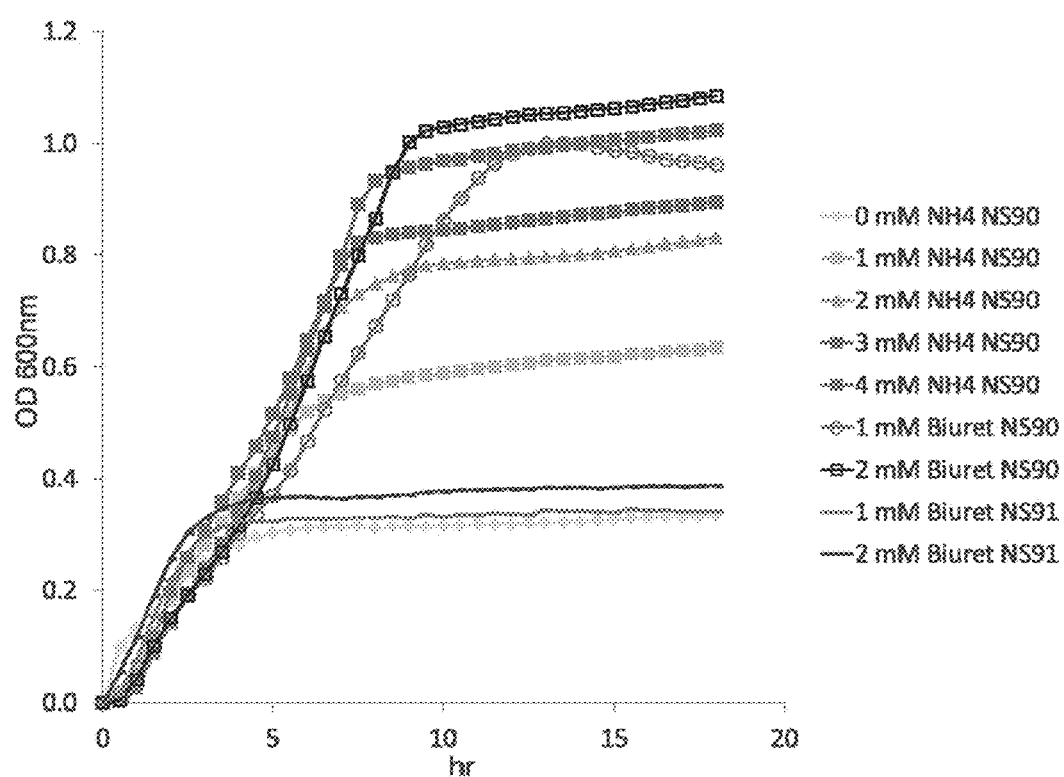
FIG. 13 depicts the growth progress of NS90 and NS91 (control) in media containing various concentrations of ammonium ion or biuret.

FIG. 13 shows the growth progress of NS90 and NS91 (control) in media containing various concentrations of ammonium chloride or biuret. NS90 grown on 1 mM biuret reaches an optical density comparable to that of the equivalent use of 3 mM ammonium chloride, suggesting that 3 mM ammonia are liberated from biuret by trzE and the DUR1,2. The control strain NS91 does not grow with biuret as nitrogen source.

FIG. 24 shows the growth progress of NS91, NS103, NS109, and NS110 in medium containing 0.25 mM melamine as sole nitrogen source. An average of all four strains grown on different ammonium chloride concentrations from 0 to 1.5 mM is also shown as a standard curve for growth with limiting nitrogen. NS91 grown on melamine is similar to the 0 mM ammonium chloride control. NS103 grown on 0.25 mM melamine is similar to 1-0.75 mM ammonium chloride, suggesting it is approximately utilizating the predicted 3 mM ammonia per 1 mM melamine Strains NS109 and NS110 grown on 0.25 mM melamine are similar to 1.5-1.25 mM ammonium chloride, suggesting it is approximately utilizating the predicted 6 mM ammonia per 1 mM melamine.

Figure 25:
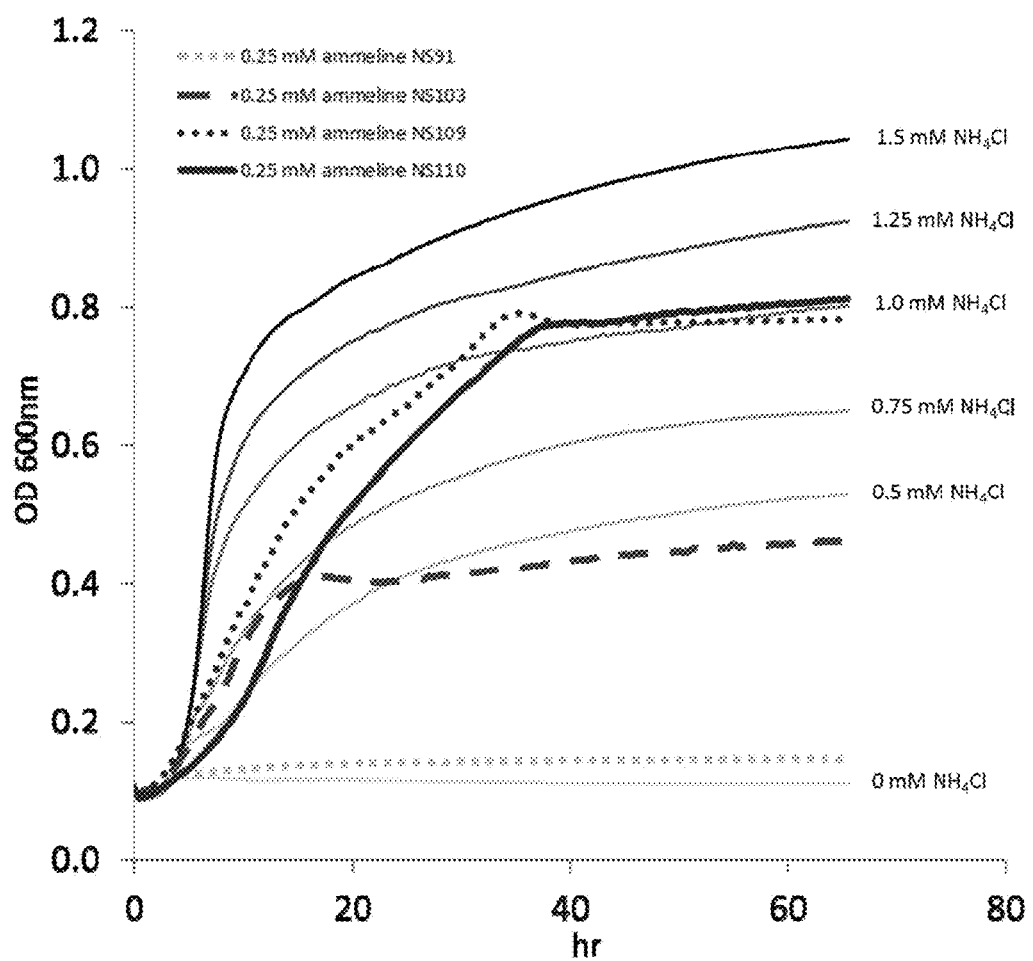
FIG. 25 depicts the growth of four organisms of the invention (NS91=control) on 0.25 mM ammeline, as compared to the standard curves for a native organism on $NH_4Cl$.

FIG. 25 shows the growth progress of NS91, NS103, NS109, and NS110 in medium containing 0.25 mM ammeline as sole nitrogen source. An average of all four strains grown on different ammonium chloride concentrations from 0 to 1.5 mM is also shown as a standard curve for growth with limiting nitrogen. NS91 grown on ammeline is similar to the 0 mM ammonium chloride control. NS103 grown on 0.25 mM ammeline is similar to 0.5 mM ammonium chloride, suggesting it is approximately utilizating the predicted 2 mM ammonia per 1 mM ammeline. Strains NS109 and NS110 grown on 0.25 mM ammeline are similar to 1.25-1.0 mM ammonium chloride, suggesting it is approximately utilizating the predicted 5 mM ammonia per 1 mM ammeline.

FIGS. 26, 27, and 28 show *E. coli* strains derived from *E. coli* K12, *E. coli* MG1655, *E. coli* B, and *E. coli* Crooks (C) containing either pNC121 with the complete melamine utilization pathway, or pNC53, a control vector. See FIGS. 29 and 30 for strain details. All the strains containing pNC121 are able to grow on 0.5 mM melamine as sole nitrogen source (FIG. 28). This indicates that the melamine utilization pathway is broadly applicable to *E. coli* strains that are commonly utilized for biotechnology applications.

Figure 14:
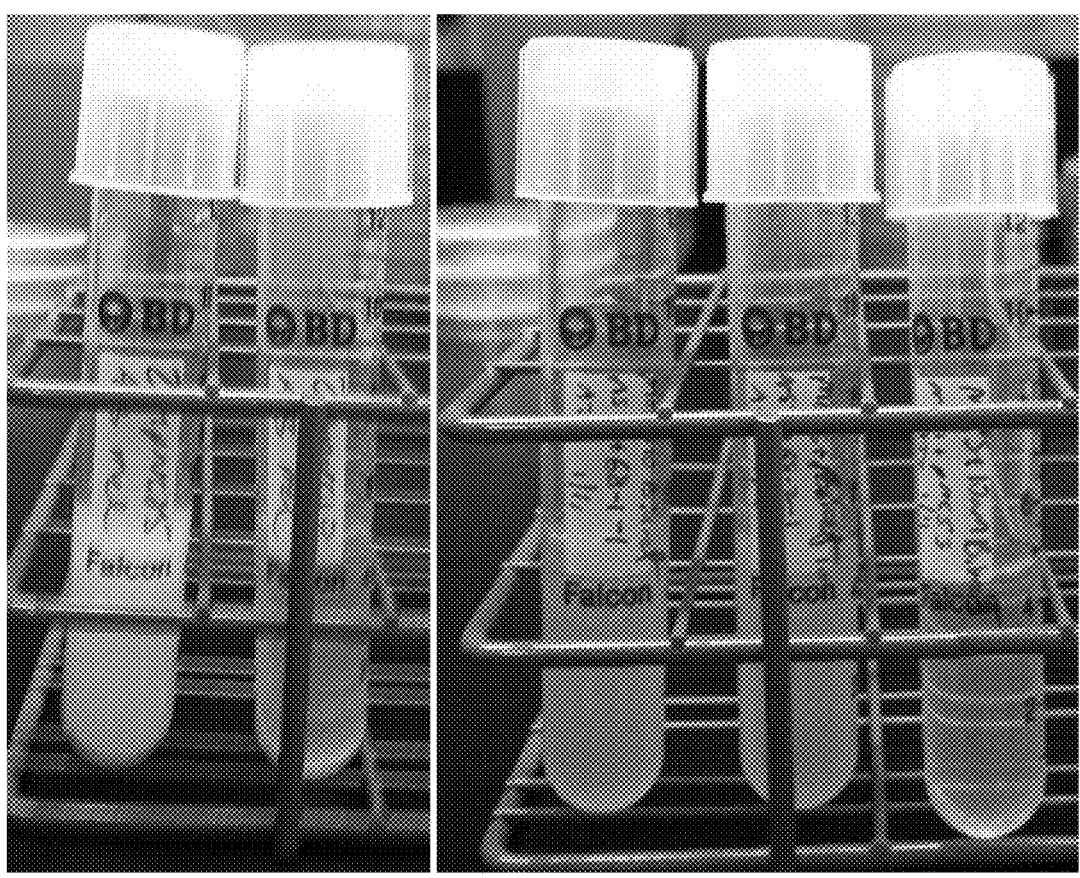
FIG. 14 depicts images, taken after 48 h, of cultures grown in MOPS media with different nitrogen sources. From left to right: NS88 with 10 mM melamine; NS91 with 10 mM melamine; NS90 with 10 mM biuret (replicate 1); NS90 with 10 mM biuret (replicate 2); and NS91 with 10 mM biuret.
Figure 15:
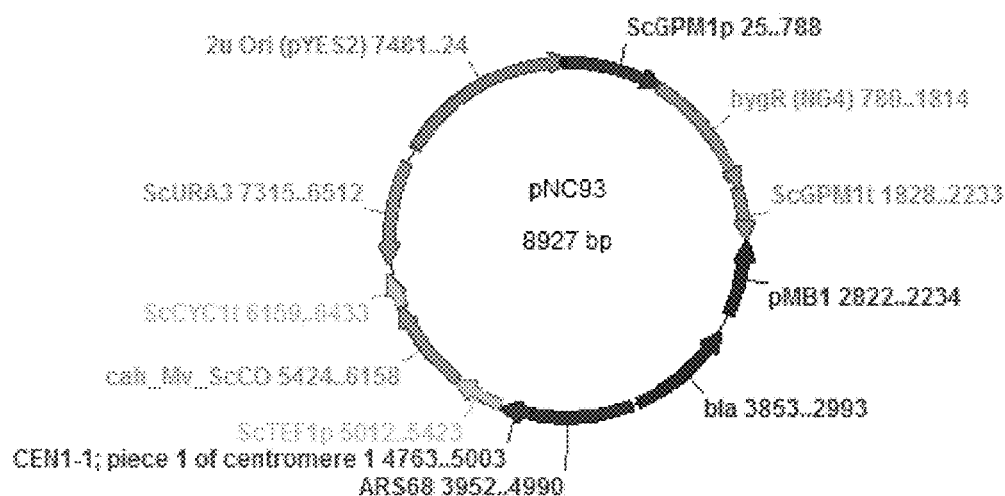
FIG. 15 depicts a plasmid of the invention.

Strains can also be selected for improved utilization of melamine derived nitrogen sources, in one example NS88 was passaged for 11 serial transfers in MOPS defined medium with 0.5 mM ammeline as sole nitrogen source. After the final passage, single colonies were isolated, and one was designated as NS93. NS93 and NS91 were grown overnight in medium with 0.5 mM ammonium chloride as sole nitrogen source, and then inoculated in medium with 0.5 mM ammeline as sole nitrogen source. NS91 exhibited a maximum growth rate of 0.024 $hr^{-1}$ on ammeline, while NS93 exhibited a maximum growth rate of 0.087 $hr^{-1}$.
Media Utilization Cultures grown aerobically at 37° C. with 100 mg/L ampicillin. Pre-cultures were grown in LB media with 100 mg/L ampicillin, washed once with an equal volume of MOPS media containing no nitrogen, and inoculated at 5% v/v of the final fermentation volume. The content of the MOPS medium is outlined in FIG. 11.
Imaging Cultures in Various Media Precultures were grown in LB media with 100 mg/L ampicillin, 0.1 mL were directly inoculated into 5 mL MOPS media with 100 mg/L ampicillin and the indicated nitrogen source. Grown at 37° C. in a drum roller at 30 rpm. See FIG. 14.

Example 10

Organisms Engineered to Utilize Cyanamide

Figure 16:
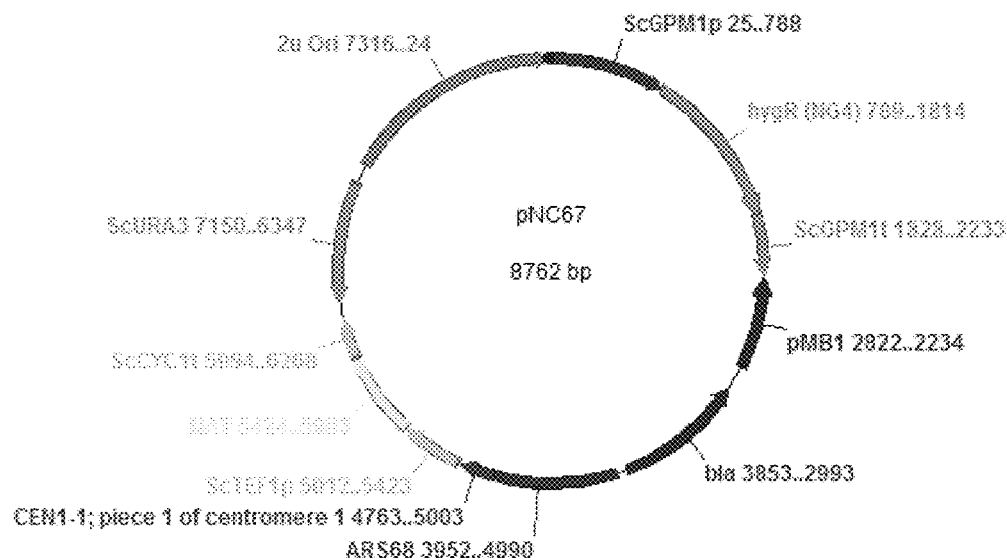
FIG. 16 depicts a plasmid of the invention.
Figure 17:
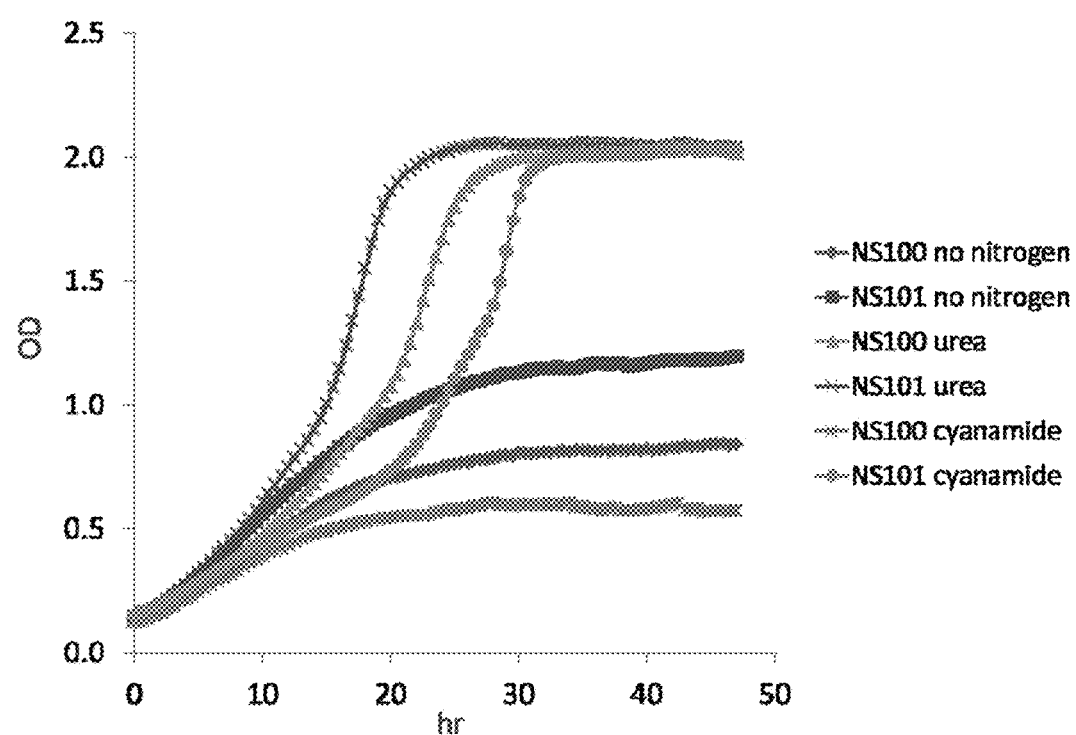
FIG. 17 depicts the growth progress of NS100 (control) and NS101 in media containing no nitrogen source, urea, or cyanamide.

Organisms
NS100—industrial *S. cerevisiae* strain with pNC67 ($hyg^R$, $nat^R$)
NS101—industrial *S. cerevisiae* strain with pNC93 ($hyg^R$, cah)
NS111—*S. cerevisiae* NRRL Y-2223 with pNC93 ($hyg^R$, cah)
NS112—*S. cerevisiae* NRRL Y-2223 with pNC67 ($hyg^R$, $nat^R$)
See FIG. 16.
Utilization of Cyanamide in Defined Medium Optical density of NS100 and NS101 grown in defined medium with different nitrogen sources. NS100 and NS101 were grown overnight in YPD medium, washed once in an equal volume of sterile water, and inoculated at 3.33% v/v. Strain NS101 is able to grow to an optical density with cyanamide comparable to that with urea, while NS100 grows to an optical density comparable to that with no nitrogen present in the medium. Data are averages of 3 replicate wells in a 96 well plate; 150 μL per well. 30° C., YNB medium contained 20 g/L glucose, 1.7 g/L YNB base medium without amino acids or ammonium sulfate, 5 g/L sodium sulfate, 100 μg/mL hygromycin, and either 10 mM urea, 10 mM cyanamide, or no nitrogen source. Inoculation was with 5 μL of culture pregrown for 24 hrs in the same medium with urea as nitrogen source. See FIG. 17.

Figures 21, 22:
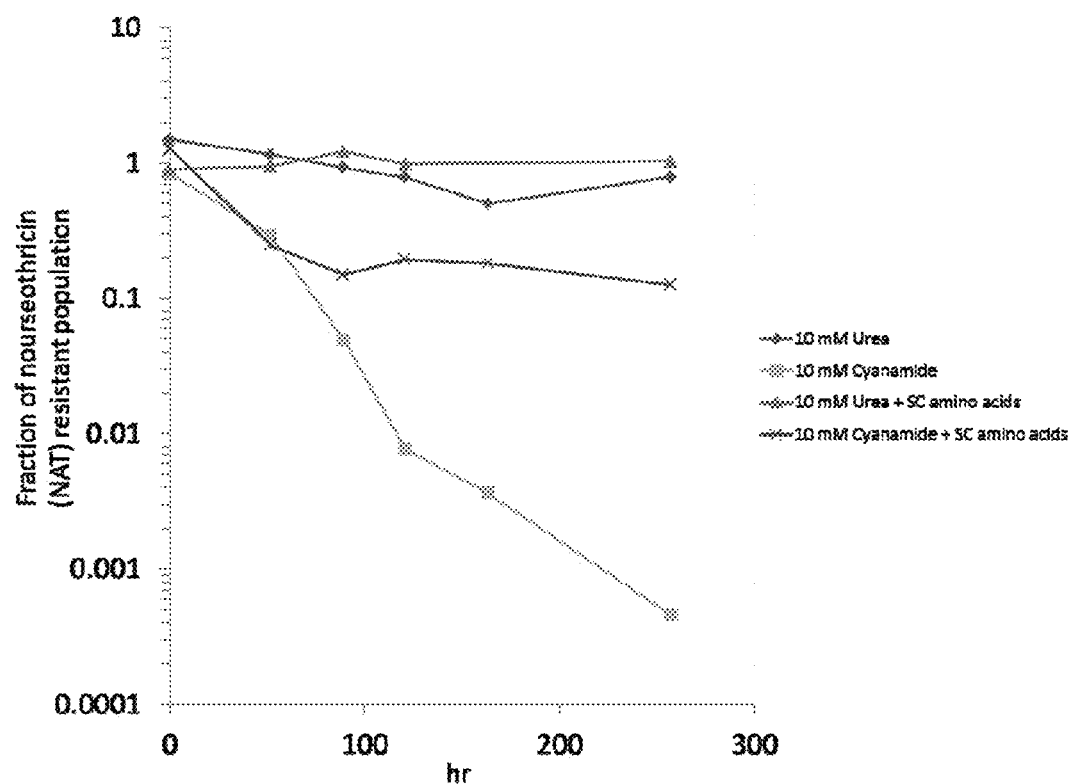
FIG. 21 depicts the growth of an organism of the invention in the presence of an antibiotic on various nitrogen-containing media (see FIG. 33 for composition of SC amino acid media).
FIG. 22 tabulates the optical density at 600 nm after growth of four organisms of the invention on various media.

Additionally, strains NS100, NS101, NS111, and NS112 were grown in defined YNB medium with 10 mM urea and 100 μg/mL hygromycin to stationary phase aerobically at 30° C. 1/1000 v/v inoculations were then made into the same defined medium with either 10 mM urea, 10 mM cyanamide, or no additional nitrogen and grown under the same conditions. Optical density was measured after 72 hours, as shown in FIG. 22. Strains NS101 and NS111, two different *S. cerevisiae* strains carrying the cah gene, were able to grow to an optical density comparable to that with urea; however, NS100 and NS112 only were able to grow to an optical density equal to or lower than in media with no nitrogen source. This shows that multiple *S. cerevisiae* strains are able to utilize cyanamide in the presence of the cah gene.

Competition in Defined Medium

Strains NS100 (hyg$^R$, nat$^R$) and NS101 (hyg$^R$, cah) were grown in defined medium with 100 μg/mL hygromycin with urea as nitrogen source, and then both inoculated into defined medium containing either 10 mM urea or 10 mM cyanamide as nitrogen source.

Figure 18:
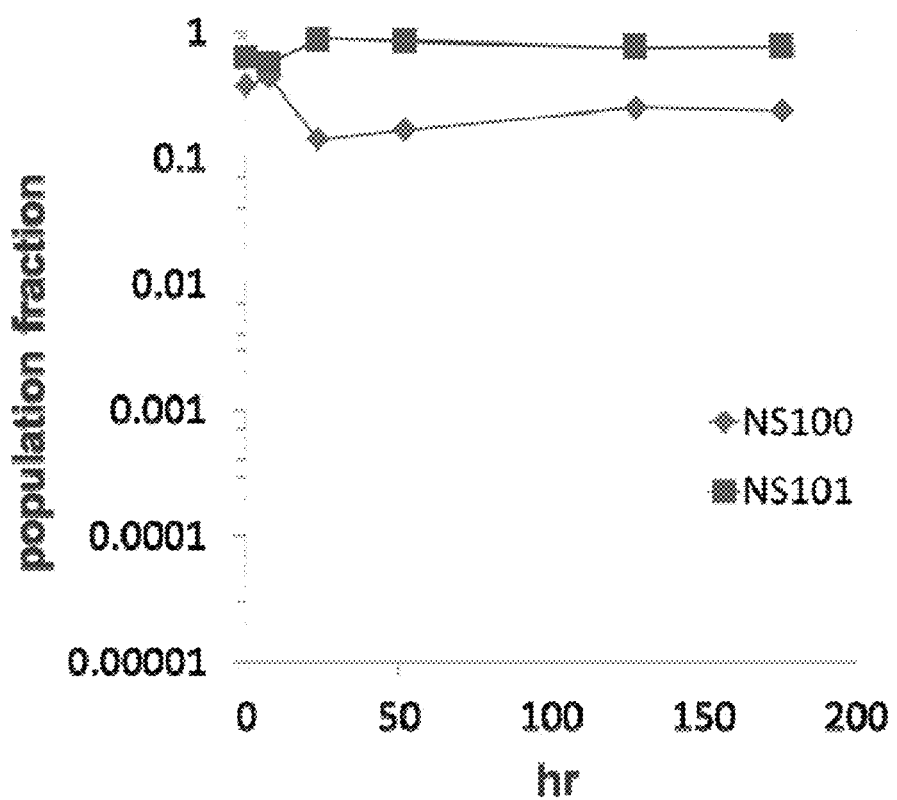
FIG. 18 depicts the population fraction of NS100 (control) and NS101 in a urea-containing medium.
Figure 19:
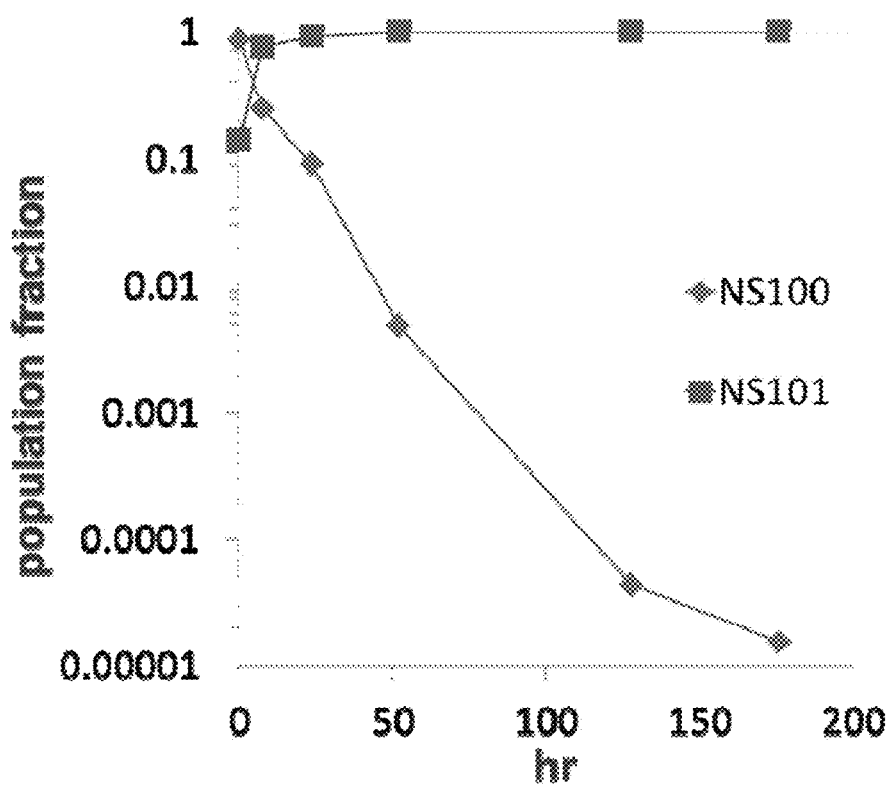
FIG. 19 depicts the population fraction of NS100 (control) and NS101 in a cyanamide-containing medium.

Upon growth to stationary phase, 1/100 v/v serial transfers were made to fresh medium with the same composition. The culture population was monitored via counting the number of hyg$^R$, nat$^R$ colony forming units and subtracting from the number of hyg$^R$ colony forming units. See FIG. 18 and FIG. 19 for one experiment in defined minimal medium. A second experiment is shown in FIG. 21. The second experiment included both defined minimal (YNB) and defined complex (YNB+SC amino acids) medium compositions. The defined YNB medium contained 20 g/L glucose, 1.7 g/L YNB base medium without amino acids or ammonium sulfate, 5 g/L sodium sulfate, and either 10 mM urea, 10 mM cyanamide, or no nitrogen source. Medium compositions are additionally given in FIGS. 32 and 33. Growth occurred aerobically at 30° C. Colony forming units were counted by serial dilutions in YPD media with either 300 μg/mL hygromycin or 100 μg/mL nourseothricin, and are the average of 3 dilution counts. See FIG. 18 and FIG. 19.

Utilization of Cyanamide in Rich Medium

Optical density of NS100 and NS101 grown in rich YPD medium with 100 μg/mL hydgromycin and with and without 10 mM cyanamide. NS100 and NS101 were grown overnight in YNB medium, and inoculated at 3.33% v/v. NS101 experiences a shorter lag phase than NS100 in the presence of 10 mM cyanamide. Thus, cyanamide, in addition to functioning as a sole source of nitrogen, can also act as a deterrent for microbial growth. Data are averages of 3 replicate wells in a 96 well plate; 150 μL per well. 30° C., YPD medium or YPD medium with 10 mM cyanamide. Inoculation was with 5 μL of culture pregrown for 24 hrs in the YNB medium with urea as nitrogen source.

Figure 20:
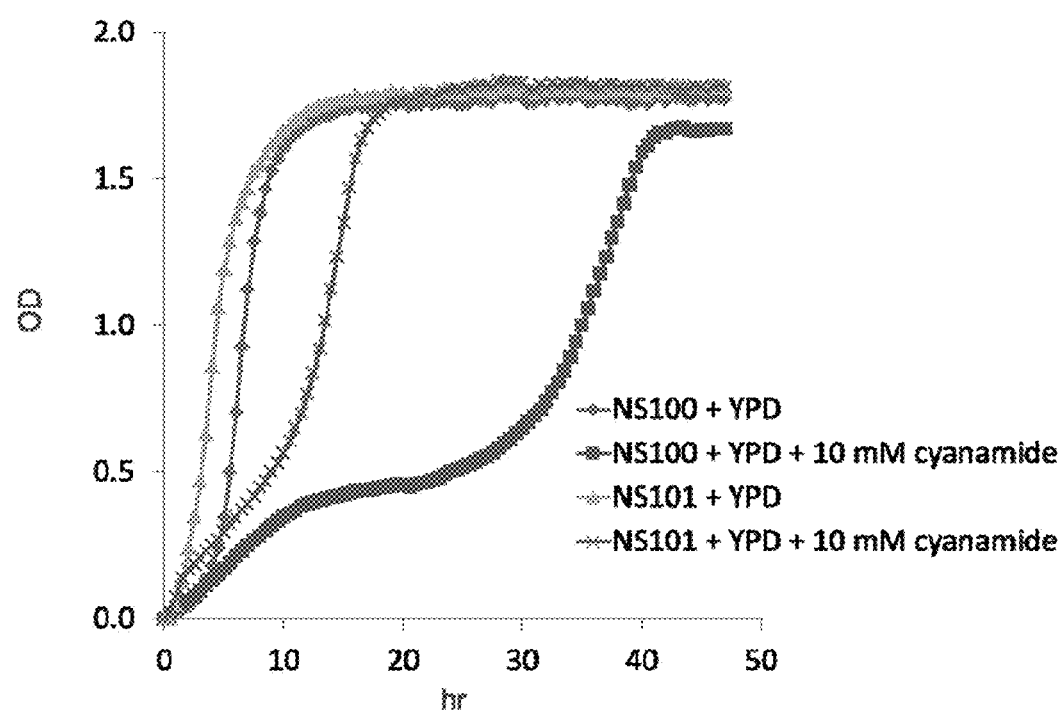
FIG. 20 depicts the growth progress of NS100 (control) and NS101 in media containing no nitrogen source, or media containing cyanamide.

See FIG. 20.

Example 11

Cyanamide Hydratase Activity Assay

This assay measured the conversion rate of cyanamide to urea. In the first step, cyanamide was hydrated to urea by cyanamide hydratase, which was detected in cell free extract of a *S. cerevisiae* strain expressing the cah gene and a control strain without cah. In the second step of the assay, a commercial kit (Megazyme, Ireland) was used to detect urea via enzymatic conversion of urea to ammonia followed by NADPH linked conversion of ammonia and 2-oxoglutarate to NADP+, $H_2O$, and glutamic acid.

Cell free extracts were prepared by growing *S. cerevisiae* strains in 50 mL yeast extract, peptone, dextrose (YPD) medium with 300 μg/mL hygromycin to an optical density between 1-2. Cells were harvested by centrifugation, washed once in an equal volume of water, and re-suspended in Y-PER lysis buffer (Thermo Scientific, USA) following the manufacturer's instructions. After incubation at room temperature for 20 minutes, the lysate was centrifuged at 14,000×g for 10 min and the supernatant was recovered as the cell free extract. Total protein was measured by a Nanodrop spectrophotometer (Thermo Scientific, USA).

Protocol

Add together in a 100 μL volume:
  10 μL of 50 mM NaPO4, pH 7.7;
  10 μL of 200 mM cyanamide made fresh
  5-20 μL cell free extract
  balance water (60 μL for 20 μL CFE)
add 100 uL of above sample to 2.9 mL Megazyme urea/ammonia assay reagents and monitor at 340 nm.

| Strain | Genotype | Cyanamide hydratase activity | |
|---|---|---|---|
| | | μmol min$^{-1}$ mg$^{-1}$ | Standard Deviation |
| NS100 | hyg$^R$ nat$^R$ | 0.019 | 0.001 |
| NS101 | hyg$^R$ cah | 0.073 | 0.002 |

Example 12

Exemplary Sequences of the Invention

Sequence 1 is the DNA sequence of the allophanate hydrolase atzF gene in *Pseudomonas* sp. strain ADP.

Sequence 2 is the DNA sequence of allophanate hydrolase DUR1,2 gene in *S. cerevisiae*.

Sequence 3 is the DNA sequence of allophanate hydrolase YALI0E07271g gene in *Y. lipolytica* CLIB122.

Sequence 4 is the DNA sequence of the biuret amidohydrolase atzE gene in *Pseudomonas* sp. strain ADP.

Sequence 5 is the DNA sequence of the cyanuric acid amidohydrolase atzD gene in *Pseudomonas* sp. strain ADP.

Sequence 6 is the DNA sequence of the cyanuric acid amidohydrolase trzD gene in *Pseudomonas* sp. strain NRRLB-12227 (formerly *Acidovorax citrulli*).

Sequence 7 is the DNA sequence of the cyanuric acid amidohydrolase atzD trzD gene in *Rhodococcus* sp. Mel.

Sequence 8 is the DNA sequence of the guanine deaminase guaD gene in *E. coli* K12 strain MG1566.

Sequence 9 is the DNA sequence of the guanine deaminase blr3880 gene in *Bradyrhizobium japonicum* USDA 110.

Sequence 10 is the DNA sequence of the guanine deaminase GUD1/YDL238C gene in *S. cerevisiae*.

Sequence 11 is the DNA sequence of the guanine deaminase YALI0E25740p gene in *Y. lipolytica* CLIB122.

Sequence 12 is the DNA sequence of the melamine deaminase trzA gene in *Williamsia* sp. NRRL B-15444R (formerly *R. corallinus*).

Sequence 13 is the DNA sequence of the melamine deaminase triA gene in *Pseudomonas* sp. strain NRRL B-12227 (formerly *Acidovorax citrulli*).

Sequence 14 is the DNA sequence of the isopropylammelide isopropylamino-hydrolase atzC gene in *Pseudomonas* sp. strain ADP.

Sequence 15 is the cDNA sequence of the *Myrothecium verrucaria* cyanamide hydratase (cah) gene.

Sequences 16-21 are DNA sequences of the invention.

Sequences 22-37 are the sequences of various cyanamide hydratase (cah) genes for use in the invention.

Sequences 38 and 39 are the sequences of various trzC genes for use in the invention.

Sequences 40 and 41 are the sequences of various trzE genes for use in the invention.

Sequence 42 is the sequence of plasmid pNC10.
Sequence 43 is the sequence of plasmid pNC53.
Sequence 44 is the sequence of plasmid pNC67.
Sequence 45 is the sequence of plasmid pNC85.
Sequence 46 is the sequence of plasmid pNC86.
Sequence 47 is the sequence of plasmid pNC87.
Sequence 48 is the sequence of plasmid pNC93.
Sequence 49 is the sequence of plasmid pNC96.
Sequence 50 is the sequence of plasmid pNC97.
Sequence 51 is the sequence of plasmid pNC101.
Sequence 52 is the sequence of plasmid pNC120.
Sequence 53 is the sequence of plasmid pNC121.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A genetically engineered organism, wherein the genetically engineered organism has been transformed by a nucleic acid molecule; the nucleic acid molecule comprises the non-native triA gene and at least one of the following additional non-native genes: DUR1,2 atzD, trzC, trzE, and guaD.

2. The genetically engineered organism of claim 1, wherein the nucleic acid molecule comprises the sequence of SEQ ID NO: 13.

3. The genetically engineered organism of claim 1, wherein the organism comprises at least two additional non-native genes.

4. The genetically engineered organism of claim 1, wherein the non-native gene is trzE from *Rhodococcus* sp. strain Mel, trzE from *Rhizobium leguminosarum*, trzC MEL, trzC 12227, DUR1,2 from *S. cerevisiae*, atzD from *Pseudomonas* sp. strain ADP, atzD from *Rhodococcus* sp. Mel, guaD from *E. coli* K12 strain MG1566, and/or triA from *Pseudomonas* sp. strain NRRL B-12227.

5. The genetically engineered organism of claim 1, wherein the genetically engineered organism is a species of the genus *Yarrowia*, *Saccharomyces*, *Ogataea*, *Pichia*, or *Escherichia*.

6. The genetically engineered organism of claim 5, wherein the genetically engineered organism is selected from the group consisting of *Yarrowia lipolytica*, *Saccharomyces cerevisiae*, *Ogataea polymorpha*, *Pichia pastoris*, and *Escherichia coli*.

7. A recombinant vector comprising a gene operably linked to a promoter, wherein the gene encodes an enzyme; and the enzyme is melamine deaminase, and the vector comprises at least one of the following additional genes: DUR1,2 atzD, trzC, trzE, and guaD.

8. The recombinant vector of claim 7, wherein the gene is trzE from *Rhodococcus* sp. strain Mel, trzE from *Rhizobium leguminosarum*, trzC MEL, trzC 12227 DUR1,2 from *S. cerevisiae*, atzD from *Pseudomonas* sp. strain ADP, guaD from *E. coli* K12 strain MG1566, and/or triA from *Pseudomonas* sp. strain NRRL B-12227.

9. The recombinant vector of claim 7, wherein the vector comprises the sequence set forth in SEQ ID NO:13.

10. The genetically engineered organism of claim 1, wherein the organism comprises at least three additional non-native genes.

11. The genetically engineered organism of claim 10, wherein the organism comprises at least four additional non-native genes.

12. The genetically engineered organism of claim 11, wherein the organism comprises all five additional non-native genes.

13. The genetically engineered organism of claim 1, wherein the non-native triA gene and the at least one additional non-native gene are expressed from a single promoter as part of a gene operon.

14. The recombinant vector of claim 7, wherein the vector further comprises at least two of the following additional genes: DUR1,2, atzD, trzC, trzE, and guaD.

15. The recombinant vector of claim 14, wherein the vector comprises at least three of the additional genes.

16. The recombinant vector of claim 15, wherein the vector comprises at least four of the additional genes.

17. The recombinant vector of claim 16, wherein the vector comprises all five additional genes.

18. The recombinant vector of claim 17, wherein the gene encoding melamine deaminase and all five additional genes are operably linked to the same promoter as part of a gene operon.

19. The recombinant vector of claim 7, wherein the gene encoding melamine deaminase and the at least one additional gene are operably linked to the same promoter as part of a gene operon.

* * * * *